US010233458B2

(12) United States Patent
Sayre et al.

(10) Patent No.: US 10,233,458 B2
(45) Date of Patent: Mar. 19, 2019

(54) CARBON FIXATION SYSTEMS IN PLANTS AND ALGAE

(71) Applicant: NMC, INC., Los Alamos, NM (US)

(72) Inventors: Richard Thomas Sayre, Los Alamos, NM (US); Somya S. Subramanian, Los Alamos, NM (US); Natalia Friedland, Los Alamos, NM (US)

(73) Assignee: NMC, INC., Los Alamos, NM (US)

( * ) Notice: Subject to any disclaimer, the term of this patent is extended or adjusted under 35 U.S.C. 154(b) by 0 days.

(21) Appl. No.: 15/411,854

(22) Filed: Jan. 20, 2017

(65) Prior Publication Data

US 2017/0211086 A1 Jul. 27, 2017

Related U.S. Application Data

(63) Continuation of application No. PCT/US2015/041617, filed on Jul. 22, 2015.

(60) Provisional application No. 62/027,354, filed on Jul. 22, 2014.

(51) Int. Cl.

| | |
|---|---|
| ***C12N 15/82*** | (2006.01) |
| ***C12N 1/12*** | (2006.01) |
| ***C07K 14/415*** | (2006.01) |
| ***C12P 1/00*** | (2006.01) |

(52) U.S. Cl.

CPC ........ *C12N 15/8269* (2013.01); *C07K 14/415* (2013.01); *C12N 1/12* (2013.01); *C12N 15/8243* (2013.01); *C12N 15/8261* (2013.01); *C12P 1/00* (2013.01); *C12N 2800/22* (2013.01); *Y02A 40/146* (2018.01)

(58) Field of Classification Search

CPC .................................................. C12N 15/8269

See application file for complete search history.

(56) References Cited

U.S. PATENT DOCUMENTS

| | | | |
|---|---|---|---|
| 4,554,101 | A | 11/1985 | Hopp |
| 5,164,316 | A | 11/1992 | McPherson et al. |
| 5,196,525 | A | 3/1993 | McPherson et al. |
| 5,322,938 | A | 6/1994 | McPherson et al. |
| 5,352,605 | A | 10/1994 | Fraley et al. |
| 5,359,142 | A | 10/1994 | McPherson et al. |
| 5,424,200 | A | 6/1995 | McPherson et al. |
| 5,510,474 | A | 4/1996 | Quail et al. |
| 5,589,583 | A | 12/1996 | Klee et al. |
| 5,593,874 | A | 1/1997 | Brown et al. |
| 5,599,686 | A | 2/1997 | Defeo-Jones et al. |
| 5,641,876 | A | 6/1997 | McElroy et al. |
| 5,659,122 | A | 8/1997 | Austin |
| 6,784,340 | B1 | 8/2004 | Aoyama et al. |
| 6,989,265 | B2 | 1/2006 | Blattner et al. |
| 7,053,205 | B1 | 5/2006 | Verdaguer et al. |
| 7,303,906 | B2 | 12/2007 | Blattner et al. |
| 8,039,243 | B2 | 10/2011 | Blattner |
| 8,043,842 | B2 | 10/2011 | Blattner et al. |
| 8,119,365 | B2 | 2/2012 | Blattner et al. |
| 8,178,339 | B2 | 5/2012 | Campbell et al. |
| 2011/0256605 | A1 | 10/2011 | Liphardt et al. |
| 2012/0219994 | A1 | 8/2012 | Blattner et al. |
| 2013/0007916 | A1 | 1/2013 | Spalding |

FOREIGN PATENT DOCUMENTS

| | | |
|---|---|---|
| EP | 0507698 | 10/1992 |
| EP | 0633317 | 1/1995 |
| EP | 1483367 | 5/2010 |
| WO | 84/02913 | 8/1984 |
| WO | 87/007644 | 12/1987 |
| WO | 95/006742 | 3/1995 |
| WO | 96/06932 | 3/1996 |
| WO | 97/48819 | 12/1997 |
| WO | 2004/053135 | 6/2004 |
| WO | 07/098042 | 8/2007 |
| WO | 2012/101118 | 8/2012 |
| WO | 2012/125737 | 9/2012 |
| WO | 2017/218959 | 12/2017 |

OTHER PUBLICATIONS

Blanco, N. et al., Plant Physiology; Feb. 2013, vol. 161, pp. 866-879.*

Suorsa, M. et al. Molecular Plant; vol. 9, Feb. 2016, pp. 271-288.*

Ainley, W. Michael, et al., "Regulatable endogenous production of cytokinins up to 'toxic' levels in transgenic plants and plant tissues", Plant Molecular Biology, vol. 22, 1993, 13-23.

Allen, Doug K., et al., "Carbon and Nitrogen Provisions Alter the Metabolic Flux in Developing Soybean Embryos", Plant Physiology, vol. 161, 2013, 1458-1475.

Allen, Doug K., et al., "Comparing Photosynthetic and Photovoltaic Efficiencies and Recognizing the Potential for Improvement", Phytochemistry, vol. 68, 2007, 2197-2210.

Allen, Doug K., et al., "Isotope labelling of Rubisco subunits provides in vivo information on subcellular biosynthesis and exchange of amino acids between compartments", Plant, Cell and Environment, Vo. 35, 2012, 1232-1244.

(Continued)

*Primary Examiner* — Russell Kallis

(74) *Attorney, Agent, or Firm* — Peacock Law P.C.; Janeen Vilven

(57) ABSTRACT

Provided are methods for elevating cyclic electron transfer activity, improving carbon concentration, and enhancing carbon fixation in C3 and C4 plants, and algae, and producing biomass or other products from C3 or C4 plants, and algae, selected from among, for example, starches, oils, fatty acids, lipids, cellulose or other carbohydrates, alcohols, sugars, nutraceuticals, pharmaceuticals, fragrance and flavoring compounds, and organic acids, as well as transgenic plants produced thereby. These methods and transgenic plants and algae encompass the expression, or overexpression, of various combinations of genes that improve carbon concentrating systems in plants and algae, such as bicarbonate transport proteins, carbonic anhydrase, light driven proton pump, cyclic electron flow regulators, etc.

12 Claims, 13 Drawing Sheets

Specification includes a Sequence Listing.

(56) References Cited

OTHER PUBLICATIONS

Allen, Doug K., et al., "Metabolic flux analysis in plants: coping with complexity", Plant, Cell and Environment, vol. 32, 2009, 1241-1257.
Allen, Doug K., et al., "Quantification of Peptide m/z Distributions from 13C-Labeled Cultures with High-Resolution Mass Spectrometry", Anal. Chem., vol. 86, 2014, 1894-1901.
Allen, Doug K., et al., "The role of light in soybean seed filling metabolism", The Plant Journal, vol. 58, 2009, 220-234.
Alric, Jean , "Cyclic electron flow around photosystem I in unicellular green algae", Photosynth Res, vol. 106, 2010, 47-56.
Altschul, Stephen F., et al., "Basic Local Alignment Search Tool", J. Mol. Biol., vol. 215, 1990, 403-410.
Altschul, Stephen F., et al., "Gapped BLAST and PSI-BLAST: a new generation of protein database search programs", Nucleic Acids Research, vol. 25, No. 17, 1997, 3389-3402.
Amunts, Alexey , et al., "The structure of a plant photosystem I supercomplex at 3.4A° resolution", Nature, vol. 447, 2007, 58-63.
Arrivault, Stephanie , "Use of reverse-phase liquid chromatography, linked to tandem mass spectrometry, to profile the Calvin cycle and other metabolic intermediates in *Arabidopsis* rosettes at different carbon dioxide concentrations", The Plant Journal, vol. 59, 2009, 824-839.
Avsian-Kretchmer, Orna , et al., "The Salt-Stress Signal Transduction Pathway That Activates the gpxl Promoter Is Mediated by Intracellular H2O2, Different from the Pathway Induced by Extracellular H2O2", Plant Physiology, vol. 135, 2004, 1685-1696.
Baumann, Kim , et al., "The DNA Binding Site of the Dof Protein NtBBF1 Is Essential for Tissue-Specific and Auxin-Regulated Expression of the rolB Oncogene in Plants", The Plant Cell, vol. 11, 1999, 323-333.
Beja, Oded , et al., "Bacterial Rhodopsin: Evidence for a New Type of Phototrophy in the Sea", Science, vol. 289, 2000, 1902-1906.
Benfey, Philip N., et al., "The CaMV 35S enhancer contains at least two domains which can confer different developmental and tissuespecific expression patterns", The EMBO Journal, vol. 8, No. 8, 1989, 2195-2202.
Bihmidine, Saadia , et al., "Regulation of assimilate import into sink organs: update on molecular drivers of sink strength", Frontiers in Plant Science, vol. 4, Issue 177, 2013, 1-15.
Blankenship, Robert E., "Comparing Photosynthetic and Photovoltaic Efficiencies and Recognizing the Potential for Improvement", Science, vol. 332, 2011, 805-809.
Blázquez, Miguel A., et al., "Gibberellins Promote Flowering of *Arabidopsis* by Activating the LEAFY Promoter", The Plant Cell, vol. 10, 1998, 791-800.
Blume, Beatrix , et al., "Expression of ACC oxidase promoter-GUS fusions in tomato and Nicotiana plumbaginifolia regulated by developmental and environmental stimuli", The Plant Journal, vol. 12, No. 4, 1997, 731-746.
Breyton, Cecile , et al., "Redox Modulation of Cyclic Electron Flow around Photosystem I in C3 Plants", Biochemistry, vol. 45, 2006, 13465-13475.
Buchel, Annemarie , et al., "Mutation of GT-1 binding sites in the Pr-1A promoter influences the level of inducible gene expression in vivo", Plant Molecular Biology, vol. 40, No. 3, 1999, 387-396.
Busch, Karin B., et al., "Dynamics of bioenergetic microcompartments", Biol. Chem., vol. 394, No. 2, 2013, 163-188.
Busk, Peter Kamp, et al., "Regulatory elements in vivo in the promoter of the abscisic acid responsive gene rab17 from maize", The Plant Journal, vol. 11, No. 6, 1997, 1285-1295.
Callis, Judy , et al., "Introns increase gene expression in cultured maize cells", Genes & Development, vol. 1, 1987, 1183-1200.
Cao, Yi , et al., "Relationship of Proton Release at the Extracellular Surface to Deprotonation of the Schiff Base in the Bacteriorhodopsin Photocycle", Biophysical Journal, vol. 68, 1995, 1518-1530.
Cardol, Pierre , et al., "Regulation of electron transport in microalgae", Biochimica et Biophysica Acta, vol. 1807, 2011, 912-918.
Cardon, Guillermo H., et al., "Functional analyis of the *Arabidopsis thaliana* SBP-box gene SPL3: a novel gene involved in the floral transition", The Plant Journal, vol. 12, No. 2, 1997, 367-377.
Carrillo, Humberto , et al., "The Multiple Sequence Alignment Problem in Biology", SIAM Journal on Applied Mathematics, vol. 48, No. 5, 1988, 1073-1082.
Carrington, James C., et al., "Cap-Independent Enhancement of Translation by a Plant Potyvirus 5' Nontranslated Region", Journal of Virology, vol. 64, No. 4, 1990, 1590-1597.
Chaubet-Gigot, Nicole , et al., "Tissue-dependent enhancement of transgene expression by introns of replacement histone H3 genes of *Arabidopsis*", Plant Molecular Biology, vol. 45, 2001, 17-30.
Chen, Wenqiong , et al., "The promoter of a H2O2-inducible, *Arabidopsis* glutathione S-transferase gene contains closely closely linked OBF- and OBP1-binding sites", The Plant Journal, vol. 10, No. 6, 1996, 955-966.
Choi, Jungik , et al., "Tandem massspectrometry:Anovelapproachf ormetabolicfluxanalysis", Metabolic Engineering, vol. 13, 2011, 225-233.
Clancy, Maureen , et al., "Splicing of the Maize Sh1 First Intron Is Essential for Enhancement of Gene Expression, and a T-Rich Motif Increases Expression without Affecting Splicing", Plant Physiol. vol. 130, 2002, 918-929.
Claverie, Jean-Michel , "Information Enhancement Methods for Large Scale Sequence Analysis", Computers Che., vol. 17, No. 2, 1993, 191-201.
Dalcorso, Giovanni , et al., "A Complex Containing PGRL1 and PGR5 Is Involved in the Switch Between Linear and Cyclic Electron Flow in *Arabidopsis*", Cell 132, 2008, 273-285.
Dalcorso, Giovanni , et al., "A Complex Containing PGRL1 and PGR5 Is Involved in the Switch between Linear and Cyclic Electron Flow in *Arabidopsis*", Cell, vol. 132, 2008, 273-285.
Datla, Raju S.S., et al., "Improved high-level constitutive foreign gene expression in plants using an AMV RNA4 untranslated leader sequence", Plant Science, vol. 94, 1993, 139-149.
De Veylder, Lieven , et al., "Herbicide Safener-Inducible Gene Expression in *Arabidopsis thaliana*", Plant Cell Physiol., vol. 38, No. 5, 1997, 568-577.
Dioumaev, Andrei K., et al., "Proton Transfers in the Photochemical Reaction Cycle of Proteorhodopsin", Biochemistry, vol. 41, 5348-5358, 2002.
Duanmu, Deqiang , et al., "Knockdown of limiting-CO2-induced gene HLA3 decreases HCO3 transport and photosynthetic Ci affinity in Chlamydomonas reinhardtii", PNAS, vol. 106, No. 14, 2009, 5990-5995.
Duckwall, Casey Scott, et al., "Mapping cancer cell metabolism with 13C flux analysis: Recent progress and future challenges", Journal of Carcinogenesis, vol. 12, No. 13, 2013, 1-7.
Egnatchik, R. A., et al., "Palmitate-induced activation of mitochondrial metabolism promotes oxidative stress and apoptosis in H4IIEC3 rat hepatocytes", Metabolism, vol. 62, No. 2, 2014, 283-295.
Elleby, Bjorn , et al., "Characterization of carbonic anhydrase from Neisseria gonorrhoeae", Eur. J. Biochem, vol. 268, 2001, 1613-1619.
Fabre, Nicolas , et al., "Characterization and expression analysis of genes encoding a and b carbonic anhydrases in *Arabidopsis* ", Plant, Cell and Environment, vol. 30, 2007, 617-629.
Farquhar, G. D., et al., "Carbon Isotope Discrimination and Photosynthesis", Annu. Rev. Plant Physiol. Plant Mol. Biol., vol. 40, 1989, 503-537.
Friedrich, Thomas , et al., "Proteorhodopsin is a Light-driven Proton Pump with Variable Vectoriality", J. Mol. Biol., vol. 321, 2002, 821-838.
Froehlich, John E., et al., "The role of the transmembrane domain in determining the targeting of membrane proteins to either the inner envelope or thylakoid membrane", The Plant Journal, vol. 68, 2011, 844-856.
Furbank, Robert T., et al., "C4 rice: a challenge for plant phenomics", Functional Plant Biology, vol. 36, No. 11, 2009, 845-856.
Gatz, C. , et al., "Chemical Control of Gene Expression", Annu. Rev. Plant Physiol. Plant Mol. Biol., vol. 18, 1997, 89-108.
Sakai, Tatsuya , et al., "Analysis of the Promoter of the Auxin-Inducible Gene, parC, of Tobacco", Plant Cell Physiol., vol. 37, No. 7, 1996, 906-913.

(56) References Cited

OTHER PUBLICATIONS

Sakamoto, Masahiro , et al., "Structure and Characterization of a Gene for Light-Harvesting Chi a/b Binding Protein from Rice", Plant Cell Physiol., vol. 32, No. 3, 1991, 385-393.
Samac, Deborah A., et al., "A comparison of constitutive promoters for expression of transgenes in alfalfa (Medicago sativa)", Transgenic Research, vol. 13, 2004, 349-361.
Sanger, Margaret , et al., "Characteristics of a strong promoter from figwort mosaic virus: comparison with the analogous 35S promoter from cauliflower mosaic virus and the regulated mannopine synthase promoter", Plant Molecular Biology, vol. 14, 1990, 433-443.
Schaffner, Anton R., et al., "Maize rbcS Promoter Activity Depends on Sequence Elements Not Found in Dicot rbcS Promoters", lhe Plant Cell, vol. 3, 1991, 997-1012.
Sekiyama, Yasuyo , et al., "Towards dynamic metabolic network measurements by multi-dimensional NMR-based fluxomics", Phytochemistry, vol. 68, 2007, 2320-2329.
Shastri, Avantika A., et al., "A transient isotopic labeling methodology for 13C metabolic flux analysis of photoautotrophic microorganisms", Phytochemistry, vol. 68, 2007, 2302-2312.
Sheen, Jen , "Ca2+-dependent protein kinases and stress signal transduction in plants", Science, vol. 274, No. 5294, 1996, 1900-1902.
Shi, Rebecca , et al., "Engineering *Oryza sativa* to Express the Photeorhodopsin Photosystem", http://openwetware.org/wiki/20.109(F12):Mod3_OrangeTR_Pre-proposal, 2012, 1-4.
Shi, Lifang , et al., "Gibberellin and abscisic acid regulate GAST1 expression at the level of transcription", Plant Molecular Biology, vol. 38, 1998, 1053-1060.
Shikanai, Toshiharu , "Central role of cyclic electron transport around photosystem I in the regulation of photosynthesis", Current Opinion in Biotechnology, vol. 26, 2014, 25-30.
Si, Li-Zhen , et al., "Isolation of a 1 195 bp 5-Flanking Region of Rice Cytosolic Fructose-1, 6-bisphosphatase and Analysis of Its Expression in Transgenic Rice", Acta Botanica Sinica, vol. 3, 2003, 359-364.
Siebertz, Barbara , et al., "cis-Analysis of the Wound-Inducible Promoter wun7 in Transgenic Tobacco Plants and Histochemical Localization of Its Expression", The Plant Cell, vol. 1, 1989, 961-968.
Sinclair, Thomas R., "Historical Changes in Harvest Index and Crop Nitrogen Accumulation", Crop Science, vol. 38, No. 3, 1998, 638-643.
Slewinski, Thomas L., et al., "Current perspectives on the regulation of whole-plant carbohydrate partitioning", Plant Science, vol. 178, 2010, 341-349.
Sonnewald, U. , "Mianipulation of sink-source relations in transgenic plants", Plant, Cell and Environment, vol. 17, 1994, 649-658.
Sonnewald, Uwe , et al., "Molecular Approaches to Sink-Source Interactions", Plant Physiol., vol. 99, 1992, 1267-1270.
Srour, Orr , et al., "Fluxomers: a new approach for 13C metabolic flux analysis", BMC Systems Biology, vol. 5, No. 129, 2011, 1-15.
Stange, Claudia , et al., "Phosphorylation of nuclear proteins directs binding to salicylic acid-responsive elements", The Plant Journal, vol. 11, No. 6, 1997, 1315-1324.
Streit, Wolfgang R., et al., "A Biotin-Regulated Locus, bioS, in a Possible Survival Operon of Rhizobium meliloti", MPMI vol. 10, No. 7, 1997, 933-937.
Subramanian, Sowmya , "Comparative energetics and kinetics of autotrophic lipid and starch metabolism in chlorophytic microalgae: implications for biomass and biofuel production", Biotechnology for Biofuels, vol. 6, No. 150, 2013, 1-12.
Sweetlove, L. J., et al., "Source metabolism dominates the control of source to sink carbon flux in tuberizing potato plants throughout the diurnal cycle and under a range of environmental conditions", Plant, Cell and Environment, vol. 23, 2000, 523-529.
Szecowka, Marek , et al., "Metabolic Fluxes in an Illuminated *Arabidopsis* Rosette", The Plant Cell, vol. 25, 2013, 694-714.
Takahashi, Hiroko , et al., "Cyclic electron flow is redox-controlled but independent of state transition", Nature communication, vol. 4, No. 1954, 2013, 1-8.
Van Der Kop, Dianne A.M., et al., "Selection of *Arabidopsis* mutants overexpressing genes driven by the promoter of an auxin-inducible glutathione S-transferase gene", Plant Molecular Biology, vol. 39, 1999, 970-990.
Victorio, Reynaldo G., et al., "Growth, Partitioning, and Harvest Index of Tuber-Bearing Solanum Genotypes Grown in Two Contrasting Peruvian Environments", Plant Physiol., vol. 82, 1986, 103-108.
Vos, J. , "The nitrogen response of potato (*Solanum tuberosum* L.) in the field: nitrogen uptake and yield, harvest index and nitrogen concentration.", Potato Research, vol. 40, 1997, 237-248.
Walter, Jessica M., et al., "Light-powering *Escherichia coli* with proteorhodopsin", PNAS, vol. 104, No. 7, 2007, 2408-2412.
Walter, Jessica M., et al., "Potential of light-harvesting proton pumps for bioenergy applications", Current Opinion in Biotechnology, vol. 21, 2010, 265-270.
Wang, Yingjun , et al., "Carbon dioxide concentrating mechanism in Chlamydomonas reinhardtyy: inorganic carbon transport and CO2 recapture", Photosynth Res, vol. 109, 2011, 115-122.
Weber, Andreas PM, et al., "Plastid transport and metabolism of C3 and C4 plants—comparative analysis and possible biotechnological exploitation", Current Opinion in Plant Biology, vol. 13, 2010, 257-265.
Willmott, Ruth L., et al., "DNase1 footprints suggest the involvement of at least three types of transcription factors in the regulation of alpha-Amy2/A by gibberellin", Plant Molecular Biology, vol. 38, 1998, 817-825.
Wootton, John C., et al., "Statistics of Local Complexity in Amino Acid Sequences and Sequence Databases", Computers Chem. vol. 17, No. 2, 1993, 149-163.
Wunsche, Jens N., et al., "Physiological and biochemical leaf and tree responses to crop load in apple", Tree Physiology, vol. 25, 2005, 1253-1263.
Yamaguchi-Shinozaki, Kazuko , et al., "A Novel cis-Acting Element in an *Arabidopsis* Gene 1s Involved in Responsiveness to Drought, Lowqemperature, or High-Salt Stress", The Plant Cell, vol. 6, 1994, 251-264.
Young, Jamey D., et al., "An Elementary Metabolite Unit (EMU) Based Method of Isotopically Nonstationary Flux Analysis", Biotechnology and Bioengineering, vol. 99, No. 3, 2008, 686-699.
Young, Jamey D., "INCA: a computational platform for isotopically non-stationary metabolic flux analysis", Bioinformatics, vol. 30, No. 9, 2014, 1333-1335.
Young, Jamey D., et al., "Isotopomer Measurement Techniques in Metabolic Flux Analysis II: Mass Spectrometry", Methods in Molecular Biology, vol. 1083, Chapter 7, 2014, 85-108.
Young, Jamey D., "Mapping photoautotrophic metabolism with isotopically nonstationary 13C flux analysis", Metabolic Engineering, vol. 13, 2011, 656-665.
Young, Jamey D., "Metabolic flux rewiring in mammalian cell cultures", Current Opinion in Biotechnology, vol. 24, 2013, 1108-1115.
Zhu, Xin-Guang , et al., "C4 Rice—an Ideal Arena for Systems Biology Research", Journal of Integrative Plant Biology, vol. 52, Issue 8, 2010, 762-770.
Zuo, Jianru et al., "An estrogen receptor-based transactivator XVE mediates highly inducible gene expression in transgenic plants", The Plant Journal, vol. 24, No. 2, 2000, 265-273.
Leamy, Alexandra , et al., "Modulating lipid fate controls lipotoxicity in palmitate-treated hepatic cells", The FASEB Journal, vol. 27, No. 1, 2013, 1.
Lindqvist, Annika , et al., "Biochemical Properties of Purified Recombinand Human Beta-Carotene 15, 15'-Monooxygenase", The Journal of Biological Chemistry, vol. 277, No. 26, 2002, 23942-23948.
Liu, Zhan-Bin , et al., "A G-Box-Binding Protein from Soybean Binds to the E1 Auxin-Response Element in the Soybean CH3 Promoter and Contains a Proline-Rich Repression Domain", Plant Physiol., vol. 115, 1997, 397-407.

(56) References Cited

OTHER PUBLICATIONS

Lu, Chaofu , et al., "Generation of transgenic plants of a potential oilseed crop Camelina sativa by Agrobacterium-mediated transformation", Plant Cell Rep, vol. 27, 2008, 273-278.
Ma, Fangfang , et al., "Isotopically nonstationary 13C flux analysis of changes in *Arabidopsis thaliana* leaf metabolism due to high light acclimation", PNAS, vol. 111, No. 7, 2014, 16967-16972.
Mandel, Therese , et al., "Definition of constitutive gene expression in plants: the translation initiation factor 4A gene as a model", Plant Molecular Biology, vol. 29, 1995, 995-1004.
Mandy, Dominic E., et al., "Metabolic flux analysis using 13C peptide label measurements", The Plant Journal, vol. 77, 2014, 476-486.
Manners, John M., et al., "The promoter of the plant defensin gene PDF1.2 from *Arabidopsis* is systemically activated by fungal pathogens and responds to methyl jasmonate but not to salicylic acid", Plant Molecular Biology, vol. 38, 1998, 1071-1080.
Martinez, A. , "Proterhodopsin photosystem gene expression enables photophosphorylation in a heterologous host", PNAS, vol. 104, No. 13, 2007, 5590-5595.
Mascarenhas, Desmond , et al., "Intron-mediated enhancement of heterologous gene expression in maize", Plant Molecular Biology, vol. 15, 1990, 913-920.
Masclaux-Daubresse, Celine , et al., "Exploring nitrogen remobilization for seed filling using natural variation in *Arabidopsis thaliana*", Journal of Experimental Botany, vol. 62, No. 6, 2011, 2131-2142.
Masgrau, Carles , et al., "Inducible overexpression of oat arginine decarboxylase in transgenic tobacco plants", The Plant Journal, vol. 11, No. 3, 1997, 465-473.
McAtee, Allison G., et al., "Role of Chinese hamster ovary central carbon metabolism in controlling the quality of secreted biotherapeutic proteins", Pharm. Bioprocess., vol. 2, No. 1, 2014, 63-74.
Minagawa, Jun , "State transitions—The molecular remodeling of photosynthetic supercomplexes that controls energy flow in the chloroplast", Biochimica et Biophysica Acta, vol. 1807, 2011, 897-905.
Miyagawa, Yoshiko , et al., "Overexpression of a cyanobacterial fructose-1,6-/sedoheptulose-1,7-bisphosphatase in tobacco enhances photosynthesis and growth", Nature Biotechnology, vol. 19, 2001, 965-969.
Moroney, James V., et al., "Photorespiration and carbon concentrating mechanisms: two adaptations to high O2, low CO2 conditions", Photosynth Res, vol. 117, 2013, 121-131.
Nakamura, Naoy , et al., "Promotion of cyclic electron transport around photosystem I during the evolution of NADP-malic enzyme-type C4 photosynthesis in the genus *Flaveria*", New Phytologist, vol. 199, 2013, 832-842.
Odell, Joan T., et al., "Identification of DNA sequences required for activity of the cauliflower mosaic virus 35S promoter", Nature, vol. 313, No. 6005, 1985, 810-812.
Odell, Joan T., "Seed-Specific Gene Activation Mediated by the Cre/lox Site-Specif ic Recombination System", Plant Physiol., vol. 106, 1994, 447-458.
Okutani, Satoshi , "Three Maize Leaf Ferredoxin:NADPH Oxidoreductases Vary in Subchloroplast Location, Expression, and Interaction with Ferredoxin", Plant Physiology, vol. 139, 2005, 1451-1459.
Outchkourov, N. S., et al., "The promoter-terminator of chrysanthemum rbcS1 directs very high expression levels in plants", Planta, vol. 216, 2003, 1003-1012.
Parry, Martin A.J., et al., "Rubisco activity and regulation as targets for crop improvement", Journal of Experimental Botany, vol. 64, No. 3, 2013, 717-730.
Paul, Matthew J., et al., "Sink regulation of photosynthesis", Journal of Experimental Botany, vol. 52, No. 360, 2001, 1383-1400.
Peltier, Gilles , "Auxiliary electron transport pathways in chloroplasts of microalgae", Photosynth Res, vol. 106, 2010, 19-31.
Peng, Lianwei , et al., "Supercomplex Formation with Photosystem I Is Required for the Stabilization of the Chloroplast NADH Dehydrogenase-Like Complex in *Arabidopsis*", Plant Physiology, vol. 155, 2011, 1629-1639.
Perrine, Zoee , et al., "Optimization of photosynthetic light energy utilization by microalgae", Algal Research, vol. 1, 2012, 134-142.
Peterhansel, Christoph , et al., "Photorespiratory bypasses: how can they work?", Journal of Experimental Botany, vol. 64, No. 3, 2013, 709-715.
Price, G. Dean, et al., "The cyanobacterial CCM as a source of genes for improving photosynthetic CO2 fixation in crop species", Journal of Experimental Botany, vol. 64, No. 3, 2013, 753-768.
Reeck, Gerald R., et al., ""Homology" in Proteins and Nucleic Acids: A Terminology Muddle and a Way out of It", Cell, vol. 50, 1987, 667.
Reiser, Leonore , et al., "The BELL7 Gene Encodes a Homeodomain Protein Involved in Pattern Formation in the *Arabidopsis* Ovule Primordium", Cell, vol. 83, 1995, 735-742.
Ringli, Christoph , et al., "Specific interaction of the tomato bZIP transcription factor VSF-1 with a non-palindromic DNA sequence that controls vascular gene expression", Plant Molecular Biology, vol. 37, 1998, 977-988.
Romisch-Margl, Werner , et al., "13CO2 as a universal metabolic tracer in isotopologue perturbation experiments", Phytochemistry, vol. 68, 2007, 2273-2289.
Roslan, Hairul A., et al., "Characterization of the ethanol-inducible alc geneexpression system in *Arabidopsis thaliana*", The Plant Journal, vol. 28, No. 2, 2001, 225-235.
Sage, Tammy L., et al., "The Functional Anatomy of Rice Leaves: Implications for Refixation of Photorespiratory CO2 and Efforts to Engineer C4 Photosynthesis into Rice", Plant Cell Physiol. vol. 50, No. 4, 2009, 756-772.
Sage, Rowan F., "Variation in the Kcat of Rubisco in C3 and C4 plants and some implications for photosynthetic performance at high and low temperature", Journal of Experimental Botany, vol. 53, No. 369, 2002, 609-620.
Goldschmidt, Eliezer E., et al., "Regulation of Photosynthesis by End-Product Accumulation in Leaves of Plants Storing Starch, Sucrose, and Hexose Sugars", Plant Physiol., vol. 99, 1992, 1443-1448.
Govindjee, Rajni , et al., "Arginine-82 Regulates the PKa of the Group Responsible for the Light-Driven Proton Release in Bacteriorhodopsin", Biophysical Journal, vol. 71, 1996, 1011-1023.
Govindjee, Rajni , et al., "Mutation of a Surface Residue, Lysine-129, Reverses the Order of Proton Release and Uptake in Bacteriorhodopsin; Guanidine Hydrochloride Restores It", Biophysical Journal, vol. 72, 1997, 886-898.
Govindjee, Rajni , et al., "The Quantum Efficiency of Proton Pumping by the Purple Membrane of Halobacterium Halobium", Biophys. J., vol. 30, 1980, 231-242.
Guevara-Garcia, Arturo , et al., "A 42 bp fragment of the pmas10 promoter containing an ocs-like element confers a developmental, wound- and chemically inducible expression pattern", Plant Molecular Biology, vol. 38, 1998, 743-753.
Hanke, Guy Thomas, et al., "Multiple iso-proteins of FNR in *Arabidopsis*: evidence for different contributions to chloroplast function and nitrogen assimilation", Plant, Cell and Environment, vol. 28, 2005, 1146-1157.
Harpster, Mark H., et al., "Relative strengths of the 35S califlower mosaic virus, 1', 2', and nopaline synthase promoters in transformed tobacco sugarbeet and oilseed rape callus tissue", Mol Gen Genet, vol. 212, 1988, 182-190.
Hausler, Rainer E., "Overexpression of C4-cycle enzymes in transgenic C3 plants: a biotechnilogical approach to mprove C3-photosynthesis", Journal of Experimental Botany, vol. 53, No. 369, 2002, 591-607.
Hay, R. K. M., et al., "Variation in the harvest index of tropical maize: evaluation of recent evidence from Mexico and Malawi", Ann. appl. Biol., vol. 138, 2001, 103-109.
Henikoff, Steven , et al., "Amino acid substitution matrices from protein blocks", Proc. Natl. Acad. Sci. USA, vol. 89, 1992, 10915-10919.

(56) References Cited

OTHER PUBLICATIONS

Henkes, Stefan , et al., "A Small Decrease of Plastid Transketolase Activity in Antisense Tobacco Transformants Has Dramatic Effects on Photosynthesis and Phenylpropanoid Metabolism", The Plant Cell, vol. 13, 2001, 535-551.
Hertle, Alexander P., et al., "PGRL1 Is the Elusive Ferredoxin-Plastoquinone Reductase in Photosynthetic Cyclic Electron Flow", Molecular Cell, vol. 49, 2013, 511-523.
Holtorf, Sonke , et al., "Comparison of different constitutive and inducible promoters for the overexpression of transgenes in *Arabidopsis thaliana*", Plant Molecular Biology, vol. 29, 1995, 637-646.
Huege, Jan , et al., "GC-EI-TOF-MS analysis of in vivo carbon-partitioning into soluble metabolite pools of higher plants by monitoring isotope dilution after 13CO2 labelling", Phytochemistry, vol. 68, 2007, 2258-2272.
Ihemere, Uzoma , "Genetic modification of cassava for enhanced starch production", Plant Biotechnology Journal, vol. 4, 2006, 453-465.
Jazmin, Lara J., "Isotopically Nonstationary 13C Metabolic Flux Analysis", Systems Metabolic Engineering: Methods and Protocols, Methods in Molecular Biology, vol. 985, Chapter 18, 2013, 367-390.
Jazmin, Lara J., "Isotopically Nonstationary MFA (INST-MFA) of Autotrophic Metabolism", Methods in Molecular Biology, vol. 1090, Chapter 12, 2014, 181-210.
Johnson, Giles N., "Physiology of PSI cyclic electron transport in higher plants", Biochimica et Biophysica Acta, vol. 1807, 2011, 384-389.
Joliot, Pierre , et al., "Regulation of cyclic and linear electron flow in higher plants", PNAS, vol. 108, No. 32, 2011, 13317-13322.
Jonik, Claudia , et al., "Simultaneous boosting of source and sink capacities doubles tuber starch yield of potato plants", Plant Biotechnology Journal, vol. 10, 2012, 1088-1098.
Karlin, Samuel , et al., "Applications and statistics for multiple high-scoring segments in molecular sequences", Proc. Natl. Acad. Sci. USA, vol. 90, 1993, 5873-5877.
Kay, Robert , et al., "Duplication of CaMV 35S promoter sequences creates a strong enhancer for plant genes", Science, vol. 236, 1987, 1299-1302.
Kelemen, Zsolt , et al., "Transformation vector based on promoter and intron sequences of a replacement histone H3 gene. A tool for high, constitutive gene expression in plants", Transgenic Research, vol. 11, 2002, 69-72.
Kim, Jaoon YH, et al., "Improved production of biohydrogen in lightpowered *Escherichia coli* by co-expression of proteorhodopsin and heterologous hydrogenase", Microbial Cell Factories, vol. 11, No. 2, 2012, 1-7.
Kramer, David M., et al., "The Importance of Energy Balance in Improving Photosynthetic Productivity", Plant Physiology, vol. 155, 2011, 70-78.
Kramer, David M., et al., "The Importance of Energy Balance in Improving Photosynthetic Productivity 1[W]", Plant Physiology, vol. 155, 2011, 70-78.
Kuhlemeier, Cris , et al., "The Pea rbcS-3A Promoter Mediates Light Responsiveness but not Organ Specificity", The Plant Cell, vol. 1, 1989, 471-478.
Kyte, Jack , "A simple method for displaying the hydropathic character of a protein", J. Mol. Biol., vol. 157, No. 1, 1982, 105-132.
Lakatos, Melinda , et al., "The Photochemical Reaction Cycle of Proteorhodopsin at Low pH", Biophysical Journal, vol. 84, 2003, 3252-3256.
Leamy, Alexandra K., "Molecular mechanisms and the role of saturated fatty acids in the progression of non-alcoholic fatty liver disease", Progress in Lipid Research, vol. 52, 2013, 165-174.

* cited by examiner

MS $NO_3^-$
WT #1 #2 #9 #20
FIG. 2A
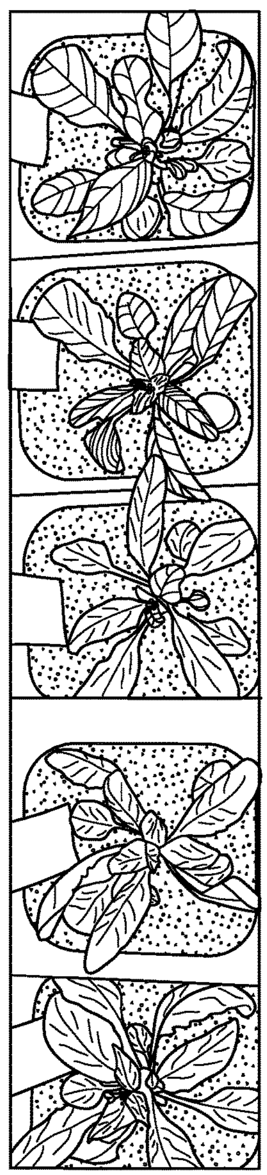
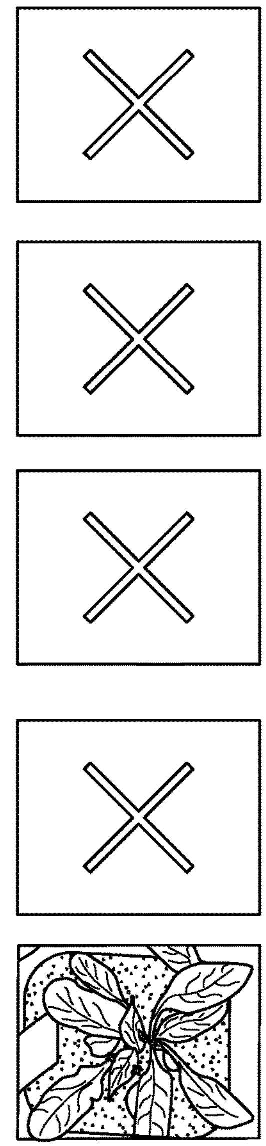
FIG. 2B

| | | | | | |
|---|---|---|---|---|---|
| ATP | 28.2±4.2 | 27.5±3.8 | 27.0±1.6 | 21.5±1.6 | 24.4±2.0 |
| ADP | 11.0±2.4 | 8.4±0.8 | 8.2±1.1 | 6.8±1.1 | 7.7±0.8 |
| AMP | 3.3±0.6 | 2.8±0.1 | 5.2±0.5 | 10.1±3.4 | 7.9±4.5 |
| $P_1$ | 4.55±0.31 | 4.59±0.38 | 4.87±0.24 | 6.06±0.92 | 8.11±0.46 |
| EC | 0.80±0.00 | 0.82±0.02 | 0.77±0.01 | 0.66±0.06 | 0.71±0.09 |
| NADPH | 21.4±2.0 | 22.2±3.0 | 19.4±3.8 | 14.9±3.3 | 18.6±4.3 |
| NADH | 5.71±0.85 | 7.27±0.63 | 4.46±0.72 | 2.71±0.43 | 2.35±0.63 |
| NADP | 1.50±0.21 | 1.06±0.05 | 1.17±0.13 | 1.48±0.37 | 1.68±0.10 |
| NAD | 22.1±0.04 | 22.7±6.6 | 27.4±0.7 | 23.1±1.7 | 21.6±3.0 |
| $RP_1$ | 0.53±0.03 | 0.57±0.05 | 0.45±0.05 | 0.41±0.05 | 0.46±0.07 |
| $RP_2$ | 0.21±0.03 | 0.27±0.07 | 0.14±0.02 | 0.11±0.02 | 0.10±0.03 |

$$EC=\frac{ATP+0.5ADP}{ATP+ADP+AMP} \quad RP_1=\frac{NADPH+NADH}{NADP(H)+NAD(H)} \quad RP_2=\frac{NADH}{NADH+NAD}$$

SEQUENCE LISTING

```
<160> NUMBER OF SEQ ID NOS: 108

<210> SEQ ID NO 1
<211> LENGTH: 132
<212> TYPE: PRT
<213> ORGANISM: Arabidopsis thaliana
<220> FEATURE:
<221> NAME/KEY: MISC_FEATURE
<222> LOCATION: (1)..(44)
<223> OTHER INFORMATION: PGR5 Amino acid sequence with chloroplast
      transit peptide

<400> SEQUENCE: 1

Met Ala Ala Ala Ser Ile Ser Ala Ile Gly Cys Asn Gln Thr Leu Ile
1               5                   10                  15

Gly Thr Ser Phe Tyr Gly Gly Trp Gly Ser Ser Ile Ser Gly Glu Asp
            20                  25                  30

Tyr Gln Thr Met Leu Ser Lys Thr Val Ala Pro Pro Gln Gln Ala Arg
        35                  40                  45

Val Ser Arg Lys Ala Ile Arg Ala Val Pro Met Met Lys Asn Val Asn
    50                  55                  60

Glu Gly Lys Gly Leu Phe Ala Pro Leu Val Val Val Thr Arg Asn Leu
65                  70                  75                  80

Val Gly Lys Lys Arg Phe Asn Gln Leu Arg Gly Lys Ala Ile Ala Leu
                85                  90                  95

His Ser Gln Val Ile Thr Glu Phe Cys Lys Ser Ile Gly Ala Asp Ala
            100                 105                 110

Lys Gln Arg Gln Gly Leu Ile Arg Leu Ala Lys Lys Asn Gly Glu Arg
        115                 120                 125

Leu Gly Phe Leu
    130


<210> SEQ ID NO 2
<211> LENGTH: 402
<212> TYPE: DNA
<213> ORGANISM: Arabidopsis thaliana

<400> SEQUENCE: 2

atggctgctg cttcgatttc tgcaatagga tgtaatcaaa ctttgatagg aacttccttc      60

tatggaggat ggggaagttc catctccgga gaagattacc aaaccatgct ctccaagaca     120

gttgcgccac cgcaacaagc cagagtctca aggaaagcaa tcagagcagt tccaatgatg     180

aagaatgtca atgaaggcaa aggcttattt gcacctctag ttgttgtcac acgcaaccta     240

gtaggcaaga agaggtttaa tcagctcaga ggaaaagcca ttgccttaca ctctcaggtg     300
```

```
atcactgagt tttgcaaatc gattggagca gatgcaaaac agagacaagg gcttatcagg    360

cttgctaaga agaatggaga gaggcttggt ttccttgctt ag                       402


<210> SEQ ID NO 3
<211> LENGTH: 324
<212> TYPE: PRT
<213> ORGANISM: Arabidopsis thaliana

<400> SEQUENCE: 3

Met Gly Ser Lys Met Leu Phe Ser Leu Thr Ser Pro Arg Leu Phe Ser
1               5                   10                  15

Ala Val Ser Arg Lys Pro Ser Ser Ser Phe Ser Pro Ser Pro Pro Ser
            20                  25                  30

Pro Ser Ser Arg Thr Gln Trp Thr Gln Leu Ser Pro Gly Lys Ser Ile
        35                  40                  45

Ser Leu Arg Arg Arg Val Phe Leu Leu Pro Ala Lys Ala Thr Thr Glu
    50                  55                  60

Gln Ser Gly Pro Val Gly Gly Asp Asn Val Asp Ser Asn Val Leu Pro
65                  70                  75                  80

Tyr Cys Ser Ile Asn Lys Ala Glu Lys Lys Thr Ile Gly Glu Met Glu
                85                  90                  95

Gln Glu Phe Leu Gln Ala Leu Gln Ser Phe Tyr Tyr Asp Gly Lys Ala
            100                 105                 110

Ile Met Ser Asn Glu Glu Phe Asp Asn Leu Lys Glu Glu Leu Met Trp
        115                 120                 125

Glu Gly Ser Ser Val Val Met Leu Ser Ser Asp Glu Gln Arg Phe Leu
    130                 135                 140

Glu Ala Ser Met Ala Tyr Val Ser Gly Asn Pro Ile Leu Asn Asp Glu
145                 150                 155                 160

Glu Tyr Asp Lys Leu Lys Leu Lys Leu Lys Ile Asp Gly Ser Asp Ile
                165                 170                 175

Val Ser Glu Gly Pro Arg Cys Ser Leu Arg Ser Lys Lys Val Tyr Ser
            180                 185                 190

Asp Leu Ala Val Asp Tyr Phe Lys Met Leu Leu Leu Asn Val Pro Ala
        195                 200                 205

Thr Val Val Ala Leu Gly Leu Phe Phe Phe Leu Asp Asp Ile Thr Gly
    210                 215                 220

Phe Glu Ile Thr Tyr Ile Met Glu Leu Pro Glu Pro Tyr Ser Phe Ile
225                 230                 235                 240

Phe Thr Trp Phe Ala Ala Val Pro Val Ile Val Tyr Leu Ala Leu Ser
                245                 250                 255

Ile Thr Lys Leu Ile Ile Lys Asp Phe Leu Ile Leu Lys Gly Pro Cys
            260                 265                 270

Pro Asn Cys Gly Thr Glu Asn Thr Ser Phe Phe Gly Thr Ile Leu Ser
        275                 280                 285

Ile Ser Ser Gly Gly Lys Thr Asn Thr Val Lys Cys Thr Asn Cys Gly
    290                 295                 300

Thr Ala Met Val Tyr Asp Ser Gly Ser Arg Leu Ile Thr Leu Pro Glu
305                 310                 315                 320

Gly Ser Gln Ala


<210> SEQ ID NO 4
<211> LENGTH: 975
<212> TYPE: DNA
<213> ORGANISM: Neisseria gonorrhoeae
```

```
<220> FEATURE:
<221> NAME/KEY: misc_feature
<223> OTHER INFORMATION: codon optimized for Arabidopsis thaliana

<400> SEQUENCE: 4

atgggtagca agatgttgtt tagtttgaca agtcctcgac ttttctccgc cgtttctcgc      60

aaaccttcct cttctttctc tccttctcct ccgtcgccgt cttcgaggac tcaatggact     120

cagctcagcc ctggaaaatc gatttctttg agaagaagag tcttcttgtt gcctgctaaa     180

gccacaacag agcaatcagg tccagtagga ggagacaacg tcgatagcaa tgttttgccc     240

tattgtagca tcaacaaggc tgagaagaaa acaattggtg aaatggaaca agagtttctc     300

caagcgttgc aatctttcta ttatgatggc aaagcgatca tgtctaatga agagtttgat     360

aaccttaaag aagagttaat gtgggaagga agcagtgttg tgatgctaag ttccgatgaa     420

caaagattct tggaagcttc catggcttat gtttctggaa atccaatctt gaatgatgaa     480

gaatatgata agctcaaact caaactaaag attgatggta gcgacattgt gagcgagggt     540

ccaagatgca gtctccgtag taaaaaggtg tatagtgatc tcgctgtaga ttatttcaaa     600

atgttattgt tgaatgttcc agcaaccgtt gttgctctcg gactcttttt cttcctggac     660

gacattacag gttttgagat cacatacatc atggagcttc cagaaccata cagtttcata     720

ttcacttggt tcgctgctgt gcctgtgatt gtatatctgg ctttatcaat caccaaattg     780

atcatcaagg acttcttgat cttgaagggt ccttgtccga attgtggaac ggaaaacacc     840

tccttctttg gaacaattct gtcaatctcc agcggcggca aaaccaacac tgtcaaatgc     900

accaactgcg gaaccgcgat ggtgtatgac tcgggttcta ggttgatcac attgccagaa     960

ggaagccaag cttaa                                                      975


<210> SEQ ID NO 5
<211> LENGTH: 280
<212> TYPE: PRT
<213> ORGANISM: Neisseria gonorrhoeae
<220> FEATURE:
<221> NAME/KEY: MISC_FEATURE
<222> LOCATION: (1)..(54)
<223> OTHER INFORMATION: Bacterial carbonic anhydrase (BCA) amino acid
      sequence with rbcs-1a transit peptide

<400> SEQUENCE: 5

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn His Gly Asn His Thr His Trp Gly Tyr Thr
    50                  55                  60

Gly His Asp Ser Pro Glu Ser Trp Gly Asn Leu Ser Glu Glu Phe Arg
65                  70                  75                  80

Leu Cys Ser Thr Gly Lys Asn Gln Ser Pro Val Asn Ile Thr Glu Thr
                85                  90                  95

Val Ser Gly Lys Leu Pro Ala Ile Lys Val Asn Tyr Lys Pro Ser Met
            100                 105                 110

Val Asp Val Glu Asn Asn Gly His Thr Ile Gln Val Asn Tyr Pro Glu
        115                 120                 125

Gly Gly Asn Thr Leu Thr Val Asn Gly Arg Thr Tyr Thr Leu Lys Gln
    130                 135                 140
```

```
Phe His Phe His Val Pro Ser Glu Asn Gln Ile Lys Gly Arg Thr Phe
145                 150                 155                 160

Pro Met Glu Ala His Phe Val His Leu Asp Glu Asn Lys Gln Pro Leu
                165                 170                 175

Val Leu Ala Val Leu Tyr Glu Ala Gly Lys Thr Asn Gly Arg Leu Ser
            180                 185                 190

Ser Ile Trp Asn Val Met Pro Met Thr Ala Gly Lys Val Lys Leu Asn
        195                 200                 205

Gln Pro Phe Asp Ala Ser Thr Leu Leu Pro Lys Arg Leu Lys Tyr Tyr
    210                 215                 220

Arg Phe Ala Gly Ser Leu Thr Thr Pro Pro Cys Thr Glu Gly Val Ser
225                 230                 235                 240

Trp Leu Val Leu Lys Thr Tyr Asp His Ile Asp Gln Ala Gln Ala Glu
                245                 250                 255

Lys Phe Thr Arg Ala Val Gly Ser Glu Asn Asn Arg Pro Val Gln Pro
            260                 265                 270

Leu Asn Ala Arg Val Val Ile Glu
        275                 280
```

<210> SEQ ID NO 6
<211> LENGTH: 684
<212> TYPE: DNA
<213> ORGANISM: Neisseria gonorrhoeae

<400> SEQUENCE: 6

```
aaccacggca atcacaccca ttggggctat accggacacg actctcccga aagctggggc     60

aatctgtcag aagaattccg tttgtgctcc accggcaaaa accaatctcc ggtaaacatt    120

accgaaaccg tttccggcaa actgcccgcc atcaaagtca attacaaacc gagtatggtt    180

gacgtggaaa acaacggcca caccattcag gtcaattatc ccgaaggcgg caataccctg    240

accgtgaacg gcagaaccta taccctgaaa cagttccact tccacgtgcc gagcgaaaac    300

caaatcaaag gcagaacttt cccgatggaa gctcacttcg tccacttaga cgaaaacaaa    360

cagcctttag tattagccgt gctgtatgaa gccggcaaaa ccaacgggag actgtcttcc    420

atctggaacg tcatgccgat gaccgcagga aaagtgaaac tcaaccaacc gttcgacgca    480

tccaccctac tgccgaaaag attgaaatac tacagatttg ccggttcgct gaccacgccg    540

ccgtgcacag agggcgtatc atggttggtg ttgaaaactt atgaccacat cgaccaagcg    600

caagcggaaa aattcaccag agccgtcggt tcggaaaaca acagacccgt acagcctctg    660

aatgcacgtg tagttattga ataa                                           684
```

<210> SEQ ID NO 7
<211> LENGTH: 356
<212> TYPE: DNA
<213> ORGANISM: Arabidopsis thaliana

<400> SEQUENCE: 7

```
ggtttacatt gatgctctca ggatttcata aggatagaga gatctattcg tatacgtgtc     60

acgtcatgag tgggtgtttc gccaatccat gaaacgcacc tagatatcta aaacacatat    120

caattgcgaa tctgcgaagt gcgagccatt aaccacgtaa gcaaacaaac aatctaaacc    180

ccaaaaaaaa tctatgacta gccaatagca acctcagaga ttgatatttc aagataagac    240

agtatttaga tttctgtatt atatatagcg aaaatcgcat caataccaaa ccacccattt    300

cttggcttac aacaacaaat cttaaacgtt ttactttgtg ctgcactact caacct        356
```

<210> SEQ ID NO 8
<211> LENGTH: 162
<212> TYPE: DNA
<213> ORGANISM: Arabidopsis thaliana
<220> FEATURE:
<221> NAME/KEY: misc_feature
<223> OTHER INFORMATION: Rbcs-1a transit peptide

<400> SEQUENCE: 8
atggcttcct ctatgctctc ttccgctact atggttgcct ctccggctca ggccactatg 60
gtcgctcctt tcaacggact taagtcctcc gctgccttcc cagccaccag aaaggctaac 120
aacgacatta cttccatcac aagcaacggc ggaagagtta ac 162

<210> SEQ ID NO 9
<211> LENGTH: 207
<212> TYPE: DNA
<213> ORGANISM: Artificial Sequence
<220> FEATURE:
<223> OTHER INFORMATION: NOS terminator from cloning vector.
<220> FEATURE:
<221> NAME/KEY: misc_feature
<223> OTHER INFORMATION: Nos terminator

<400> SEQUENCE: 9
atcgttcaaa catttggcaa taaagtttct taagattgaa tcctgttgcc ggtcttgcga 60
tgattatcat ataatttctg ttgaattacg ttaagcatgt aataattaac atgtaatgca 120
tgacgttatt tatgagatgg gtttttatga ttagagtccc gcaattatac atttaatacg 180
cgatagaaaa caaaatatag cgcgcaa 207

<210> SEQ ID NO 10
<211> LENGTH: 251
<212> TYPE: DNA
<213> ORGANISM: Nicotiana sylvestris

<400> SEQUENCE: 10
tgtggtcaca cctcaaacta aatcaaccag tttgcatttt tttccttctc aatgttaatt 60
tgctgacttg gctagggtgc gaatcaaatc acacgttcta attgggcaaa atccgtatat 120
caccttatcc tatatccttt ttctccacca cccatcatct cttctatgca acaaaaatag 180
cttcttcctt ttcatttttc acttctctca atccaacttt tctatggcca tggcatccca 240
agcttccctt t 251

<210> SEQ ID NO 11
<211> LENGTH: 255
<212> TYPE: DNA
<213> ORGANISM: Arabidopsis thaliana

<400> SEQUENCE: 11
tatacaaagc aaccgatcaa gtggagacta gtaaaccata cacaatcact catttcctca 60
caaaagaaag ataagataag ggtgtcaaca cctttcctta atcatgtggt agtgaacgag 120
ttatcatgaa tcccggaccc tttgatcatt agggcttttt gcctcttacg gttctcacta 180
tataaagatg acaaaaccaa tagaaaaaca attaagcaaa agaagaagaa gaagaagtaa 240
tggcttcctc tatgc 255

<210> SEQ ID NO 12
<211> LENGTH: 3249
<212> TYPE: DNA

<213> ORGANISM: Chlamydomonas reinhardtii

<400> SEQUENCE: 12

```
atgcttcctg gtcttggtgt catccttctt gtgcttccta tgcagtacta cttcggttac     60
aagatcgtgc agatcaagct tcagaacgct aagcacgtcg ctcttcgttc tgctatcatg    120
caggaggtgc ttcctgctat caagcttgtc aagtactacg cttgggagca gttctttgag    180
aaccagatct ctaaggtccg tcgtgaggag atccgtctca acttctggaa ctgcgtgatg    240
aaggtcatca acgtggcttg cgtgttctgc gtgccgccta tgaccgcttt cgtcatcttc    300
accacctacg agttccagcg tgctcgtctt gtgtcttctg tcgctttcac caccctttct    360
cttttcaaca ttcttcgttt ccctcttgtc gtgcttccta aggctcttcg tgctgtgtct    420
gaggctaacg cttctctcca gcgtcttgag gcttaccttc ttgaggaggt gccttctggt    480
actgctgctg tcaagacccc taagaacgct cctcctggtg ctgtcatcga gaacggtgtg    540
ttccaccacc cttctaaccc taactggcac cttcacgtgc ctaagttcga ggtcaagcct    600
ggtcaggtcg ttgctgtggt gggtcgtatc gctgctggta agtcttctct tgtgcaggct    660
atcctcggta acatggtcaa ggagcacggt tctttcaacg tgggtggtcg tatctcttac    720
gtgccgcaga acccttggct tcagaacctt tctcttcgtg acaacgtgct tttggtgag     780
cagttcgatg agaacaagta caccgacgtc atcgagtctt gcgctcttac ccttgacctt    840
cagatccttt ctaacggtga ccagtctaag gctggtatcc gtggtgtcaa cttctctggt    900
ggtcagcgtc agcgtgtgaa ccttgctcgt tgcgcttacg ctgacgctga ccttgtgctt    960
ctcgacaacg ctctttctgc tgtggaccac cacaccgctc accacatctt cgacaagtgc   1020
atcaagggtc ttttctctga caaggctgtg gtgcttgtca cccaccagat cgagttcatg   1080
cctcgttgcg acaacgtggc tatcatggac gagggtcgtt gcctttactt cggtaagtgg   1140
aacgaggagg ctcagcacct tctcggtaag cttcttccta tcacccacct tcttcacgct   1200
gctggttctc aggaggctcc tcctgctcct aagaagaagg ctgaggacaa ggctggtcct   1260
cagaagtctc agtctcttca gcttaccctt gctcctacct ctatcggtaa gcctaccgag   1320
aagcctaagg acgtccagaa gcttactgct taccaggctg ctctcatcta cacctggtac   1380
ggtaaccttt tccttgttgg tgtgtgcttc ttcttcttcc ttgctgctca gtgctctcgt   1440
cagatctctg atttctgggt gcgttggtgg gtgaacgacg agtacaagaa gttccctgtg   1500
aagggtgagc aggactctgc tgctaccacc ttctactgcc tcatctacct tcttcttgtg   1560
ggtcttttct acatcttcat gatcttccgt ggtgctactt tcctttggtg ggtgctcaag   1620
tcttctgaga ccatccgtag gaaggctctt cacaacgtcc tcaacgctcc tatgggtttc   1680
ttccttgtca cgccggtcgg tgaccttctt ctcaacttca ccaaggacca ggacattatg   1740
gatgagaacc ttcctgatgc tgttcacttc atgggtatct acggtcttat tcttcttgct   1800
accaccatca ccgtgtctgt caccatcaac ttcttcgctg ctttcaccgg tgctcttatc   1860
atcatgaccc tcatcatgct ctctatctac cttcctgctg ctactgctct taagaaggct   1920
cgtgctgtgt ctggtggtat gcttgtcggt cttgttgctg aggttcttga gggtcttggt   1980
gtggttcagg ctttcaacaa gcaggagtac ttcattgagg aggctgctcg tcgtaccaac   2040
atcaccaact ctgctgtctt caacgctgag gctcttaacc tttggcttgc tttctggtgc   2100
gacttcatcg gtgcttgcct tgtgggtgtg gtgtctgctt tcgctgtggg tatggctaag   2160
gaccttggtg gtgctaccgt cggtcttgct ttctctaaca tcattcagat gcttgtgttc   2220
tacacctggg tggtccgttt catctctgag tctatctctc tcttcaactc tgtcgagggt   2280
```

```
atggcttacc tcgctgacta cgtgcctcac gatggtgtct tctatgacca gcgtcagaag   2340

gacggtgtcg ctaagcaaat cgtccttcct gacggtaaca tcgtgcctgc tgcttctaag   2400

gtccaggtcg tggttgacga cgctgctctc gctcgttggc ctgctaccgg taacatccgt   2460

ttcgaggacg tgtggatgca gtaccgtctt gacgctcctt gggctcttaa gggtgtcacc   2520

ttcaagatca acgacggtga gaaggtcggt gctgtgggtc gtaccggttc tggtaagtct   2580

accacgcttc ttgctcttta ccgtatgttc gagcttggta agggtcgtat ccttgtcgac   2640

ggtgtggaca tcgctaccct ttctctcaag cgtcttcgta ccggtctttc tatcattcct   2700

caggagcctg tcatgttcac cggtaccgtg cgttctaacc ttgacccttt cggtgagttc   2760

aaggacgatg ctattctttg ggaggtgctt aagaaggtcg gtctcgagga ccaggctcag   2820

cacgctggtg gtcttgacgg tcaggtcgat ggtaccggtg gtaaggcttg gtctcttggt   2880

cagatgcagc ttgtgtgcct tgctcgtgct gctcttcgtg ctgtgcctat cctttgcctt   2940

gacgaggcta ccgctgctat ggacccgcac actgaggcta tcgtgcagca gaccatcaag   3000

aaggtgttcg acgaccgtac caccatcacc attgctcacc gtcttgacac catcatcgag   3060

tctgacaaga tcatcgtgat ggagcagggt tctcttatgg agtacgagtc tccttctaag   3120

cttctcgcta accgtgactc tatgttctct aagcttgtcg acaagaccgg tcctgctgct   3180

gctgctgctc ttcgtaagat ggctgaggac ttctggtcta ctcgttctgc tcagggtcgt   3240

aaccagtaa                                                           3249
```

```
<210> SEQ ID NO 13
<211> LENGTH: 35
<212> TYPE: PRT
<213> ORGANISM: Arabidopsis thaliana

<400> SEQUENCE: 13

Met Ala Ala Ser Thr Met Ala Leu Ser Ser Pro Ala Phe Ala Gly Lys
1               5                   10                  15

Ala Val Asn Leu Ser Pro Ala Ala Ser Glu Val Leu Gly Ser Gly Arg
            20                  25                  30

Val Thr Met
        35


<210> SEQ ID NO 14
<211> LENGTH: 44
<212> TYPE: PRT
<213> ORGANISM: Arabidopsis thaliana
<220> FEATURE:
<221> NAME/KEY: MISC_FEATURE
<223> OTHER INFORMATION: PGR5 transit peptide

<400> SEQUENCE: 14

Met Ala Ala Ala Ser Ile Ser Ala Ile Gly Cys Asn Gln Thr Leu Ile
1               5                   10                  15

Gly Thr Ser Phe Tyr Gly Gly Trp Gly Ser Ser Ile Ser Gly Glu Asp
            20                  25                  30

Tyr Gln Thr Met Leu Ser Lys Thr Val Ala Pro Pro
        35                  40


<210> SEQ ID NO 15
<211> LENGTH: 45
<212> TYPE: PRT
<213> ORGANISM: Arabidopsis thaliana
<220> FEATURE:
<221> NAME/KEY: MISC_FEATURE
```

<223> OTHER INFORMATION: psaD transit eptide

<400> SEQUENCE: 15

```
Met Ala Thr Gln Ala Ala Gly Ile Phe Asn Ser Ala Ile Thr Thr Ala
1               5                   10                  15

Ala Thr Ser Gly Val Lys Lys Leu His Phe Phe Ser Thr Thr His Arg
            20                  25                  30

Pro Lys Ser Leu Ser Phe Thr Lys Thr Ala Ile Arg Ala
        35                  40                  45
```

<210> SEQ ID NO 16
<211> LENGTH: 1011
<212> TYPE: DNA
<213> ORGANISM: Chlamydomonas reinhardtii

<400> SEQUENCE: 16

```
atgcagacca ctatgactcg cccttgcctt gcccagcccg tgctgcgatc tcgtgtgctc     60
cggtcgccta tgcgggtggt tgcagcgagc gctcctaccg cggtgacgac agtcgtgacc    120
tcgaatggaa atggcaacgg tcatttccaa gctgctacta cgcccgtgcc ccctactccc    180
gctcccgtcg ctgtttccgc gcctgtgcgc gctgtgtcgg tgctgactcc tcctcaagtg    240
tatgagaacg ccattaatgt tggcgcctac aaggccgggc taacgcctct ggcaacgttt    300
gtccagggca tccaagccgg tgcctacatt gcgttcggcg ccttcctcgc catctccgtg    360
ggaggcaaca tccccggcgt cgccgccgcc aaccccggcc tggccaagct gctatttgct    420
ctggtgttcc ccgtgggtct gtccatggtg accaactgcg gcgccgagct gttcacgggc    480
aacaccatga tgctcacatg cgcgctcatc gagaagaagg ccacttgggg gcagcttctg    540
aagaactgga gcgtgtccta cttcggcaac ttcgtgggct ccatcgccat ggtcgccgcc    600
gtggtggcca ccggctgcct gaccaccaac accctgcctg tgcagatggc caccctcaag    660
gccaacctgg gcttcaccga ggtgctgtcg cgctccatcc tgtgcaactg gctggtgtgc    720
tgcgccgtgt ggtccgcctc cgccgccacc tcgctgcccg gccgcatcct ggcgctgtgg    780
ccctgcatca ccgccttcgt ggccatcggc ctggagcact ccgtcgccaa catgttcgtg    840
attcctctgg gcatgatgct gggcgctgag gtcacgtgga gccagttctt tttcaacaac    900
ctgatccccg tcaccctggg caacaccatt gctggcgttc tcatgatggc catcgcctac    960
tccatctcgt tcggctccct cggcaagtcc gccaagcccg ccaccgcgta a            1011
```

<210> SEQ ID NO 17
<211> LENGTH: 892
<212> TYPE: DNA
<213> ORGANISM: Homo sapiens

<400> SEQUENCE: 17

```
atgatatcct cttcagctgt gactacagtc agccgtgctt ctacggtgca atcggccgcg     60
gtggctccat tcggcggcct caaatccatg actggattcc cagttaagaa ggtcaacact    120
gacattactt ccattacaag caatggtgga agagtaaagt gcatgcaggt ggagctctct    180
catcattggg gttatggtaa acacaatggt cctgaacact ggcataaaga ctttccaatt    240
gcaaaaggtg aacgtcaatc acctgttgat attgacactc atacagctaa atatgaccct    300
tctttaaaac cattatctgt ttcatatgat caagcaactt ctttacgtat tttaaacaat    360
ggtcatgctt ttaatgtaga atttgatgac tctcaagata aagcagtatt aaaaggtggt    420
ccattagatg gtacttaccg tttaattcaa tttcactttc actggggttc attagatggt    480
```

```
caaggttcag aacatactgt agataaaaaa aaatatgctg cagaattaca cttagttcac    540

tggaacacaa aatatggtga ttttggtaaa gctgtacaac aacctgatgg tttagctgtt    600

ttaggtattt ttttaaaagt tggtagtgct aaaccaggtc ttcaaaaagt tgttgatgta    660

ttagattcaa ttaaaacaaa aggtaaaagt gctgacttta ctaatttcga tcctcgtggt    720

ttacttcctg aatctttaga ttactggaca tatccaggtt cattaacaac acctcctctt    780

ttagaatgtg taacatggat tgtattaaaa gaaccaatta gtgtaagtag tgaacaagta    840

ttaaaattcc gtaaacttaa tttcaatggt gaaggtgaac cagaagaatt aa            892
```

```
<210> SEQ ID NO 18
<211> LENGTH: 336
<212> TYPE: PRT
<213> ORGANISM: Chlamydomonas reinhardtii

<400> SEQUENCE: 18

Met Gln Thr Thr Met Thr Arg Pro Cys Leu Ala Gln Pro Val Leu Arg
1               5                   10                  15

Ser Arg Val Leu Arg Ser Pro Met Arg Val Val Ala Ala Ser Ala Pro
            20                  25                  30

Thr Ala Val Thr Thr Val Val Thr Ser Asn Gly Asn Gly Asn Gly His
        35                  40                  45

Phe Gln Ala Ala Thr Thr Pro Val Pro Pro Thr Pro Ala Pro Val Ala
    50                  55                  60

Val Ser Ala Pro Val Arg Ala Val Ser Val Leu Thr Pro Pro Gln Val
65                  70                  75                  80

Tyr Glu Asn Ala Ile Asn Val Gly Ala Tyr Lys Ala Gly Leu Thr Pro
                85                  90                  95

Leu Ala Thr Phe Val Gln Gly Ile Gln Ala Gly Ala Tyr Ile Ala Phe
            100                 105                 110

Gly Ala Phe Leu Ala Ile Ser Val Gly Gly Asn Ile Pro Gly Val Ala
        115                 120                 125

Ala Ala Asn Pro Gly Leu Ala Lys Leu Leu Phe Ala Leu Val Phe Pro
    130                 135                 140

Val Gly Leu Ser Met Val Thr Asn Cys Gly Ala Glu Leu Phe Thr Gly
145                 150                 155                 160

Asn Thr Met Met Leu Thr Cys Ala Leu Ile Glu Lys Lys Ala Thr Trp
                165                 170                 175

Gly Gln Leu Leu Lys Asn Trp Ser Val Ser Tyr Phe Gly Asn Phe Val
            180                 185                 190

Gly Ser Ile Ala Met Val Ala Ala Val Val Ala Thr Gly Cys Leu Thr
        195                 200                 205

Thr Asn Thr Leu Pro Val Gln Met Ala Thr Leu Lys Ala Asn Leu Gly
    210                 215                 220

Phe Thr Glu Val Leu Ser Arg Ser Ile Leu Cys Asn Trp Leu Val Cys
225                 230                 235                 240

Cys Ala Val Trp Ser Ala Ser Ala Ala Thr Ser Leu Pro Gly Arg Ile
                245                 250                 255

Leu Ala Leu Trp Pro Cys Ile Thr Ala Phe Val Ala Ile Gly Leu Glu
            260                 265                 270

His Ser Val Ala Asn Met Phe Val Ile Pro Leu Gly Met Met Leu Gly
        275                 280                 285

Ala Glu Val Thr Trp Ser Gln Phe Phe Phe Asn Asn Leu Ile Pro Val
    290                 295                 300
```

```
Thr Leu Gly Asn Thr Ile Ala Gly Val Leu Met Met Ala Ile Ala Tyr
305                 310                 315                 320

Ser Ile Ser Phe Gly Ser Leu Gly Lys Ser Ala Lys Pro Ala Thr Ala
                325                 330                 335


<210> SEQ ID NO 19
<211> LENGTH: 260
<212> TYPE: PRT
<213> ORGANISM: Homo sapiens

<400> SEQUENCE: 19

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260


<210> SEQ ID NO 20
<211> LENGTH: 159
<212> TYPE: PRT
<213> ORGANISM: Homo sapiens

<400> SEQUENCE: 20

Met Val Met Leu Ser Thr Trp Ser Leu Met Thr Leu Arg Thr Lys Gln
1               5                   10                  15

Leu His Leu Val His Trp Asn Thr Lys Tyr Gly Asp Phe Gly Lys Ala
            20                  25                  30
```

```
Val Gln Gln Pro Asp Gly Leu Ala Val Leu Gly Ile Phe Leu Lys Val
        35                  40                  45

Gly Ser Ala Lys Pro Gly Leu Gln Lys Val Val Asp Val Leu Asp Ser
    50                  55                  60

Ile Lys Thr Lys Gly Lys Ser Ala Asp Phe Thr Asn Phe Asp Pro Arg
65                  70                  75                  80

Gly Leu Leu Pro Glu Ser Leu Asp Tyr Trp Thr Tyr Pro Gly Ser Leu
                85                  90                  95

Thr Thr Pro Pro Leu Leu Glu Cys Val Thr Trp Ile Val Leu Lys Glu
            100                 105                 110

Pro Ile Ser Val Ser Ser Glu Gln Val Leu Lys Phe Arg Lys Leu Asn
        115                 120                 125

Phe Asn Gly Glu Gly Glu Pro Glu Glu Leu Met Val Asp Asn Trp Arg
    130                 135                 140

Pro Ala Gln Pro Leu Lys Asn Arg Gln Ile Lys Ala Ser Phe Lys
145                 150                 155


<210> SEQ ID NO 21
<211> LENGTH: 252
<212> TYPE: PRT
<213> ORGANISM: Neisseria gonorrhoeae

<400> SEQUENCE: 21

Met Pro Arg Phe Pro Arg Thr Leu Pro Arg Leu Thr Ala Val Leu Leu
1               5                   10                  15

Leu Ala Cys Thr Ala Phe Ser Ala Ala Ala His Gly Asn His Thr His
            20                  25                  30

Trp Gly Tyr Thr Gly His Asp Ser Pro Glu Ser Trp Gly Asn Leu Ser
        35                  40                  45

Glu Glu Phe Arg Leu Cys Ser Thr Gly Lys Asn Gln Ser Pro Val Asn
    50                  55                  60

Ile Thr Glu Thr Val Ser Gly Lys Leu Pro Ala Ile Lys Val Asn Tyr
65                  70                  75                  80

Lys Pro Ser Met Val Asp Val Glu Asn Asn Gly His Thr Ile Gln Val
                85                  90                  95

Asn Tyr Pro Glu Gly Gly Asn Thr Leu Thr Val Asn Gly Arg Thr Tyr
            100                 105                 110

Thr Leu Lys Gln Phe His Phe His Val Pro Ser Glu Asn Gln Ile Lys
        115                 120                 125

Gly Arg Thr Phe Pro Met Glu Ala His Phe Val His Leu Asp Glu Asn
    130                 135                 140

Lys Gln Pro Leu Val Leu Ala Val Leu Tyr Glu Ala Gly Lys Thr Asn
145                 150                 155                 160

Gly Arg Leu Ser Ser Ile Trp Asn Val Met Pro Met Thr Ala Gly Lys
                165                 170                 175

Val Lys Leu Asn Gln Pro Phe Asp Ala Ser Thr Leu Leu Pro Lys Arg
            180                 185                 190

Leu Lys Tyr Tyr Arg Phe Ala Gly Ser Leu Thr Thr Pro Pro Cys Thr
        195                 200                 205

Glu Gly Val Ser Trp Leu Val Leu Lys Thr Tyr Asp His Ile Asp Gln
    210                 215                 220

Ala Gln Ala Glu Lys Phe Thr Arg Ala Val Gly Ser Glu Asn Asn Arg
225                 230                 235                 240

Pro Val Gln Pro Leu Asn Ala Arg Val Val Ile Glu
                245                 250
```

<210> SEQ ID NO 22
<211> LENGTH: 217
<212> TYPE: PRT
<213> ORGANISM: Arabidopsis thaliana
<220> FEATURE:
<221> NAME/KEY: MISC_FEATURE
<223> OTHER INFORMATION: DNAJ transit peptide

<400> SEQUENCE: 22

```
Met Ala Ser Leu Ser Thr Ile Thr Gln Pro Ser Leu Val His Ile Pro
1               5                   10                  15

Gly Glu Ser Val Leu His His Val Pro Ser Thr Cys Ser Phe Pro Trp
            20                  25                  30

Lys Pro Thr Ile Asn Thr Lys Arg Ile Ile Cys Ser Pro Ala Arg Asn
        35                  40                  45

Ser Ser Glu Val Ser Ala Glu Ala Glu Thr Glu Gly Gly Ser Ser Thr
    50                  55                  60

Ala Val Asp Glu Ala Pro Lys Glu Ser Pro Ser Leu Ile Ser Ala Leu
65                  70                  75                  80

Asn Val Glu Arg Ala Leu Arg Gly Leu Pro Ile Thr Asp Val Asp His
                85                  90                  95

Tyr Gly Arg Leu Gly Ile Phe Arg Asn Cys Ser Tyr Asp Gln Val Thr
            100                 105                 110

Ile Gly Tyr Lys Glu Arg Val Lys Glu Leu Lys Glu Gln Gly Leu Asp
        115                 120                 125

Glu Glu Gln Leu Lys Thr Lys Met Asp Leu Ile Lys Ser Tyr Thr Ile
    130                 135                 140

Leu Ser Thr Val Glu Glu Arg Arg Met Tyr Asp Trp Ser Leu Ala Arg
145                 150                 155                 160

Ser Glu Lys Ala Glu Arg Tyr Val Trp Pro Phe Glu Val Asp Ile Met
                165                 170                 175

Glu Pro Ser Arg Glu Glu Pro Pro Pro Gln Glu Pro Glu Asp Val Gly
            180                 185                 190

Pro Thr Arg Ile Leu Gly Tyr Phe Ile Gly Ala Trp Leu Val Leu Gly
        195                 200                 205

Val Ala Leu Ser Val Ala Phe Asn Arg
    210                 215
```

<210> SEQ ID NO 23
<211> LENGTH: 67
<212> TYPE: PRT
<213> ORGANISM: Arabidopsis thaliana

<400> SEQUENCE: 23

```
Met Asp Lys Ala Leu Thr Gly Ile Ser Ala Ala Ala Leu Thr Ala Ser
1               5                   10                  15

Met Val Ile Pro Glu Ile Ala Glu Ala Ala Gly Ser Gly Ile Ser Pro
            20                  25                  30

Ser Leu Lys Asn Phe Leu Leu Ser Ile Ala Ser Gly Gly Leu Val Leu
        35                  40                  45

Thr Val Ile Ile Gly Val Val Val Gly Val Ser Asn Phe Asp Pro Val
    50                  55                  60

Lys Arg Thr
65
```

<210> SEQ ID NO 24

<211> LENGTH: 260
<212> TYPE: PRT
<213> ORGANISM: Macaca fascicularis

<400> SEQUENCE: 24

Met Ser His His Trp Gly Tyr Gly Lys His Asn Gly Pro Glu His Trp
1               5                   10                  15

His Lys Asp Phe Pro Ile Ala Lys Gly Gln Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ser Phe Asn Val Glu Phe Asp Asp Ser Gln Asp Lys Ala Val Ile Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Ser Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260

<210> SEQ ID NO 25
<211> LENGTH: 260
<212> TYPE: PRT
<213> ORGANISM: Pan troglodytes

<400> SEQUENCE: 25

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Gly Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

```
Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro His Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260
```

<210> SEQ ID NO 26
<211> LENGTH: 260
<212> TYPE: PRT
<213> ORGANISM: Pongo abelii

<400> SEQUENCE: 26

```
Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Cys Tyr Asp Gln Ala Thr Ser Leu Arg Ile Leu Asn Asn Gly His
    50                  55                  60

Ser Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Cys Ala Asp Phe Thr
                165                 170                 175

Asn Phe Asp Pro Arg Gly Leu Leu Pro Ala Ser Leu Asp Tyr Trp Thr
```

```
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Lys Arg Gln Ile Lys
                245                 250                 255

Ala Ser Phe Lys
            260


<210> SEQ ID NO 27
<211> LENGTH: 260
<212> TYPE: PRT
<213> ORGANISM: Pongo abelii

<400> SEQUENCE: 27

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Cys Tyr Asp Gln Ala Thr Ser Leu Arg Ile Leu Asn Asn Gly His
    50                  55                  60

Ser Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Cys Ala Asp Phe Thr
                165                 170                 175

Asn Phe Asp Pro Arg Gly Leu Leu Pro Ala Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Lys Arg Gln Ile Lys
                245                 250                 255

Ala Ser Phe Lys
            260


<210> SEQ ID NO 28
<211> LENGTH: 260
```

```
<212> TYPE: PRT
<213> ORGANISM: Callithrix jacchus

<400> SEQUENCE: 28

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Trp Arg Ile Leu Asn Asn Gly His
    50                  55                  60

Ser Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Thr Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Ala Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Ser Val Thr Trp
        195                 200                 205

Ile Val Leu Lys Glu Pro Ile Ser Val Ser Ser Glu Gln Ile Leu Lys
    210                 215                 220

Phe Arg Lys Leu Asn Phe Ser Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260


<210> SEQ ID NO 29
<211> LENGTH: 260
<212> TYPE: PRT
<213> ORGANISM: Lemur catta

<400> SEQUENCE: 29

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asn Thr Gly Ala Ala Lys His Asp Pro Ser Leu Lys Pro Leu Ser
        35                  40                  45

Val Tyr Tyr Glu Gln Ala Thr Ser Arg Arg Ile Leu Asn Asn Gly His
    50                  55                  60

Ser Phe Asn Val Glu Phe Asp Asp Ser Gln Asp Lys Ala Val Leu Lys
65                  70                  75                  80
```

```
Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Leu Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Met Lys
    210                 215                 220

Phe Arg Lys Leu Ser Phe Ser Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260


<210> SEQ ID NO 30
<211> LENGTH: 260
<212> TYPE: PRT
<213> ORGANISM: Ailuropoda melanoleuca

<400> SEQUENCE: 30

Met Ala His His Trp Gly Tyr Gly Lys His Asn Gly Pro Glu His Trp
1               5                   10                  15

Tyr Lys Asp Phe Pro Ile Ala Lys Gly Gln Arg Gln Ser Pro Val Asp
            20                  25                  30

Ile Asp Thr Lys Ala Ala Ile His Asp Pro Ala Leu Lys Ala Leu Cys
        35                  40                  45

Pro Thr Tyr Glu Gln Ala Val Ser Gln Arg Val Ile Asn Asn Gly His
    50                  55                  60

Ser Phe Asn Val Glu Phe Asp Asp Ser Gln Asp Asn Ala Val Leu Lys
65                  70                  75                  80

Gly Gly Pro Leu Thr Gly Thr Tyr Arg Leu Ile Gln Phe His Phe His
                85                  90                  95

Trp Gly Ser Ser Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Ile Gly Asp Ala Arg Pro Gly Leu Gln Lys Val Leu
145                 150                 155                 160

Asp Ala Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190
```

```
Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Leu Lys
    210                 215                 220

Phe Arg Arg Leu Asn Phe Asn Lys Glu Gly Glu Pro Glu Glu Leu Met
225                 230                 235                 240

Val Asp Asn Trp Arg Pro Ala Gln Pro Leu His Asn Arg Gln Ile Asn
                245                 250                 255

Ala Ser Phe Lys
            260


<210> SEQ ID NO 31
<211> LENGTH: 260
<212> TYPE: PRT
<213> ORGANISM: Equus caballus

<400> SEQUENCE: 31

Met Ser His His Trp Gly Tyr Gly Gln His Asn Gly Pro Lys His Trp
1               5                   10                  15

His Lys Asp Phe Pro Ile Ala Lys Gly Gln Arg Gln Ser Pro Val Asp
            20                  25                  30

Ile Asp Thr Lys Ala Ala Val His Asp Ala Ala Leu Lys Pro Leu Ala
        35                  40                  45

Val His Tyr Glu Gln Ala Thr Ser Arg Arg Ile Val Asn Asn Gly His
    50                  55                  60

Ser Phe Asn Val Glu Phe Asp Asp Ser Gln Asp Lys Ala Val Leu Gln
65                  70                  75                  80

Gly Gly Pro Leu Thr Gly Thr Tyr Arg Leu Ile Gln Phe His Phe His
                85                  90                  95

Trp Gly Ser Ser Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Val Gly
    130                 135                 140

Val Phe Leu Lys Val Gly Gly Ala Lys Pro Gly Leu Gln Lys Val Leu
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Arg Glu Pro Ile Ser Val Ser Ser Glu Gln Leu Leu Lys
    210                 215                 220

Phe Arg Ser Leu Asn Phe Asn Ala Glu Gly Lys Pro Glu Asp Pro Met
225                 230                 235                 240

Val Asp Asn Trp Arg Pro Ala Gln Pro Leu Asn Ser Arg Gln Ile Arg
                245                 250                 255

Ala Ser Phe Lys
            260


<210> SEQ ID NO 32
<211> LENGTH: 260
<212> TYPE: PRT
```

```
<213> ORGANISM: Canis lupus

<400> SEQUENCE: 32

Met Ala His His Trp Gly Tyr Ala Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr Lys Ala Ala Val His Asp Pro Ala Leu Lys Ser Leu Cys
        35                  40                  45

Pro Cys Tyr Asp Gln Ala Val Ser Gln Arg Ile Ile Asn Asn Gly His
    50                  55                  60

Ser Phe Asn Val Glu Phe Asp Asp Ser Gln Asp Lys Thr Val Leu Lys
65                  70                  75                  80

Gly Gly Pro Leu Thr Gly Thr Tyr Arg Leu Ile Gln Phe His Phe His
                85                  90                  95

Trp Gly Ser Ser Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Glu Phe Gly Lys Ala Val Gln Gln Pro Asp Gly Leu Ala Val Leu Gly
    130                 135                 140

Ile Phe Leu Lys Ile Gly Gly Ala Asn Pro Gly Leu Gln Lys Ile Leu
145                 150                 155                 160

Asp Ala Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Met Leu Lys
    210                 215                 220

Phe Arg Lys Leu Asn Phe Asn Lys Glu Gly Glu Pro Glu Glu Leu Met
225                 230                 235                 240

Met Asp Asn Trp Arg Pro Ala Gln Pro Leu His Ser Arg Gln Ile Asn
                245                 250                 255

Ala Ser Phe Lys
            260


<210> SEQ ID NO 33
<211> LENGTH: 260
<212> TYPE: PRT
<213> ORGANISM: Oryctolagus cuniculus

<400> SEQUENCE: 33

Met Ser His His Trp Gly Tyr Gly Lys His Asn Gly Pro Glu His Trp
1               5                   10                  15

His Lys Asp Phe Pro Ile Ala Asn Gly Glu Arg Gln Ser Pro Ile Asp
            20                  25                  30

Ile Asp Thr Asn Ala Ala Lys His Asp Pro Ser Leu Lys Pro Leu Arg
        35                  40                  45

Val Cys Tyr Glu His Pro Ile Ser Arg Arg Ile Ile Asn Asn Gly His
    50                  55                  60

Ser Phe Asn Val Glu Phe Asp Asp Ser His Asp Lys Thr Val Leu Lys
65                  70                  75                  80

Glu Gly Pro Leu Glu Gly Thr Tyr Arg Leu Ile Gln Phe His Phe His
```

```
                85                  90                  95

Trp Gly Ser Ser Asp Gly Gln Gly Ser Glu His Thr Val Asn Lys Lys
            100                 105                 110

Lys Tyr Ala Ala Glu Leu His Leu Val His Trp Asn Thr Lys Tyr Gly
        115                 120                 125

Asp Phe Gly Lys Ala Val Lys His Pro Asp Gly Leu Ala Val Leu Gly
    130                 135                 140

Ile Phe Leu Lys Ile Gly Ser Ala Thr Pro Gly Leu Gln Lys Val Val
145                 150                 155                 160

Asp Thr Leu Ser Ser Ile Lys Thr Lys Gly Lys Ser Val Asp Phe Thr
                165                 170                 175

Asp Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Thr Val Ser Ser Glu Gln Met Leu Lys
    210                 215                 220

Phe Arg Asn Leu Asn Phe Asn Lys Glu Ala Glu Pro Glu Glu Pro Met
225                 230                 235                 240

Val Asp Asn Trp Arg Pro Thr Gln Pro Leu Lys Gly Arg Gln Val Lys
                245                 250                 255

Ala Ser Phe Val
            260


<210> SEQ ID NO 34
<211> LENGTH: 249
<212> TYPE: PRT
<213> ORGANISM: Ailuropoda melanoleuca

<400> SEQUENCE: 34

Gly Pro Glu His Trp Tyr Lys Asp Phe Pro Ile Ala Lys Gly Gln Arg
1               5                   10                  15

Gln Ser Pro Val Asp Ile Asp Thr Lys Ala Ala Ile His Asp Pro Ala
            20                  25                  30

Leu Lys Ala Leu Cys Pro Thr Tyr Glu Gln Ala Val Ser Gln Arg Val
        35                  40                  45

Ile Asn Asn Gly His Ser Phe Asn Val Glu Phe Asp Asp Ser Gln Asp
    50                  55                  60

Asn Ala Val Leu Lys Gly Gly Pro Leu Thr Gly Thr Tyr Arg Leu Ile
65                  70                  75                  80

Gln Phe His Phe His Trp Gly Ser Ser Asp Gly Gln Gly Ser Glu His
                85                  90                  95

Thr Val Asp Lys Lys Lys Tyr Ala Ala Glu Leu His Leu Val His Trp
            100                 105                 110

Asn Thr Lys Tyr Gly Asp Phe Gly Lys Ala Val Gln Gln Pro Asp Gly
        115                 120                 125

Leu Ala Val Leu Gly Ile Phe Leu Lys Ile Gly Asp Ala Arg Pro Gly
    130                 135                 140

Leu Gln Lys Val Leu Asp Ala Leu Asp Ser Ile Lys Thr Lys Gly Lys
145                 150                 155                 160

Ser Ala Asp Phe Thr Asn Phe Asp Pro Arg Gly Leu Leu Pro Glu Ser
                165                 170                 175

Leu Asp Tyr Trp Thr Tyr Pro Gly Ser Leu Thr Thr Pro Pro Leu Leu
            180                 185                 190
```

```
Glu Cys Val Thr Trp Ile Val Leu Lys Glu Pro Ile Ser Val Ser Ser
        195                 200                 205

Glu Gln Met Leu Lys Phe Arg Arg Leu Asn Phe Asn Lys Glu Gly Glu
    210                 215                 220

Pro Glu Glu Leu Met Val Asp Asn Trp Arg Pro Ala Gln Pro Leu His
225                 230                 235                 240

Asn Arg Gln Ile Asn Ala Ser Phe Lys
                245


<210> SEQ ID NO 35
<211> LENGTH: 260
<212> TYPE: PRT
<213> ORGANISM: Sus scrofa

<400> SEQUENCE: 35

Met Ser His His Trp Gly Tyr Asp Lys His Asn Gly Pro Glu His Trp
1               5                   10                  15

His Lys Asp Phe Pro Ile Ala Lys Gly Asp Arg Gln Ser Pro Val Asp
            20                  25                  30

Ile Asn Thr Ser Thr Ala Val His Asp Pro Ala Leu Lys Pro Leu Ser
        35                  40                  45

Leu Cys Tyr Glu Gln Ala Thr Ser Gln Arg Ile Val Asn Asn Gly His
    50                  55                  60

Ser Phe Asn Val Glu Phe Asp Ser Ser Gln Asp Lys Gly Val Leu Glu
65                  70                  75                  80

Gly Gly Pro Leu Ala Gly Thr Tyr Arg Leu Ile Gln Phe His Phe His
                85                  90                  95

Trp Gly Ser Ser Asp Gly Gln Gly Ser Glu His Thr Val Asp Lys Lys
            100                 105                 110

Lys Tyr Ala Ala Glu Leu His Leu Val His Trp Asn Thr Lys Tyr Lys
        115                 120                 125

Asp Phe Gly Glu Ala Ala Gln Gln Pro Asp Gly Leu Ala Val Leu Gly
    130                 135                 140

Val Phe Leu Lys Ile Gly Asn Ala Gln Pro Gly Leu Gln Lys Ile Val
145                 150                 155                 160

Asp Val Leu Asp Ser Ile Lys Thr Lys Gly Lys Ser Val Glu Phe Thr
                165                 170                 175

Gly Phe Asp Pro Arg Asp Leu Leu Pro Gly Ser Leu Asp Tyr Trp Thr
            180                 185                 190

Tyr Pro Gly Ser Leu Thr Thr Pro Pro Leu Leu Glu Ser Val Thr Trp
        195                 200                 205

Ile Val Leu Arg Glu Pro Ile Ser Val Ser Ser Gly Gln Met Met Lys
    210                 215                 220

Phe Arg Thr Leu Asn Phe Asn Lys Glu Gly Glu Pro Glu His Pro Met
225                 230                 235                 240

Val Asp Asn Trp Arg Pro Thr Gln Pro Leu Lys Asn Arg Gln Ile Arg
                245                 250                 255

Ala Ser Phe Gln
            260


<210> SEQ ID NO 36
<211> LENGTH: 235
<212> TYPE: PRT
<213> ORGANISM: Callithrix jacchus

<400> SEQUENCE: 36
```

```
Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Trp Arg Ile Leu Asn Asn Gly His
    50                  55                  60

Ser Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Leu His Leu Val
                85                  90                  95

His Trp Asn Thr Lys Tyr Gly Asp Phe Gly Lys Ala Ala Gln Gln Pro
            100                 105                 110

Asp Gly Leu Ala Val Leu Gly Ile Phe Leu Lys Val Gly Ser Ala Lys
        115                 120                 125

Pro Gly Leu Gln Lys Val Val Asp Val Leu Asp Ser Ile Lys Thr Lys
    130                 135                 140

Gly Lys Ser Ala Asp Phe Thr Asn Phe Asp Pro Arg Gly Leu Leu Pro
145                 150                 155                 160

Glu Ser Leu Asp Tyr Trp Thr Tyr Pro Gly Ser Leu Thr Thr Pro Pro
                165                 170                 175

Leu Leu Glu Ser Val Thr Trp Ile Val Leu Lys Glu Pro Ile Ser Val
            180                 185                 190

Ser Ser Glu Gln Ile Leu Lys Phe Arg Lys Leu Asn Phe Ser Gly Glu
        195                 200                 205

Gly Glu Pro Glu Glu Leu Met Val Asp Asn Trp Arg Pro Ala Gln Pro
    210                 215                 220

Leu Lys Asn Arg Gln Ile Lys Ala Ser Phe Lys
225                 230                 235


<210> SEQ ID NO 37
<211> LENGTH: 260
<212> TYPE: PRT
<213> ORGANISM: Mus musculus

<400> SEQUENCE: 37

Met Ser His His Trp Gly Tyr Ser Lys His Asn Gly Pro Glu Asn Trp
1               5                   10                  15

His Lys Asp Phe Pro Ile Ala Asn Gly Asp Arg Gln Ser Pro Val Asp
            20                  25                  30

Ile Asp Thr Ala Thr Ala Gln His Asp Pro Ala Leu Gln Pro Leu Leu
        35                  40                  45

Ile Ser Tyr Asp Lys Ala Ala Ser Lys Ser Ile Val Asn Asn Gly His
    50                  55                  60

Ser Phe Asn Val Glu Phe Asp Asp Ser Gln Asp Asn Ala Val Leu Lys
65                  70                  75                  80

Gly Gly Pro Leu Ser Asp Ser Tyr Arg Leu Ile Gln Phe His Phe His
                85                  90                  95

Trp Gly Ser Ser Asp Gly Gln Gly Ser Glu His Thr Val Asn Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140
```

```
Ile Phe Leu Lys Ile Gly Pro Ala Ser Gln Gly Leu Gln Lys Val Leu
145                 150                 155                 160

Glu Ala Leu His Ser Ile Lys Thr Lys Gly Lys Arg Ala Ala Phe Ala
                165                 170                 175

Asn Phe Asp Pro Cys Ser Leu Leu Pro Gly Asn Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Arg Glu Pro Ile Thr Val Ser Ser Glu Gln Met Ser His
    210                 215                 220

Phe Arg Thr Leu Asn Phe Asn Glu Glu Gly Asp Ala Glu Glu Ala Met
225                 230                 235                 240

Val Asp Asn Trp Arg Pro Ala Gln Pro Leu Lys Asn Arg Lys Ile Lys
                245                 250                 255

Ala Ser Phe Lys
            260


<210> SEQ ID NO 38
<211> LENGTH: 260
<212> TYPE: PRT
<213> ORGANISM: Bos taurus

<400> SEQUENCE: 38

Met Ser His His Trp Gly Tyr Gly Lys His Asn Gly Pro Glu His Trp
1               5                   10                  15

His Lys Asp Phe Pro Ile Ala Asn Gly Glu Arg Gln Ser Pro Val Asp
            20                  25                  30

Ile Asp Thr Lys Ala Val Val Gln Asp Pro Ala Leu Lys Pro Leu Ala
        35                  40                  45

Leu Val Tyr Gly Glu Ala Thr Ser Arg Arg Met Val Asn Asn Gly His
    50                  55                  60

Ser Phe Asn Val Glu Tyr Asp Asp Ser Gln Asp Lys Ala Val Leu Lys
65                  70                  75                  80

Asp Gly Pro Leu Thr Gly Thr Tyr Arg Leu Val Gln Phe His Phe His
                85                  90                  95

Trp Gly Ser Ser Asp Asp Gln Gly Ser Glu His Thr Val Asp Arg Lys
            100                 105                 110

Lys Tyr Ala Ala Glu Leu His Leu Val His Trp Asn Thr Lys Tyr Gly
        115                 120                 125

Asp Phe Gly Thr Ala Ala Gln Gln Pro Asp Gly Leu Ala Val Val Gly
    130                 135                 140

Val Phe Leu Lys Val Gly Asp Ala Asn Pro Ala Leu Gln Lys Val Leu
145                 150                 155                 160

Asp Ala Leu Asp Ser Ile Lys Thr Lys Gly Lys Ser Thr Asp Phe Pro
                165                 170                 175

Asn Phe Asp Pro Gly Ser Leu Leu Pro Asn Val Leu Asp Tyr Trp Thr
            180                 185                 190

Tyr Pro Gly Ser Leu Thr Thr Pro Pro Leu Leu Glu Ser Val Thr Trp
        195                 200                 205

Ile Val Leu Lys Glu Pro Ile Ser Val Ser Ser Gln Gln Met Leu Lys
    210                 215                 220

Phe Arg Thr Leu Asn Phe Asn Ala Glu Gly Glu Pro Glu Leu Leu Met
225                 230                 235                 240

Leu Ala Asn Trp Arg Pro Ala Gln Pro Leu Lys Asn Arg Gln Val Arg
```

```
                245                 250                 255

Gly Phe Pro Lys
            260


<210> SEQ ID NO 39
<211> LENGTH: 232
<212> TYPE: PRT
<213> ORGANISM: Oryctolagus cuniculus

<400> SEQUENCE: 39

Gly Lys His Asn Gly Pro Glu His Trp His Lys Asp Phe Pro Ile Ala
1               5                   10                  15

Asn Gly Glu Arg Gln Ser Pro Ile Asp Ile Asp Thr Asn Ala Ala Lys
            20                  25                  30

His Asp Pro Ser Leu Lys Pro Leu Arg Val Cys Tyr Glu His Pro Ile
        35                  40                  45

Ser Arg Arg Ile Ile Asn Asn Gly His Ser Phe Asn Val Glu Phe Asp
    50                  55                  60

Asp Ser His Asp Lys Thr Val Leu Lys Glu Gly Pro Leu Glu Gly Thr
65                  70                  75                  80

Tyr Arg Leu Ile Gln Phe His Phe His Trp Gly Ser Ser Asp Gly Gln
                85                  90                  95

Gly Ser Glu His Thr Val Asn Lys Lys Lys Tyr Ala Ala Glu Leu His
            100                 105                 110

Leu Val His Trp Asn Thr Lys Tyr Gly Asp Phe Gly Lys Ala Val Lys
        115                 120                 125

His Pro Asp Gly Leu Ala Val Leu Gly Ile Phe Leu Lys Ile Gly Ser
    130                 135                 140

Ala Thr Pro Gly Leu Gln Lys Val Val Asp Thr Leu Ser Ser Ile Lys
145                 150                 155                 160

Thr Lys Gly Lys Ser Val Asp Phe Thr Asp Phe Asp Pro Arg Gly Leu
                165                 170                 175

Leu Pro Glu Ser Leu Asp Tyr Trp Thr Tyr Pro Gly Ser Leu Thr Thr
            180                 185                 190

Pro Pro Leu Leu Glu Cys Val Thr Trp Ile Val Leu Lys Glu Pro Ile
        195                 200                 205

Thr Val Ser Ser Glu Gln Met Leu Lys Phe Arg Asn Leu Asn Phe Asn
    210                 215                 220

Lys Glu Ala Glu Pro Glu Glu Pro
225                 230


<210> SEQ ID NO 40
<211> LENGTH: 260
<212> TYPE: PRT
<213> ORGANISM: Rattus norvegicus

<400> SEQUENCE: 40

Met Ser His His Trp Gly Tyr Ser Lys Ser Asn Gly Pro Glu Asn Trp
1               5                   10                  15

His Lys Glu Phe Pro Ile Ala Asn Gly Asp Arg Gln Ser Pro Val Asp
            20                  25                  30

Ile Asp Thr Gly Thr Ala Gln His Asp Pro Ser Leu Gln Pro Leu Leu
        35                  40                  45

Ile Cys Tyr Asp Lys Val Ala Ser Lys Ser Ile Val Asn Asn Gly His
    50                  55                  60

Ser Phe Asn Val Glu Phe Asp Asp Ser Gln Asp Phe Ala Val Leu Lys
```

```
65                  70                  75                  80

Glu Gly Pro Leu Ser Gly Ser Tyr Arg Leu Ile Gln Phe His Phe His
                85                  90                  95

Trp Gly Ser Ser Asp Gly Gln Gly Ser Glu His Thr Val Asn Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln His Pro Asp Gly Leu Ala Val Leu Gly
    130                 135                 140

Ile Phe Leu Lys Ile Gly Pro Ala Ser Gln Gly Leu Gln Lys Ile Thr
145                 150                 155                 160

Glu Ala Leu His Ser Ile Lys Thr Lys Gly Lys Arg Ala Ala Phe Ala
                165                 170                 175

Asn Phe Asp Pro Cys Ser Leu Leu Pro Gly Asn Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Thr Val Ser Ser Glu Gln Met Ser His
    210                 215                 220

Phe Arg Lys Leu Asn Phe Asn Ser Glu Gly Glu Ala Glu Glu Leu Met
225                 230                 235                 240

Val Asp Asn Trp Arg Pro Ala Gln Pro Leu Lys Asn Arg Lys Ile Lys
                245                 250                 255

Ala Ser Phe Lys
            260


<210> SEQ ID NO 41
<211> LENGTH: 208
<212> TYPE: PRT
<213> ORGANISM: Homo sapiens

<400> SEQUENCE: 41

Met Ser Leu Ser Ile Thr Asn Asn Gly His Ser Val Gln Val Asp Phe
1               5                   10                  15

Asn Asp Ser Asp Asp Arg Thr Val Val Thr Gly Gly Pro Leu Glu Gly
            20                  25                  30

Pro Tyr Arg Leu Lys Gln Phe His Phe His Trp Gly Lys Lys His Asp
        35                  40                  45

Val Gly Ser Glu His Thr Val Asp Gly Lys Ser Phe Pro Ser Glu Leu
    50                  55                  60

His Leu Val His Trp Asn Ala Lys Lys Tyr Ser Thr Phe Gly Glu Ala
65                  70                  75                  80

Ala Ser Ala Pro Asp Gly Leu Ala Val Val Gly Val Phe Leu Glu Thr
                85                  90                  95

Gly Asp Glu His Pro Ser Met Asn Arg Leu Thr Asp Ala Leu Tyr Met
            100                 105                 110

Val Arg Phe Lys Gly Thr Lys Ala Gln Phe Ser Cys Phe Asn Pro Lys
        115                 120                 125

Cys Leu Leu Pro Ala Ser Arg His Tyr Trp Thr Tyr Pro Gly Ser Leu
    130                 135                 140

Thr Thr Pro Pro Leu Ser Glu Ser Val Thr Trp Ile Val Leu Arg Glu
145                 150                 155                 160

Pro Ile Cys Ile Ser Glu Arg Gln Met Gly Lys Phe Arg Ser Leu Leu
                165                 170                 175
```

```
Phe Thr Ser Glu Asp Asp Glu Arg Ile His Met Val Asn Asn Phe Arg
            180                 185                 190

Pro Pro Gln Pro Leu Lys Gly Arg Val Val Lys Ala Ser Phe Arg Ala
        195                 200                 205


<210> SEQ ID NO 42
<211> LENGTH: 264
<212> TYPE: PRT
<213> ORGANISM: Pongo abelii

<400> SEQUENCE: 42

Met Thr Gly His His Gly Trp Gly Tyr Gly Gln Asp Asp Gly Pro Ser
1               5                   10                  15

His Trp His Lys Leu Tyr Pro Ile Ala Gln Gly Asp Arg Gln Ser Pro
            20                  25                  30

Ile Asn Ile Ile Ser Ser Gln Ala Val Tyr Ser Pro Ser Leu Gln Pro
        35                  40                  45

Leu Glu Leu Ser Tyr Glu Ala Cys Met Ser Leu Ser Ile Thr Asn Asn
    50                  55                  60

Gly His Ser Val Gln Val Asp Phe Asn Asp Ser Asp Asp Arg Thr Val
65                  70                  75                  80

Val Thr Gly Gly Pro Leu Glu Gly Pro Tyr Arg Leu Lys Gln Phe His
                85                  90                  95

Phe His Trp Gly Lys Lys His Asp Val Gly Ser Glu His Thr Val Asp
            100                 105                 110

Gly Lys Ser Phe Pro Ser Glu Leu His Leu Val His Trp Asn Ala Lys
        115                 120                 125

Lys Tyr Ser Thr Phe Gly Glu Ala Ala Ser Ala Pro Asp Gly Leu Ala
    130                 135                 140

Val Val Gly Val Phe Leu Glu Thr Gly Asp Glu His Pro Ser Met Asn
145                 150                 155                 160

Arg Leu Thr Asp Ala Leu Tyr Met Val Arg Phe Lys Gly Thr Lys Ala
                165                 170                 175

Gln Phe Ser Cys Phe Asn Pro Lys Ser Leu Leu Pro Ala Ser Arg His
            180                 185                 190

Tyr Trp Thr Tyr Pro Gly Ser Leu Thr Thr Pro Pro Leu Ser Glu Ser
        195                 200                 205

Val Thr Trp Ile Val Leu Arg Glu Pro Ile Cys Ile Ser Glu Arg Gln
    210                 215                 220

Met Gly Lys Phe Arg Ser Leu Leu Phe Thr Ser Glu Asp Asp Glu Arg
225                 230                 235                 240

Ile His Met Val Asn Asn Phe Arg Pro Pro Gln Pro Leu Lys Gly Arg
                245                 250                 255

Val Val Lys Ala Ser Phe Arg Ala
            260


<210> SEQ ID NO 43
<211> LENGTH: 264
<212> TYPE: PRT
<213> ORGANISM: Pan troglodytes

<400> SEQUENCE: 43

Met Thr Gly His His Gly Trp Gly Tyr Gly Gln Asp Asp Gly Pro Ser
1               5                   10                  15

His Trp His Lys Leu Tyr Pro Ile Ala Gln Gly Asp Arg Gln Ser Pro
            20                  25                  30
```

```
Ile Asn Ile Ile Ser Ser Gln Ala Val Tyr Ser Pro Ser Leu Gln Pro
        35                  40                  45

Leu Glu Leu Ser Tyr Glu Ala Cys Met Ser Leu Ser Ile Thr Asn Asn
    50                  55                  60

Gly His Ser Val Gln Val Asp Phe Asn Asp Ser Asp Asp Arg Thr Val
65                  70                  75                  80

Val Thr Gly Gly Pro Leu Glu Gly Pro Tyr Arg Leu Lys Gln Phe His
                85                  90                  95

Phe His Trp Gly Lys Lys His Asp Val Gly Ser Glu His Thr Val Asp
            100                 105                 110

Gly Lys Ser Phe Pro Ser Glu Leu His Leu Val His Trp Asn Ala Lys
        115                 120                 125

Lys Tyr Ser Thr Phe Gly Glu Ala Ala Ser Ala Pro Asp Gly Leu Ala
    130                 135                 140

Val Val Gly Val Phe Leu Glu Thr Gly Asp Glu His Pro Ser Met Asn
145                 150                 155                 160

Arg Leu Thr Asp Ala Leu Tyr Met Val Arg Phe Lys Gly Thr Lys Ala
                165                 170                 175

Gln Phe Ser Cys Phe Asn Pro Lys Cys Leu Leu Pro Ala Ser Arg His
            180                 185                 190

Tyr Trp Thr Tyr Pro Gly Ser Leu Thr Thr Pro Pro Leu Ser Glu Ser
        195                 200                 205

Val Thr Trp Ile Val Leu Arg Glu Pro Ile Cys Ile Ser Glu Arg Gln
    210                 215                 220

Met Arg Lys Phe Arg Ser Leu Leu Phe Thr Ser Glu Asp Asp Glu Arg
225                 230                 235                 240

Ile His Met Val Asn Asn Phe Arg Pro Pro Gln Pro Leu Lys Gly Arg
                245                 250                 255

Val Val Lys Ala Ser Phe Arg Ala
            260


<210> SEQ ID NO 44
<211> LENGTH: 264
<212> TYPE: PRT
<213> ORGANISM: Callithrix jacchus

<400> SEQUENCE: 44

Met Thr Gly His His Gly Trp Gly Tyr Gly Gln Asp Asp Gly Pro Ser
1               5                   10                  15

His Trp His Lys Leu Tyr Pro Ile Ala Gln Gly Asp Arg Gln Ser Pro
            20                  25                  30

Ile Asn Ile Ile Ser Ser Gln Ala Val Tyr Ser Pro Ser Leu Gln Pro
        35                  40                  45

Leu Glu Leu Ser Tyr Glu Ala Cys Met Ser Leu Ser Ile Thr Asn Asn
    50                  55                  60

Gly His Ser Val Gln Val Asp Phe Asn Asp Ser Asp Asp Arg Thr Val
65                  70                  75                  80

Val Thr Gly Gly Pro Leu Glu Gly Pro Tyr Arg Leu Lys Gln Phe His
                85                  90                  95

Phe His Trp Gly Lys Lys His Asp Val Gly Ser Glu His Thr Val Asp
            100                 105                 110

Gly Lys Ser Phe Pro Ser Glu Leu His Leu Val His Trp Asn Ala Lys
        115                 120                 125

Lys Tyr Ser Thr Phe Gly Glu Ala Ala Ser Ala Pro Asp Gly Leu Ala
    130                 135                 140
```

```
Val Val Gly Val Phe Leu Glu Thr Gly Asp Glu His Pro Ser Met Asn
145                 150                 155                 160

Arg Leu Thr Asp Ala Leu Tyr Met Val Arg Phe Lys Gly Thr Lys Ala
                165                 170                 175

Gln Phe Ser Cys Phe Asn Pro Lys Cys Leu Leu Pro Ala Ser Trp His
            180                 185                 190

Tyr Trp Thr Tyr Pro Gly Ser Leu Thr Thr Pro Pro Leu Ser Glu Ser
        195                 200                 205

Val Thr Trp Ile Val Leu Arg Glu Pro Ile Cys Ile Ser Glu Arg Gln
    210                 215                 220

Met Gly Lys Phe Arg Ser Leu Leu Phe Thr Ser Glu Asp Asp Glu Arg
225                 230                 235                 240

Val His Met Val Asn Asn Phe Arg Pro Pro Gln Pro Leu Lys Gly Arg
                245                 250                 255

Val Val Lys Ala Ser Phe Arg Ala
            260


<210> SEQ ID NO 45
<211> LENGTH: 251
<212> TYPE: PRT
<213> ORGANISM: Ailuropoda melanoleuca

<400> SEQUENCE: 45

Gly Pro Ser Gln Trp His Lys Leu Tyr Pro Ile Ala Gln Gly Asp Arg
1               5                   10                  15

Gln Ser Pro Ile Asn Ile Val Ser Ser Gln Ala Val Tyr Ser Pro Ser
            20                  25                  30

Leu Lys Pro Leu Glu Leu Ser Tyr Glu Ala Cys Ile Ser Leu Ser Ile
        35                  40                  45

Ala Asn Asn Gly His Ser Val Gln Val Asp Phe Asn Asp Ser Asp Asp
    50                  55                  60

Arg Thr Val Val Thr Gly Gly Pro Leu Asp Gly Pro Tyr Arg Leu Lys
65                  70                  75                  80

Gln Phe His Phe His Trp Gly Lys Lys His Ser Val Gly Ser Glu His
                85                  90                  95

Thr Val Asp Gly Lys Ser Phe Pro Ser Glu Leu His Leu Val His Trp
            100                 105                 110

Asn Ala Lys Lys Tyr Ser Thr Phe Gly Glu Ala Ala Ser Ala Pro Asp
        115                 120                 125

Gly Leu Ala Val Val Gly Val Phe Leu Glu Thr Gly Asp Glu His Pro
    130                 135                 140

Ser Met Asn Arg Leu Thr Asp Ala Leu Tyr Met Val Arg Phe Lys Gly
145                 150                 155                 160

Thr Lys Ala Gln Phe Ser Cys Phe Asn Pro Lys Cys Leu Leu Pro Ala
                165                 170                 175

Ser Arg His Tyr Trp Thr Tyr Pro Gly Ser Leu Thr Thr Pro Pro Leu
            180                 185                 190

Ser Glu Ser Val Thr Trp Ile Val Leu Arg Glu Pro Ile Ser Ile Ser
        195                 200                 205

Glu Arg Gln Met Glu Lys Phe Arg Ser Leu Leu Phe Thr Ser Glu Asp
    210                 215                 220

Asp Glu Arg Ile His Met Val Asn Asn Phe Arg Pro Pro Gln Pro Leu
225                 230                 235                 240

Lys Gly Arg Val Val Lys Ala Ser Phe Arg Ala
```

245 250

<210> SEQ ID NO 46
<211> LENGTH: 264
<212> TYPE: PRT
<213> ORGANISM: Canis familiaris

<400> SEQUENCE: 46

```
Met Thr Gly His His Cys Trp Gly Tyr Gly Gln Asn Asp Gly Pro Ser
1               5                   10                  15

Gln Trp His Lys Leu Tyr Pro Ile Ala Gln Gly Asp Arg Gln Ser Pro
            20                  25                  30

Ile Asn Ile Val Ser Ser Gln Ala Val Tyr Ser Pro Ser Leu Lys Pro
        35                  40                  45

Leu Glu Leu Ser Tyr Glu Ala Cys Ile Ser Leu Ser Ile Thr Asn Asn
    50                  55                  60

Gly His Ser Val Gln Val Asp Phe Asn Asp Ser Asp Asp Arg Thr Ala
65                  70                  75                  80

Val Thr Gly Gly Pro Leu Asp Gly Pro Tyr Arg Leu Lys Gln Leu His
                85                  90                  95

Phe His Trp Gly Lys Lys His Ser Val Gly Ser Glu His Thr Val Asp
            100                 105                 110

Gly Lys Ser Phe Pro Ser Glu Leu His Leu Val His Trp Asn Ala Lys
        115                 120                 125

Lys Tyr Ser Thr Phe Gly Glu Ala Ala Ser Ala Pro Asp Gly Leu Ala
    130                 135                 140

Val Val Gly Ile Phe Leu Glu Thr Gly Asp Glu His Pro Ser Met Asn
145                 150                 155                 160

Arg Leu Thr Asp Ala Leu Tyr Met Val Arg Phe Lys Gly Thr Lys Ala
                165                 170                 175

Gln Phe Ser Cys Phe Asn Pro Lys Cys Leu Leu Pro Ala Ser Arg His
            180                 185                 190

Tyr Trp Thr Tyr Pro Gly Ser Leu Thr Thr Pro Pro Leu Ser Glu Ser
        195                 200                 205

Val Thr Trp Ile Val Leu Arg Glu Pro Ile Ser Ile Ser Glu Arg Gln
    210                 215                 220

Met Glu Lys Phe Arg Ser Leu Leu Phe Thr Ser Glu Glu Asp Glu Arg
225                 230                 235                 240

Ile His Met Val Asn Asn Phe Arg Pro Pro Gln Pro Leu Lys Gly Arg
                245                 250                 255

Val Val Lys Ala Ser Phe Arg Ala
            260
```

<210> SEQ ID NO 47
<211> LENGTH: 264
<212> TYPE: PRT
<213> ORGANISM: Bos taurus

<400> SEQUENCE: 47

```
Met Thr Gly His His Gly Trp Gly Tyr Gly Gln Asn Asp Gly Pro Ser
1               5                   10                  15

His Trp His Lys Leu Tyr Pro Ile Ala Gln Gly Asp Arg Gln Ser Pro
            20                  25                  30

Ile Asn Ile Val Ser Ser Gln Ala Val Tyr Ser Pro Ser Leu Lys Pro
        35                  40                  45

Leu Glu Ile Ser Tyr Glu Ser Cys Thr Ser Leu Ser Ile Ala Asn Asn
```

```
    50                  55                  60

Gly His Ser Val Gln Val Asp Phe Asn Asp Ser Asp Asp Arg Thr Val
65                  70                  75                  80

Val Ser Gly Gly Pro Leu Asp Gly Pro Tyr Arg Leu Lys Gln Phe His
                85                  90                  95

Phe His Trp Gly Lys Lys His Gly Val Gly Ser Glu His Thr Val Asp
            100                 105                 110

Gly Lys Ser Phe Pro Ser Glu Leu His Leu Val His Trp Asn Ala Lys
        115                 120                 125

Lys Tyr Ser Thr Phe Gly Glu Ala Ala Ser Ala Pro Asp Gly Leu Ala
    130                 135                 140

Val Val Gly Val Phe Leu Glu Thr Gly Asp Glu His Pro Ser Met Asn
145                 150                 155                 160

Arg Leu Thr Asp Ala Leu Tyr Met Val Arg Phe Lys Gly Thr Lys Ala
                165                 170                 175

Gln Phe Ser Cys Phe Asn Pro Lys Cys Leu Leu Pro Ala Ser Arg His
            180                 185                 190

Tyr Trp Thr Tyr Pro Gly Ser Leu Thr Thr Pro Pro Leu Ser Glu Ser
        195                 200                 205

Val Thr Trp Ile Val Leu Arg Glu Pro Ile Arg Ile Ser Glu Arg Gln
    210                 215                 220

Met Glu Lys Phe Arg Ser Leu Leu Phe Thr Ser Glu Glu Asp Glu Arg
225                 230                 235                 240

Ile His Met Val Asn Asn Phe Arg Pro Pro Gln Pro Leu Lys Gly Arg
                245                 250                 255

Val Val Lys Ala Ser Phe Arg Ala
            260


<210> SEQ ID NO 48
<211> LENGTH: 271
<212> TYPE: PRT
<213> ORGANISM: Rattus norvegicus

<400> SEQUENCE: 48

Met Thr Val Leu Trp Trp Pro Met Leu Arg Glu Glu Leu Met Ser Lys
1               5                   10                  15

Leu Arg Thr Gly Gly Pro Ser Asn Trp His Lys Leu Tyr Pro Ile Ala
            20                  25                  30

Gln Gly Asp Arg Gln Ser Pro Ile Asn Ile Ile Ser Ser Gln Ala Val
        35                  40                  45

Tyr Ser Pro Ser Leu Gln Pro Leu Glu Leu Phe Tyr Glu Ala Cys Met
    50                  55                  60

Ser Leu Ser Ile Thr Asn Asn Gly His Ser Val Gln Val Asp Phe Asn
65                  70                  75                  80

Asp Ser Asp Asp Arg Thr Val Val Ala Gly Gly Pro Leu Glu Gly Pro
                85                  90                  95

Tyr Arg Leu Lys Gln Leu His Phe His Trp Gly Lys Lys Arg Asp Val
            100                 105                 110

Gly Ser Glu His Thr Val Asp Gly Lys Ser Phe Pro Ser Glu Leu His
        115                 120                 125

Leu Val His Trp Asn Ala Lys Lys Tyr Ser Thr Phe Gly Glu Ala Ala
    130                 135                 140

Ala Ala Pro Asp Gly Leu Ala Val Val Gly Ile Phe Leu Glu Thr Gly
145                 150                 155                 160
```

```
Asp Glu His Pro Ser Met Asn Arg Leu Thr Asp Ala Leu Tyr Met Val
                165                 170                 175

Arg Phe Lys Asp Thr Lys Ala Gln Phe Ser Cys Phe Asn Pro Lys Cys
            180                 185                 190

Leu Leu Pro Thr Ser Arg His Tyr Trp Thr Tyr Pro Gly Ser Leu Thr
        195                 200                 205

Thr Pro Pro Leu Ser Glu Ser Val Thr Trp Ile Val Leu Arg Glu Pro
    210                 215                 220

Ile Arg Ile Ser Glu Arg Gln Met Glu Lys Phe Arg Ser Leu Leu Phe
225                 230                 235                 240

Thr Ser Glu Asp Asp Glu Arg Ile His Met Val Asn Asn Phe Arg Pro
                245                 250                 255

Pro Gln Pro Leu Lys Gly Arg Val Val Lys Ala Ser Phe Gln Ser
            260                 265                 270


<210> SEQ ID NO 49
<211> LENGTH: 266
<212> TYPE: PRT
<213> ORGANISM: Oryctolagus cuniculus

<400> SEQUENCE: 49

Met Thr Gly His His Gly Trp Gly Tyr Gly Gln Asp Asp Gly Gly Arg
1               5                   10                  15

Pro Ser His Trp His Lys Leu Tyr Pro Ile Ala Gln Gly Asp Arg Gln
            20                  25                  30

Ser Pro Ile Asn Ile Val Ser Ser Gln Ala Val Tyr Ser Pro Gly Leu
        35                  40                  45

Gln Pro Leu Glu Leu Ser Tyr Glu Ala Cys Thr Ser Leu Ser Ile Ala
    50                  55                  60

Asn Asn Gly His Ser Val Gln Val Asp Phe Asn Asp Ser Asp Asp Arg
65                  70                  75                  80

Thr Val Val Thr Gly Gly Pro Leu Glu Gly Pro Tyr Arg Leu Lys Gln
                85                  90                  95

Phe His Phe His Trp Gly Lys Arg Arg Asp Ala Gly Ser Glu His Thr
            100                 105                 110

Val Asp Gly Lys Ser Phe Pro Ser Glu Leu His Leu Val His Trp Asn
        115                 120                 125

Ala Arg Lys Tyr Ser Thr Phe Gly Glu Ala Ala Ser Ala Pro Asp Gly
    130                 135                 140

Leu Ala Val Val Gly Val Phe Leu Glu Thr Gly Asn Glu His Pro Ser
145                 150                 155                 160

Met Asn Arg Leu Thr Asp Ala Leu Tyr Met Val Arg Phe Lys Gly Thr
                165                 170                 175

Lys Ala Gln Phe Ser Cys Phe Asn Pro Lys Cys Leu Leu Pro Ser Ser
            180                 185                 190

Arg His Tyr Trp Thr Tyr Pro Gly Ser Leu Thr Thr Pro Pro Leu Ser
        195                 200                 205

Glu Ser Val Thr Trp Ile Val Leu Arg Glu Pro Ile Ser Ile Ser Glu
    210                 215                 220

Arg Gln Met Glu Lys Phe Arg Ser Leu Leu Phe Thr Ser Glu Asp Asp
225                 230                 235                 240

Glu Arg Val His Met Val Asn Asn Phe Arg Pro Pro Gln Pro Leu Arg
                245                 250                 255

Gly Arg Val Val Lys Ala Ser Phe Arg Ala
            260                 265
```

<210> SEQ ID NO 50
<211> LENGTH: 255
<212> TYPE: PRT
<213> ORGANISM: Mus musculus

<400> SEQUENCE: 50

```
Gly Gln Asp Asp Gly Pro Ser Asn Trp His Lys Leu Tyr Pro Ile Ala
1               5                   10                  15

Gln Gly Asp Arg Gln Ser Pro Ile Asn Ile Ile Ser Ser Gln Ala Val
            20                  25                  30

Tyr Ser Pro Ser Leu Gln Pro Leu Glu Leu Phe Tyr Glu Ala Cys Met
        35                  40                  45

Ser Leu Ser Ile Thr Asn Asn Gly His Ser Val Gln Val Asp Phe Asn
    50                  55                  60

Asp Ser Asp Asp Arg Thr Val Val Ser Gly Gly Pro Leu Glu Gly Pro
65                  70                  75                  80

Tyr Arg Leu Lys Gln Leu His Phe His Trp Gly Lys Lys Arg Asp Met
                85                  90                  95

Gly Ser Glu His Thr Val Asp Gly Lys Ser Phe Pro Ser Glu Leu His
            100                 105                 110

Leu Val His Trp Asn Ala Lys Lys Tyr Ser Thr Phe Gly Glu Ala Ala
        115                 120                 125

Ala Ala Pro Asp Gly Leu Ala Val Val Gly Val Phe Leu Glu Thr Gly
    130                 135                 140

Asp Glu His Pro Ser Met Asn Arg Leu Thr Asp Ala Leu Tyr Met Val
145                 150                 155                 160

Arg Phe Lys Asp Thr Lys Ala Gln Phe Ser Cys Phe Asn Pro Lys Cys
                165                 170                 175

Leu Leu Pro Thr Ser Arg His Tyr Trp Thr Tyr Pro Gly Ser Leu Thr
            180                 185                 190

Thr Pro Pro Leu Ser Glu Ser Val Thr Trp Ile Val Leu Arg Glu Pro
        195                 200                 205

Ile Arg Ile Ser Glu Arg Gln Met Glu Lys Phe Arg Ser Leu Leu Phe
    210                 215                 220

Thr Ser Glu Asp Asp Glu Arg Ile His Met Val Asp Asn Phe Arg Pro
225                 230                 235                 240

Pro Gln Pro Leu Lys Gly Arg Val Val Lys Ala Ser Phe Gln Ala
                245                 250                 255
```

<210> SEQ ID NO 51
<211> LENGTH: 264
<212> TYPE: PRT
<213> ORGANISM: Monodelphis domestica

<400> SEQUENCE: 51

```
Met Thr Gly His His Gly Trp Gly Tyr Gly Gln Glu Asp Gly Pro Ser
1               5                   10                  15

Glu Trp His Lys Leu Tyr Pro Ile Ala Gln Gly Asp Arg Gln Ser Pro
            20                  25                  30

Ile Asp Ile Val Ser Ser Gln Ala Val Tyr Asp Pro Thr Leu Lys Pro
        35                  40                  45

Leu Val Leu Ala Tyr Glu Ser Cys Met Ser Leu Ser Ile Ala Asn Asn
    50                  55                  60

Gly His Ser Val Met Val Glu Phe Asp Asp Val Asp Asp Arg Thr Val
65                  70                  75                  80
```

Val Asn Gly Gly Pro Leu Asp Gly Pro Tyr Arg Leu Lys Gln Phe His
85 90 95

Phe His Trp Gly Lys Lys His Ser Leu Gly Ser Glu His Thr Val Asp
100 105 110

Gly Lys Ser Phe Ser Ser Glu Leu His Leu Val His Trp Asn Gly Lys
115 120 125

Lys Tyr Lys Thr Phe Ala Glu Ala Ala Ala Ala Pro Asp Gly Leu Ala
130 135 140

Val Val Gly Ile Phe Leu Glu Thr Gly Asp Glu His Ala Ser Met Asn
145 150 155 160

Arg Leu Thr Asp Ala Leu Tyr Met Val Arg Phe Lys Gly Thr Lys Ala
165 170 175

Gln Phe Asn Ser Phe Asn Pro Lys Cys Leu Leu Pro Met Asn Leu Ser
180 185 190

Tyr Trp Thr Tyr Pro Gly Ser Leu Thr Thr Pro Pro Leu Ser Glu Ser
195 200 205

Val Thr Trp Ile Val Leu Lys Glu Pro Ile Thr Ile Ser Glu Lys Gln
210 215 220

Met Glu Lys Phe Arg Ser Leu Leu Phe Thr Ala Glu Glu Asp Glu Lys
225 230 235 240

Val Arg Met Val Asn Asn Phe Arg Pro Pro Gln Pro Leu Lys Gly Arg
245 250 255

Val Val Gln Ala Ser Phe Arg Ser
260

<210> SEQ ID NO 52
<211> LENGTH: 264
<212> TYPE: PRT
<213> ORGANISM: Gallus gallus

<400> SEQUENCE: 52

Met Thr Gly His His Ser Trp Gly Tyr Gly Gln Asp Asp Gly Pro Ser
1 5 10 15

Glu Trp His Lys Ser Tyr Pro Ile Ala Gln Gly Asn Arg Gln Ser Pro
20 25 30

Ile Asp Ile Ile Ser Ala Lys Ala Val Tyr Asp Pro Lys Leu Met Pro
35 40 45

Leu Val Ile Ser Tyr Glu Ser Cys Thr Ser Leu Asn Ile Ser Asn Asn
50 55 60

Gly His Ser Val Met Val Glu Phe Glu Asp Ile Asp Asp Lys Thr Val
65 70 75 80

Ile Ser Gly Gly Pro Phe Glu Ser Pro Phe Arg Leu Lys Gln Phe His
85 90 95

Phe His Trp Gly Ala Lys His Ser Glu Gly Ser Glu His Thr Ile Asp
100 105 110

Gly Lys Pro Phe Pro Cys Glu Leu His Leu Val His Trp Asn Ala Lys
115 120 125

Lys Tyr Ala Thr Phe Gly Glu Ala Ala Ala Ala Pro Asp Gly Leu Ala
130 135 140

Val Val Gly Val Phe Leu Glu Ile Gly Lys Glu His Ala Asn Met Asn
145 150 155 160

Arg Leu Thr Asp Ala Leu Tyr Met Val Lys Phe Lys Gly Thr Lys Ala
165 170 175

Gln Phe Arg Ser Phe Asn Pro Lys Cys Leu Leu Pro Leu Ser Leu Asp

```
            180                 185                 190

Tyr Trp Thr Tyr Leu Gly Ser Leu Thr Thr Pro Pro Leu Asn Glu Ser
        195                 200                 205

Val Ile Trp Val Val Leu Lys Glu Pro Ile Ser Ile Ser Glu Lys Gln
    210                 215                 220

Leu Glu Lys Phe Arg Met Leu Leu Phe Thr Ser Glu Glu Asp Gln Lys
225                 230                 235                 240

Val Gln Met Val Asn Asn Phe Arg Pro Pro Gln Pro Leu Lys Gly Arg
                245                 250                 255

Thr Val Arg Ala Ser Phe Lys Ala
            260


<210> SEQ ID NO 53
<211> LENGTH: 264
<212> TYPE: PRT
<213> ORGANISM: Taeniopygia guttata

<400> SEQUENCE: 53

Met Thr Gly Gln His Ser Trp Gly Tyr Gly Gln Ala Asp Gly Pro Ser
1               5                   10                  15

Glu Trp His Lys Ala Tyr Pro Ile Ala Gln Gly Asn Arg Gln Ser Pro
            20                  25                  30

Ile Asp Ile Asp Ser Ala Arg Ala Val Tyr Asp Pro Ser Leu Gln Pro
        35                  40                  45

Leu Leu Ile Ser Tyr Glu Ser Cys Ser Ser Leu Ser Ile Ser Asn Thr
    50                  55                  60

Gly His Ser Val Met Val Glu Phe Glu Asp Thr Asp Asp Arg Thr Ala
65                  70                  75                  80

Ile Ser Gly Gly Pro Phe Gln Asn Pro Phe Arg Leu Lys Gln Phe His
                85                  90                  95

Phe His Trp Gly Thr Thr His Ser Gln Gly Ser Glu His Thr Ile Asp
            100                 105                 110

Gly Lys Pro Phe Pro Cys Glu Leu His Leu Val His Trp Asn Ala Arg
        115                 120                 125

Lys Tyr Thr Thr Phe Gly Glu Ala Ala Ala Ala Pro Asp Gly Leu Ala
    130                 135                 140

Val Val Gly Val Phe Leu Glu Ile Gly Lys Glu His Ala Ser Met Asn
145                 150                 155                 160

Arg Leu Thr Asp Ala Leu Tyr Met Val Lys Phe Lys Gly Thr Lys Ala
                165                 170                 175

Gln Phe Arg Gly Phe Asn Pro Lys Cys Leu Leu Pro Leu Ser Leu Asp
            180                 185                 190

Tyr Trp Thr Tyr Leu Gly Ser Leu Thr Thr Pro Pro Leu Asn Glu Ser
        195                 200                 205

Val Thr Trp Ile Val Leu Lys Glu Pro Ile Arg Ile Ser Val Lys Gln
    210                 215                 220

Leu Glu Lys Phe Arg Met Leu Leu Phe Thr Gly Glu Glu Asp Gln Arg
225                 230                 235                 240

Ile Gln Met Ala Asn Asn Phe Arg Pro Pro Gln Pro Leu Lys Gly Arg
                245                 250                 255

Ile Val Arg Ala Ser Phe Lys Ala
            260


<210> SEQ ID NO 54
<211> LENGTH: 262
```

```
<212> TYPE: PRT
<213> ORGANISM: Homo sapiens

<400> SEQUENCE: 54

Met Ser Arg Leu Ser Trp Gly Tyr Arg Glu His Asn Gly Pro Ile His
1               5                   10                  15

Trp Lys Glu Phe Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Pro Ser Ser Ala Lys Ile Ile Ser Asn Ser Gly
    50                  55                  60

His Ser Phe Asn Val Asp Phe Asp Asp Thr Glu Asn Lys Ser Val Leu
65                  70                  75                  80

Arg Gly Gly Pro Leu Thr Gly Ser Tyr Arg Leu Arg Gln Val His Leu
                85                  90                  95

His Trp Gly Ser Ala Asp Asp His Gly Ser Glu His Ile Val Asp Gly
            100                 105                 110

Val Ser Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu Pro Asn Ser Gln Leu Gln Lys
145                 150                 155                 160

Ile Thr Asp Thr Leu Asp Ser Ile Lys Glu Lys Gly Lys Gln Thr Arg
                165                 170                 175

Phe Thr Asn Phe Asp Leu Leu Ser Leu Leu Pro Pro Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Asn Ile Ser Ser Gln Gln Leu
    210                 215                 220

Ala Lys Phe Arg Ser Leu Leu Cys Thr Ala Glu Gly Glu Ala Ala Ala
225                 230                 235                 240

Phe Leu Val Ser Asn His Arg Pro Pro Gln Pro Leu Lys Gly Arg Lys
                245                 250                 255

Val Arg Ala Ser Phe His
            260


<210> SEQ ID NO 55
<211> LENGTH: 262
<212> TYPE: PRT
<213> ORGANISM: Pan troglodytes

<400> SEQUENCE: 55

Met Ser Arg Leu Ser Trp Gly Tyr Arg Glu His Asn Gly Pro Ile His
1               5                   10                  15

Trp Lys Glu Phe Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Pro Ser Ser Ala Lys Ile Ile Ser Asn Ser Gly
    50                  55                  60

His Ser Phe Asn Val Asp Phe Asp Asp Thr Glu Asn Lys Ser Val Leu
65                  70                  75                  80
```

```
Arg Gly Gly Pro Leu Thr Gly Ser Tyr Arg Leu Arg Gln Phe His Leu
                85                  90                  95

His Trp Gly Ser Ala Asp Asp His Gly Ser Glu His Ile Val Asp Gly
            100                 105                 110

Val Ser Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu Pro Asn Ser Gln Leu Gln Lys
145                 150                 155                 160

Ile Thr Asp Thr Leu Asp Ser Ile Lys Glu Lys Gly Lys Gln Thr Arg
                165                 170                 175

Phe Thr Asn Phe Asp Pro Leu Ser Leu Leu Pro Pro Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Asn Ile Ser Ser Gln Gln Leu
    210                 215                 220

Ala Lys Phe Arg Ser Leu Leu Cys Thr Ala Glu Gly Glu Ala Ala Ala
225                 230                 235                 240

Phe Leu Val Ser Asn His Arg Pro Pro Gln Pro Leu Lys Gly Arg Lys
                245                 250                 255

Val Arg Ala Ser Phe His
            260


<210> SEQ ID NO 56
<211> LENGTH: 262
<212> TYPE: PRT
<213> ORGANISM: Macaca mulatta

<400> SEQUENCE: 56

Met Ser Arg Leu Ser Trp Gly Tyr Arg Glu His Asn Gly Pro Ile His
1               5                   10                  15

Trp Lys Glu Phe Phe Pro Ile Ala Asp Gly Asp Gln Gln Ser Pro Ile
            20                  25                  30

Glu Ile Lys Thr Gln Glu Val Lys Tyr Asp Ser Ser Leu Arg Pro Leu
        35                  40                  45

Ser Ile Lys Tyr Asp Pro Ser Ser Ala Lys Ile Ile Ser Asn Ser Gly
    50                  55                  60

His Ser Phe Asn Val Asp Phe Asp Asp Thr Glu Asp Lys Ser Val Leu
65                  70                  75                  80

Arg Gly Gly Pro Leu Ala Gly Ser Tyr Arg Leu Arg Gln Phe His Leu
                85                  90                  95

His Trp Gly Ser Ala Asp Asp His Gly Ser Glu His Ile Val Asp Gly
            100                 105                 110

Val Ser Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu Pro Asn Ser Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Ser Leu Leu Pro Pro Ser Trp Asp Tyr
            180                 185                 190
```

```
Trp Thr Tyr Pro Gly Ser Leu Thr Val Pro Pro Leu Leu Glu Ser Val
        195                 200                 205

Ile Trp Ile Val Leu Lys Gln Pro Ile Asn Val Ser Ser Gln Gln Leu
    210                 215                 220

Ala Lys Phe Arg Ser Leu Leu Cys Thr Ala Glu Gly Glu Ala Ala Ala
225                 230                 235                 240

Phe Leu Leu Ser Asn His Arg Pro Pro Gln Pro Leu Lys Gly Arg Lys
                245                 250                 255

Val Arg Ala Ser Phe Arg
            260


<210> SEQ ID NO 57
<211> LENGTH: 262
<212> TYPE: PRT
<213> ORGANISM: Oryctolagus cuniculus

<400> SEQUENCE: 57

Met Ser Arg Ile Ser Trp Gly Tyr Gly Glu His Asn Gly Pro Ile His
1               5                   10                  15

Trp Asn Gln Phe Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Pro Ser Ser Ala Lys Ile Ile Ser Asn Ser Gly
    50                  55                  60

His Ser Phe Asn Val Asp Phe Asp Asp Thr Glu Asp Lys Ser Val Leu
65                  70                  75                  80

Arg Gly Gly Pro Leu Thr Gly Asn Tyr Arg Leu Arg Gln Phe His Leu
                85                  90                  95

His Trp Gly Ser Ala Asp Asp His Gly Ser Glu His Val Val Asp Gly
            100                 105                 110

Val Arg Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu Tyr Asn Ser Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Ser Leu Leu Pro Ser Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Asn Ile Ser Ser Gln Gln Leu
    210                 215                 220

Ala Lys Phe Arg Ser Leu Leu Cys Ser Ala Glu Gly Glu Ser Ala Ala
225                 230                 235                 240

Phe Leu Leu Ser Asn His Arg Pro Pro Gln Pro Leu Lys Gly Arg Lys
                245                 250                 255

Val Arg Ala Ser Phe His
            260


<210> SEQ ID NO 58
<211> LENGTH: 262
<212> TYPE: PRT
```

<213> ORGANISM: Ailuropoda melanoleuca

<400> SEQUENCE: 58

```
Met Ser Arg Leu Ser Trp Gly Tyr Gly Glu His Asn Gly Pro Ile His
1               5                   10                  15

Trp Asn Lys Phe Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Ala Asn Ser Ala Lys Ile Ile Ser Asn Ser Gly
    50                  55                  60

His Ser Phe Ser Val Asp Phe Asp Asp Thr Glu Asp Lys Ser Val Leu
65                  70                  75                  80

Arg Gly Gly Pro Leu Thr Gly Ser Tyr Arg Leu Arg Gln Phe His Leu
                85                  90                  95

His Trp Gly Ser Ala Asp Asp His Gly Ser Glu His Val Val Asp Gly
            100                 105                 110

Val Arg Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu His Asn Ser Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Ser Leu Leu Pro Pro Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Asn Ile Ser Ser Glu Gln Leu
    210                 215                 220

Ala Thr Phe Arg Thr Leu Leu Cys Thr Ala Glu Gly Glu Ala Ala Ala
225                 230                 235                 240

Phe Leu Leu Ser Asn His Arg Pro Pro Gln Pro Leu Lys Gly Arg Lys
                245                 250                 255

Val Arg Ala Ser Phe His
            260
```

<210> SEQ ID NO 59
<211> LENGTH: 262
<212> TYPE: PRT
<213> ORGANISM: Sus scrofa

<400> SEQUENCE: 59

```
Met Ser Arg Phe Ser Trp Gly Tyr Gly Glu His Asn Gly Pro Val His
1               5                   10                  15

Trp Asn Glu Phe Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Pro Ser Ser Ala Lys Ile Ile Ser Asn Ser Gly
    50                  55                  60

His Ser Phe Ser Val Asp Phe Asp Asp Thr Glu Asp Lys Ser Val Leu
65                  70                  75                  80

Arg Gly Gly Pro Leu Thr Gly Ser Tyr Arg Leu Arg Gln Phe His Leu
```

```
                85                  90                  95

His Trp Gly Ser Ala Asp Asp His Gly Ser Glu His Val Val Asp Gly
            100                 105                 110

Val Lys Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu His Asn Ser Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Ser Leu Leu Pro Pro Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Ile Leu Lys Gln Pro Ile Asn Ile Ser Ser Gln Gln Leu
    210                 215                 220

Ala Thr Phe Arg Thr Leu Leu Cys Thr Lys Glu Gly Glu Glu Ala Ala
225                 230                 235                 240

Phe Leu Leu Ser Asn His Arg Pro Leu Gln Pro Leu Lys Gly Arg Lys
                245                 250                 255

Val Arg Ala Ser Phe His
            260


<210> SEQ ID NO 60
<211> LENGTH: 262
<212> TYPE: PRT
<213> ORGANISM: Callithrix jacchus

<400> SEQUENCE: 60

Met Ser Arg Leu Ser Trp Gly Tyr Gly Glu His Asn Gly Pro Ile His
1               5                   10                  15

Trp Asn Glu Phe Phe Pro Ile Ala Asp Gly Asp Arg Gln Ser Pro Ile
            20                  25                  30

Glu Ile Lys Ala Lys Glu Val Lys Tyr Asp Ser Ser Leu Arg Pro Leu
        35                  40                  45

Ser Ile Lys Tyr Asp Pro Ser Ser Ala Lys Ile Ile Ser Asn Ser Gly
    50                  55                  60

His Ser Phe Asn Val Asp Phe Asp Asp Thr Glu Asp Lys Ser Val Leu
65                  70                  75                  80

His Gly Gly Pro Leu Thr Gly Ser Tyr Arg Leu Arg Gln Phe His Leu
                85                  90                  95

His Trp Gly Ser Ala Asp Asp His Gly Ser Glu His Val Val Asp Gly
            100                 105                 110

Val Arg Tyr Ala Ala Glu Leu His Val Val His Trp Asn Ser Glu Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu Pro Asn Ser Gln Leu Gln Lys
145                 150                 155                 160

Ile Ile Asp Ile Leu Asp Ser Ile Lys Glu Lys Gly Lys Gln Ile Arg
                165                 170                 175

Phe Thr Asn Phe Asp Pro Leu Ser Leu Phe Pro Pro Ser Trp Asp Tyr
            180                 185                 190
```

```
Trp Thr Tyr Ser Gly Ser Leu Thr Val Pro Pro Leu Leu Glu Ser Val
        195                 200                 205

Thr Trp Ile Leu Leu Lys Gln Pro Ile Asn Ile Ser Ser Gln Gln Leu
    210                 215                 220

Ala Lys Phe Arg Ser Leu Leu Cys Thr Ala Glu Gly Glu Ala Ala Ala
225                 230                 235                 240

Phe Leu Leu Ser Asn Tyr Arg Pro Pro Gln Pro Leu Lys Gly Arg Lys
                245                 250                 255

Val Arg Ala Ser Phe Arg
            260


<210> SEQ ID NO 61
<211> LENGTH: 262
<212> TYPE: PRT
<213> ORGANISM: Rattus norvegicus

<400> SEQUENCE: 61

Met Ala Arg Leu Ser Trp Gly Tyr Asp Glu His Asn Gly Pro Ile His
1               5                   10                  15

Trp Asn Glu Leu Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Pro Ala Ser Ala Lys Ile Ile Ser Asn Ser Gly
    50                  55                  60

His Ser Phe Asn Val Asp Phe Asp Asp Thr Glu Asp Lys Ser Val Leu
65                  70                  75                  80

Arg Gly Gly Pro Leu Thr Gly Ser Tyr Arg Leu Arg Gln Phe His Leu
                85                  90                  95

His Trp Gly Ser Ala Asp Asp His Gly Ser Glu His Val Val Asp Gly
            100                 105                 110

Val Arg Tyr Ala Ala Glu Leu His Val Val His Trp Asn Ser Asp Lys
        115                 120                 125

Tyr Pro Ser Phe Val Glu Ala Ala His Glu Ser Asp Gly Leu Ala Val
    130                 135                 140

Leu Gly Val Phe Leu Gln Ile Gly Glu His Asn Pro Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Cys Leu Leu Pro Ser Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Ser Ile Ser Ser Gln Gln Leu
    210                 215                 220

Ala Arg Phe Arg Ser Leu Leu Cys Thr Ala Glu Gly Glu Ser Ala Ala
225                 230                 235                 240

Phe Leu Leu Ser Asn His Arg Pro Pro Gln Pro Leu Lys Gly Arg Arg
                245                 250                 255

Val Arg Ala Ser Phe Tyr
            260


<210> SEQ ID NO 62
<211> LENGTH: 262
<212> TYPE: PRT
<213> ORGANISM: Mus musculus
```

<400> SEQUENCE: 62

```
Met Ala Arg Leu Ser Trp Gly Tyr Gly Glu His Asn Gly Pro Ile His
1               5                   10                  15

Trp Asn Glu Leu Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Pro Ala Ser Ala Lys Ile Ile Ser Asn Ser Gly
    50                  55                  60

His Ser Phe Asn Val Asp Phe Asp Asp Thr Glu Asp Lys Ser Val Leu
65                  70                  75                  80

Arg Gly Gly Pro Leu Thr Gly Asn Tyr Arg Leu Arg Gln Phe His Leu
                85                  90                  95

His Trp Gly Ser Ala Asp Asp His Gly Ser Glu His Val Val Asp Gly
            100                 105                 110

Val Arg Tyr Ala Ala Glu Leu His Val Val His Trp Asn Ser Asp Lys
        115                 120                 125

Tyr Pro Ser Phe Val Glu Ala Ala His Glu Ser Asp Gly Leu Ala Val
    130                 135                 140

Leu Gly Val Phe Leu Gln Ile Gly Glu His Asn Pro Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Cys Leu Leu Pro Ser Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Ser Ile Ser Ser Gln Gln Leu
    210                 215                 220

Ala Arg Phe Arg Ser Leu Leu Cys Thr Ala Glu Gly Glu Ser Ala Ala
225                 230                 235                 240

Phe Leu Leu Ser Asn His Arg Pro Pro Gln Pro Leu Lys Gly Arg Arg
                245                 250                 255

Val Arg Ala Ser Phe Tyr
            260
```

<210> SEQ ID NO 63
<211> LENGTH: 262
<212> TYPE: PRT
<213> ORGANISM: Canis familiaris

<400> SEQUENCE: 63

```
Met Ser Arg Leu Ser Trp Gly Tyr Gly Glu His Asn Gly Pro Ile His
1               5                   10                  15

Trp Asn Lys Phe Phe Pro Ile Ala Asp Gly Asp Gln Gln Ser Pro Ile
            20                  25                  30

Glu Ile Lys Thr Lys Glu Val Lys Tyr Asp Ser Ser Leu Arg Pro Leu
        35                  40                  45

Ser Ile Lys Tyr Asp Ala Asn Ser Ala Lys Ile Ile Ser Asn Ser Gly
    50                  55                  60

His Ser Phe Ser Val Asp Phe Asp Asp Thr Glu Asp Lys Ser Val Leu
65                  70                  75                  80

Arg Gly Gly Pro Leu Thr Gly Ser Tyr Arg Leu Arg Gln Phe His Leu
                85                  90                  95
```

```
His Trp Gly Ser Ala Asp Asp His Gly Ser Glu His Val Val Asp Gly
            100                 105                 110

Val Arg Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Val Phe Leu Gln Ile Gly Glu His Asn Ser Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Leu Ser Leu Leu Pro Pro Ser Trp Asp Tyr
            180                 185                 190

Trp Thr Tyr Pro Gly Ser Leu Thr Val Pro Pro Leu Leu Glu Ser Val
        195                 200                 205

Thr Trp Ile Val Leu Lys Gln Pro Ile Asn Ile Ser Ser Gln Gln Leu
    210                 215                 220

Ala Thr Phe Arg Thr Leu Leu Cys Thr Ala Glu Gly Glu Ala Ala Ala
225                 230                 235                 240

Phe Leu Leu Ser Asn His Arg Pro Pro Gln Pro Leu Lys Gly Arg Lys
                245                 250                 255

Val Arg Ala Ser Phe His
            260


<210> SEQ ID NO 64
<211> LENGTH: 252
<212> TYPE: PRT
<213> ORGANISM: Equus caballus

<400> SEQUENCE: 64

Met Ser Gly Pro Val His Trp Asn Glu Phe Phe Pro Ile Ala Asp Gly
1               5                   10                  15

Asp Gln Gln Ser Pro Ile Glu Ile Lys Thr Lys Glu Val Lys Tyr Asp
            20                  25                  30

Ser Ser Leu Arg Pro Leu Thr Ile Lys Tyr Asp Pro Ser Ser Ala Lys
        35                  40                  45

Ile Ile Ser Asn Ser Gly His Ser Phe Ser Val Gly Phe Asp Asp Thr
    50                  55                  60

Glu Asn Lys Ser Val Leu Arg Gly Gly Pro Leu Thr Gly Ser Tyr Arg
65                  70                  75                  80

Leu Arg Gln Phe His Leu His Trp Gly Ser Ala Asp Asp His Gly Ser
                85                  90                  95

Glu His Val Val Asp Gly Val Arg Tyr Ala Ala Glu Leu His Ile Val
            100                 105                 110

His Trp Asn Ser Asp Lys Tyr Pro Ser Phe Val Glu Ala Ala His Glu
        115                 120                 125

Pro Asp Gly Leu Ala Val Leu Gly Val Phe Leu Gln Val Gly Glu His
    130                 135                 140

Asn Ser Gln Leu Gln Lys Ile Thr Asp Thr Leu Asp Ser Ile Lys Glu
145                 150                 155                 160

Lys Gly Lys Gln Thr Leu Phe Thr Asn Phe Asp Pro Leu Ser Leu Leu
                165                 170                 175

Pro Pro Ser Trp Asp Tyr Trp Thr Tyr Pro Gly Ser Leu Thr Val Pro
            180                 185                 190

Pro Leu Leu Glu Ser Val Thr Trp Ile Ile Leu Lys Gln Pro Ile Asn
```

```
        195                 200                 205

Ile Ser Ser Gln Gln Leu Val Lys Phe Arg Thr Leu Leu Cys Thr Ala
    210                 215                 220

Glu Gly Glu Thr Ala Ala Phe Leu Leu Ser Asn His Arg Pro Pro Gln
225                 230                 235                 240

Pro Leu Lys Gly Arg Lys Val Arg Ala Ser Phe Arg
                245                 250


<210> SEQ ID NO 65
<211> LENGTH: 262
<212> TYPE: PRT
<213> ORGANISM: Bos taurus

<400> SEQUENCE: 65

Met Ser Gly Phe Ser Trp Gly Tyr Gly Glu Arg Asp Gly Pro Val His
1               5                   10                  15

Trp Asn Glu Phe Phe Pro Ile Ala Asp Gly Asp Gln Gln Ser Pro Ile
            20                  25                  30

Glu Ile Lys Thr Lys Glu Val Arg Tyr Asp Ser Ser Leu Arg Pro Leu
        35                  40                  45

Gly Ile Lys Tyr Asp Ala Ser Ser Ala Lys Ile Ile Ser Asn Ser Gly
    50                  55                  60

His Ser Phe Asn Val Asp Phe Asp Asp Thr Asp Asp Lys Ser Val Leu
65                  70                  75                  80

Arg Gly Gly Pro Leu Thr Gly Ser Tyr Arg Leu Arg Gln Phe His Leu
                85                  90                  95

His Trp Gly Ser Thr Asp Asp His Gly Ser Glu His Val Val Asp Gly
            100                 105                 110

Val Arg Tyr Ala Ala Glu Leu His Val Val His Trp Asn Ser Asp Lys
        115                 120                 125

Tyr Pro Ser Phe Val Glu Ala Ala His Glu Pro Asp Gly Leu Ala Val
    130                 135                 140

Leu Gly Ile Phe Leu Gln Ile Gly Glu His Asn Pro Gln Leu Gln Lys
145                 150                 155                 160

Ile Thr Asp Ile Leu Asp Ser Ile Lys Glu Lys Gly Lys Gln Thr Arg
                165                 170                 175

Phe Thr Asn Phe Asp Pro Val Cys Leu Leu Pro Pro Cys Arg Asp Tyr
            180                 185                 190

Trp Thr Tyr Pro Gly Ser Leu Thr Val Pro Pro Leu Leu Glu Ser Val
        195                 200                 205

Thr Trp Ile Ile Leu Lys Gln Pro Ile Asn Ile Ser Ser Gln Gln Leu
    210                 215                 220

Ala Ala Phe Arg Thr Leu Leu Cys Ser Arg Glu Gly Glu Thr Ala Ala
225                 230                 235                 240

Phe Leu Leu Ser Asn His Arg Pro Pro Gln Pro Leu Lys Gly Arg Lys
                245                 250                 255

Val Arg Ala Ser Phe Arg
            260


<210> SEQ ID NO 66
<211> LENGTH: 419
<212> TYPE: PRT
<213> ORGANISM: Monodelphis domestica

<400> SEQUENCE: 66

Met Ala Ser Val Phe Ala Gly Trp Gly Pro Gly Arg Thr His Leu Phe
```

-continued

```
1               5                   10                  15

Phe Arg Phe Phe Pro Gly Pro Phe Ser Ala Leu Pro Ala Gln Thr Ser
            20                  25                  30

Arg Gly Val Leu Val Phe Thr Ala Pro Gly Pro Ser Pro Arg Arg Val
        35                  40                  45

Pro Asp Pro Val His Pro Gly Arg Asp Val Val Arg Pro Ser Gly Ser
    50                  55                  60

Leu Phe Ser Cys Arg Leu Pro Pro Pro Arg Pro Ser Ala Pro Ala Arg
65                  70                  75                  80

Glu Arg Arg Pro Leu Ala Glu Lys Val Gly Arg Ser Ser Ala Pro His
                85                  90                  95

Leu Pro Leu Asp Asn Phe Glu Phe Ile Ala Lys Arg Leu Arg Arg Arg
            100                 105                 110

Val Leu Ser Gly Leu Ala Ala Glu Ser Ala Gly Ala Leu Ala Pro Ser
        115                 120                 125

Leu Pro Arg Ser Leu His Ser Ser Leu Gly Leu Arg Ser Ser Leu Lys
    130                 135                 140

Ser Gln Arg Val Phe Pro Ser Pro His Ser Glu Glu Thr Met Ser Arg
145                 150                 155                 160

Leu Ser Trp Gly Tyr Cys Glu His Asn Gly Pro Val His Trp Ser Glu
                165                 170                 175

Leu Phe Pro Ile Ala Asp Gly Asp Tyr Gln Ser Pro Ile Glu Ile Asn
            180                 185                 190

Thr Lys Glu Val Lys Tyr Asp Ser Ser Leu Arg Pro Leu Ser Ile Lys
        195                 200                 205

Tyr Asp Pro Ala Ser Ala Lys Ile Ile Ser Asn Ser Gly His Ser Phe
    210                 215                 220

Ser Val Asp Phe Asp Asp Ser Glu Asp Lys Ser Val Leu Arg Gly Gly
225                 230                 235                 240

Pro Leu Ile Gly Thr Tyr Arg Leu Arg Gln Phe His Leu His Trp Gly
                245                 250                 255

Ser Thr Asp Asp Gln Gly Ser Glu His Thr Val Asp Gly Met Lys Tyr
            260                 265                 270

Ala Ala Glu Leu His Val Val His Trp Asn Ser Asp Lys Tyr Pro Ser
        275                 280                 285

Phe Val Glu Ala Ala His Glu Pro Asp Gly Leu Ala Val Leu Gly Ile
    290                 295                 300

Phe Leu Gln Thr Gly Glu His Asn Leu Gln Met Gln Lys Ile Thr Asp
305                 310                 315                 320

Ile Leu Asp Ser Ile Lys Glu Lys Gly Lys Gln Ile Arg Phe Thr Asn
                325                 330                 335

Phe Asp Pro Ala Thr Leu Leu Pro Gln Ser Trp Asp Tyr Trp Thr Tyr
            340                 345                 350

Pro Gly Ser Leu Thr Val Pro Pro Leu Leu Glu Ser Val Thr Trp Ile
        355                 360                 365

Val Leu Lys Gln Pro Ile Thr Ile Ser Ser Gln Gln Leu Ala Lys Phe
    370                 375                 380

Arg Ser Leu Leu Tyr Thr Gly Glu Gly Glu Ala Ala Ala Phe Leu Leu
385                 390                 395                 400

Ser Asn Tyr Arg Pro Pro Gln Pro Leu Lys Gly Arg Lys Val Arg Ala
                405                 410                 415

Ser Phe Arg
```

<210> SEQ ID NO 67
<211> LENGTH: 428
<212> TYPE: PRT
<213> ORGANISM: Ornithorhynchus anatinus

<400> SEQUENCE: 67

```
Met Lys Lys Gly Val Gly Ser Phe Tyr Glu Leu Ala Val Asn Arg Trp
1               5                   10                  15

Ser Val Val Asn Arg Val Gln Ile Met Ile Val Glu Ser Ile Thr Glu
            20                  25                  30

Pro Leu Leu Cys Gly Ser Ala Leu Ala Val Ala Pro Ala Leu Ala Leu
        35                  40                  45

Ala Val Val Gln Ala Leu Ala Leu Thr Val Val Gln Ala Leu Ala Leu
    50                  55                  60

Ala Val Ser Pro Ala Leu Ala Leu Ser Val Ala Pro Ala Leu Ala Leu
65                  70                  75                  80

Ala Val Val Gln Ala Leu Ala Leu Ala Val Val Gln Ala Leu Ala Leu
                85                  90                  95

Ala Val Ala Gln Ala Leu Ala Leu Ala Val Ala Gln Ala Leu Ala Leu
            100                 105                 110

Ala Val Ala Gln Ala Leu Ala Leu Ala Leu Pro Gln Ala Leu Ala Leu
        115                 120                 125

Thr Leu Pro Gln Ala Leu Ala Leu Thr Leu Ser Pro Thr Leu Ala Leu
    130                 135                 140

Ser Val Ala Pro Ala Leu Ala Leu Ala Val Ala Pro Ala Leu Ala Leu
145                 150                 155                 160

Ala Asp Ser Pro Ala Leu Ala Leu Ala Leu Ala Arg Pro His Pro Ser
                165                 170                 175

Ser Gly Pro Ile His Trp Asn Glu Leu Phe Pro Ile Ala Asp Gly Asp
            180                 185                 190

Arg Gln Ser Pro Ile Glu Ile Lys Thr Lys Glu Val Lys Tyr Asp Ser
        195                 200                 205

Ser Leu Arg Pro Leu Ser Ile Lys Tyr Asp Pro Thr Ser Ala Lys Ile
    210                 215                 220

Ile Ser Asn Ser Gly His Ser Phe Ser Val Asp Phe Asp Asp Thr Glu
225                 230                 235                 240

Asp Lys Ser Val Leu Arg Gly Gly Pro Leu Ser Gly Thr Tyr Arg Leu
                245                 250                 255

Arg Gln Phe His Phe His Trp Gly Ser Ala Asp Asp His Gly Ser Glu
            260                 265                 270

His Thr Val Asp Gly Met Glu Tyr Ser Ala Glu Leu His Val Val His
        275                 280                 285

Trp Asn Ser Asp Lys Tyr Ser Ser Phe Val Glu Ala Ala His Glu Pro
    290                 295                 300

Asp Gly Leu Ala Val Leu Gly Ile Phe Leu Lys Arg Gly Glu His Asn
305                 310                 315                 320

Leu Gln Leu Gln Lys Ile Thr Asp Ile Leu Asp Ala Ile Lys Glu Lys
                325                 330                 335

Gly Lys Gln Met Arg Phe Thr Asn Phe Asp Pro Leu Ser Leu Leu Pro
            340                 345                 350

Leu Thr Arg Asp Tyr Trp Thr Tyr Pro Gly Ser Leu Thr Val Pro Pro
        355                 360                 365

Leu Leu Glu Ser Val Ile Trp Ile Ile Phe Lys Gln Pro Ile Ser Ile
    370                 375                 380
```

```
Ser Ser Gln Gln Leu Ala Lys Phe Arg Asn Leu Leu Tyr Thr Ala Glu
385                 390                 395                 400

Gly Glu Ala Ala Asp Phe Met Leu Ser Asn His Arg Pro Pro Gln Pro
                405                 410                 415

Leu Lys Gly Arg Lys Val Arg Ala Ser Phe Arg Ser
            420                 425


<210> SEQ ID NO 68
<211> LENGTH: 1082
<212> TYPE: PRT
<213> ORGANISM: Chlamydomonas reinhardtii

<400> SEQUENCE: 68

Met Leu Pro Gly Leu Gly Val Ile Leu Leu Val Leu Pro Met Gln Tyr
1               5                   10                  15

Tyr Phe Gly Tyr Lys Ile Val Gln Ile Lys Leu Gln Asn Ala Lys His
            20                  25                  30

Val Ala Leu Arg Ser Ala Ile Met Gln Glu Val Leu Pro Ala Ile Lys
        35                  40                  45

Leu Val Lys Tyr Tyr Ala Trp Glu Gln Phe Phe Glu Asn Gln Ile Ser
    50                  55                  60

Lys Val Arg Arg Glu Glu Ile Arg Leu Asn Phe Trp Asn Cys Val Met
65                  70                  75                  80

Lys Val Ile Asn Val Ala Cys Val Phe Cys Val Pro Pro Met Thr Ala
                85                  90                  95

Phe Val Ile Phe Thr Thr Tyr Glu Phe Gln Arg Ala Arg Leu Val Ser
            100                 105                 110

Ser Val Ala Phe Thr Thr Leu Ser Leu Phe Asn Ile Leu Arg Phe Pro
        115                 120                 125

Leu Val Val Leu Pro Lys Ala Leu Arg Ala Val Ser Glu Ala Asn Ala
    130                 135                 140

Ser Leu Gln Arg Leu Glu Ala Tyr Leu Leu Glu Glu Val Pro Ser Gly
145                 150                 155                 160

Thr Ala Ala Val Lys Thr Pro Lys Asn Ala Pro Pro Gly Ala Val Ile
                165                 170                 175

Glu Asn Gly Val Phe His His Pro Ser Asn Pro Asn Trp His Leu His
            180                 185                 190

Val Pro Lys Phe Glu Val Lys Pro Gly Gln Val Val Ala Val Val Gly
        195                 200                 205

Arg Ile Ala Ala Gly Lys Ser Ser Leu Val Gln Ala Ile Leu Gly Asn
    210                 215                 220

Met Val Lys Glu His Gly Ser Phe Asn Val Gly Gly Arg Ile Ser Tyr
225                 230                 235                 240

Val Pro Gln Asn Pro Trp Leu Gln Asn Leu Ser Leu Arg Asp Asn Val
                245                 250                 255

Leu Phe Gly Glu Gln Phe Asp Glu Asn Lys Tyr Thr Asp Val Ile Glu
            260                 265                 270

Ser Cys Ala Leu Thr Leu Asp Leu Gln Ile Leu Ser Asn Gly Asp Gln
        275                 280                 285

Ser Lys Ala Gly Ile Arg Gly Val Asn Phe Ser Gly Gly Gln Arg Gln
    290                 295                 300

Arg Val Asn Leu Ala Arg Cys Ala Tyr Ala Asp Ala Asp Leu Val Leu
305                 310                 315                 320

Leu Asp Asn Ala Leu Ser Ala Val Asp His His Thr Ala His His Ile
```

```
                325                 330                 335

Phe Asp Lys Cys Ile Lys Gly Leu Phe Ser Asp Lys Ala Val Val Leu
            340                 345                 350

Val Thr His Gln Ile Glu Phe Met Pro Arg Cys Asp Asn Val Ala Ile
        355                 360                 365

Met Asp Glu Gly Arg Cys Leu Tyr Phe Gly Lys Trp Asn Glu Glu Ala
    370                 375                 380

Gln His Leu Leu Gly Lys Leu Leu Pro Ile Thr His Leu Leu His Ala
385                 390                 395                 400

Ala Gly Ser Gln Glu Ala Pro Pro Ala Pro Lys Lys Lys Ala Glu Asp
                405                 410                 415

Lys Ala Gly Pro Gln Lys Ser Gln Ser Leu Gln Leu Thr Leu Ala Pro
            420                 425                 430

Thr Ser Ile Gly Lys Pro Thr Glu Lys Pro Lys Asp Val Gln Lys Leu
        435                 440                 445

Thr Ala Tyr Gln Ala Ala Leu Ile Tyr Thr Trp Tyr Gly Asn Leu Phe
    450                 455                 460

Leu Val Gly Val Cys Phe Phe Phe Phe Leu Ala Ala Gln Cys Ser Arg
465                 470                 475                 480

Gln Ile Ser Asp Phe Trp Val Arg Trp Trp Val Asn Asp Glu Tyr Lys
                485                 490                 495

Lys Phe Pro Val Lys Gly Glu Gln Asp Ser Ala Ala Thr Thr Phe Tyr
            500                 505                 510

Cys Leu Ile Tyr Leu Leu Leu Val Gly Leu Phe Tyr Ile Phe Met Ile
        515                 520                 525

Phe Arg Gly Ala Thr Phe Leu Trp Trp Val Leu Lys Ser Ser Glu Thr
    530                 535                 540

Ile Arg Arg Lys Ala Leu His Asn Val Leu Asn Ala Pro Met Gly Phe
545                 550                 555                 560

Phe Leu Val Thr Pro Val Gly Asp Leu Leu Leu Asn Phe Thr Lys Asp
                565                 570                 575

Gln Asp Ile Met Asp Glu Asn Leu Pro Asp Ala Val His Phe Met Gly
            580                 585                 590

Ile Tyr Gly Leu Ile Leu Leu Ala Thr Thr Ile Thr Val Ser Val Thr
        595                 600                 605

Ile Asn Phe Phe Ala Ala Phe Thr Gly Ala Leu Ile Ile Met Thr Leu
    610                 615                 620

Ile Met Leu Ser Ile Tyr Leu Pro Ala Ala Thr Ala Leu Lys Lys Ala
625                 630                 635                 640

Arg Ala Val Ser Gly Gly Met Leu Val Gly Leu Val Ala Glu Val Leu
                645                 650                 655

Glu Gly Leu Gly Val Val Gln Ala Phe Asn Lys Gln Glu Tyr Phe Ile
            660                 665                 670

Glu Glu Ala Ala Arg Arg Thr Asn Ile Thr Asn Ser Ala Val Phe Asn
        675                 680                 685

Ala Glu Ala Leu Asn Leu Trp Leu Ala Phe Trp Cys Asp Phe Ile Gly
    690                 695                 700

Ala Cys Leu Val Gly Val Val Ser Ala Phe Ala Val Gly Met Ala Lys
705                 710                 715                 720

Asp Leu Gly Gly Ala Thr Val Gly Leu Ala Phe Ser Asn Ile Ile Gln
                725                 730                 735

Met Leu Val Phe Tyr Thr Trp Val Val Arg Phe Ile Ser Glu Ser Ile
            740                 745                 750
```

```
Ser Leu Phe Asn Ser Val Glu Gly Met Ala Tyr Leu Ala Asp Tyr Val
        755                 760                 765

Pro His Asp Gly Val Phe Tyr Asp Gln Arg Gln Lys Asp Gly Val Ala
    770                 775                 780

Lys Gln Ile Val Leu Pro Asp Gly Asn Ile Val Pro Ala Ala Ser Lys
785                 790                 795                 800

Val Gln Val Val Val Asp Asp Ala Ala Leu Ala Arg Trp Pro Ala Thr
                805                 810                 815

Gly Asn Ile Arg Phe Glu Asp Val Trp Met Gln Tyr Arg Leu Asp Ala
            820                 825                 830

Pro Trp Ala Leu Lys Gly Val Thr Phe Lys Ile Asn Asp Gly Glu Lys
        835                 840                 845

Val Gly Ala Val Gly Arg Thr Gly Ser Gly Lys Ser Thr Thr Leu Leu
    850                 855                 860

Ala Leu Tyr Arg Met Phe Glu Leu Gly Lys Gly Arg Ile Leu Val Asp
865                 870                 875                 880

Gly Val Asp Ile Ala Thr Leu Ser Leu Lys Arg Leu Arg Thr Gly Leu
                885                 890                 895

Ser Ile Ile Pro Gln Glu Pro Val Met Phe Thr Gly Thr Val Arg Ser
            900                 905                 910

Asn Leu Asp Pro Phe Gly Glu Phe Lys Asp Asp Ala Ile Leu Trp Glu
        915                 920                 925

Val Leu Lys Lys Val Gly Leu Glu Asp Gln Ala Gln His Ala Gly Gly
    930                 935                 940

Leu Asp Gly Gln Val Asp Gly Thr Gly Gly Lys Ala Trp Ser Leu Gly
945                 950                 955                 960

Gln Met Gln Leu Val Cys Leu Ala Arg Ala Ala Leu Arg Ala Val Pro
                965                 970                 975

Ile Leu Cys Leu Asp Glu Ala Thr Ala Ala Met Asp Pro His Thr Glu
            980                 985                 990

Ala Ile Val Gln Gln Thr Ile Lys  Lys Val Phe Asp Asp  Arg Thr Thr
        995                 1000                1005

Ile Thr  Ile Ala His Arg Leu  Asp Thr Ile Ile Glu  Ser Asp Lys
    1010                1015                1020

Ile Ile  Val Met Glu Gln Gly  Ser Leu Met Glu Tyr  Glu Ser Pro
    1025                1030                1035

Ser Lys  Leu Leu Ala Asn Arg  Asp Ser Met Phe Ser  Lys Leu Val
    1040                1045                1050

Asp Lys  Thr Gly Pro Ala Ala  Ala Ala Ala Leu Arg  Lys Met Ala
    1055                1060                1065

Glu Asp  Phe Trp Ser Thr Arg  Ser Ala Gln Gly Arg  Asn Gln
    1070                1075                1080
```

<210> SEQ ID NO 69
<211> LENGTH: 1321
<212> TYPE: PRT
<213> ORGANISM: Volvox carteri

<400> SEQUENCE: 69

```
Met Gly Thr Ile Ser His Pro Ala Arg Gly Asn Asp Pro Thr Ala Gly
1               5                   10                  15

Phe Phe Asn Lys Phe Ala Phe Gly Trp Met Phe Lys His Val Ser Glu
            20                  25                  30

Ala Arg Lys Asn Gly Asp Ile Asp Leu Asp Lys Met Gly Met Pro Pro
```

```
        35                  40                  45

Glu Asn His Ala His Glu Ala Tyr Asp Met Phe Ala Ser Asn Trp Ala
    50                  55                  60

Ala Glu Met Lys Leu Lys Asp Ser Gly Ala Lys Pro Ser Leu Val Arg
65                  70                  75                  80

Ala Leu Arg Lys Ser Phe Gly Leu Val Tyr Leu Leu Gly Gly Val Phe
                85                  90                  95

Lys Cys Phe Trp Ser Thr Phe Val Ile Thr Gly Ala Phe Tyr Phe Val
            100                 105                 110

Arg Ser Leu Leu Ala His Val Asn Gly Ile Lys Asp Gly Arg Leu Tyr
        115                 120                 125

Ser Lys Thr Val Ser Gly Trp Cys Leu Met Ala Gly Phe Thr Leu Asp
    130                 135                 140

Ala Trp Leu Leu Gly Leu Ser Leu Gln Arg Met Gly Tyr Ile Cys Met
145                 150                 155                 160

Ser Val Gly Ile Arg Ala Arg Ala Ala Leu Val Gln Ala Val Thr His
                165                 170                 175

Lys Ala Phe Arg Leu Ser Ser Val Arg Ala Asp Gln Ser Ala Ala Ile
            180                 185                 190

Val Asn Phe Val Ser Ser Asp Ile Gln Lys Ile Tyr Asp Gly Ala Leu
        195                 200                 205

Glu Phe His Tyr Leu Trp Thr Ala Pro Phe Glu Ala Ala Ala Ile Leu
    210                 215                 220

Ala Leu Leu Gly Tyr Leu Thr Asn Asp Ser Met Leu Pro Gly Leu Gly
225                 230                 235                 240

Val Ile Leu Leu Val Leu Pro Leu Gln Tyr Phe Phe Gly Tyr Lys Ile
                245                 250                 255

Ile Gln Ile Lys Leu Gln Asn Ala Lys His Val Ala Leu Arg Ser Ser
            260                 265                 270

Ile Leu Gln Glu Val Leu Pro Ala Ile Lys Leu Val Lys Tyr Tyr Ala
        275                 280                 285

Trp Glu Gln Phe Phe Glu Asp Glu Ile Ser Lys Ile Arg Arg Glu Glu
    290                 295                 300

Met Arg Leu Ser Phe Trp Asn Ala Met Met Lys Val Ile Asn Val Ala
305                 310                 315                 320

Cys Val Phe Cys Val Pro Pro Met Thr Ala Phe Val Ile Phe Thr Thr
                325                 330                 335

Tyr Glu Phe Gln Lys Ala Arg Leu Val Ser Gly Val Ala Phe Thr Thr
            340                 345                 350

Leu Ser Leu Phe Asn Ile Leu Arg Phe Pro Leu Val Val Leu Pro Lys
        355                 360                 365

Ala Leu Arg Ala Val Ser Glu Ala His Ala Ser Leu Gln Arg Leu Glu
    370                 375                 380

Ser Tyr Leu Leu Glu Asp Val Pro Gln Gly Thr Ala Ser Gly Gly Lys
385                 390                 395                 400

Ser Ser Lys Ser Ser Ala Pro Gly Val His Ile Asp Asn Ala Val Tyr
                405                 410                 415

His His Pro Ser Asn Pro Asn Trp His Leu His Val Pro Arg Phe Asp
            420                 425                 430

Val Arg Pro Gly Gln Val Val Ala Val Val Gly Arg Ile Gly Ala Gly
        435                 440                 445

Lys Ser Ser Leu Val Gln Ala Ile Leu Gly Asn Met Val Lys Glu His
    450                 455                 460
```

```
Gly Ser Gln Gln Val Gly Gly Arg Ile Ser Tyr Val Pro Gln Asn Pro
465                 470                 475                 480

Trp Leu Gln Asn Leu Ser Ile Arg Asp Asn Val Thr Phe Gly Glu Gly
                485                 490                 495

Trp Asp Glu Asn Lys Tyr Glu Ala Val Ile Asp Ala Cys Ala Leu Thr
            500                 505                 510

Met Asp Leu Gln Ile Leu Pro Gln Gly Asp Gln Ser Lys Ala Gly Ile
        515                 520                 525

Arg Gly Val Asn Phe Ser Gly Gly Gln Arg Gln Arg Val Asn Leu Ala
    530                 535                 540

Arg Cys Ala Tyr Ala Asp Ala Asp Leu Val Leu Leu Asp Asn Ala Leu
545                 550                 555                 560

Ser Ala Val Asp His His Thr Ala His His Ile Phe Asp Lys Cys Ile
                565                 570                 575

Lys Gly Leu Phe Ser Asp Lys Ala Val Val Leu Ile Thr His Gln Ile
            580                 585                 590

Glu Phe Met Pro Arg Cys Asp Ala Val Ala Ile Met Asp Glu Gly Arg
        595                 600                 605

Cys Leu Tyr Phe Gly Lys Trp Asn Glu Glu Ser Gln His Leu Leu Gly
    610                 615                 620

Lys Leu Leu Pro Ile Thr His Leu Leu His Ala Ala Gly Ser Gln Glu
625                 630                 635                 640

Ala Pro Pro Ala Ala Pro Lys Lys Lys Asp Asp Lys Ala Thr Pro Gln
                645                 650                 655

Lys Ser Gln Ser Leu Gln Leu Thr Leu Ala Pro Thr Ser Ile Gly Lys
            660                 665                 670

Pro Thr Gln Lys Asp Thr Lys Ala Ala Pro Lys Leu Thr Ala Phe Lys
        675                 680                 685

Ala Ala Leu Ile Tyr Thr Tyr Tyr Gly Asn Ile Leu Leu Val Phe Val
    690                 695                 700

Cys Phe Ile Thr Phe Leu Ala Ala Gln Thr Cys Arg Gln Met Ser Asp
705                 710                 715                 720

Phe Trp Val Arg Trp Trp Val Asn Asp Glu Tyr Lys His Phe Pro Lys
                725                 730                 735

Arg Thr Gly Val Arg Glu Glu Ser Ala Thr Lys Phe Tyr Ala Leu Ile
            740                 745                 750

Tyr Leu Leu Leu Val Gly Leu Phe Tyr Phe Thr Met Val Ala Arg Gly
        755                 760                 765

Ser Thr Phe Leu Trp Trp Val Leu Arg Ser Ser Glu Asn Ile Arg Lys
    770                 775                 780

Lys Ala Leu Asn Asn Val Leu Asn Ala Pro Met Gly Phe Phe Leu Val
785                 790                 795                 800

Thr Pro Val Gly Asp Leu Leu Leu Asn Phe Thr Lys Asp Gln Asp Ile
                805                 810                 815

Met Asp Glu Asn Leu Pro Asp Ala Ile His Phe Met Gly Ile Tyr Gly
            820                 825                 830

Leu Ile Leu Leu Ala Thr Thr Ile Thr Val Ser Val Thr Ile Asn Phe
        835                 840                 845

Phe Gly Ala Phe Thr Gly Phe Leu Ile Ile Met Thr Leu Ile Met Leu
    850                 855                 860

Ala Ile Tyr Leu Pro Ala Ala Thr Ala Leu Lys Lys Ala Arg Ala Val
865                 870                 875                 880
```

```
Ser Gly Gly Gln Leu Val Gly Leu Val Ala Glu Val Leu Glu Gly Leu
                885                 890                 895

Asn Val Val Gln Ala Phe Ser Lys Gln Glu Tyr Phe Ile Glu Glu Ala
            900                 905                 910

Ala Arg Arg Thr Asp Val Thr Asn Ala Ala Val Phe Asn Ala Glu Ser
        915                 920                 925

Leu Asn Leu Trp Leu Ala Phe Trp Cys Asp Leu Ile Gly Ala Ser Leu
    930                 935                 940

Val Gly Val Val Ser Ala Phe Ala Val Gly Leu Lys Asp Gln Leu Gly
945                 950                 955                 960

Ala Ala Thr Val Gly Leu Ala Phe Ser Asn Ile Ile Gln Met Leu Val
                965                 970                 975

Phe Tyr Thr Trp Val Val Arg Phe Ile Ala Glu Ser Ile Ser Leu Phe
            980                 985                 990

Asn Ser Val Glu Ala Met Ala Trp  Leu Ala Asp Tyr Val  Pro Lys Asp
        995                 1000                1005

Gly Ile  Phe Tyr Asp Gln Lys  Gln Leu Asp Gly Val  Ala Lys Ser
    1010                1015                1020

Ile Thr  Leu Pro Asp Gly Gln  Ile Val Pro Ala Thr  Ser Lys Val
    1025                1030                1035

Gln Val  Val Val Asp Asp Ala  Ala Leu Ala Arg Trp  Pro Ala Thr
    1040                1045                1050

Gly Asn  Ile Arg Phe Glu Asp  Val Trp Met Gln Tyr  Arg Leu Asp
    1055                1060                1065

Ala Ala  Trp Ala Leu Lys Gly  Val Thr Phe Lys Ile  Asn Asp Gly
    1070                1075                1080

Glu Lys  Val Gly Ala Val Gly  Arg Thr Gly Ser Gly  Lys Ser Thr
    1085                1090                1095

Thr Leu  Leu Ala Leu Tyr Arg  Met Phe Glu Leu Gly  Lys Gly Arg
    1100                1105                1110

Ile Leu  Ile Asp Gly Val Asp  Ile Ala Thr Leu Ser  Leu Lys Arg
    1115                1120                1125

Leu Arg  Thr Gly Leu Ser Ile  Ile Pro Gln Glu Pro  Val Met Phe
    1130                1135                1140

Thr Gly  Thr Val Arg Ser Asn  Leu Asp Pro Phe Gly  Glu Phe Lys
    1145                1150                1155

Asp Asp  Ser Val Leu Trp Glu  Val Leu Gln Lys Val  Gly Leu Glu
    1160                1165                1170

Ala Gln  Ala Gln His Ala Gly  Gly Leu Asp Gly Arg  Val Asp Gly
    1175                1180                1185

Thr Gly  Gly Lys Ala Trp Ser  Leu Gly Gln Met Gln  Leu Val Cys
    1190                1195                1200

Leu Ala  Arg Ala Ala Leu Arg  Ala Val Pro Ile Leu  Cys Leu Asp
    1205                1210                1215

Glu Ala  Thr Ala Ala Met Asp  Pro His Thr Glu Gln  Val Val Gln
    1220                1225                1230

Glu Thr  Ile Lys Lys Val Phe  Asp Asp Arg Thr Thr  Ile Thr Ile
    1235                1240                1245

Ala His  Arg Leu Asp Thr Ile  Ile Glu Ser Asp Lys  Val Leu Val
    1250                1255                1260

Met Glu  Ala Gly Glu Leu Lys  Glu Phe Ala Pro Pro  Ala Gln Leu
    1265                1270                1275

Leu Ala  Asn Arg Glu Thr Met  Phe Ser Lys Leu Val  Asp Lys Thr
```

```
    1280                1285                1290

Gly Pro  Ala Ala Ala Ala Ala  Leu Arg Lys Met Ala  Asp Glu His
    1295                1300                1305

Phe Ser  Lys Ser Gln Ala Arg  Ala Ala Ala Gln Arg  His
    1310                1315                1320


<210> SEQ ID NO 70
<211> LENGTH: 2297
<212> TYPE: PRT
<213> ORGANISM: Chlorella variabilis

<400> SEQUENCE: 70

Met Val Pro Leu Leu Ala Gln Arg Gly Arg Ile Arg Ser Gln Ala Pro
1               5                   10                  15

Arg Thr Trp His Pro Asp Pro Gln Pro Leu His Ala Glu Arg Ser Arg
            20                  25                  30

Gln Cys Pro Gly Arg Gly Val Arg Ala Ala Ala Lys Arg Gly Gly Gly
        35                  40                  45

Ser Gly Gly Ala Thr His Lys Ser Lys Lys Ser Lys Glu Leu Asp Glu
    50                  55                  60

Val Ala Ala Phe Glu Gln Leu Met Cys Asp Trp Asp Asp Ala Phe Ala
65                  70                  75                  80

Ala Asp Cys Tyr Asp Asn Glu Arg Ala Ala Arg Met Ala Arg Leu Ala
                85                  90                  95

Glu Glu Gly Tyr Gln His His Gly Arg Gly Phe Val Phe Val Arg Ser
            100                 105                 110

Arg Leu Asp Lys Arg Ser Arg Lys Ala Arg Asn Asp Ser Gly Ala Ser
        115                 120                 125

Lys Gly Phe Gly Ala Ala Ala Lys Ala Leu Ser Val Glu Gln Gly Thr
    130                 135                 140

Pro Leu Glu Asn Asn Pro Gln Leu His Leu Leu Ser Trp Thr Ala Cys
145                 150                 155                 160

Tyr Ile Ala Ser Ser Gln Leu Asp Ser Leu Gly Gly Leu Phe Ser Thr
                165                 170                 175

Gln Glu Gly Val Leu Leu Pro Asp Ser Gly Ser Leu Leu Thr Asp Gly
            180                 185                 190

Gly Ser Gly Ala Ser Gly Ser Asn Ala Ala Asp Ala Val Gly Glu Leu
        195                 200                 205

Gln Arg Val Leu Arg Gly Gln Asp Leu Ser Gln Leu Arg Gly Tyr Val
    210                 215                 220

Gly Ala Pro Pro Gln Ala Arg Pro Ala Ser Gly Ser Asp Asp Asp Gly
225                 230                 235                 240

Ser Ser Thr Thr Gly Ser Asn Asn Gly Ala Ala Gly Glu Gly Ser Glu
                245                 250                 255

Val Glu Glu Gly Thr Ala Met Gly Gly Ile Arg Arg Tyr Glu Pro Glu
            260                 265                 270

Ser Gly Glu Leu Val Val Leu Leu Ser Cys Lys Ile Gly Gly Lys Pro
        275                 280                 285

Ala Val Gly Ala Glu Leu Leu Ala Val Ala Gln Ala Glu Asp Gly Lys
    290                 295                 300

His Ala Pro Gly Ala Ser Pro Asp Thr Arg Leu Cys Lys Glu Pro Ser
305                 310                 315                 320

Gln Ser Ala Phe Asp Leu Trp Ser Phe Gly Trp Met Asn Lys Ile Val
                325                 330                 335
```

```
Pro Ala Ala Arg Arg Gly Glu Val Glu Val Ala Asp Leu Pro Leu Pro
            340                 345                 350

Glu Ala Gln Gln Ala Glu Pro Cys Tyr Glu Glu Leu Asn Thr Asn Trp
        355                 360                 365

Glu Ala Ala Val Gln Glu Ala Lys Lys Ala Gly Lys Glu Pro Lys Leu
    370                 375                 380

Met Lys Val Leu Trp Lys Thr Tyr Gly Lys Asp Ile Val Leu Ala Gly
385                 390                 395                 400

Ile Phe Lys Leu Met Trp Ser Val Phe Val Ile Leu Gly Ala Tyr Tyr
                405                 410                 415

Phe Thr Arg Ser Ile Leu Met Cys Ile Arg Thr Leu Glu Gly Lys Asp
            420                 425                 430

Asp Ser Ile Tyr Asp Thr Glu Trp Lys Gly Trp Val Leu Thr Gly Phe
        435                 440                 445

Phe Phe Leu Asp Ala Trp Leu Leu Gly Met Met Leu Gln Arg Met Ala
    450                 455                 460

Phe Asn Cys Leu Lys Val Gly Ile Lys Ala Arg Ala Ala Leu Thr Thr
465                 470                 475                 480

Met Ile Ala Arg Lys Cys Tyr Asn Met Ala His Leu Thr Lys Asp Thr
                485                 490                 495

Ala Ala Glu Ala Val Gly Phe Val Ala Ser Asp Ile Asn Lys Val Phe
            500                 505                 510

Glu Gly Ile Gln Glu Val His Tyr Leu Trp Gly Ala Pro Val Glu Ala
        515                 520                 525

Gly Ala Ile Leu Ala Leu Leu Gly Thr Leu Val Gly Val Tyr Cys Ile
    530                 535                 540

Gly Gly Val Ile Ile Val Cys Met Val Val Pro Leu Gln Tyr Tyr Phe
545                 550                 555                 560

Gly Tyr Lys Ile Ile Lys Asn Lys Ile Lys Asn Ala Pro Asn Val Thr
                565                 570                 575

Glu Arg Trp Ser Ile Ile Gln Glu Ile Leu Pro Ala Met Lys Leu Val
            580                 585                 590

Lys Tyr Tyr Ala Trp Glu Arg Phe Phe Glu Lys His Val Ala Asp Met
        595                 600                 605

Arg Thr Arg Glu Arg His Tyr Met Phe Trp Asn Ala Val Val Lys Thr
    610                 615                 620

Val Asn Val Thr Met Val Phe Gly Val Pro Pro Met Val Thr Phe Ala
625                 630                 635                 640

Val Leu Val Pro Tyr Glu Leu Trp His Val Asp Ser Ser Thr Ser Glu
                645                 650                 655

Pro Tyr Ile Lys Pro Gln Thr Ala Phe Thr Met Leu Ser Leu Phe Asn
            660                 665                 670

Val Leu Arg Phe Pro Leu Val Val Leu Pro Lys Ala Met Arg Cys Val
        675                 680                 685

Ser Glu Ala Leu Arg Ser Val Gly Asn Leu Glu Lys Phe Leu Ala Glu
    690                 695                 700

Pro Val Ala Pro Arg Gln Asp Leu Glu Gly Lys Pro Gly Ala Gln Leu
705                 710                 715                 720

Ser Lys Ala Val Leu Arg His Glu Met Asp Thr Ser Gly Phe Thr Leu
                725                 730                 735

Arg Val Pro Glu Phe Ser Val Lys Ala Gly Glu Leu Val Ala Val Val
            740                 745                 750

Gly Arg Val Gly Ala Gly Lys Ser Ser Ile Leu Gln Ala Met Leu Gly
```

-continued

```
        755                 760                 765

Asn Met Gln Thr Ala Ser Gly Leu Ala Lys Cys Gln His Ser Ala Ser
    770                 775                 780

Ser Cys Leu Pro Phe Leu Val Glu Gly Thr Ala His Ser Gly Gly Arg
785                 790                 795                 800

Ile Ala Tyr Val Pro Gln Thr Ala Trp Cys Gln Asn Leu Ser Leu Arg
                805                 810                 815

Asp Asn Ile Thr Phe Gly Gln Pro Trp Asp Glu Ala Lys Tyr Lys Gln
            820                 825                 830

Val Ile His Ala Cys Ala Leu Glu Leu Asp Leu Ala Ile Leu Ala Ala
        835                 840                 845

Gly Asp Gln Ser Lys Ala Gly Leu Arg Gly Ile Asn Leu Ser Gly Gly
    850                 855                 860

Gln Arg Gln Arg Leu Asn Leu Ala Arg Cys Ala Tyr Phe Asp Gly Asp
865                 870                 875                 880

Leu Val Leu Leu Asp Asn Ala Leu Ser Ala Val Asp His His Thr Ala
                885                 890                 895

His His Ile Phe Glu His Cys Val Arg Gly Met Phe Arg Asp Lys Ala
            900                 905                 910

Thr Val Leu Val Thr His Gln Val Glu Phe Leu Pro Gln Cys Asp Lys
        915                 920                 925

Val Ala Ile Met Asp Asp Gly Thr Cys Val Tyr Phe Gly Pro Trp Asn
    930                 935                 940

Ala Ala Ala Gln Gln Leu Leu Ser Lys Tyr Leu Pro Ala Ser His Leu
945                 950                 955                 960

Leu Ala Ala Gly Gly Asn Ala Glu Gln Pro Arg Asp Thr Lys Lys Lys
                965                 970                 975

Val Val Lys Lys Glu Glu Thr Lys Lys Thr Glu Asp Ala Gly Lys Ala
            980                 985                 990

Lys Arg Val His Ser Ala Ser Leu  Thr Leu Lys Ser Ala  Leu Trp Glu
        995                 1000                1005

Tyr Cys  Trp Asp Ala Arg Trp  Ile Ile Phe Cys Leu  Ser Leu Phe
    1010                1015                1020

Phe Phe  Leu Thr Ala Gln Ala  Ser Arg Gln Leu Ala  Asp Tyr Phe
    1025                1030                1035

Ile Arg  Trp Trp Thr Arg Asp  His Tyr Asn Lys Tyr  Gly Val Leu
    1040                1045                1050

Cys Ile  Asp Glu Gly Asp Asn  Pro Cys Gly Pro Leu  Phe Tyr Val
    1055                1060                1065

Gln Tyr  Tyr Gly Ile Leu Gly  Leu Leu Cys Phe Ile  Val Leu Met
    1070                1075                1080

Ala Phe  Arg Gly Ala Phe Leu  Tyr Thr Trp Ser Leu  Gly Ala Ser
    1085                1090                1095

Tyr Arg  Gln His Glu Lys Ser  Ile His Arg Val Leu  Tyr Ala Pro
    1100                1105                1110

Leu Gly  Phe Phe Leu Thr Thr  Pro Val Gly Asp Leu  Leu Val Ser
    1115                1120                1125

Phe Thr  Lys Asp Gln Asp Val  Met Asp Asp Ala Leu  Pro Asp Ala
    1130                1135                1140

Leu Tyr  Tyr Ala Gly Ile Tyr  Gly Leu Ile Leu Leu  Ala Thr Ala
    1145                1150                1155

Ile Thr  Val Ser Val Thr Ile  Pro Leu Phe Ser Ala  Leu Ala Gly
    1160                1165                1170
```

```
Gly Leu  Phe Val Val Ser Gly  Ile Met Leu Ala Ile  Tyr Leu Pro
    1175                 1180                 1185

Ala Ala  Thr His Leu Lys Lys  Leu Arg Met Gly Thr  Ser Gly Asp
    1190                 1195                 1200

Val Val  Thr Leu Ile Ala Glu  Ala Leu Asp Gly Leu  Gly Val Ile
    1205                 1210                 1215

Gln Ala  Tyr Gly Lys Gln Ala  Tyr Phe Thr Thr Ile  Thr Ser Gln
    1220                 1225                 1230

Tyr Val  Asn Asp Ala His Arg  Ala Leu Phe Gly Ala  Glu Ser Leu
    1235                 1240                 1245

Asn Leu  Trp Leu Ala Phe Ile  Cys Asp Phe Phe Gly  Ala Cys Met
    1250                 1255                 1260

Val Leu  Ser Val Ala Cys Phe  Gly Ile Gly Gln Trp  Ser Thr Leu
    1265                 1270                 1275

Gly Ser  Ser Ser Val Gly Leu  Ala Phe Ser Gln Ser  Ile Gln Met
    1280                 1285                 1290

Leu Val  Phe Tyr Thr Trp Ser  Ile Arg Leu Val Ala  Glu Cys Ile
    1295                 1300                 1305

Gly Leu  Phe Gly Ser Ala Glu  Lys Ile Ala Trp Leu  Ala Asn His
    1310                 1315                 1320

Thr Pro  Gln Glu Ala Gly Ser  Leu Asp Pro Pro Ser  Leu Pro Gly
    1325                 1330                 1335

Ser Gly  Glu Thr Lys Ala Ala  Pro Lys Lys Arg Gly  Thr Ala Gly
    1340                 1345                 1350

Lys Phe  Leu Pro Pro Leu Lys  Asp Glu Asp Leu Ala  Ile Val Pro
    1355                 1360                 1365

Thr Gly  Gly Pro Lys Leu Pro  Ser Gly Trp Pro Arg  Thr Gly Val
    1370                 1375                 1380

Leu Glu  Phe Asn Gln Val Val  Met Lys Tyr Ala Pro  His Leu Pro
    1385                 1390                 1395

Pro Ala  Leu Arg Gly Val Ser  Phe Lys Val Lys Ser  Gly Asp Lys
    1400                 1405                 1410

Val Gly  Val Val Gly Arg Thr  Gly Ser Gly Lys Ser  Thr Leu Leu
    1415                 1420                 1425

Leu Ala  Leu Tyr Arg Met Phe  Asn Leu Glu Ser Gly  Ala Ile Thr
    1430                 1435                 1440

Leu Asp  Gly Ile Asp Ile Ser  Thr Leu Thr Leu Glu  Gln Leu Arg
    1445                 1450                 1455

Arg Gly  Leu Ser Val Ile Pro  Gln Glu Pro Thr Val  Phe Ser Gly
    1460                 1465                 1470

Thr Val  Arg Thr Asn Leu Asp  Pro Phe Gly Glu Phe  Gly Ala Asp
    1475                 1480                 1485

Ala Ile  Leu Trp Glu Ala Leu  Arg Asp Cys Gly Leu  Glu Glu Gln
    1490                 1495                 1500

Val Lys  Ala Cys Gly Gly Leu  Asp Ala Lys Leu Asp  Gly Thr Gly
    1505                 1510                 1515

Gly Asn  Ala Trp Ser Ile Gly  Gln Gln Gln Leu Met  Cys Leu Ala
    1520                 1525                 1530

Arg Ala  Ala Leu Lys Lys Val  Pro Val Leu Cys Leu  Asp Glu Ala
    1535                 1540                 1545

Thr Ala  Ala Met Asp Pro His  Thr Glu Ala His Val  Leu Glu Ile
    1550                 1555                 1560
```

```
Ile Glu  Arg Ile Phe Ser Asp  Arg Thr Met Leu Thr  Ile Ala His
    1565                 1570                 1575

Arg Leu  Asp Asn Val Ile Arg  Ser Asp Leu Val Val  Val Met Asp
    1580                 1585                 1590

Ala Gly  Gln Val Cys Glu Met  Gly Thr Pro Asp Glu  Leu Leu Ala
    1595                 1600                 1605

Asn Pro  Gln Ser Ala Phe Ser  Gln Leu Val Asp Lys  Thr Gly Ala
    1610                 1615                 1620

Ala Ser  Ala Ala Ala Leu Arg  Lys Met Ala Ala Asp  Phe Leu Asp
    1625                 1630                 1635

Glu Arg  Ala Arg Gly Gln Lys  Leu Gly Phe Lys Pro  Arg Pro Ser
    1640                 1645                 1650

Leu Glu  Glu Ser His Ile Cys  Val Ala Pro Ser Pro  Ser Leu Ile
    1655                 1660                 1665

Leu Ser  Thr Leu Leu Phe Pro  Pro Ala Phe Met Ala  Asn Val Thr
    1670                 1675                 1680

Ala Leu  Leu Leu Pro Lys Pro  Val Leu Ser His Ala  Pro Val Ser
    1685                 1690                 1695

Ser Gln  Thr Val Asn Thr Tyr  Ile Arg Leu Asn Ile  Ile Gln Leu
    1700                 1705                 1710

Gln Cys  Asn Val Leu His Pro  Ala Thr Lys Glu Ala  Thr Trp Ser
    1715                 1720                 1725

Ser Arg  Arg Ile Thr Phe Thr  Ala His Leu Ser Ser  Ser Gly Ser
    1730                 1735                 1740

Lys Pro  Pro Pro Pro Leu Pro  Pro Leu Thr Glu Leu  Pro Glu Gly
    1745                 1750                 1755

Arg Gly  Leu Asp Trp Ser Ser  Ala Gly Tyr Arg Asp  Gly Arg Glu
    1760                 1765                 1770

Ala Ile  Pro Ser Pro Ser Ala  Lys Tyr Ser Ala Ala  Asp Tyr Gly
    1775                 1780                 1785

Ala Ala  Gly Asp Gly Val Thr  Asp Asp Thr Gln Ala  Leu Gln Val
    1790                 1795                 1800

Ala Val  Ala Ala Ala His Glu  Asp Asp Glu Gly Gly  Val Val Tyr
    1805                 1810                 1815

Leu Gly  Ala Gly Thr Phe Val  Leu Thr Gln Pro Leu  Ser Ile Ala
    1820                 1825                 1830

Gly Ser  Asn Val Val Ile Arg  Gly Ala Gly Glu Asp  Ala Thr Thr
    1835                 1840                 1845

Ile Phe  Val Pro Leu Pro Leu  Ser Asp Val Phe Pro  Gly Thr Trp
    1850                 1855                 1860

Ser Met  Asp Ala Ser Gly Lys  Val Thr Ser Pro Trp  Ile Thr Arg
    1865                 1870                 1875

Gly Gly  Phe Leu Ala Phe Ser  Gly Arg Arg Thr Lys  Ser Ser Asp
    1880                 1885                 1890

Ser Ser  Thr Leu Leu Ala Thr  Val Ala Gly Ser Val  Glu Gln Gly
    1895                 1900                 1905

Ala Ser  Val Ile Pro Val Asp  Ser Thr Ala Glu Phe  Arg Leu Gly
    1910                 1915                 1920

Gln Trp  Val Arg Ile Ile Ile  Asn Asp Ala Ser Thr  Asp Ala Ser
    1925                 1930                 1935

Ala Gly  Gly Gly Thr Leu Glu  Arg Gly Ser Ser Glu  Val Gln Glu
    1940                 1945                 1950

Ser Glu  Thr Met Ile Ala Glu  Gly Ala Thr Gly Gly  Gly Ala Gly
```

```
    1955                1960                1965

Val Arg  Ala Gln Trp Thr Gly  Val Leu His Ala Phe  Glu Pro Thr
    1970                1975                1980

Val Gln  Cys Ser Gly Val Glu  Gln Leu Thr Ile Arg  Phe Asn His
    1985                1990                1995

Ser Met  Met Ala Ala His Leu  Ala Glu Arg Gly Tyr  Asn Ala Ile
    2000                2005                2010

Glu Leu  Glu Asp Val Val Asp  Cys Trp Ile Arg Gln  Val Thr Ile
    2015                2020                2025

Leu Asn  Ala Asp Asn Ala Ile  Arg Leu Arg Gly Thr  Asp His Ser
    2030                2035                2040

Thr Leu  Ser Gly Gln Ala Cys  Ser Gly Gly Gly Val  Val Ala Val
    2045                2050                2055

Val Pro  Val Trp Cys Arg Arg  Gly Leu Pro Ser Pro  Ala Asp Val
    2060                2065                2070

Thr Val  Gly Val Thr Glu Leu  Arg Trp Glu Pro Asp  Thr Arg Glu
    2075                2080                2085

Val Asn  Gly His His Ala Ile  Thr Val Ser Lys Gly  His Ala Asn
    2090                2095                2100

Leu Val  Thr Arg Phe Arg Ile  Thr Ala Pro Phe Tyr  His Asp Ile
    2105                2110                2115

Ser Leu  Glu Gly Gly Ala Leu  Leu Asn Val Ile Ser  Ser Gly Gly
    2120                2125                2130

Gly Ala  Asn Leu Asn Leu Asp  Leu His Arg Ser Gly  Pro Trp Gly
    2135                2140                2145

Asn Leu  Phe Ser Gln Leu Gly  Met Gly Leu Ala Ala  Arg Pro Phe
    2150                2155                2160

Asp Ala  Gly Gly Arg Asp Gly  Arg Gly Ala His Ala  Gly Arg Gln
    2165                2170                2175

Asn Thr  Phe Trp Asn Leu Gln  Pro Gly Asp Val Ala  Ala Ala Ala
    2180                2185                2190

Pro Ala  Leu Gln Pro Ser Ala  Ala Ala Gly Asp Ala  Arg Arg Leu
    2195                2200                2205

Leu Val  Asp Gly Asp Ser Leu  Leu His Ala Gly Thr  Gly Gln Ala
    2210                2215                2220

Arg Leu  Leu Arg Gln Leu Glu  Ala Asp Asp Ser Ala  Glu Pro Leu
    2225                2230                2235

Leu Leu  Pro Ser Cys Glu Phe  Gly Pro Leu Leu Asn  Phe Val Gly
    2240                2245                2250

Gly Phe  Ala Gly Glu Leu Cys  Lys Ser Ser Gly Trp  Leu Val Ala
    2255                2260                2265

Gly Leu  Pro Asp Asp Arg Pro  Asp Leu His Ala Ser  Gln Val Thr
    2270                2275                2280

Ala Arg  Leu Gln His Gly Ala  Ala Asp Asn Lys Thr  His Ala
    2285                2290                2295


<210> SEQ ID NO 71
<211> LENGTH: 373
<212> TYPE: PRT
<213> ORGANISM: Synechocystis PCC6803

<400> SEQUENCE: 71

Met Asp Phe Leu Ser Asn Phe Leu Met Asp Phe Val Lys Gln Leu Gln
1               5                   10                  15
```

```
Ser Pro Thr Leu Ser Phe Leu Ile Gly Gly Met Val Ile Ala Ala Cys
            20                  25                  30

Gly Ser Gln Leu Gln Ile Pro Glu Ser Ile Cys Lys Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Val Leu Pro Ala Leu Phe Ser Val Ala Ile
65                  70                  75                  80

Gly Ile Leu Ile Val Phe Ile Ala Arg Tyr Thr Leu Ala Arg Met Pro
                85                  90                  95

Lys Val Lys Thr Val Asp Ala Ile Ala Thr Gly Gly Leu Phe Gly Ala
            100                 105                 110

Val Ser Gly Ser Thr Met Ala Ala Ala Leu Thr Leu Leu Glu Glu Gln
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Arg Lys Glu Ala Ala Phe Ala Ser Ala Gln Gly Ala Tyr
                165                 170                 175

Ser Lys Gln Pro Val Ala Ala Gly Asp Tyr Ser Ser Ser Ser Asp Tyr
            180                 185                 190

Pro Ser Ser Arg Arg Glu Tyr Ala Gln Gln Glu Ser Gly Asp His Arg
        195                 200                 205

Val Lys Ile Trp Pro Ile Val Glu Glu Ser Leu Gln Gly Pro Ala Leu
    210                 215                 220

Ser Ala Met Leu Leu Gly Val Ala Leu Gly Leu Phe Ala Arg Pro Glu
225                 230                 235                 240

Ser Val Tyr Glu Gly Phe Tyr Asp Pro Leu Phe Arg Gly Leu Leu Ser
                245                 250                 255

Ile Leu Met Leu Val Met Gly Met Glu Ala Trp Ser Arg Ile Ser Glu
            260                 265                 270

Leu Arg Lys Val Ala Gln Trp Tyr Val Val Tyr Ser Ile Val Ala Pro
        275                 280                 285

Leu Ala His Gly Phe Ile Ala Phe Gly Leu Gly Met Ile Ala His Tyr
    290                 295                 300

Ala Thr Gly Phe Ser Met Gly Gly Val Val Val Leu Ala Val Ile Ala
305                 310                 315                 320

Ala Ser Ser Ser Asp Ile Ser Gly Pro Pro Thr Leu Arg Ala Gly Ile
                325                 330                 335

Pro Ser Ala Asn Pro Ser Ala Tyr Ile Gly Ala Ser Thr Ala Ile Gly
            340                 345                 350

Thr Pro Val Ala Ile Gly Ile Ala Ile Pro Leu Phe Leu Gly Leu Ala
        355                 360                 365

Gln Thr Ile Gly Gly
    370
```

<210> SEQ ID NO 72
<211> LENGTH: 374
<212> TYPE: PRT
<213> ORGANISM: Synechocystis PCC 6803

<400> SEQUENCE: 72

```
Met Asp Phe Leu Ser Asn Phe Leu Thr Asp Phe Val Gly Gln Leu Gln
1               5                   10                  15
```

```
Ser Pro Thr Leu Ala Phe Leu Ile Gly Gly Met Val Ile Ala Ala Leu
            20                  25                  30

Gly Thr Gln Leu Val Ile Pro Glu Ala Ile Ser Thr Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Leu Leu Pro Val Ala Phe Ser Val Ile Leu
65                  70                  75                  80

Gly Ile Leu Ile Val Phe Ile Ala Arg Phe Thr Leu Ala Lys Leu Pro
                85                  90                  95

Asn Val Arg Thr Val Asp Ala Leu Ala Thr Gly Gly Leu Phe Gly Ala
            100                 105                 110

Val Ser Gly Ser Thr Met Ala Ala Ala Leu Thr Thr Leu Glu Glu Ser
        115                 120                 125

Lys Ile Ser Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Arg Lys Arg Lys Ser Ala Ala Ala Ser Ile Glu Glu Ser Phe Ser
                165                 170                 175

Lys Gln Pro Val Ala Ala Gly Asp Tyr Gly Asp Gln Thr Asp Tyr Pro
            180                 185                 190

Arg Thr Arg Gln Glu Tyr Leu Ser Gln Gln Glu Pro Glu Asp Asn Arg
        195                 200                 205

Val Lys Ile Trp Pro Ile Ile Glu Glu Ser Leu Gln Gly Pro Ala Leu
    210                 215                 220

Ser Ala Met Leu Leu Gly Leu Ala Leu Gly Ile Phe Thr Lys Pro Glu
225                 230                 235                 240

Ser Val Tyr Glu Gly Phe Tyr Asp Pro Leu Phe Arg Gly Leu Leu Ser
                245                 250                 255

Ile Leu Met Leu Ile Met Gly Met Glu Ala Trp Ser Arg Ile Gly Glu
            260                 265                 270

Leu Arg Lys Val Ala Gln Trp Tyr Val Val Tyr Ser Leu Ile Ala Pro
        275                 280                 285

Ile Val His Gly Phe Ile Ala Phe Gly Leu Gly Met Ile Ala His Tyr
    290                 295                 300

Ala Thr Gly Phe Ser Leu Gly Gly Val Val Val Leu Ala Val Ile Ala
305                 310                 315                 320

Ala Ser Ser Ser Asp Ile Ser Gly Pro Pro Thr Leu Arg Ala Gly Ile
                325                 330                 335

Pro Ser Ala Asn Pro Ser Ala Tyr Ile Gly Ser Ser Thr Ala Ile Gly
            340                 345                 350

Thr Pro Ile Ala Ile Gly Val Cys Ile Pro Leu Phe Ile Gly Leu Ala
        355                 360                 365

Gln Thr Leu Gly Ala Gly
    370
```

```
<210> SEQ ID NO 73
<211> LENGTH: 370
<212> TYPE: PRT
<213> ORGANISM: Nostoc PCC 7120
<220> FEATURE:
<221> NAME/KEY: MISC_FEATURE
<223> OTHER INFORMATION: Anabaena
```

<400> SEQUENCE: 73

```
Met Asp Phe Phe Ser Leu Phe Leu Met Asp Phe Val Lys Gln Leu Gln
1               5                   10                  15

Ser Pro Thr Leu Gly Phe Leu Ile Gly Gly Met Val Ile Ala Ala Leu
            20                  25                  30

Gly Ser Glu Leu Ile Ile Pro Glu Ala Ile Cys Gln Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Ala Ala Ser Ala Val Ala Val
65                  70                  75                  80

Gly Val Leu Val Val Phe Ile Ala Arg Tyr Thr Leu Ala Lys Leu Pro
                85                  90                  95

Lys Val Asn Thr Val Asp Ala Ile Ala Thr Gly Gly Leu Phe Gly Ala
            100                 105                 110

Val Ser Gly Ser Thr Met Ala Ala Ala Leu Thr Leu Leu Glu Glu Gln
        115                 120                 125

Lys Ile Gln Tyr Glu Ala Trp Ala Ala Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Arg Ser Ala Ala Gly Glu Tyr Leu Ser Lys Gln Ser Val
                165                 170                 175

Ala Ala Gly Glu Tyr Pro Asp Gln Gln Asp Tyr Pro Ser Ser Arg Gln
            180                 185                 190

Glu Tyr Leu Arg Lys Gln Gln Ser Ala Asp Asn Arg Val Lys Ile Trp
        195                 200                 205

Pro Ile Val Lys Glu Ser Leu Gln Gly Pro Ala Leu Ser Ala Met Leu
    210                 215                 220

Leu Gly Ile Ala Leu Gly Leu Phe Thr Gln Pro Glu Ser Val Tyr Lys
225                 230                 235                 240

Ser Phe Tyr Asp Pro Leu Phe Arg Gly Leu Leu Ser Ile Leu Met Leu
                245                 250                 255

Val Met Gly Met Glu Ala Trp Ser Arg Ile Gly Glu Leu Arg Lys Val
            260                 265                 270

Ala Gln Trp Tyr Val Val Tyr Ser Val Val Ala Pro Leu Val His Gly
        275                 280                 285

Phe Ile Ala Phe Gly Leu Gly Met Ile Ala His Tyr Ala Thr Gly Phe
    290                 295                 300

Ser Leu Gly Gly Val Val Ile Leu Ala Val Ile Ala Ala Ser Ser Ser
305                 310                 315                 320

Asp Ile Ser Gly Pro Pro Thr Leu Arg Ala Gly Ile Pro Ser Ala Asn
                325                 330                 335

Pro Ser Ala Tyr Ile Gly Ala Ser Thr Ala Ile Gly Thr Pro Ile Ala
            340                 345                 350

Ile Gly Leu Ala Ile Pro Leu Phe Leu Gly Leu Ala Gln Ala Ile Gly
        355                 360                 365

Gly Arg
    370
```

<210> SEQ ID NO 74
<211> LENGTH: 377
<212> TYPE: PRT
<213> ORGANISM: Cyanothece sp. PCC 7425

```
<400> SEQUENCE: 74

Met Asp Phe Trp Ser Tyr Phe Leu Met Asp Phe Val Lys Gln Leu Gln
1               5                   10                  15

Ser Pro Thr Leu Gly Phe Leu Ile Gly Gly Met Val Ile Ala Ala Leu
            20                  25                  30

Gly Ser Gln Leu Val Ile Pro Glu Ala Ile Cys Gln Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Val Leu Pro Ala Ala Phe Ser Val Ile Ser
65                  70                  75                  80

Gly Ile Leu Ile Val Phe Ile Ala Arg Tyr Thr Leu Ala Lys Leu Pro
                85                  90                  95

Lys Val Arg Thr Val Asp Ala Ile Ala Thr Gly Gly Leu Phe Gly Ala
            100                 105                 110

Val Ser Gly Ser Thr Met Ala Ala Ala Leu Thr Leu Leu Glu Glu Glu
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Ile Ala Asn Ile Tyr Leu Asn
145                 150                 155                 160

Lys Lys Lys Arg Arg Ala Glu Ser Glu Ala Leu Ser Lys Gln Glu Tyr
                165                 170                 175

Leu Gly Lys Gln Ser Ile Val Ala Gly Asp Tyr Pro Ala Gln Gln Asp
            180                 185                 190

Tyr Pro Ser Thr Arg Gln Glu Tyr Leu Ser Lys Gln Gln Gly Pro Glu
        195                 200                 205

Asn Asn Arg Val Lys Ile Trp Pro Ile Val Gln Glu Ser Leu Gln Gly
    210                 215                 220

Pro Ala Leu Ser Ala Met Leu Leu Gly Val Ala Leu Gly Ile Leu Thr
225                 230                 235                 240

Lys Pro Glu Ser Val Tyr Glu Ser Phe Tyr Asp Pro Leu Phe Arg Gly
                245                 250                 255

Leu Leu Ser Ile Leu Met Leu Val Met Gly Met Glu Ala Trp Ser Arg
            260                 265                 270

Ile Gly Glu Leu Arg Lys Val Ala Gln Trp Tyr Val Val Tyr Ser Val
        275                 280                 285

Val Ala Pro Phe Val His Gly Leu Ile Ala Phe Gly Leu Gly Met Phe
    290                 295                 300

Ala His Tyr Thr Met Gly Phe Ser Met Gly Gly Val Val Val Leu Ala
305                 310                 315                 320

Val Ile Ala Ser Ser Ser Ser Asp Ile Ser Gly Pro Pro Thr Leu Arg
                325                 330                 335

Ala Gly Ile Pro Ser Ala Asn Pro Ser Ala Tyr Ile Gly Ala Ser Thr
            340                 345                 350

Ala Ile Gly Thr Pro Ile Ala Ile Gly Leu Cys Ile Pro Phe Phe Ile
        355                 360                 365

Gly Leu Ala Gln Thr Leu Gly Gly Gly
    370                 375

<210> SEQ ID NO 75
<211> LENGTH: 373
<212> TYPE: PRT
```

```
<213> ORGANISM: Microcystis aeruginosa

<400> SEQUENCE: 75

Met Asp Phe Phe Ser Leu Phe Val Met Asp Phe Ile Gln Gln Leu Gln
1               5                   10                  15

Ser Pro Thr Leu Ala Phe Leu Ile Gly Gly Met Ile Ile Ala Ala Leu
            20                  25                  30

Gly Ser Glu Leu Val Ile Pro Glu Ser Ile Cys Thr Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Met Ile Phe Ala Val Ile Val
65                  70                  75                  80

Gly Ile Ile Val Val Phe Val Ala Arg Tyr Thr Leu Ala Asn Leu Pro
                85                  90                  95

Lys Val Lys Val Val Asp Ala Ile Ala Thr Gly Gly Leu Phe Gly Ala
            100                 105                 110

Val Ser Gly Ser Thr Met Ala Ala Gly Leu Thr Val Leu Glu Glu Gln
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Gln Lys Glu Ala Ala Tyr Asp Gln Glu Ser Phe Ser Lys
                165                 170                 175

Gln Pro Val Ala Ala Gly Asn Tyr Ser Asp Gln Gln Asp Tyr Pro Ser
            180                 185                 190

Ser Arg Gln Glu Tyr Leu Ser Gln Gln Gln Pro Ala Asp Asn Arg Val
        195                 200                 205

Lys Ile Trp Pro Ile Ile Glu Glu Ser Leu Arg Gly Pro Ala Leu Ser
    210                 215                 220

Ala Met Leu Leu Gly Leu Ala Leu Gly Ile Phe Thr Gln Pro Glu Ser
225                 230                 235                 240

Val Tyr Lys Ser Phe Tyr Asp Pro Leu Phe Arg Gly Leu Leu Ser Val
                245                 250                 255

Leu Met Leu Val Met Gly Met Glu Ala Trp Ser Arg Val Gly Glu Leu
            260                 265                 270

Arg Lys Val Ala Gln Trp Tyr Val Val Tyr Ser Val Ile Ala Pro Phe
        275                 280                 285

Val His Gly Leu Ile Ala Phe Gly Leu Gly Met Ile Ala His Tyr Ala
    290                 295                 300

Thr Gly Phe Ser Trp Gly Gly Val Val Met Leu Ala Val Ile Ala Ser
305                 310                 315                 320

Ser Ser Ser Asp Ile Ser Gly Pro Pro Thr Leu Arg Ala Gly Ile Pro
                325                 330                 335

Ser Ala Asn Pro Ser Ala Tyr Ile Gly Ala Ser Thr Ala Ile Gly Thr
            340                 345                 350

Pro Val Ala Ile Gly Leu Cys Ile Pro Phe Phe Val Gly Leu Ala Gln
        355                 360                 365

Ala Leu Ser Gly Gly
    370

<210> SEQ ID NO 76
<211> LENGTH: 369
```

```
<212> TYPE: PRT
<213> ORGANISM: Anabaena variabilis

<400> SEQUENCE: 76

Met Asp Phe Val Ser Leu Phe Val Lys Asp Phe Ile Ala Gln Leu Gln
1               5                   10                  15

Ser Pro Thr Leu Ala Phe Leu Ile Gly Gly Met Ile Ile Ala Ala Leu
            20                  25                  30

Gly Ser Glu Leu Val Ile Pro Glu Ser Ile Cys Thr Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Met Ile Phe Ala Val Ile Thr
65                  70                  75                  80

Gly Ile Thr Ile Val Phe Ile Ser Arg Tyr Thr Leu Ala Lys Leu Pro
                85                  90                  95

Lys Val Lys Val Val Asp Ala Ile Ala Thr Gly Gly Leu Phe Gly Ala
            100                 105                 110

Val Ser Gly Ser Thr Met Ala Ala Gly Leu Thr Val Leu Glu Glu Gln
        115                 120                 125

Lys Met Ala Tyr Glu Ala Trp Ala Gly Ala Leu Tyr Pro Phe Met Asp
    130                 135                 140

Ile Pro Ala Leu Val Thr Ala Ile Val Ile Ala Asn Ile Tyr Leu Asn
145                 150                 155                 160

Lys Lys Lys Arg Lys Glu Ala Val Tyr Ser Thr Glu Gln Pro Val Ala
                165                 170                 175

Ala Gly Asp Tyr Pro Asp Gln Lys Asp Tyr Pro Ser Ser Arg Gln Glu
            180                 185                 190

Tyr Leu Ser Gln Gln Lys Gly Asp Glu Asp Asn Arg Val Lys Ile Trp
        195                 200                 205

Pro Ile Ile Glu Glu Ser Leu Arg Gly Pro Ala Leu Ser Ala Met Leu
    210                 215                 220

Leu Gly Leu Ala Leu Gly Leu Phe Thr Gln Pro Glu Ser Val Tyr Lys
225                 230                 235                 240

Ser Phe Tyr Asp Pro Ala Phe Arg Gly Leu Leu Ser Ile Leu Met Leu
                245                 250                 255

Val Met Gly Met Glu Ala Trp Ser Arg Ile Gly Glu Leu Arg Lys Val
            260                 265                 270

Ala Gln Trp Tyr Val Val Tyr Ser Val Val Ala Pro Phe Val His Gly
        275                 280                 285

Leu Ile Ala Phe Gly Leu Gly Met Ile Ala His Tyr Thr Met Asn Phe
    290                 295                 300

Ser Met Gly Gly Val Val Ile Leu Ala Val Ile Ala Ser Ser Ser Ser
305                 310                 315                 320

Asp Ile Ser Gly Pro Pro Thr Leu Arg Ala Gly Ile Pro Ser Ala Asn
                325                 330                 335

Pro Ser Ala Tyr Ile Gly Ala Ser Thr Ala Val Gly Thr Pro Val Ala
            340                 345                 350

Ile Gly Leu Cys Ile Pro Phe Phe Leu Gly Leu Ala Gln Ala Ile Gly
        355                 360                 365

Gly

<210> SEQ ID NO 77
<211> LENGTH: 1082
```

<212> TYPE: PRT
<213> ORGANISM: Chlamydomonas reinhardtii

<400> SEQUENCE: 77

```
Met Leu Pro Gly Leu Gly Val Ile Leu Leu Val Leu Pro Met Gln Tyr
1               5                   10                  15

Tyr Phe Gly Tyr Lys Ile Val Gln Ile Lys Leu Gln Asn Ala Lys His
            20                  25                  30

Val Ala Leu Arg Ser Ala Ile Met Gln Glu Val Leu Pro Ala Ile Lys
        35                  40                  45

Leu Val Lys Tyr Tyr Ala Trp Glu Gln Phe Phe Glu Asn Gln Ile Ser
    50                  55                  60

Lys Val Arg Arg Glu Glu Ile Arg Leu Asn Phe Trp Asn Cys Val Met
65                  70                  75                  80

Lys Val Ile Asn Val Ala Cys Val Phe Cys Val Pro Pro Met Thr Ala
                85                  90                  95

Phe Val Ile Phe Thr Thr Tyr Glu Phe Gln Arg Ala Arg Leu Val Ser
            100                 105                 110

Ser Val Ala Phe Thr Thr Leu Ser Leu Phe Asn Ile Leu Arg Phe Pro
        115                 120                 125

Leu Val Val Leu Pro Lys Ala Leu Arg Ala Val Ser Glu Ala Asn Ala
    130                 135                 140

Ser Leu Gln Arg Leu Glu Ala Tyr Leu Leu Glu Glu Val Pro Ser Gly
145                 150                 155                 160

Thr Ala Ala Val Lys Thr Pro Lys Asn Ala Pro Pro Gly Ala Val Ile
                165                 170                 175

Glu Asn Gly Val Phe His His Pro Ser Asn Pro Asn Trp His Leu His
            180                 185                 190

Val Pro Lys Phe Glu Val Lys Pro Gly Gln Val Val Ala Val Val Gly
        195                 200                 205

Arg Ile Ala Ala Gly Lys Ser Ser Leu Val Gln Ala Ile Leu Gly Asn
    210                 215                 220

Met Val Lys Glu His Gly Ser Phe Asn Val Gly Gly Arg Ile Ser Tyr
225                 230                 235                 240

Val Pro Gln Asn Pro Trp Leu Gln Asn Leu Ser Leu Arg Asp Asn Val
                245                 250                 255

Leu Phe Gly Glu Gln Phe Asp Glu Asn Lys Tyr Thr Asp Val Ile Glu
            260                 265                 270

Ser Cys Ala Leu Thr Leu Asp Leu Gln Ile Leu Ser Asn Gly Asp Gln
        275                 280                 285

Ser Lys Ala Gly Ile Arg Gly Val Asn Phe Ser Gly Gly Gln Arg Gln
    290                 295                 300

Arg Val Asn Leu Ala Arg Cys Ala Tyr Ala Asp Ala Asp Leu Val Leu
305                 310                 315                 320

Leu Asp Asn Ala Leu Ser Ala Val Asp His His Thr Ala His His Ile
                325                 330                 335

Phe Asp Lys Cys Ile Lys Gly Leu Phe Ser Asp Lys Ala Val Val Leu
            340                 345                 350

Val Thr His Gln Ile Glu Phe Met Pro Arg Cys Asp Asn Val Ala Ile
        355                 360                 365

Met Asp Glu Gly Arg Cys Leu Tyr Phe Gly Lys Trp Asn Glu Glu Ala
    370                 375                 380

Gln His Leu Leu Gly Lys Leu Leu Pro Ile Thr His Leu Leu His Ala
385                 390                 395                 400
```

```
Ala Gly Ser Gln Glu Ala Pro Pro Ala Pro Lys Lys Lys Ala Glu Asp
                405                 410                 415

Lys Ala Gly Pro Gln Lys Ser Gln Ser Leu Gln Leu Thr Leu Ala Pro
            420                 425                 430

Thr Ser Ile Gly Lys Pro Thr Glu Lys Pro Lys Asp Val Gln Lys Leu
        435                 440                 445

Thr Ala Tyr Gln Ala Ala Leu Ile Tyr Thr Trp Tyr Gly Asn Leu Phe
    450                 455                 460

Leu Val Gly Val Cys Phe Phe Phe Phe Leu Ala Ala Gln Cys Ser Arg
465                 470                 475                 480

Gln Ile Ser Asp Phe Trp Val Arg Trp Trp Val Asn Asp Glu Tyr Lys
                485                 490                 495

Lys Phe Pro Val Lys Gly Glu Gln Asp Ser Ala Ala Thr Thr Phe Tyr
            500                 505                 510

Cys Leu Ile Tyr Leu Leu Leu Val Gly Leu Phe Tyr Ile Phe Met Ile
        515                 520                 525

Phe Arg Gly Ala Thr Phe Leu Trp Trp Val Leu Lys Ser Ser Glu Thr
    530                 535                 540

Ile Arg Arg Lys Ala Leu His Asn Val Leu Asn Ala Pro Met Gly Phe
545                 550                 555                 560

Phe Leu Val Thr Pro Val Gly Asp Leu Leu Leu Asn Phe Thr Lys Asp
                565                 570                 575

Gln Asp Ile Met Asp Glu Asn Leu Pro Asp Ala Val His Phe Met Gly
            580                 585                 590

Ile Tyr Gly Leu Ile Leu Leu Ala Thr Thr Ile Thr Val Ser Val Thr
        595                 600                 605

Ile Asn Phe Phe Ala Ala Phe Thr Gly Ala Leu Ile Ile Met Thr Leu
    610                 615                 620

Ile Met Leu Ser Ile Tyr Leu Pro Ala Ala Thr Ala Leu Lys Lys Ala
625                 630                 635                 640

Arg Ala Val Ser Gly Gly Met Leu Val Gly Leu Val Ala Glu Val Leu
                645                 650                 655

Glu Gly Leu Gly Val Val Gln Ala Phe Asn Lys Gln Glu Tyr Phe Ile
            660                 665                 670

Glu Glu Ala Ala Arg Arg Thr Asn Ile Thr Asn Ser Ala Val Phe Asn
        675                 680                 685

Ala Glu Ala Leu Asn Leu Trp Leu Ala Phe Trp Cys Asp Phe Ile Gly
    690                 695                 700

Ala Cys Leu Val Gly Val Val Ser Ala Phe Ala Val Gly Met Ala Lys
705                 710                 715                 720

Asp Leu Gly Gly Ala Thr Val Gly Leu Ala Phe Ser Asn Ile Ile Gln
                725                 730                 735

Met Leu Val Phe Tyr Thr Trp Val Val Arg Phe Ile Ser Glu Ser Ile
            740                 745                 750

Ser Leu Phe Asn Ser Val Glu Gly Met Ala Tyr Leu Ala Asp Tyr Val
        755                 760                 765

Pro His Asp Gly Val Phe Tyr Asp Gln Arg Gln Lys Asp Gly Val Ala
    770                 775                 780

Lys Gln Ile Val Leu Pro Asp Gly Asn Ile Val Pro Ala Ala Ser Lys
785                 790                 795                 800

Val Gln Val Val Val Asp Asp Ala Ala Leu Ala Arg Trp Pro Ala Thr
                805                 810                 815
```

```
Gly Asn Ile Arg Phe Glu Asp Val Trp Met Gln Tyr Arg Leu Asp Ala
            820                 825                 830

Pro Trp Ala Leu Lys Gly Val Thr Phe Lys Ile Asn Asp Gly Glu Lys
        835                 840                 845

Val Gly Ala Val Gly Arg Thr Gly Ser Gly Lys Ser Thr Thr Leu Leu
    850                 855                 860

Ala Leu Tyr Arg Met Phe Glu Leu Gly Lys Gly Arg Ile Leu Val Asp
865                 870                 875                 880

Gly Val Asp Ile Ala Thr Leu Ser Leu Lys Arg Leu Arg Thr Gly Leu
                885                 890                 895

Ser Ile Ile Pro Gln Glu Pro Val Met Phe Thr Gly Thr Val Arg Ser
            900                 905                 910

Asn Leu Asp Pro Phe Gly Glu Phe Lys Asp Asp Ala Ile Leu Trp Glu
        915                 920                 925

Val Leu Lys Lys Val Gly Leu Glu Asp Gln Ala Gln His Ala Gly Gly
    930                 935                 940

Leu Asp Gly Gln Val Asp Gly Thr Gly Gly Lys Ala Trp Ser Leu Gly
945                 950                 955                 960

Gln Met Gln Leu Val Cys Leu Ala Arg Ala Ala Leu Arg Ala Val Pro
                965                 970                 975

Ile Leu Cys Leu Asp Glu Ala Thr Ala Ala Met Asp Pro His Thr Glu
            980                 985                 990

Ala Ile Val Gln Gln Thr Ile Lys  Lys Val Phe Asp Asp  Arg Thr Thr
        995                 1000                1005

Ile Thr  Ile Ala His Arg Leu  Asp Thr Ile Ile Glu  Ser Asp Lys
    1010                1015                1020

Ile Ile  Val Met Glu Gln Gly  Ser Leu Met Glu Tyr  Glu Ser Pro
    1025                1030                1035

Ser Lys  Leu Leu Ala Asn Arg  Asp Ser Met Phe Ser  Lys Leu Val
    1040                1045                1050

Asp Lys  Thr Gly Pro Ala Ala  Ala Ala Ala Leu Arg  Lys Met Ala
    1055                1060                1065

Glu Asp  Phe Trp Ser Thr Arg  Ser Ala Gln Gly Arg  Asn Gln
    1070                1075                1080
```

<210> SEQ ID NO 78
<211> LENGTH: 366
<212> TYPE: PRT
<213> ORGANISM: Cyanothece

<400> SEQUENCE: 78

```
Met Asp Phe Leu Ser Leu Phe Val Lys Asp Phe Ile Ile Gln Leu Gln
1               5                   10                  15

Ser Pro Thr Leu Ala Phe Leu Ile Gly Gly Met Val Ile Ala Ala Leu
            20                  25                  30

Gly Ser Glu Leu Val Ile Pro Glu Ser Ile Cys Thr Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Met Ile Cys Ala Val Ile Val
65                  70                  75                  80

Gly Ile Val Val Val Phe Ile Ala Arg Tyr Thr Leu Ala Lys Leu Pro
                85                  90                  95

Lys Val Asn Val Val Asp Ala Ile Ala Thr Gly Gly Leu Phe Gly Ala
            100                 105                 110
```

```
Val Ser Gly Ser Thr Met Ala Ala Gly Leu Thr Val Leu Glu Glu Gln
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Arg Lys Ala Thr Val Met Gln Glu Ser Leu Ser Lys Gln
                165                 170                 175

Pro Val Ala Ala Gly Asp Tyr Pro Ser Ser Arg Gln Glu Tyr Val Ser
            180                 185                 190

Gln Gln Gln Pro Glu Asp Asn Arg Val Lys Ile Trp Pro Ile Ile Glu
        195                 200                 205

Glu Ser Leu Arg Gly Pro Ala Leu Ser Ala Met Leu Leu Gly Leu Ala
    210                 215                 220

Leu Gly Ile Leu Thr Gln Pro Glu Ser Val Tyr Lys Gly Phe Tyr Asp
225                 230                 235                 240

Pro Pro Phe Arg Gly Leu Leu Ser Ile Leu Met Leu Val Met Gly Met
                245                 250                 255

Glu Ala Trp Ser Arg Ile Gly Glu Leu Arg Lys Val Ala Gln Trp Tyr
            260                 265                 270

Val Val Tyr Ser Val Ala Ala Pro Phe Ile His Gly Leu Leu Ala Phe
        275                 280                 285

Gly Leu Gly Met Ile Ala His Tyr Thr Met Gly Phe Ser Met Gly Gly
    290                 295                 300

Val Val Ile Leu Ala Val Ile Ala Ser Ser Ser Ser Asp Ile Ser Gly
305                 310                 315                 320

Pro Pro Thr Leu Arg Ala Gly Ile Pro Ser Ala Asn Pro Ser Ala Tyr
                325                 330                 335

Ile Gly Ala Ser Thr Ala Ile Gly Thr Pro Val Ala Ile Gly Leu Cys
            340                 345                 350

Ile Pro Phe Phe Val Gly Leu Ala Gln Ala Ile Gly Gly Phe
        355                 360                 365


<210> SEQ ID NO 79
<211> LENGTH: 337
<212> TYPE: PRT
<213> ORGANISM: Volvox carteri
<220> FEATURE:
<221> NAME/KEY: MISC_FEATURE
<223> OTHER INFORMATION: f. nagariensis

<400> SEQUENCE: 79

Met Gln Thr Thr Met Ser Val Thr Arg Pro Cys Val Gly Leu Arg Pro
1               5                   10                  15

Leu Pro Val Arg Asn Val Arg Ser Leu Ile Arg Ala Gln Ala Ala Pro
            20                  25                  30

Gln Gln Val Ser Thr Ala Val Ser Thr Asn Gly Asn Gly Asn Gly Val
        35                  40                  45

Ala Ala Ala Ser Leu Ser Val Pro Ala Pro Val Ala Ala Pro Ala Gln
    50                  55                  60

Ala Val Ser Thr Pro Val Arg Ala Val Ser Val Leu Thr Pro Pro Gln
65                  70                  75                  80

Val Tyr Glu Asn Ala Ala Asn Val Gly Ala Tyr Lys Ala Ser Leu Gly
                85                  90                  95

Val Leu Ala Thr Phe Val Gln Gly Ile Gln Ala Gly Ala Tyr Ile Ala
```

```
            100                 105                 110

Phe Gly Ala Phe Leu Ala Cys Ser Val Gly Gly Asn Ile Pro Gly Ile
        115                 120                 125

Thr Ala Ser Asn Pro Gly Leu Ala Lys Leu Leu Phe Ala Leu Val Phe
    130                 135                 140

Pro Val Gly Leu Ser Met Val Thr Asn Cys Gly Ala Glu Leu Tyr Thr
145                 150                 155                 160

Gly Asn Thr Met Met Leu Thr Cys Ala Ile Phe Glu Lys Lys Ala Thr
                165                 170                 175

Trp Ala Gln Leu Val Lys Asn Trp Val Val Ser Tyr Ala Gly Asn Phe
            180                 185                 190

Val Gly Ser Ile Ala Met Val Ala Ala Val Val Ala Thr Gly Leu Met
        195                 200                 205

Ala Ser Asn Gln Leu Pro Val Asn Met Ala Thr Ala Lys Ser Ser Leu
    210                 215                 220

Gly Phe Thr Glu Val Leu Ser Arg Ser Ile Leu Cys Asn Trp Leu Val
225                 230                 235                 240

Cys Cys Ala Val Trp Ser Ala Ser Ala Ala Thr Ser Leu Pro Gly Arg
                245                 250                 255

Ile Leu Gly Leu Trp Pro Pro Ile Thr Ala Phe Val Ala Ile Gly Leu
            260                 265                 270

Glu His Ser Val Ala Asn Met Phe Val Ile Pro Leu Gly Met Met Leu
        275                 280                 285

Gly Ala Asp Val Thr Trp Ser Gln Phe Phe Phe Asn Asn Leu Val Pro
    290                 295                 300

Val Thr Leu Gly Asn Thr Ile Ala Gly Val Val Met Met Ala Val Ala
305                 310                 315                 320

Tyr Ser Val Ser Tyr Gly Ser Leu Gly Lys Thr Pro Lys Pro Ala Thr
                325                 330                 335

Ala


<210> SEQ ID NO 80
<211> LENGTH: 2297
<212> TYPE: PRT
<213> ORGANISM: Chlorella variabilis

<400> SEQUENCE: 80

Met Val Pro Leu Leu Ala Gln Arg Gly Arg Ile Arg Ser Gln Ala Pro
1               5                   10                  15

Arg Thr Trp His Pro Asp Pro Gln Pro Leu His Ala Glu Arg Ser Arg
            20                  25                  30

Gln Cys Pro Gly Arg Gly Val Arg Ala Ala Ala Lys Arg Gly Gly Gly
        35                  40                  45

Ser Gly Gly Ala Thr His Lys Ser Lys Lys Ser Lys Glu Leu Asp Glu
    50                  55                  60

Val Ala Ala Phe Glu Gln Leu Met Cys Asp Trp Asp Asp Ala Phe Ala
65                  70                  75                  80

Ala Asp Cys Tyr Asp Asn Glu Arg Ala Ala Arg Met Ala Arg Leu Ala
                85                  90                  95

Glu Glu Gly Tyr Gln His His Gly Arg Gly Phe Val Phe Val Arg Ser
            100                 105                 110

Arg Leu Asp Lys Arg Ser Arg Lys Ala Arg Asn Asp Ser Gly Ala Ser
        115                 120                 125

Lys Gly Phe Gly Ala Ala Ala Lys Ala Leu Ser Val Glu Gln Gly Thr
```

```
    130                 135                 140

Pro Leu Glu Asn Asn Pro Gln Leu His Leu Leu Ser Trp Thr Ala Cys
145                 150                 155                 160

Tyr Ile Ala Ser Ser Gln Leu Asp Ser Leu Gly Gly Leu Phe Ser Thr
                165                 170                 175

Gln Glu Gly Val Leu Leu Pro Asp Ser Gly Ser Leu Leu Thr Asp Gly
            180                 185                 190

Gly Ser Gly Ala Ser Gly Ser Asn Ala Ala Asp Ala Val Gly Glu Leu
        195                 200                 205

Gln Arg Val Leu Arg Gly Gln Asp Leu Ser Gln Leu Arg Gly Tyr Val
    210                 215                 220

Gly Ala Pro Pro Gln Ala Arg Pro Ala Ser Gly Ser Asp Asp Asp Gly
225                 230                 235                 240

Ser Ser Thr Thr Gly Ser Asn Asn Gly Ala Ala Gly Glu Gly Ser Glu
                245                 250                 255

Val Glu Glu Gly Thr Ala Met Gly Gly Ile Arg Arg Tyr Glu Pro Glu
            260                 265                 270

Ser Gly Glu Leu Val Val Leu Leu Ser Cys Lys Ile Gly Gly Lys Pro
        275                 280                 285

Ala Val Gly Ala Glu Leu Leu Ala Val Ala Gln Ala Glu Asp Gly Lys
    290                 295                 300

His Ala Pro Gly Ala Ser Pro Asp Thr Arg Leu Cys Lys Glu Pro Ser
305                 310                 315                 320

Gln Ser Ala Phe Asp Leu Trp Ser Phe Gly Trp Met Asn Lys Ile Val
                325                 330                 335

Pro Ala Ala Arg Arg Gly Glu Val Glu Val Ala Asp Leu Pro Leu Pro
            340                 345                 350

Glu Ala Gln Gln Ala Glu Pro Cys Tyr Glu Glu Leu Asn Thr Asn Trp
        355                 360                 365

Glu Ala Ala Val Gln Glu Ala Lys Lys Ala Gly Lys Glu Pro Lys Leu
    370                 375                 380

Met Lys Val Leu Trp Lys Thr Tyr Gly Lys Asp Ile Val Leu Ala Gly
385                 390                 395                 400

Ile Phe Lys Leu Met Trp Ser Val Phe Val Ile Leu Gly Ala Tyr Tyr
                405                 410                 415

Phe Thr Arg Ser Ile Leu Met Cys Ile Arg Thr Leu Glu Gly Lys Asp
            420                 425                 430

Asp Ser Ile Tyr Asp Thr Glu Trp Lys Gly Trp Val Leu Thr Gly Phe
        435                 440                 445

Phe Phe Leu Asp Ala Trp Leu Leu Gly Met Met Leu Gln Arg Met Ala
    450                 455                 460

Phe Asn Cys Leu Lys Val Gly Ile Lys Ala Arg Ala Ala Leu Thr Thr
465                 470                 475                 480

Met Ile Ala Arg Lys Cys Tyr Asn Met Ala His Leu Thr Lys Asp Thr
                485                 490                 495

Ala Ala Glu Ala Val Gly Phe Val Ala Ser Asp Ile Asn Lys Val Phe
            500                 505                 510

Glu Gly Ile Gln Glu Val His Tyr Leu Trp Gly Ala Pro Val Glu Ala
        515                 520                 525

Gly Ala Ile Leu Ala Leu Leu Gly Thr Leu Val Gly Val Tyr Cys Ile
    530                 535                 540

Gly Gly Val Ile Ile Val Cys Met Val Val Pro Leu Gln Tyr Tyr Phe
545                 550                 555                 560
```

```
Gly Tyr Lys Ile Ile Lys Asn Lys Ile Lys Asn Ala Pro Asn Val Thr
                565                 570                 575

Glu Arg Trp Ser Ile Ile Gln Glu Ile Leu Pro Ala Met Lys Leu Val
            580                 585                 590

Lys Tyr Tyr Ala Trp Glu Arg Phe Phe Glu Lys His Val Ala Asp Met
        595                 600                 605

Arg Thr Arg Glu Arg His Tyr Met Phe Trp Asn Ala Val Val Lys Thr
    610                 615                 620

Val Asn Val Thr Met Val Phe Gly Val Pro Pro Met Val Thr Phe Ala
625                 630                 635                 640

Val Leu Val Pro Tyr Glu Leu Trp His Val Asp Ser Ser Thr Ser Glu
                645                 650                 655

Pro Tyr Ile Lys Pro Gln Thr Ala Phe Thr Met Leu Ser Leu Phe Asn
            660                 665                 670

Val Leu Arg Phe Pro Leu Val Val Leu Pro Lys Ala Met Arg Cys Val
        675                 680                 685

Ser Glu Ala Leu Arg Ser Val Gly Asn Leu Glu Lys Phe Leu Ala Glu
    690                 695                 700

Pro Val Ala Pro Arg Gln Asp Leu Glu Gly Lys Pro Gly Ala Gln Leu
705                 710                 715                 720

Ser Lys Ala Val Leu Arg His Glu Met Asp Thr Ser Gly Phe Thr Leu
                725                 730                 735

Arg Val Pro Glu Phe Ser Val Lys Ala Gly Glu Leu Val Ala Val Val
            740                 745                 750

Gly Arg Val Gly Ala Gly Lys Ser Ser Ile Leu Gln Ala Met Leu Gly
        755                 760                 765

Asn Met Gln Thr Ala Ser Gly Leu Ala Lys Cys Gln His Ser Ala Ser
    770                 775                 780

Ser Cys Leu Pro Phe Leu Val Glu Gly Thr Ala His Ser Gly Gly Arg
785                 790                 795                 800

Ile Ala Tyr Val Pro Gln Thr Ala Trp Cys Gln Asn Leu Ser Leu Arg
                805                 810                 815

Asp Asn Ile Thr Phe Gly Gln Pro Trp Asp Glu Ala Lys Tyr Lys Gln
            820                 825                 830

Val Ile His Ala Cys Ala Leu Glu Leu Asp Leu Ala Ile Leu Ala Ala
        835                 840                 845

Gly Asp Gln Ser Lys Ala Gly Leu Arg Gly Ile Asn Leu Ser Gly Gly
    850                 855                 860

Gln Arg Gln Arg Leu Asn Leu Ala Arg Cys Ala Tyr Phe Asp Gly Asp
865                 870                 875                 880

Leu Val Leu Leu Asp Asn Ala Leu Ser Ala Val Asp His His Thr Ala
                885                 890                 895

His His Ile Phe Glu His Cys Val Arg Gly Met Phe Arg Asp Lys Ala
            900                 905                 910

Thr Val Leu Val Thr His Gln Val Glu Phe Leu Pro Gln Cys Asp Lys
        915                 920                 925

Val Ala Ile Met Asp Asp Gly Thr Cys Val Tyr Phe Gly Pro Trp Asn
    930                 935                 940

Ala Ala Ala Gln Gln Leu Leu Ser Lys Tyr Leu Pro Ala Ser His Leu
945                 950                 955                 960

Leu Ala Ala Gly Gly Asn Ala Glu Gln Pro Arg Asp Thr Lys Lys Lys
                965                 970                 975
```

```
Val Val Lys Lys Glu Glu Thr Lys Lys Thr Glu Asp Ala Gly Lys Ala
            980                 985                 990

Lys Arg Val His Ser Ala Ser Leu  Thr Leu Lys Ser Ala  Leu Trp Glu
        995                 1000                 1005

Tyr Cys  Trp Asp Ala Arg Trp  Ile Ile Phe Cys Leu  Ser Leu Phe
    1010                 1015                 1020

Phe Phe  Leu Thr Ala Gln Ala  Ser Arg Gln Leu Ala  Asp Tyr Phe
    1025                 1030                 1035

Ile Arg  Trp Trp Thr Arg Asp  His Tyr Asn Lys Tyr  Gly Val Leu
    1040                 1045                 1050

Cys Ile  Asp Glu Gly Asp Asn  Pro Cys Gly Pro Leu  Phe Tyr Val
    1055                 1060                 1065

Gln Tyr  Tyr Gly Ile Leu Gly  Leu Leu Cys Phe Ile  Val Leu Met
    1070                 1075                 1080

Ala Phe  Arg Gly Ala Phe Leu  Tyr Thr Trp Ser Leu  Gly Ala Ser
    1085                 1090                 1095

Tyr Arg  Gln His Glu Lys Ser  Ile His Arg Val Leu  Tyr Ala Pro
    1100                 1105                 1110

Leu Gly  Phe Phe Leu Thr Thr  Pro Val Gly Asp Leu  Leu Val Ser
    1115                 1120                 1125

Phe Thr  Lys Asp Gln Asp Val  Met Asp Asp Ala Leu  Pro Asp Ala
    1130                 1135                 1140

Leu Tyr  Tyr Ala Gly Ile Tyr  Gly Leu Ile Leu Leu  Ala Thr Ala
    1145                 1150                 1155

Ile Thr  Val Ser Val Thr Ile  Pro Leu Phe Ser Ala  Leu Ala Gly
    1160                 1165                 1170

Gly Leu  Phe Val Val Ser Gly  Ile Met Leu Ala Ile  Tyr Leu Pro
    1175                 1180                 1185

Ala Ala  Thr His Leu Lys Lys  Leu Arg Met Gly Thr  Ser Gly Asp
    1190                 1195                 1200

Val Val  Thr Leu Ile Ala Glu  Ala Leu Asp Gly Leu  Gly Val Ile
    1205                 1210                 1215

Gln Ala  Tyr Gly Lys Gln Ala  Tyr Phe Thr Thr Ile  Thr Ser Gln
    1220                 1225                 1230

Tyr Val  Asn Asp Ala His Arg  Ala Leu Phe Gly Ala  Glu Ser Leu
    1235                 1240                 1245

Asn Leu  Trp Leu Ala Phe Ile  Cys Asp Phe Phe Gly  Ala Cys Met
    1250                 1255                 1260

Val Leu  Ser Val Ala Cys Phe  Gly Ile Gly Gln Trp  Ser Thr Leu
    1265                 1270                 1275

Gly Ser  Ser Ser Val Gly Leu  Ala Phe Ser Gln Ser  Ile Gln Met
    1280                 1285                 1290

Leu Val  Phe Tyr Thr Trp Ser  Ile Arg Leu Val Ala  Glu Cys Ile
    1295                 1300                 1305

Gly Leu  Phe Gly Ser Ala Glu  Lys Ile Ala Trp Leu  Ala Asn His
    1310                 1315                 1320

Thr Pro  Gln Glu Ala Gly Ser  Leu Asp Pro Pro Ser  Leu Pro Gly
    1325                 1330                 1335

Ser Gly  Glu Thr Lys Ala Ala  Pro Lys Lys Arg Gly  Thr Ala Gly
    1340                 1345                 1350

Lys Phe  Leu Pro Pro Leu Lys  Asp Glu Asp Leu Ala  Ile Val Pro
    1355                 1360                 1365

Thr Gly  Gly Pro Lys Leu Pro  Ser Gly Trp Pro Arg  Thr Gly Val
```

```
    1370                1375                1380

Leu Glu  Phe Asn Gln Val Val  Met Lys Tyr Ala Pro  His Leu Pro
    1385                1390                1395

Pro Ala  Leu Arg Gly Val Ser  Phe Lys Val Lys Ser  Gly Asp Lys
    1400                1405                1410

Val Gly  Val Val Gly Arg Thr  Gly Ser Gly Lys Ser  Thr Leu Leu
    1415                1420                1425

Leu Ala  Leu Tyr Arg Met Phe  Asn Leu Glu Ser Gly  Ala Ile Thr
    1430                1435                1440

Leu Asp  Gly Ile Asp Ile Ser  Thr Leu Thr Leu Glu  Gln Leu Arg
    1445                1450                1455

Arg Gly  Leu Ser Val Ile Pro  Gln Glu Pro Thr Val  Phe Ser Gly
    1460                1465                1470

Thr Val  Arg Thr Asn Leu Asp  Pro Phe Gly Glu Phe  Gly Ala Asp
    1475                1480                1485

Ala Ile  Leu Trp Glu Ala Leu  Arg Asp Cys Gly Leu  Glu Glu Gln
    1490                1495                1500

Val Lys  Ala Cys Gly Gly Leu  Asp Ala Lys Leu Asp  Gly Thr Gly
    1505                1510                1515

Gly Asn  Ala Trp Ser Ile Gly  Gln Gln Gln Leu Met  Cys Leu Ala
    1520                1525                1530

Arg Ala  Ala Leu Lys Lys Val  Pro Val Leu Cys Leu  Asp Glu Ala
    1535                1540                1545

Thr Ala  Ala Met Asp Pro His  Thr Glu Ala His Val  Leu Glu Ile
    1550                1555                1560

Ile Glu  Arg Ile Phe Ser Asp  Arg Thr Met Leu Thr  Ile Ala His
    1565                1570                1575

Arg Leu  Asp Asn Val Ile Arg  Ser Asp Leu Val Val  Val Met Asp
    1580                1585                1590

Ala Gly  Gln Val Cys Glu Met  Gly Thr Pro Asp Glu  Leu Leu Ala
    1595                1600                1605

Asn Pro  Gln Ser Ala Phe Ser  Gln Leu Val Asp Lys  Thr Gly Ala
    1610                1615                1620

Ala Ser  Ala Ala Ala Leu Arg  Lys Met Ala Ala Asp  Phe Leu Asp
    1625                1630                1635

Glu Arg  Ala Arg Gly Gln Lys  Leu Gly Phe Lys Pro  Arg Pro Ser
    1640                1645                1650

Leu Glu  Glu Ser His Ile Cys  Val Ala Pro Ser Pro  Ser Leu Ile
    1655                1660                1665

Leu Ser  Thr Leu Leu Phe Pro  Pro Ala Phe Met Ala  Asn Val Thr
    1670                1675                1680

Ala Leu  Leu Leu Pro Lys Pro  Val Leu Ser His Ala  Pro Val Ser
    1685                1690                1695

Ser Gln  Thr Val Asn Thr Tyr  Ile Arg Leu Asn Ile  Ile Gln Leu
    1700                1705                1710

Gln Cys  Asn Val Leu His Pro  Ala Thr Lys Glu Ala  Thr Trp Ser
    1715                1720                1725

Ser Arg  Arg Ile Thr Phe Thr  Ala His Leu Ser Ser  Ser Gly Ser
    1730                1735                1740

Lys Pro  Pro Pro Pro Leu Pro  Pro Leu Thr Glu Leu  Pro Glu Gly
    1745                1750                1755

Arg Gly  Leu Asp Trp Ser Ser  Ala Gly Tyr Arg Asp  Gly Arg Glu
    1760                1765                1770
```

```
Ala Ile  Pro Ser Pro Ser Ala  Lys Tyr Ser Ala Ala  Asp Tyr Gly
    1775                 1780                 1785

Ala Ala  Gly Asp Gly Val Thr  Asp Asp Thr Gln Ala  Leu Gln Val
    1790                 1795                 1800

Ala Val  Ala Ala Ala His Glu  Asp Asp Glu Gly Gly  Val Val Tyr
    1805                 1810                 1815

Leu Gly  Ala Gly Thr Phe Val  Leu Thr Gln Pro Leu  Ser Ile Ala
    1820                 1825                 1830

Gly Ser  Asn Val Val Ile Arg  Gly Ala Gly Glu Asp  Ala Thr Thr
    1835                 1840                 1845

Ile Phe  Val Pro Leu Pro Leu  Ser Asp Val Phe Pro  Gly Thr Trp
    1850                 1855                 1860

Ser Met  Asp Ala Ser Gly Lys  Val Thr Ser Pro Trp  Ile Thr Arg
    1865                 1870                 1875

Gly Gly  Phe Leu Ala Phe Ser  Gly Arg Arg Thr Lys  Ser Ser Asp
    1880                 1885                 1890

Ser Ser  Thr Leu Leu Ala Thr  Val Ala Gly Ser Val  Glu Gln Gly
    1895                 1900                 1905

Ala Ser  Val Ile Pro Val Asp  Ser Thr Ala Glu Phe  Arg Leu Gly
    1910                 1915                 1920

Gln Trp  Val Arg Ile Ile Ile  Asn Asp Ala Ser Thr  Asp Ala Ser
    1925                 1930                 1935

Ala Gly  Gly Gly Thr Leu Glu  Arg Gly Ser Ser Glu  Val Gln Glu
    1940                 1945                 1950

Ser Glu  Thr Met Ile Ala Glu  Gly Ala Thr Gly Gly  Gly Ala Gly
    1955                 1960                 1965

Val Arg  Ala Gln Trp Thr Gly  Val Leu His Ala Phe  Glu Pro Thr
    1970                 1975                 1980

Val Gln  Cys Ser Gly Val Glu  Gln Leu Thr Ile Arg  Phe Asn His
    1985                 1990                 1995

Ser Met  Met Ala Ala His Leu  Ala Glu Arg Gly Tyr  Asn Ala Ile
    2000                 2005                 2010

Glu Leu  Glu Asp Val Val Asp  Cys Trp Ile Arg Gln  Val Thr Ile
    2015                 2020                 2025

Leu Asn  Ala Asp Asn Ala Ile  Arg Leu Arg Gly Thr  Asp His Ser
    2030                 2035                 2040

Thr Leu  Ser Gly Gln Ala Cys  Ser Gly Gly Gly Val  Val Ala Val
    2045                 2050                 2055

Val Pro  Val Trp Cys Arg Arg  Gly Leu Pro Ser Pro  Ala Asp Val
    2060                 2065                 2070

Thr Val  Gly Val Thr Glu Leu  Arg Trp Glu Pro Asp  Thr Arg Glu
    2075                 2080                 2085

Val Asn  Gly His His Ala Ile  Thr Val Ser Lys Gly  His Ala Asn
    2090                 2095                 2100

Leu Val  Thr Arg Phe Arg Ile  Thr Ala Pro Phe Tyr  His Asp Ile
    2105                 2110                 2115

Ser Leu  Glu Gly Gly Ala Leu  Leu Asn Val Ile Ser  Ser Gly Gly
    2120                 2125                 2130

Gly Ala  Asn Leu Asn Leu Asp  Leu His Arg Ser Gly  Pro Trp Gly
    2135                 2140                 2145

Asn Leu  Phe Ser Gln Leu Gly  Met Gly Leu Ala Ala  Arg Pro Phe
    2150                 2155                 2160
```

```
Asp Ala  Gly Gly Arg Asp Gly  Arg Gly Ala His Ala  Gly Arg Gln
    2165                 2170                 2175

Asn Thr  Phe Trp Asn Leu Gln  Pro Gly Asp Val Ala  Ala Ala Ala
    2180                 2185                 2190

Pro Ala  Leu Gln Pro Ser Ala  Ala Ala Gly Asp Ala  Arg Arg Leu
    2195                 2200                 2205

Leu Val  Asp Gly Asp Ser Leu  Leu His Ala Gly Thr  Gly Gln Ala
    2210                 2215                 2220

Arg Leu  Leu Arg Gln Leu Glu  Ala Asp Asp Ser Ala  Glu Pro Leu
    2225                 2230                 2235

Leu Leu  Pro Ser Cys Glu Phe  Gly Pro Leu Leu Asn  Phe Val Gly
    2240                 2245                 2250

Gly Phe  Ala Gly Glu Leu Cys  Lys Ser Ser Gly Trp  Leu Val Ala
    2255                 2260                 2265

Gly Leu  Pro Asp Asp Arg Pro  Asp Leu His Ala Ser  Gln Val Thr
    2270                 2275                 2280

Ala Arg  Leu Gln His Gly Ala  Ala Asp Asn Lys Thr  His Ala
    2285                 2290                 2295


<210> SEQ ID NO 81
<211> LENGTH: 373
<212> TYPE: PRT
<213> ORGANISM: Synechococcus PCC7942
<220> FEATURE:
<221> NAME/KEY: MISC_FEATURE
<223> OTHER INFORMATION: PCC 7942

<400> SEQUENCE: 81

Met Asp Phe Leu Ser Asn Phe Leu Met Asp Phe Val Lys Gln Leu Gln
1               5                   10                  15

Ser Pro Thr Leu Ser Phe Leu Ile Gly Gly Met Val Ile Ala Ala Cys
            20                  25                  30

Gly Ser Gln Leu Gln Ile Pro Glu Ser Ile Cys Lys Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Val Leu Pro Ala Leu Phe Ser Val Ala Ile
65                  70                  75                  80

Gly Ile Leu Ile Val Phe Ile Ala Arg Tyr Thr Leu Ala Arg Met Pro
                85                  90                  95

Lys Val Lys Thr Val Asp Ala Ile Ala Thr Gly Gly Leu Phe Gly Ala
            100                 105                 110

Val Ser Gly Ser Thr Met Ala Ala Ala Leu Thr Leu Leu Glu Glu Gln
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Arg Lys Glu Ala Ala Phe Ala Ser Ala Gln Gly Ala Tyr
                165                 170                 175

Ser Lys Gln Pro Val Ala Ala Gly Asp Tyr Ser Ser Ser Ser Asp Tyr
            180                 185                 190

Pro Ser Ser Arg Arg Glu Tyr Ala Gln Gln Glu Ser Gly Asp His Arg
        195                 200                 205

Val Lys Ile Trp Pro Ile Val Glu Glu Ser Leu Gln Gly Pro Ala Leu
    210                 215                 220
```

```
Ser Ala Met Leu Leu Gly Val Ala Leu Gly Leu Phe Ala Arg Pro Glu
225                 230                 235                 240

Ser Val Tyr Glu Gly Phe Tyr Asp Pro Leu Phe Arg Gly Leu Leu Ser
                245                 250                 255

Ile Leu Met Leu Val Met Gly Met Glu Ala Trp Ser Arg Ile Ser Glu
            260                 265                 270

Leu Arg Lys Val Ala Gln Trp Tyr Val Val Tyr Ser Ile Val Ala Pro
        275                 280                 285

Leu Ala His Gly Phe Ile Ala Phe Gly Leu Gly Met Ile Ala His Tyr
    290                 295                 300

Ala Thr Gly Phe Ser Met Gly Gly Val Val Val Leu Ala Val Ile Ala
305                 310                 315                 320

Ala Ser Ser Ser Asp Ile Ser Gly Pro Pro Thr Leu Arg Ala Gly Ile
                325                 330                 335

Pro Ser Ala Asn Pro Ser Ala Tyr Ile Gly Ala Ser Thr Ala Ile Gly
            340                 345                 350

Thr Pro Val Ala Ile Gly Ile Ala Ile Pro Leu Phe Leu Gly Leu Ala
        355                 360                 365

Gln Thr Ile Gly Gly
    370


<210> SEQ ID NO 82
<211> LENGTH: 374
<212> TYPE: PRT
<213> ORGANISM: Synechocystis PCC6803

<400> SEQUENCE: 82

Met Asp Phe Leu Ser Asn Phe Leu Thr Asp Phe Val Gly Gln Leu Gln
1               5                   10                  15

Ser Pro Thr Leu Ala Phe Leu Ile Gly Gly Met Val Ile Ala Ala Leu
            20                  25                  30

Gly Thr Gln Leu Val Ile Pro Glu Ala Ile Ser Thr Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Leu Leu Pro Val Ala Phe Ser Val Ile Leu
65                  70                  75                  80

Gly Ile Leu Ile Val Phe Ile Ala Arg Phe Thr Leu Ala Lys Leu Pro
                85                  90                  95

Asn Val Arg Thr Val Asp Ala Leu Ala Thr Gly Gly Leu Phe Gly Ala
            100                 105                 110

Val Ser Gly Ser Thr Met Ala Ala Ala Leu Thr Thr Leu Glu Glu Ser
        115                 120                 125

Lys Ile Ser Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Arg Lys Arg Lys Ser Ala Ala Ala Ser Ile Glu Glu Ser Phe Ser
                165                 170                 175

Lys Gln Pro Val Ala Ala Gly Asp Tyr Gly Asp Gln Thr Asp Tyr Pro
            180                 185                 190

Arg Thr Arg Gln Glu Tyr Leu Ser Gln Gln Glu Pro Glu Asp Asn Arg
        195                 200                 205

Val Lys Ile Trp Pro Ile Ile Glu Glu Ser Leu Gln Gly Pro Ala Leu
```

```
    210                 215                 220

Ser Ala Met Leu Leu Gly Leu Ala Leu Gly Ile Phe Thr Lys Pro Glu
225                 230                 235                 240

Ser Val Tyr Glu Gly Phe Tyr Asp Pro Leu Phe Arg Gly Leu Leu Ser
                245                 250                 255

Ile Leu Met Leu Ile Met Gly Met Glu Ala Trp Ser Arg Ile Gly Glu
            260                 265                 270

Leu Arg Lys Val Ala Gln Trp Tyr Val Val Tyr Ser Leu Ile Ala Pro
        275                 280                 285

Ile Val His Gly Phe Ile Ala Phe Gly Leu Gly Met Ile Ala His Tyr
    290                 295                 300

Ala Thr Gly Phe Ser Leu Gly Gly Val Val Val Leu Ala Val Ile Ala
305                 310                 315                 320

Ala Ser Ser Ser Asp Ile Ser Gly Pro Pro Thr Leu Arg Ala Gly Ile
                325                 330                 335

Pro Ser Ala Asn Pro Ser Ala Tyr Ile Gly Ser Ser Thr Ala Ile Gly
            340                 345                 350

Thr Pro Ile Ala Ile Gly Val Cys Ile Pro Leu Phe Ile Gly Leu Ala
        355                 360                 365

Gln Thr Leu Gly Ala Gly
    370


<210> SEQ ID NO 83
<211> LENGTH: 370
<212> TYPE: PRT
<213> ORGANISM: Nostoc sp. PCC 7120 (Anabaena sp. PCC 7120)

<400> SEQUENCE: 83

Met Asp Phe Phe Ser Leu Phe Leu Met Asp Phe Val Lys Gln Leu Gln
1               5                   10                  15

Ser Pro Thr Leu Gly Phe Leu Ile Gly Gly Met Val Ile Ala Ala Leu
            20                  25                  30

Gly Ser Glu Leu Ile Ile Pro Glu Ala Ile Cys Gln Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Ala Ala Ser Ala Val Ala Val
65                  70                  75                  80

Gly Val Leu Val Val Phe Ile Ala Arg Tyr Thr Leu Ala Lys Leu Pro
                85                  90                  95

Lys Val Asn Thr Val Asp Ala Ile Ala Thr Gly Gly Leu Phe Gly Ala
            100                 105                 110

Val Ser Gly Ser Thr Met Ala Ala Ala Leu Thr Leu Leu Glu Glu Gln
        115                 120                 125

Lys Ile Gln Tyr Glu Ala Trp Ala Ala Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Arg Ser Ala Ala Gly Glu Tyr Leu Ser Lys Gln Ser Val
                165                 170                 175

Ala Ala Gly Glu Tyr Pro Asp Gln Gln Asp Tyr Pro Ser Ser Arg Gln
            180                 185                 190

Glu Tyr Leu Arg Lys Gln Gln Ser Ala Asp Asn Arg Val Lys Ile Trp
        195                 200                 205
```

```
Pro Ile Val Lys Glu Ser Leu Gln Gly Pro Ala Leu Ser Ala Met Leu
    210                 215                 220

Leu Gly Ile Ala Leu Gly Leu Phe Thr Gln Pro Glu Ser Val Tyr Lys
225                 230                 235                 240

Ser Phe Tyr Asp Pro Leu Phe Arg Gly Leu Leu Ser Ile Leu Met Leu
                245                 250                 255

Val Met Gly Met Glu Ala Trp Ser Arg Ile Gly Glu Leu Arg Lys Val
            260                 265                 270

Ala Gln Trp Tyr Val Val Tyr Ser Val Val Ala Pro Leu Val His Gly
        275                 280                 285

Phe Ile Ala Phe Gly Leu Gly Met Ile Ala His Tyr Ala Thr Gly Phe
    290                 295                 300

Ser Leu Gly Gly Val Val Ile Leu Ala Val Ile Ala Ala Ser Ser Ser
305                 310                 315                 320

Asp Ile Ser Gly Pro Pro Thr Leu Arg Ala Gly Ile Pro Ser Ala Asn
                325                 330                 335

Pro Ser Ala Tyr Ile Gly Ala Ser Thr Ala Ile Gly Thr Pro Ile Ala
            340                 345                 350

Ile Gly Leu Ala Ile Pro Leu Phe Leu Gly Leu Ala Gln Ala Ile Gly
        355                 360                 365

Gly Arg
    370


<210> SEQ ID NO 84
<211> LENGTH: 377
<212> TYPE: PRT
<213> ORGANISM: Cyanothece PCC 7425

<400> SEQUENCE: 84

Met Asp Phe Trp Ser Tyr Phe Leu Met Asp Phe Val Lys Gln Leu Gln
1               5                   10                  15

Ser Pro Thr Leu Gly Phe Leu Ile Gly Gly Met Val Ile Ala Ala Leu
            20                  25                  30

Gly Ser Gln Leu Val Ile Pro Glu Ala Ile Cys Gln Ile Ile Val Phe
        35                  40                  45

Met Leu Leu Thr Lys Ile Gly Leu Thr Gly Gly Met Ala Ile Arg Asn
    50                  55                  60

Ser Asn Leu Thr Glu Met Val Leu Pro Ala Ala Phe Ser Val Ile Ser
65                  70                  75                  80

Gly Ile Leu Ile Val Phe Ile Ala Arg Tyr Thr Leu Ala Lys Leu Pro
                85                  90                  95

Lys Val Arg Thr Val Asp Ala Ile Ala Thr Gly Gly Leu Phe Gly Ala
            100                 105                 110

Val Ser Gly Ser Thr Met Ala Ala Ala Leu Thr Leu Leu Glu Glu Glu
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Ile Ala Asn Ile Tyr Leu Asn
145                 150                 155                 160

Lys Lys Lys Arg Arg Ala Glu Ser Glu Ala Leu Ser Lys Gln Glu Tyr
                165                 170                 175

Leu Gly Lys Gln Ser Ile Val Ala Gly Asp Tyr Pro Ala Gln Gln Asp
            180                 185                 190

Tyr Pro Ser Thr Arg Gln Glu Tyr Leu Ser Lys Gln Gln Gly Pro Glu
        195                 200                 205
```

```
Asn Asn Arg Val Lys Ile Trp Pro Ile Val Gln Glu Ser Leu Gln Gly
    210                 215                 220

Pro Ala Leu Ser Ala Met Leu Leu Gly Val Ala Leu Gly Ile Leu Thr
225                 230                 235                 240

Lys Pro Glu Ser Val Tyr Glu Ser Phe Tyr Asp Pro Leu Phe Arg Gly
                245                 250                 255

Leu Leu Ser Ile Leu Met Leu Val Met Gly Met Glu Ala Trp Ser Arg
            260                 265                 270

Ile Gly Glu Leu Arg Lys Val Ala Gln Trp Tyr Val Val Tyr Ser Val
        275                 280                 285

Val Ala Pro Phe Val His Gly Leu Ile Ala Phe Gly Leu Gly Met Phe
    290                 295                 300

Ala His Tyr Thr Met Gly Phe Ser Met Gly Gly Val Val Val Leu Ala
305                 310                 315                 320

Val Ile Ala Ser Ser Ser Ser Asp Ile Ser Gly Pro Pro Thr Leu Arg
                325                 330                 335

Ala Gly Ile Pro Ser Ala Asn Pro Ser Ala Tyr Ile Gly Ala Ser Thr
            340                 345                 350

Ala Ile Gly Thr Pro Ile Ala Ile Gly Leu Cys Ile Pro Phe Phe Ile
        355                 360                 365

Gly Leu Ala Gln Thr Leu Gly Gly Gly
    370                 375


<210> SEQ ID NO 85
<211> LENGTH: 373
<212> TYPE: PRT
<213> ORGANISM: Microcystis aeruginosa

<400> SEQUENCE: 85

Met Asp Phe Phe Ser Leu Phe Val Met Asp Phe Ile Gln Gln Leu Gln
1               5                   10                  15

Ser Pro Thr Leu Ala Phe Leu Ile Gly Gly Met Ile Ile Ala Ala Leu
            20                  25                  30

Gly Ser Glu Leu Val Ile Pro Glu Ser Ile Cys Thr Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Met Ile Phe Ala Val Ile Val
65                  70                  75                  80

Gly Ile Ile Val Val Phe Val Ala Arg Tyr Thr Leu Ala Asn Leu Pro
                85                  90                  95

Lys Val Lys Val Val Asp Ala Ile Ala Thr Gly Gly Leu Phe Gly Ala
            100                 105                 110

Val Ser Gly Ser Thr Met Ala Ala Gly Leu Thr Val Leu Glu Glu Gln
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Gln Lys Glu Ala Ala Tyr Asp Gln Glu Ser Phe Ser Lys
                165                 170                 175

Gln Pro Val Ala Ala Gly Asn Tyr Ser Asp Gln Gln Asp Tyr Pro Ser
            180                 185                 190

Ser Arg Gln Glu Tyr Leu Ser Gln Gln Gln Pro Ala Asp Asn Arg Val
```

```
        195                 200                 205

Lys Ile Trp Pro Ile Ile Glu Glu Ser Leu Arg Gly Pro Ala Leu Ser
    210                 215                 220

Ala Met Leu Leu Gly Leu Ala Leu Gly Ile Phe Thr Gln Pro Glu Ser
225                 230                 235                 240

Val Tyr Lys Ser Phe Tyr Asp Pro Leu Phe Arg Gly Leu Leu Ser Val
                245                 250                 255

Leu Met Leu Val Met Gly Met Glu Ala Trp Ser Arg Val Gly Glu Leu
            260                 265                 270

Arg Lys Val Ala Gln Trp Tyr Val Val Tyr Ser Val Ile Ala Pro Phe
        275                 280                 285

Val His Gly Leu Ile Ala Phe Gly Leu Gly Met Ile Ala His Tyr Ala
    290                 295                 300

Thr Gly Phe Ser Trp Gly Gly Val Val Met Leu Ala Val Ile Ala Ser
305                 310                 315                 320

Ser Ser Ser Asp Ile Ser Gly Pro Pro Thr Leu Arg Ala Gly Ile Pro
                325                 330                 335

Ser Ala Asn Pro Ser Ala Tyr Ile Gly Ala Ser Thr Ala Ile Gly Thr
            340                 345                 350

Pro Val Ala Ile Gly Leu Cys Ile Pro Phe Phe Val Gly Leu Ala Gln
        355                 360                 365

Ala Leu Ser Gly Gly
    370


<210> SEQ ID NO 86
<211> LENGTH: 369
<212> TYPE: PRT
<213> ORGANISM: Anabaena variabilis

<400> SEQUENCE: 86

Met Asp Phe Val Ser Leu Phe Val Lys Asp Phe Ile Ala Gln Leu Gln
1               5                   10                  15

Ser Pro Thr Leu Ala Phe Leu Ile Gly Gly Met Ile Ile Ala Ala Leu
            20                  25                  30

Gly Ser Glu Leu Val Ile Pro Glu Ser Ile Cys Thr Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Met Ile Phe Ala Val Ile Thr
65                  70                  75                  80

Gly Ile Thr Ile Val Phe Ile Ser Arg Tyr Thr Leu Ala Lys Leu Pro
                85                  90                  95

Lys Val Lys Val Val Asp Ala Ile Ala Thr Gly Gly Leu Phe Gly Ala
            100                 105                 110

Val Ser Gly Ser Thr Met Ala Ala Gly Leu Thr Val Leu Glu Glu Gln
        115                 120                 125

Lys Met Ala Tyr Glu Ala Trp Ala Gly Ala Leu Tyr Pro Phe Met Asp
    130                 135                 140

Ile Pro Ala Leu Val Thr Ala Ile Val Ile Ala Asn Ile Tyr Leu Asn
145                 150                 155                 160

Lys Lys Lys Arg Lys Glu Ala Val Tyr Ser Thr Glu Gln Pro Val Ala
                165                 170                 175

Ala Gly Asp Tyr Pro Asp Gln Lys Asp Tyr Pro Ser Ser Arg Gln Glu
            180                 185                 190
```

```
Tyr Leu Ser Gln Gln Lys Gly Asp Glu Asp Asn Arg Val Lys Ile Trp
        195                 200                 205

Pro Ile Ile Glu Glu Ser Leu Arg Gly Pro Ala Leu Ser Ala Met Leu
    210                 215                 220

Leu Gly Leu Ala Leu Gly Leu Phe Thr Gln Pro Glu Ser Val Tyr Lys
225                 230                 235                 240

Ser Phe Tyr Asp Pro Ala Phe Arg Gly Leu Leu Ser Ile Leu Met Leu
                245                 250                 255

Val Met Gly Met Glu Ala Trp Ser Arg Ile Gly Glu Leu Arg Lys Val
            260                 265                 270

Ala Gln Trp Tyr Val Val Tyr Ser Val Val Ala Pro Phe Val His Gly
        275                 280                 285

Leu Ile Ala Phe Gly Leu Gly Met Ile Ala His Tyr Thr Met Asn Phe
    290                 295                 300

Ser Met Gly Gly Val Val Ile Leu Ala Val Ile Ala Ser Ser Ser Ser
305                 310                 315                 320

Asp Ile Ser Gly Pro Pro Thr Leu Arg Ala Gly Ile Pro Ser Ala Asn
                325                 330                 335

Pro Ser Ala Tyr Ile Gly Ala Ser Thr Ala Val Gly Thr Pro Val Ala
            340                 345                 350

Ile Gly Leu Cys Ile Pro Phe Phe Leu Gly Leu Ala Gln Ala Ile Gly
        355                 360                 365

Gly


<210> SEQ ID NO 87
<211> LENGTH: 366
<212> TYPE: PRT
<213> ORGANISM: Cyanothece

<400> SEQUENCE: 87

Met Asp Phe Leu Ser Leu Phe Val Lys Asp Phe Ile Ile Gln Leu Gln
1               5                   10                  15

Ser Pro Thr Leu Ala Phe Leu Ile Gly Gly Met Val Ile Ala Ala Leu
            20                  25                  30

Gly Ser Glu Leu Val Ile Pro Glu Ser Ile Cys Thr Ile Ile Val Phe
        35                  40                  45

Met Leu Leu Thr Lys Ile Gly Leu Thr Gly Gly Ile Ala Ile Arg Asn
    50                  55                  60

Ser Asn Leu Thr Glu Met Val Leu Pro Met Ile Cys Ala Val Ile Val
65                  70                  75                  80

Gly Ile Val Val Val Phe Ile Ala Arg Tyr Thr Leu Ala Lys Leu Pro
                85                  90                  95

Lys Val Asn Val Val Asp Ala Ile Ala Thr Gly Gly Leu Phe Gly Ala
            100                 105                 110

Val Ser Gly Ser Thr Met Ala Ala Gly Leu Thr Val Leu Glu Glu Gln
        115                 120                 125

Lys Ile Pro Tyr Glu Ala Trp Ala Gly Ala Leu Tyr Pro Phe Met Asp
    130                 135                 140

Ile Pro Ala Leu Val Thr Ala Ile Val Val Ala Asn Ile Tyr Leu Asn
145                 150                 155                 160

Lys Lys Lys Arg Lys Ala Thr Val Met Gln Glu Ser Leu Ser Lys Gln
                165                 170                 175

Pro Val Ala Ala Gly Asp Tyr Pro Ser Ser Arg Gln Glu Tyr Val Ser
            180                 185                 190
```

```
Gln Gln Gln Pro Glu Asp Asn Arg Val Lys Ile Trp Pro Ile Ile Glu
        195                 200                 205

Glu Ser Leu Arg Gly Pro Ala Leu Ser Ala Met Leu Leu Gly Leu Ala
    210                 215                 220

Leu Gly Ile Leu Thr Gln Pro Glu Ser Val Tyr Lys Gly Phe Tyr Asp
225                 230                 235                 240

Pro Pro Phe Arg Gly Leu Leu Ser Ile Leu Met Leu Val Met Gly Met
                245                 250                 255

Glu Ala Trp Ser Arg Ile Gly Glu Leu Arg Lys Val Ala Gln Trp Tyr
            260                 265                 270

Val Val Tyr Ser Val Ala Ala Pro Phe Ile His Gly Leu Leu Ala Phe
        275                 280                 285

Gly Leu Gly Met Ile Ala His Tyr Thr Met Gly Phe Ser Met Gly Gly
    290                 295                 300

Val Val Ile Leu Ala Val Ile Ala Ser Ser Ser Ser Asp Ile Ser Gly
305                 310                 315                 320

Pro Pro Thr Leu Arg Ala Gly Ile Pro Ser Ala Asn Pro Ser Ala Tyr
                325                 330                 335

Ile Gly Ala Ser Thr Ala Ile Gly Thr Pro Val Ala Ile Gly Leu Cys
            340                 345                 350

Ile Pro Phe Phe Val Gly Leu Ala Gln Ala Ile Gly Gly Phe
        355                 360                 365


<210> SEQ ID NO 88
<211> LENGTH: 378
<212> TYPE: PRT
<213> ORGANISM: Arthrospira platensis str. Paraca

<400> SEQUENCE: 88

Met Asp Phe Leu Ser Gly Phe Leu Thr Arg Phe Leu Ala Gln Leu Gln
1               5                   10                  15

Ser Pro Thr Leu Gly Phe Leu Ile Gly Gly Met Val Ile Ala Ala Val
            20                  25                  30

Asn Ser Gln Leu Gln Ile Pro Asp Ala Ile Tyr Lys Phe Val Val Phe
        35                  40                  45

Met Leu Leu Met Lys Val Gly Leu Ser Gly Gly Ile Ala Ile Arg Gly
    50                  55                  60

Ser Asn Leu Thr Glu Met Leu Leu Pro Ala Val Phe Ala Leu Val Thr
65                  70                  75                  80

Gly Ile Val Ile Val Phe Ile Gly Arg Tyr Thr Leu Ala Lys Leu Pro
                85                  90                  95

Asn Val Lys Thr Val Asp Ala Ile Ala Thr Ala Gly Leu Phe Gly Ala
            100                 105                 110

Val Ser Gly Ser Thr Met Ala Ala Ala Leu Thr Leu Leu Glu Glu Gln
        115                 120                 125

Gly Met Glu Tyr Glu Ala Trp Ala Ala Ala Leu Tyr Pro Phe Met Asp
    130                 135                 140

Ile Pro Ala Leu Val Ser Ala Ile Val Leu Ala Ser Ile Tyr Val Ser
145                 150                 155                 160

Lys Gln Lys His Ser Asp Met Ala Asp Glu Ser Leu Ser Lys His Glu
                165                 170                 175

Ser Leu Ser Lys Gln Pro Val Ala Ala Gly Asp Tyr Pro Ser Lys Pro
            180                 185                 190

Glu Tyr Pro Thr Thr Arg Gln Glu Tyr Leu Ser Gln Gln Arg Gly Ser
        195                 200                 205
```

```
Ala Asn Gln Gly Val Glu Ile Trp Pro Ile Ile Lys Glu Ser Leu Gln
    210                 215                 220

Gly Ser Ala Leu Ser Ala Leu Leu Leu Gly Leu Ala Leu Gly Leu Leu
225                 230                 235                 240

Thr Arg Pro Glu Ser Val Phe Gln Ser Phe Tyr Glu Pro Leu Phe Arg
                245                 250                 255

Gly Leu Leu Ser Ile Leu Met Leu Val Met Gly Met Glu Ala Thr Ala
            260                 265                 270

Arg Leu Gly Glu Leu Arg Lys Val Ala Gln Trp Tyr Ala Val Tyr Ala
        275                 280                 285

Phe Ile Ala Pro Leu Leu His Gly Leu Ile Ala Phe Gly Leu Gly Met
    290                 295                 300

Ile Ala His Val Val Thr Gly Phe Ser Leu Gly Gly Val Val Ile Leu
305                 310                 315                 320

Ala Val Ile Ala Ser Ser Ser Ser Asp Ile Ser Gly Pro Pro Thr Leu
                325                 330                 335

Arg Ala Gly Ile Pro Ser Ala Asn Pro Ser Ala Tyr Ile Gly Ser Ser
            340                 345                 350

Thr Ala Val Gly Thr Pro Val Ala Ile Ala Leu Gly Ile Pro Leu Tyr
        355                 360                 365

Ile Gly Leu Ala Gln Ala Leu Met Gly Gly
    370                 375


<210> SEQ ID NO 89
<211> LENGTH: 336
<212> TYPE: PRT
<213> ORGANISM: Chlamydomonas reinhardtii

<400> SEQUENCE: 89

Met Gln Thr Thr Met Thr Arg Pro Cys Leu Ala Gln Pro Val Leu Arg
1               5                   10                  15

Ser Arg Val Leu Arg Ser Pro Met Arg Val Val Ala Ala Ser Ala Pro
            20                  25                  30

Thr Ala Val Thr Thr Val Val Thr Ser Asn Gly Asn Gly Asn Gly His
        35                  40                  45

Phe Gln Ala Ala Thr Thr Pro Val Pro Pro Thr Pro Ala Pro Val Ala
    50                  55                  60

Val Ser Ala Pro Val Arg Ala Val Ser Val Leu Thr Pro Pro Gln Val
65                  70                  75                  80

Tyr Glu Asn Ala Ile Asn Val Gly Ala Tyr Lys Ala Gly Leu Thr Pro
                85                  90                  95

Leu Ala Thr Phe Val Gln Gly Ile Gln Ala Gly Ala Tyr Ile Ala Phe
            100                 105                 110

Gly Ala Phe Leu Ala Ile Ser Val Gly Gly Asn Ile Pro Gly Val Ala
        115                 120                 125

Ala Ala Asn Pro Gly Leu Ala Lys Leu Leu Phe Ala Leu Val Phe Pro
    130                 135                 140

Val Gly Leu Ser Met Val Thr Asn Cys Gly Ala Glu Leu Phe Thr Gly
145                 150                 155                 160

Asn Thr Met Met Leu Thr Cys Ala Leu Ile Glu Lys Lys Ala Thr Trp
                165                 170                 175

Gly Gln Leu Leu Lys Asn Trp Ser Val Ser Tyr Phe Gly Asn Phe Val
            180                 185                 190

Gly Ser Ile Ala Met Val Ala Ala Val Val Ala Thr Gly Cys Leu Thr
```

```
        195                 200                 205

Thr Asn Thr Leu Pro Val Gln Met Ala Thr Leu Lys Ala Asn Leu Gly
    210                 215                 220

Phe Thr Glu Val Leu Ser Arg Ser Ile Leu Cys Asn Trp Leu Val Cys
225                 230                 235                 240

Cys Ala Val Trp Ser Ala Ser Ala Ala Thr Ser Leu Pro Gly Arg Ile
                245                 250                 255

Leu Ala Leu Trp Pro Cys Ile Thr Ala Phe Val Ala Ile Gly Leu Glu
            260                 265                 270

His Ser Val Ala Asn Met Phe Val Ile Pro Leu Gly Met Met Leu Gly
        275                 280                 285

Ala Glu Val Thr Trp Ser Gln Phe Phe Phe Asn Asn Leu Ile Pro Val
    290                 295                 300

Thr Leu Gly Asn Thr Ile Ala Gly Val Leu Met Met Ala Ile Ala Tyr
305                 310                 315                 320

Ser Ile Ser Phe Gly Ser Leu Gly Lys Ser Ala Lys Pro Ala Thr Ala
                325                 330                 335


<210> SEQ ID NO 90
<211> LENGTH: 337
<212> TYPE: PRT
<213> ORGANISM: Volvox carteri
<220> FEATURE:
<221> NAME/KEY: MISC_FEATURE
<223> OTHER INFORMATION: f. nagariensis

<400> SEQUENCE: 90

Met Gln Thr Thr Met Ser Val Thr Arg Pro Cys Val Gly Leu Arg Pro
1               5                   10                  15

Leu Pro Val Arg Asn Val Arg Ser Leu Ile Arg Ala Gln Ala Ala Pro
            20                  25                  30

Gln Gln Val Ser Thr Ala Val Ser Thr Asn Gly Asn Gly Asn Gly Val
        35                  40                  45

Ala Ala Ala Ser Leu Ser Val Pro Ala Pro Val Ala Ala Pro Ala Gln
    50                  55                  60

Ala Val Ser Thr Pro Val Arg Ala Val Ser Val Leu Thr Pro Pro Gln
65                  70                  75                  80

Val Tyr Glu Asn Ala Ala Asn Val Gly Ala Tyr Lys Ala Ser Leu Gly
                85                  90                  95

Val Leu Ala Thr Phe Val Gln Gly Ile Gln Ala Gly Ala Tyr Ile Ala
            100                 105                 110

Phe Gly Ala Phe Leu Ala Cys Ser Val Gly Gly Asn Ile Pro Gly Ile
        115                 120                 125

Thr Ala Ser Asn Pro Gly Leu Ala Lys Leu Leu Phe Ala Leu Val Phe
    130                 135                 140

Pro Val Gly Leu Ser Met Val Thr Asn Cys Gly Ala Glu Leu Tyr Thr
145                 150                 155                 160

Gly Asn Thr Met Met Leu Thr Cys Ala Ile Phe Glu Lys Lys Ala Thr
                165                 170                 175

Trp Ala Gln Leu Val Lys Asn Trp Val Val Ser Tyr Ala Gly Asn Phe
            180                 185                 190

Val Gly Ser Ile Ala Met Val Ala Ala Val Val Ala Thr Gly Leu Met
        195                 200                 205

Ala Ser Asn Gln Leu Pro Val Asn Met Ala Thr Ala Lys Ser Ser Leu
    210                 215                 220
```

```
Gly Phe Thr Glu Val Leu Ser Arg Ser Ile Leu Cys Asn Trp Leu Val
225                 230                 235                 240

Cys Cys Ala Val Trp Ser Ala Ser Ala Ala Thr Ser Leu Pro Gly Arg
                245                 250                 255

Ile Leu Gly Leu Trp Pro Pro Ile Thr Ala Phe Val Ala Ile Gly Leu
            260                 265                 270

Glu His Ser Val Ala Asn Met Phe Val Ile Pro Leu Gly Met Met Leu
        275                 280                 285

Gly Ala Asp Val Thr Trp Ser Gln Phe Phe Phe Asn Asn Leu Val Pro
    290                 295                 300

Val Thr Leu Gly Asn Thr Ile Ala Gly Val Val Met Met Ala Val Ala
305                 310                 315                 320

Tyr Ser Val Ser Tyr Gly Ser Leu Gly Lys Thr Pro Lys Pro Ala Thr
                325                 330                 335

Ala
```

<210> SEQ ID NO 91
<211> LENGTH: 3249
<212> TYPE: DNA
<213> ORGANISM: Engineered construct (codon optimized gene)

<400> SEQUENCE: 91

```
atgctgcccg gcctgggcgt catcctgctg gtgctgccca tgcagtacta cttcggctac     60

aagatcgtgc agatcaagct gcagaacgcc aagcacgtcg ccctgcgctc cgccatcatg    120

caggaggtgc tgcccgccat caagctggtc aagtactacg cctgggagca gttctttgag    180

aaccagatca gcaaggtccg ccgcgaggag atccgcctca acttctggaa ctgcgtgatg    240

aaggtcatca acgtggcctg cgtgttctgc gtgccgccca tgaccgcctt cgtcatcttc    300

accacctacg agttccagcg cgcccgcctg gtgtccagcg tcgccttcac caccctgtcg    360

ctgttcaaca ttctgcgctt cccccctggtc gtgctgccca aggccctgcg tgccgtgtcc    420

gaggccaacg cgtctctcca gcgcctggag gcctacctgc tggaggaggt gccctcgggc    480

actgccgccg tcaagacccc caagaacgct ccccccggcg ccgtcatcga gaacggtgtg    540

ttccaccacc cctccaaccc caactggcac ctgcacgtgc ccaagttcga ggtcaagccc    600

ggccaggtcg ttgctgtggt gggccgcatc gccgccggca agtcgtccct ggtgcaggcc    660

atcctcggca acatggtcaa ggagcacggc agcttcaacg tgggcggccg catctcctac    720

gtgccgcaga acccctggct gcagaacctg tccctgcgtg acaacgtgct gtttggcgag    780

cagttcgatg agaacaagta caccgacgtc atcgagtcct gcgccctgac cctggacctg    840

cagatcctgt ccaacggtga ccagtccaag gccggcatcc gcggtgtcaa cttctccggt    900

ggccagcgcc agcgcgtgaa cctggcccgc tgcgcctacg ccgacgccga cctggtgctg    960

ctcgacaacg ccctgtccgc cgtggaccac cacaccgccc accacatctt cgacaagtgc   1020

atcaagggcc tgttctccga caaggccgtg gtgctggtca cccaccagat cgagttcatg   1080

ccccgctgcg acaacgtggc catcatggac gagggccgct gcctgtactt cggcaagtgg   1140

aacgaggagg cccagcacct gctcggcaag ctgctgccca tcacccacct gctgcacgcc   1200

gccggctccc aggaggctcc ccccgccccc aagaagaagg ccgaggacaa ggccggcccc   1260

cagaagtcgc agtcgctgca gctgaccctg gcccccacct ccatcggcaa gcccaccgag   1320

aagcccaagg acgtccagaa gctgactgcc taccaggccg ccctcatcta cacctggtac   1380

ggcaacctgt tcctggttgg cgtgtgcttc ttcttcttcc tggcggctca gtgctctcgc   1440
```

cagatctccg atttctgggt gcgctggtgg gtgaacgacg agtacaagaa gttccccgtg 1500
aagggcgagc aggactcggc cgccaccacc ttctactgcc tcatctacct gctgctggtg 1560
ggcctgttct acatcttcat gatcttccgc ggcgccactt tcctgtggtg ggtgctcaag 1620
tcctcggaga ccatccgcag gaaggccctg cacaacgtcc tcaacgcgcc catgggcttc 1680
ttcctggtca cgccggtcgg cgacctgctg ctcaacttca ccaaggacca ggacattatg 1740
gatgagaacc tgcccgatgc cgttcacttc atgggcatct acggcctgat tctgctggcg 1800
accaccatca ccgtgtccgt caccatcaac ttcttcgccg ccttcaccgg cgcgctgatc 1860
atcatgaccc tcatcatgct ctccatctac ctgcccgccg ccactgccct gaagaaggcg 1920
cgcgccgtgt ctggcggcat gctggtcggc ctggttgccg aggttctgga gggccttggc 1980
gtggttcagg ccttcaacaa gcaggagtac ttcattgagg aggccgcccg ccgcaccaac 2040
atcaccaact ccgccgtctt caacgccgag gcgctgaacc tgtggctggc tttctggtgc 2100
gacttcatcg gcgcctgcct ggtgggcgtg gtgtccgcct tcgccgtggg catggccaag 2160
gacctgggcg gcgcgaccgt cggcctggcc ttctccaaca tcattcagat gcttgtgttc 2220
tacacctggg tggtccgctt catctccgag tccatctccc tcttcaactc cgtcgagggc 2280
atggcctacc tcgccgacta cgtgccccac gatggtgtct tctatgacca gcgccagaag 2340
gacggcgtcg ccaagcaaat cgtcctgccc gacggcaaca tcgtgcccgc cgcctccaag 2400
gtccaggtcg tggttgacga cgccgccctc gcccgctggc ctgccaccgg caacatccgc 2460
ttcgaggacg tgtggatgca gtaccgcctg gacgctcctt gggctctgaa gggcgtcacc 2520
ttcaagatca acgacggcga gaaggtcggc gccgtgggcc gcaccggctc cggcaagtcc 2580
accacgctgc tggcgctgta ccgcatgttc gagctgggca agggccgcat cctggtcgac 2640
ggcgtggaca tcgccaccct gtcgctcaag cgcctgcgca ccggcctgtc catcattccc 2700
caggagcccg tcatgttcac cggcaccgtg cgctccaacc tggacccctt cggcgagttc 2760
aaggacgatg ccattctgtg ggaggtgctg aagaaggtcg gcctcgagga ccaggcgcag 2820
cacgccggcg gcctggacgg ccaggtcgat ggcaccggcg gcaaggcctg gtctctgggc 2880
cagatgcagc tggtgtgcct ggctcgcgcc gccctgcgcg ccgtgcccat cctgtgcctg 2940
gacgaggcta ccgccgccat ggacccgcac actgaggcca tcgtgcagca gaccatcaag 3000
aaggtgttcg acgaccgcac caccatcacc attgcccacc gcctggacac catcatcgag 3060
tccgacaaga tcatcgtgat ggagcagggc tcgctgatgg agtacgagtc gccctcgaag 3120
ctgctcgcca accgcgactc catgttctcc aagctggtcg acaagaccgg ccccgccgcc 3180
gccgctgcgc tgcgcaagat ggccgaggac ttctggtcca ctcgctccgc gcagggccgc 3240
aaccagtaa 3249

<210> SEQ ID NO 92
<211> LENGTH: 1008
<212> TYPE: DNA
<213> ORGANISM: Engineered construct (codon optimized gene)

<400> SEQUENCE: 92
atgcagacca ctatgactcg cccttgcctt gcccagcccg tgctgcgatc tcgtgtgctc 60
cggtcgccta tgcgggtggt tgcagcgagc gctcctaccg cggtgacgac agtcgtgacc 120
tcgaatggaa atggcaacgg tcatttccaa gctgctacta cgcccgtgcc ccctactccc 180
gctcccgtcg ctgtttccgc gcctgtgcgc gctgtgtcgg tgctgactcc tcctcaagtg 240
tatgagaacg ccattaatgt tggcgcctac aaggccgggc taacgcctct ggcaacgttt 300
gtccagggca tccaagccgg tgcctacatt gcgttcggcg ccttcctcgc catctccgtg 360
ggaggcaaca tccccggcgt cgccgccgcc aaccccggcc tggccaagct gctatttgct 420
ctggtgttcc ccgtgggtct gtccatggtg accaactgcg gcgccgagct gttcacgggc 480
aacaccatga tgctcacatg cgcgctcatc gagaagaagg ccacttgggg gcagcttctg 540
aagaactgga gcgtgtccta cttcggcaac ttcgtgggct ccatcgccat ggtcgccgcc 600
gtggtggcca ccggctgcct gaccaccaac accctgcctg tgcagatggc caccctcaag 660
gccaacctgg gcttcaccga ggtgctgtcg cgctccatcc tgtgcaactg gctggtgtgc 720
tgcgccgtgt ggtccgcctc cgccgccacc tcgctgcccg gccgcatcct ggcgctgtgg 780
ccctgcatca ccgccttcgt ggccatcggc ctggagcact ccgtcgccaa catgttcgtg 840
attcctctgg gcatgatgct gggcgctgag gtcacgtgga gccagttctt tttcaacaac 900
ctgatccccg tcaccctggg caacaccatt gctggcgttc tcatgatggc catcgcctac 960
tccatctcgt tcggctccct cggcaagtcc gccaagcccg ccaccgcg 1008

<210> SEQ ID NO 93
<211> LENGTH: 148
<212> TYPE: PRT
<213> ORGANISM: Arabidopsis thaliana
<220> FEATURE:
<221> NAME/KEY: MISC_FEATURE
<223> OTHER INFORMATION: Ferredoxin1

<400> SEQUENCE: 93

Met Ala Ser Thr Ala Leu Ser Ser Ala Ile Val Ser Thr Ser Phe Leu
1               5                   10                  15

Arg Arg Gln Gln Thr Pro Ile Ser Leu Arg Ser Leu Pro Phe Ala Asn
            20                  25                  30

Thr Gln Ser Leu Phe Gly Leu Lys Ser Ser Thr Ala Arg Gly Gly Arg
        35                  40                  45

Val Thr Ala Met Ala Thr Tyr Lys Val Lys Phe Ile Thr Pro Glu Gly
    50                  55                  60

Glu Gln Glu Val Glu Cys Glu Glu Asp Val Tyr Val Leu Asp Ala Ala
65                  70                  75                  80

Glu Glu Ala Gly Leu Asp Leu Pro Tyr Ser Cys Arg Ala Gly Ser Cys
                85                  90                  95

Ser Ser Cys Ala Gly Lys Val Val Ser Gly Ser Ile Asp Gln Ser Asp
            100                 105                 110

Gln Ser Phe Leu Asp Asp Glu Gln Met Ser Glu Gly Tyr Val Leu Thr
        115                 120                 125

Cys Val Ala Tyr Pro Thr Ser Asp Val Val Ile Glu Thr His Lys Glu
    130                 135                 140

Glu Ala Ile Met
145

<210> SEQ ID NO 94
<211> LENGTH: 783
<212> TYPE: DNA
<213> ORGANISM: Homo sapiens

<400> SEQUENCE: 94
atgtcccatc actgggggta cggcaaacac aacggacctg agcactggca taaggacttc 60
cccattgcca agggagagcg ccagtcccct gttgacatcg acactcatac agccaagtat 120
gacccttccc tgaagcccct gtctgtttcc tatgatcaag caacttccct gaggatcctc 180

```
aacaatggtc atgctttcaa cgtggagttt gatgactctc aggacaaagc agtgctcaag    240

ggaggacccc tggatggcac ttacagattg attcagtttc actttcactg ggttcactt    300

gatggacaag gttcagagca tactgtggat aaaaagaaat atgctgcaga acttcacttg    360

gttcactgga acaccaaata tggggatttt gggaaagctg tgcagcaacc tgatggactg    420

gccgttctag gtatttttt gaaggttggc agcgctaaac cgggccttca gaaagttgtt    480

gatgtgctgg attccattaa aacaaagggc aagagtgctg acttcactaa cttcgatcct    540

cgtggcctcc ttcctgaatc cttggattac tggacctacc caggctcact gaccacccct    600

cctcttctgg aatgtgtgac ctggattgtg ctcaaggaac ccatcagcgt cagcagcgag    660

caggtgttga aattccgtaa acttaacttc aatggggagg gtgaacccga agaactgatg    720

gtggacaact ggcgcccagc tcagccactg aagaacaggc aaatcaaagc ttccttcaaa    780

taa                                                                  783
```

```
<210> SEQ ID NO 95
<211> LENGTH: 148
<212> TYPE: PRT
<213> ORGANISM: Arabidopsis thaliana
<220> FEATURE:
<221> NAME/KEY: MISC_FEATURE
<223> OTHER INFORMATION: Ferredoxin2(thale cress)

<400> SEQUENCE: 95

Met Ala Ser Thr Ala Leu Ser Ser Ala Ile Val Gly Thr Ser Phe Ile
1               5                   10                  15

Arg Arg Ser Pro Ala Pro Ile Ser Leu Arg Ser Leu Pro Ser Ala Asn
            20                  25                  30

Thr Gln Ser Leu Phe Gly Leu Lys Ser Gly Thr Ala Arg Gly Gly Arg
        35                  40                  45

Val Thr Ala Met Ala Thr Tyr Lys Val Lys Phe Ile Thr Pro Glu Gly
    50                  55                  60

Glu Leu Glu Val Glu Cys Asp Asp Asp Val Tyr Val Leu Asp Ala Ala
65                  70                  75                  80

Glu Glu Ala Gly Ile Asp Leu Pro Tyr Ser Cys Arg Ala Gly Ser Cys
                85                  90                  95

Ser Ser Cys Ala Gly Lys Val Val Ser Gly Ser Val Asp Gln Ser Asp
            100                 105                 110

Gln Ser Phe Leu Asp Asp Glu Gln Ile Gly Glu Gly Phe Val Leu Thr
        115                 120                 125

Cys Ala Ala Tyr Pro Thr Ser Asp Val Thr Ile Glu Thr His Lys Glu
    130                 135                 140

Glu Asp Ile Val
145


<210> SEQ ID NO 96
<211> LENGTH: 253
<212> TYPE: PRT
<213> ORGANISM: Arabidopsis thaliana (thale cress)
<220> FEATURE:
<221> NAME/KEY: MISC_FEATURE
<223> OTHER INFORMATION: ferredoxin-NADP(+)oxidoreductase(FNR1)

<400> SEQUENCE: 96

Phe Thr Thr Glu Gly Glu Val Pro Tyr Arg Glu Gly Gln Ser Ile Gly
1               5                   10                  15

Val Ile Pro Glu Gly Ile Asp Lys Asn Gly Lys Pro His Lys Leu Arg
```

```
            20                  25                  30

Leu Tyr Ser Ile Ala Ser Ser Ala Ile Gly Asp Phe Gly Asp Ser Lys
        35                  40                  45

Thr Val Ser Leu Cys Val Lys Arg Leu Val Tyr Thr Asn Asp Gly Gly
    50                  55                  60

Glu Ile Val Lys Gly Val Cys Ser Asn Phe Leu Cys Asp Leu Lys Pro
65                  70                  75                  80

Gly Asp Glu Ala Lys Ile Thr Gly Pro Val Gly Lys Glu Met Leu Met
                85                  90                  95

Pro Lys Asp Pro Asn Ala Thr Ile Ile Met Leu Gly Thr Gly Thr Gly
            100                 105                 110

Ile Ala Pro Phe Arg Ser Phe Leu Trp Lys Met Phe Phe Glu Glu His
        115                 120                 125

Glu Asp Tyr Lys Phe Asn Gly Leu Ala Trp Leu Phe Leu Gly Val Pro
    130                 135                 140

Thr Ser Ser Ser Leu Leu Tyr Lys Glu Glu Phe Glu Lys Met Lys Glu
145                 150                 155                 160

Lys Asn Pro Asp Asn Phe Arg Leu Asp Phe Ala Val Ser Arg Glu Gln
                165                 170                 175

Thr Asn Glu Lys Gly Glu Lys Met Tyr Ile Gln Thr Arg Met Ala Glu
            180                 185                 190

Tyr Ala Glu Glu Leu Trp Glu Leu Leu Lys Lys Asp Asn Thr Phe Val
        195                 200                 205

Tyr Met Cys Gly Leu Lys Gly Met Glu Lys Gly Ile Asp Asp Ile Met
    210                 215                 220

Val Ser Leu Ala Ala Lys Asp Gly Ile Asp Trp Leu Glu Tyr Lys Lys
225                 230                 235                 240

Gln Leu Lys Arg Ser Glu Gln Trp Asn Val Glu Val Tyr
                245                 250


<210> SEQ ID NO 97
<211> LENGTH: 294
<212> TYPE: PRT
<213> ORGANISM: Arabidopsis thaliana (thale cress)
<220> FEATURE:
<221> NAME/KEY: MISC_FEATURE
<223> OTHER INFORMATION: ferredoxin-NADP(+)oxidoreductase(FNR2)

<400> SEQUENCE: 97

Met Ala Thr Thr Met Asn Ala Ala Val Ser Leu Thr Ser Ser Asn Ser
1               5                   10                  15

Ser Ser Phe Pro Ala Thr Ser Cys Ala Ile Ala Pro Glu Arg Ile Arg
            20                  25                  30

Phe Thr Lys Gly Ala Phe Tyr Tyr Lys Ser Asn Asn Val Val Thr Gly
        35                  40                  45

Lys Arg Val Phe Ser Ile Lys Ala Gln Ile Thr Thr Glu Thr Asp Thr
    50                  55                  60

Pro Thr Pro Ala Lys Lys Val Glu Lys Val Ser Lys Lys Asn Glu Glu
65                  70                  75                  80

Gly Val Ile Val Asn Arg Tyr Arg Pro Lys Glu Pro Tyr Thr Gly Lys
                85                  90                  95

Cys Leu Leu Asn Thr Lys Ile Thr Ala Asp Asp Ala Pro Gly Glu Thr
            100                 105                 110

Trp His Met Val Phe Ser His Gln Gly Glu Ile Pro Tyr Arg Glu Gly
        115                 120                 125
```

```
Gln Ser Val Gly Val Ile Ala Asp Gly Ile Asp Lys Asn Gly Lys Pro
    130                 135                 140

His Lys Val Arg Leu Tyr Ser Ile Ala Ser Ser Ala Leu Gly Asp Leu
145                 150                 155                 160

Gly Asn Ser Glu Thr Val Ser Leu Cys Val Lys Arg Leu Val Tyr Thr
                165                 170                 175

Asn Asp Gln Gly Glu Thr Val Lys Gly Val Cys Ser Asn Phe Leu Cys
            180                 185                 190

Asp Leu Ala Pro Gly Ser Asp Val Lys Leu Thr Gly Pro Val Gly Lys
        195                 200                 205

Glu Met Leu Met Pro Lys Asp Pro Asn Ala Thr Val Ile Met Leu Ala
    210                 215                 220

Thr Gly Thr Gly Ile Ala Pro Phe Arg Ser Phe Leu Trp Lys Met Phe
225                 230                 235                 240

Phe Glu Lys His Asp Asp Tyr Lys Phe Asn Gly Leu Ala Trp Leu Phe
                245                 250                 255

Leu Gly Val Pro Thr Thr Ser Ser Leu Leu Tyr Gln Glu Glu Phe Asp
            260                 265                 270

Lys Met Lys Ala Lys Ala Pro Glu Asn Phe Arg Val Asp Tyr Ala Ile
        275                 280                 285

Ser Arg Glu Gln Ala Asn
    290


<210> SEQ ID NO 98
<211> LENGTH: 249
<212> TYPE: PRT
<213> ORGANISM: Proteobacteria

<400> SEQUENCE: 98

Met Lys Leu Leu Leu Ile Leu Gly Ser Val Ile Ala Leu Pro Thr Phe
1               5                   10                  15

Ala Ala Gly Gly Gly Asp Leu Asp Ala Ser Asp Tyr Thr Gly Val Ser
            20                  25                  30

Phe Trp Leu Val Thr Ala Ala Leu Leu Ala Ser Thr Val Phe Phe Phe
        35                  40                  45

Val Glu Arg Asp Arg Val Ser Ala Lys Trp Lys Thr Ser Leu Thr Val
    50                  55                  60

Ser Gly Leu Val Thr Gly Ile Ala Phe Trp His Tyr Met Tyr Met Arg
65                  70                  75                  80

Gly Val Trp Ile Glu Thr Gly Asp Ser Pro Thr Val Phe Arg Tyr Ile
                85                  90                  95

Asp Trp Leu Leu Thr Val Pro Leu Leu Ile Cys Glu Phe Tyr Leu Ile
            100                 105                 110

Leu Ala Ala Ala Thr Asn Val Ala Gly Ser Leu Phe Lys Lys Leu Leu
        115                 120                 125

Val Gly Ser Leu Val Met Leu Val Phe Gly Tyr Met Gly Glu Ala Gly
    130                 135                 140

Ile Met Ala Ala Trp Pro Ala Phe Ile Ile Gly Cys Leu Ala Trp Val
145                 150                 155                 160

Tyr Met Ile Tyr Glu Leu Trp Ala Gly Glu Gly Lys Ser Ala Cys Asn
                165                 170                 175

Thr Ala Ser Pro Ala Val Gln Ser Ala Tyr Asn Thr Met Met Tyr Ile
            180                 185                 190

Ile Ile Phe Gly Trp Ala Ile Tyr Pro Val Gly Tyr Phe Thr Gly Tyr
        195                 200                 205
```

Leu Met Gly Asp Gly Gly Ser Ala Leu Asn Leu Asn Leu Ile Tyr Asn
    210                 215                 220

Leu Ala Asp Phe Val Asn Lys Ile Leu Phe Gly Leu Ile Ile Trp Asn
225                 230                 235                 240

Val Ala Val Lys Glu Ser Ser Asn Ala
                245

<210> SEQ ID NO 99
<211> LENGTH: 446
<212> TYPE: DNA
<213> ORGANISM: Arabidopsis thaliana (thale cress)

<400> SEQUENCE: 99
atttcgaaag agaatctcag aaagatcaat ctagagagac ccgttcgtct cctttcctta 60
agccattacc tctgaaacca tccaaggctt tggttgcaac tggaggcaga gcacagaggc 120
ttcaagttaa ggccctcaag atggacaagg ctttgaccgg tatctccgcg gctgctctta 180
ctgcttcgat ggtgattccg gagatagctg aagctgctgg ttctggaatc tctccttccc 240
tcaagaattt cttgctcagc attgcttctg gtggcctcgt cctcactgtc atcattggtg 300
tcgtcgtcgg cgtctccaac tttgaccctg tcaagagaac ctaagaccta tatatctttc 360
ttacatcatt attgtaatct gttctccttc tgtgtattcg tttcaatgtt gcagcaatga 420
acttttggat aaaaaaaaaa aaaaaa 446

<210> SEQ ID NO 100
<211> LENGTH: 642
<212> TYPE: DNA
<213> ORGANISM: Mus musculus

<400> SEQUENCE: 100
aaggcagaag caccggtcag ctgggggaag ggacacagag gaagagacgg agtgtacagg 60
gaccaaggtt gtatgtcaag gagcaaagag caggaagaca ggaggctttg agcacacacg 120
gctttgtcta ttccagtaac aacccccttg ctgccgctca ccggttccat ggagataata 180
tttggccaga ataagaaaga acagctggag ccagttcagg ccaaagtgac aggcagcatt 240
ccagcatggc tgcaggggac cctgctccga aacgggcccg ggatgcacac agtgggagag 300
agcaagtaca accattggtt tgatggcctg gcccttctcc acagtttctc catcagagat 360
ggggaggtct tctacaggag caaatacctg cagagtgaca cctacatcgc caacattgag 420
gccaacagaa tcgtggtgtc tgagttcgga accatggcct acccggaccc ctgcaaaaac 480
atcttttcca aagctttctc ctacttgtct cacaccatcc ccgacttcac agacaactgt 540
ctgatcaaca tcatgaaatg tggagaagac ttctatgcaa ccacggagac caactacatc 600
aggaaaatcg acccccagac cctagagacc ttggagaagg tg 642

<210> SEQ ID NO 101
<211> LENGTH: 217
<212> TYPE: PRT
<213> ORGANISM: Arabidopsis thaliana
<220> FEATURE:
<221> NAME/KEY: MISC_FEATURE
<223> OTHER INFORMATION: (thale cress)

<400> SEQUENCE: 101

Met Ala Ser Leu Ser Thr Ile Thr Gln Pro Ser Leu Val His Ile Pro
1               5                   10                  15

Gly Glu Ser Val Leu His His Val Pro Ser Thr Cys Ser Phe Pro Trp

```
            20                  25                  30

Lys Pro Thr Ile Asn Thr Lys Arg Ile Ile Cys Ser Pro Ala Arg Asn
        35                  40                  45

Ser Ser Glu Val Ser Ala Glu Ala Glu Thr Glu Gly Gly Ser Ser Thr
    50                  55                  60

Ala Val Asp Glu Ala Pro Lys Glu Ser Pro Ser Leu Ile Ser Ala Leu
65                  70                  75                  80

Asn Val Glu Arg Ala Leu Arg Gly Leu Pro Ile Thr Asp Val Asp His
                85                  90                  95

Tyr Gly Arg Leu Gly Ile Phe Arg Asn Cys Ser Tyr Asp Gln Val Thr
            100                 105                 110

Ile Gly Tyr Lys Glu Arg Val Lys Glu Leu Lys Glu Gln Gly Leu Asp
        115                 120                 125

Glu Glu Gln Leu Lys Thr Lys Met Asp Leu Ile Lys Ser Tyr Thr Ile
    130                 135                 140

Leu Ser Thr Val Glu Glu Arg Arg Met Tyr Asp Trp Ser Leu Ala Arg
145                 150                 155                 160

Ser Glu Lys Ala Glu Arg Tyr Val Trp Pro Phe Glu Val Asp Ile Met
                165                 170                 175

Glu Pro Ser Arg Glu Glu Pro Pro Pro Gln Glu Pro Glu Asp Val Gly
            180                 185                 190

Pro Thr Arg Ile Leu Gly Tyr Phe Ile Gly Ala Trp Leu Val Leu Gly
        195                 200                 205

Val Ala Leu Ser Val Ala Phe Asn Arg
    210                 215


<210> SEQ ID NO 102
<211> LENGTH: 53
<212> TYPE: PRT
<213> ORGANISM: Cyanophora paradoxa

<400> SEQUENCE: 102

Met Asn Ala Phe Val Ala Ser Val Ala Pro Ile Ala Val Ala Gly Ser
1               5                   10                  15

Ala Thr Leu Ser Ser Ala Val Cys Ala Gln Lys Lys Ala Phe Phe Gly
            20                  25                  30

Ala Gln Val Ala Ala Lys Lys Thr Thr Phe Glu Ala Ala Pro Ala Arg
        35                  40                  45

Phe Ile Val Arg Ala
    50


<210> SEQ ID NO 103
<211> LENGTH: 45
<212> TYPE: PRT
<213> ORGANISM: Arabidopsis thaliana

<400> SEQUENCE: 103

Met Ala Thr Gln Ala Ala Gly Ile Phe Asn Ser Ala Ile Thr Thr Ala
1               5                   10                  15

Ala Thr Ser Gly Val Lys Lys Leu His Phe Phe Ser Thr Thr His Arg
            20                  25                  30

Pro Lys Ser Leu Ser Phe Thr Lys Thr Ala Ile Arg Ala
        35                  40                  45


<210> SEQ ID NO 104
<211> LENGTH: 30
<212> TYPE: PRT
```

<213> ORGANISM: Arabidopsis thaliana
<220> FEATURE:
<221> NAME/KEY: MISC_FEATURE
<223> OTHER INFORMATION: (thale cress)
<220> FEATURE:
<221> NAME/KEY: MISC_FEATURE
<223> OTHER INFORMATION: CAB transit peptide(thale cress)

<400> SEQUENCE: 104

```
Met Gln Ser Ser Ala Val Phe Ser Leu Ser Pro Ser Leu Pro Leu Leu
1               5                   10                  15

Lys Pro Arg Arg Leu Ser Leu Arg His His Pro Ile Thr Thr
            20                  25                  30
```

<210> SEQ ID NO 105
<211> LENGTH: 44
<212> TYPE: PRT
<213> ORGANISM: Arabidopsis thaliana
<220> FEATURE:
<221> NAME/KEY: MISC_FEATURE
<223> OTHER INFORMATION: (thale cress)
<220> FEATURE:
<221> NAME/KEY: MISC_FEATURE
<223> OTHER INFORMATION: PGR5 transit peptide(thale cress)

<400> SEQUENCE: 105

```
Met Ala Ala Ala Ser Ile Ser Ala Ile Gly Cys Asn Gln Thr Leu Ile
1               5                   10                  15

Gly Thr Ser Phe Tyr Gly Gly Trp Gly Ser Ser Ile Ser Gly Glu Asp
            20                  25                  30

Tyr Gln Thr Met Leu Ser Lys Thr Val Ala Pro Pro
        35                  40
```

<210> SEQ ID NO 106
<211> LENGTH: 2955
<212> TYPE: DNA
<213> ORGANISM: Arabidopsis thaliana
<220> FEATURE:
<221> NAME/KEY: misc_feature
<223> OTHER INFORMATION: PCRL1 gene
<220> FEATURE:
<221> NAME/KEY: misc_feature
<223> OTHER INFORMATION: PCRL1 gene(thale cress)

<400> SEQUENCE: 106

```
catatttgat tttcacatgg attaacgaaa ctatattatg gaacacattc aaaattataa     60

caacaaaaaa aatacaagta ttatttcaaa actacacaag gttgtgctta tttcttgaat    120

tattttactt tcctaatgag agcaaagttt ctcaaagaag taatcatatg atgtttttct    180

ttgaatgtgc ctcacactta cttacaaaca caacacaagc caatgagagc tacatgaaaa    240

gatctgaaga ttatacaaaa cagcatacaa actttggttt ttctccttct tcttcaattt    300

ctccaccttc ttcatttgtt agtattaatt ttacatacac ttctacataa ccctgagaaa    360

aagaaaaccc taaaattttg aattttccat tgaatcaaga aagatttcat cagaaatcaa    420

agttgagata agaattaaac cttggctctt agatttaagc tttccctcct tctggtaatg    480

tgatcaaacg agaacctgag tcatagacca tctccgttcc acagctaaaa accagaagaa    540

tcataagact tcaagaaacg ttgtagacaa tttgtgtgat cgattcgagt ctacagctga    600

gaagcttacc ctgagcattt gacattgttg gtgttactat cattggggat ggatagtatc    660

gttccaaaga aagatacatt ctctgttcca cagtttgggc aagggccctg tgaaagatat    720

gttccacgaa aattaaaagc atttcataat aatcgcataa aactcgtagg atttggcact    780
```

```
ataccaatcc aaatttgtag cgtttagcac aaaatagatt attatctcaa gtctaatctc    840
ttgtttaagc atttttgata ctgagaaaac aagatttagt tctataactt ttatttttcc    900
acttcatgaa ctgatcttgg aagatgatta atgtttttac cttcaagatc aagaagtctt    960
tgaggatcag tttggtgagt gataacgcca gatatacaat tgcaggcacc gcagcgaacc   1020
atgtgaaaat gaaactgaat ggttccggaa gctgcagatt tttgtttttg tttttaatc   1080
agttgcatga atactggaac aattactacg agtatatatt ctccaaacca tagtagaata   1140
gtcgaaagag gttttacctc gagcaggtac gtgatttcaa aaccagtaat gtcatcaaga   1200
aagaaaaatc tggagaacaa ttgaagaaaa caacaatttt aaactaacta acataagcta   1260
agatcatgtg atttgaaagt tgagagagga acagaaccgg aggtactcac agtccgagag   1320
caacaacagt tgctggtaca ttcaacaaga acattttgaa gtaatcaatg gcaagatcac   1380
tataaacctg cataatcaag gaggtccaca agtctataac atctctagag tttgtcccaa   1440
acaatgaatc taatgttatg ttctgtaatg tccaaagaat atatgagcta tccgaacaat   1500
taagagtttt taccttttta ctacgaagac tgcatcttgg accctcacac acaatctcac   1560
tgccgtccat ctacagaaac caaagaaaca atcataacgt ttgtccaaat tacacatgta   1620
acaagatgga tgaaactaag aaatagtatt tgtaagtata aatagattaa gaacctttag   1680
tttcattttg agcttatcat actcttcatc actcaagatt ggatttccag agacataagc   1740
cattgaagct tcaaggaatc tttgttcatc agaacctaca atacatagat aaaattagat   1800
caagaatcaa gaacctaggc gaatggatta ttgacaaaac tataaatcat aagtgttcat   1860
tacttagcat gacaacactg cttccttccc acatcaactc ttctttaagg ttatcaaact   1920
cttcattaga cataatcgct ttgccttcgt aataaaacga ctgcaaaaga aaagaaacag   1980
aaacaatcct cgattatata gagataaacc catactaatg ataaaaacac tttatttgat   2040
gtgttacttg catcgcttgg aggaactctt gttccatttc accgatagtt ctcttctcat   2100
tcttgttgat gctacaataa ggtaaaatct tgctatcaac ttcttcccca cccacctgac   2160
ctgaagacaa gtcataaaaa tgattttaag aagtaaggaa actctcaagg agcaatcttt   2220
tagtggatta gagtataaaa actaaaaatc cacagaggaa aaaagttcca tataacaact   2280
tttcttaact agaattaaag cttgagtgat tttattctat gattgaataa aatcaaaact   2340
ttctcaaaag ccactgtgtt cccaaacaat gatcagagac aaaatcaaag ctacaataca   2400
acagcttttc tcaactaaat ttgaagattg agtgcttttt tgtttcgatc acataacgat   2460
gagttaataa cttaagaacc ttaagctaca cacaaatttt aatcctaaaa aggctacaaa   2520
ttggaaatca tttatctaat tatcttctat gatcataaaa atctcaactt ttcacaccaa   2580
tttcgttccc aaagaaagat cagaggcaaa aacaaataaa aaaatcgaaa ctttaaagag   2640
gcaaataaaa atcgagacct gattgatcag tagaagcttt aaggggcaat aaggtaagtc   2700
ttcgtctgag agaaatcgat cgtccatggg taaagggagc aggacactgt gtcctcgaag   2760
aagaacaagt gatgggtttg cgagaaattg cagaaaatct agggattgtt agagtaaaag   2820
ccatcgtctt tatccctcac gccgatgatt gagtgagatc gttgttttct cttgtccggg   2880
acgaagaaca aaaaaaaaag ttagaagctt tggatttgtg tggttgagaa ttgagatggt   2940
gatgtttttt actgt                                                    2955
```

<210> SEQ ID NO 107
<211> LENGTH: 55
<212> TYPE: PRT
<213> ORGANISM: Arabidopsis thaliana (thale cress)

```
<220> FEATURE:
<221> NAME/KEY: MISC_FEATURE
<223> OTHER INFORMATION: Rubisco
<220> FEATURE:
<221> NAME/KEY: MISC_FEATURE
<223> OTHER INFORMATION: Rubisco(thale cress)

<400> SEQUENCE: 107

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys
    50                  55


<210> SEQ ID NO 108
<211> LENGTH: 795
<212> TYPE: DNA
<213> ORGANISM: homo sapien

<400> SEQUENCE: 108

gaattcatgt ctcatcattg gggttatggt aaacacaatg gtcctgaaca ctggcataaa      60

gactttccaa ttgcaaaagg tgaacgtcaa tcacctgttg atattgacac tcatacagct     120

aaatatgacc cttctttaaa accattatct gtttcatatg atcaagcaac ttctttacgt     180

attttaaaca atggtcatgc ttttaatgta gaatttgatg actctcaaga taaagcagta     240

ttaaaaggtg gtccattaga tggtacttac cgtttaattc aatttcactt tcactggggt     300

tcattagatg gtcaaggttc agaacatact gtagataaaa aaaaatatgc tgcagaatta     360

cacttagttc actggaacac aaaatatggt gattttggta aagctgtaca acaacctgat     420

ggtttagctg ttttaggtat ttttttaaaa gttggtagtg ctaaaccagg tcttcaaaaa     480

gttgttgatg tattagattc aattaaaaca aaaggtaaaa gtgctgactt tactaatttc     540

gatcctcgtg gtttacttcc tgaatcttta gattactgga catatccagg ttcattaaca     600

acacctcctc ttttagaatg tgtaacatgg attgtattaa aagaaccaat tagtgtaagt     660

agtgaacaag tattaaaatt ccgtaaactt aatttcaatg gtgaaggtga accagaagaa     720

ttaatggttg ataactggcg tccagctcaa ccattaaaaa atcgtcaaat taaagcttca     780

ttcaaataag catgc                                                      795
```

CARBON FIXATION SYSTEMS IN PLANTS AND ALGAE

CROSS-REFERENCE TO RELATED APPLICATIONS

This application is a continuation of International Patent Application No. PCT/US2015/041617, entitled "Improved Carbon Fixation Systems in Plants and Algae", filed on Jul. 22, 2015, which claims priority to and the benefit of the filing of U.S. Provisional Patent Application No. 62/027,354, entitled "Carbon Fixation Systems in Plants and Algae", filed on Jul. 22, 2014, and the specification and claims thereof are incorporated herein by reference.

STATEMENT REGARDING FEDERALLY SPONSORED RESEARCH

This invention was made with government support under grants Nos. DOE-CECO Prime No: DE-AR0000202, Sub No: 21018-N; DOE-CABS Prime No: DE-SC0001295, Sub No: 21017-NM NSF EF-1219603, NSF No:1219603. The U.S. government has certain rights in the invention.

SEQUENCE LISTING

The instant application contains a Sequence Listing which has been submitted electronically in ASCII format and is hereby incorporated by reference in its entirety. Said ASCII copy, created on Jul. 20, 2015, is named 072215_NMC0001-101-US_Sequence_Listing_ST25.txt and is 284 bytes in size.

INCORPORATION BY REFERENCE OF MATERIAL SUBMITTED ON A COMPACT DISC

Not Applicable.

COPYRIGHTED MATERIAL

Not Applicable.

BACKGROUND

A major factor limiting photosynthetic efficiency is the competitive inhibition of $CO_2$ fixation by oxygen, due to lack of specificity of the enzyme RuBisCO. Incorporation of oxygen by RuBisCO is the first-dedicated step in photorespiration, a pathway that respires $CO_2$, compounding photosynthetic inefficiency. Overall, photorespiration reduces photosynthetic productivity by as much as 50% [1]. To date, attempts to engineer reduced oxygenase activity in RuBisCO have been largely unsuccessful.

Significantly, the cyanobacteria, eukaryotic microalgae, and C4 plants have evolved mechanisms to reduce photorespiration by concentrating $CO_2$ near RuBisCO, competitively inhibiting oxygenase activity and leading to substantial increases in yield and water use efficiency per unit carbon fixed. However, carbon concentrating systems (CCMs) are not operational in the vast majority of plant species (i.e., C3 plants).

Attempts to reconstitute functional CCMs in C3 plants have been previously attempted by us and others, mainly focusing on engineering pathways that are directly involved in facilitating $CO_2$ transport into leaf chloroplasts. Note, for example, PCT International Publication WO 2012/125737; Sage and Sage (2009) Plant and Cell Physiol. 50(4):756-772; Zhu et al. (2010) J Interg. Plant Biol. 52(8):762-770; Furbank et al. (2009) Funct. Plant Biol. 36(11):845-856; Weber and von Caemmerer (2010) Curr. Opin. Plant Biol.; Price (2013) J. Exp. Bot. 64(3):753-68; and U.S. Patent Application Publication No. 2013/0007916 A1.

However, ATP and NADPH production through light harvesting and electron transfer steps must be coordinated with carbon assimilation and additional energy requiring steps including CCM systems to prevent photoinhibition and to improve growth. Additionally, assimilatory flux and storage rates can limit carbon fixation due to feedback inhibition when sink demand is not matched to source capacity [2].

Thus, there is a critical need to improve plant productivity through integrated systems engineering approaches that balance source/sink interactions with energy and reductant production to develop energy-requiring, artificial CCMs that can effectively mimic those found in nature.

BRIEF SUMMARY OF THE INVENTION

Accordingly, in response to this need, the present disclosure provides methods for elevating cyclic electron transfer activity, improving carbon concentration, and enhancing carbon fixation in C3 and C4 plants, and algae, and producing biomass or other products from C3 or C4 plants, and algae, selected from among, for example, starches, oils, fatty acids, lipids, cellulose or other carbohydrates, alcohols, sugars, nutraceuticals, pharmaceuticals, fragrance and flavoring compounds, and organic acids, as well as transgenic plants produced thereby. These methods and transgenic plants and algae encompass the expression, or overexpression, of various combinations of genes that improve carbon concentrating systems in plants and algae, such as bicarbonate transport proteins, carbonic anhydrase, light driven proton pump, cyclic electron flow regulators, etc. Thus, among its various embodiments, the present disclosure provides the following:

A first embodiment of the present invention provides for a transgenic plant or alga, comprising within its genome, and expressing or overexpressing, a combination of heterologous nucleotide sequences encoding an ATP dependent bicarbonate anion transporter localized to the plasma membrane and a cyclic electron transfer modulator protein. The cyclic electron transfer modulator protein may be selected from a PGRL1 protein (for example SEQ ID NO:3), a PGR5 protein (for example SEQ ID NO:1), a leaf FNR1 protein (for example SEQ ID NO:96), a leaf FNR2 protein (for example SEQ ID NO:97), a Fd1 protein (for example SEQ ID NO:95), or any combination thereof and for example the ATP dependent bicarbonate anion transporter localized to the plasma membrane may be a HLA3 protein (for example SEQ ID NO:77). The transgenic plant or alga described may further comprise within its genome, and expressing or overexpressing the heterologous nucleotide sequence encoding a bicarbonate anion transporter protein localized to the chloroplast envelope. The transgenic plant or alga described herein may further comprise within its genome, and expressing or overexpressing the heterologous nucleotide sequence a carbonic anhydrase protein. In a preferred embodiment, the cyclic electron transfer modulator protein is a PGR5 protein, in another preferred embodiment the cyclic electron transfer modulator protein is Fd1 protein, in yet another preferred embodiment, in still another preferred embodiment the cyclic electron transfer modulator protein is leaf FNR1, in a further preferred embodiment the cyclic electron transfer modulator protein is PGRL1. In a preferred embodiment the heterologous nucleotide sequences of the transgenic plant or alga encode i) a PGR5 protein, and a HLA3 protein; or ii) a PGR5 protein, a HLA3 protein and a PGRL1 protein or a PGR5 protein, a HLA3 protein, and a LCIA protein or a PGR5 protein, a HLA3 protein, a PGRL1 protein, a LCIA protein, and a BCA or HCA2 protein. In another preferred embodiment the heterologous nucleotide sequences the transgenic plant or alga of wherein encode a PGR5 protein, a HLA3 protein, a LCIA protein and a BCA or optionally a HCA2 protein. The transgenic plant or alga as described wherein the PGR5 protein has an amino acid sequence at least 80% identical to SEQ ID NO:1; the HLA3 protein has an amino acid sequence at least 80% identical to SEQ ID NO:77; the PGRL1 protein has an amino acid sequence at least 80% identical to SEQ ID NO:3; the LCIA protein has an amino acid sequence at least 80% identical to SEQ ID NO:18; and/or the BCA protein has an amino acid sequence at least 80% identical to SEQ ID NO:21. Alternatively, the sequence identity/sequence similarity is about 75%, 85%, 90%, 91%, 92%, 93%, 94%, 95%, 96%, 97%, 98%, 99%, 100% to those specifically disclosed which includes for example proteins without a transit peptide sequence and the functional protein.

A second embodiment provides for a transgenic plant or alga, comprising within its genome, and expressing or overexpressing, a combination of heterologous nucleotide sequences encoding:

LCIA protein and BCA protein or HCA protein is provided. In a preferred embodiment the heterologous nucleotide sequences encode transgenic plant or alga wherein the LCIA protein has an amino acid sequence at least 80% identical to SEQ ID NO:18; and/or the BCA protein has an amino acid sequence at least 80% identical to SEQ ID NO:21 and the HCA protein has an amino acid sequence at least 80% identical to SEQ ID NO:19. Alternatively, the sequence identity/sequence similarity is about 75%, 85%, 90%, 91%, 92%, 93%, 94%, 95%, 96%, 97%, 98%, 99%, 100% to those specifically disclosed which include for example proteins without a transit peptide sequence and the functional protein.

A third embodiment provides for a transgenic plant or alga, comprising within its genome, and expressing or overexpressing, a combination of heterologous nucleotide sequences encoding an ATP dependent bicarbonate anion transporter localized to the plasma membrane (for example SEQ ID NO:77), a bicarbonate anion transporter localized to the chloroplast envelope (for example SEQ ID NO:18), a carbonic anhydrase, a proteorhodopsin protein targeted to thylakoid membranes (for example SEQ ID NO:98), and a β carotene monooxygenase protein (for example SEQ ID NO:100). In another preferred embodiment the proteorhodopsin comprises a chloroplast transit peptide selected from among a psbX stop-transfer trans-membrane domain fused to its C-terminus, a DNAJ transit peptide, a CAB transit peptide, a PGR5 transit peptide, and a psaD transit peptide. In another preferred embodiment the β-carotene monooxygenase is expressed under the control of a promoter selected from among an ethanol inducible gene promoter and a green tissue/leaf-specific promoter selected from among CAB and rbcS. The proteorhodopsin may comprise an amino acid substitution selected from among L219E/T206S, M79T, and M79Y, and combinations thereof.

The carbonic anhydrase of the first, second, or third embodiment may be a BCA or optionally a HCA2 protein. The bicarbonate anion transporter localized to the chloroplast envelope of the first, second and third embodiment may be a LCIA protein. The ATP dependent bicarbonate anion transporter localized to the plasma membrane of the first and third embodiments may be HLA3.

A fourth embodiment provides for a method of making a transgenic plant or alga of a first embodiment wherein said method comprises expressing, or overexpressing, in a C3 plant, a C4 plant, or an alga, a combination of heterologous nucleotide sequences encoding an ATP dependent bicarbonate anion transporter localized to the plasma membrane and a cyclic electron transfer modulator protein. The cyclic electron transfer modulator protein may be selected from a PGRL1 protein, a PGR5 protein, a FNR1 protein, a FNR2 protein (leaf-form isotopes), a Fd1 protein, or any combination thereof and wherein the ATP dependent bicarbonate anion transporter localized to the plasma membrane is a HLA3 protein. The heterologous nucleotide sequences of the fourth embodiment further encoding a bicarbonate anion transporter protein localized to the chloroplast envelope for example the bicarbonate anion transporter protein is LCIA. Additionally, the heterologous nucleotide sequences encode a carbonic anhydrase protein for example a BCA protein or optionally a HCA2 protein. In a preferred embodiment the cyclic electron transfer modulator protein is a PGR5 protein and optionally a PGRL1 protein and or combination thereof.

A fifth embodiment provides a method of making a transgenic plant or alga as described in a second embodiment, wherein said method comprises expressing, or overexpressing, in a C3 plant, a C4 plant, or an alga, a combination of heterologous nucleotide sequences encoding a LCIA protein and a BCA protein or optionally a HCA protein.

A sixth embodiment provides a method of making a transgenic plant or alga of a third embodiment wherein said method comprises expressing, or overexpressing, in a C3 plant, a C4 plant, or an alga, a combination of heterologous nucleotide sequences encoding an ATP dependent bicarbonate anion transporter localized to the plasma membrane, a bicarbonate anion transporter, a carbonic anhydrase, a proteorhodopsin protein targeted to thylakoid membranes, and a β carotene monooxygenase protein. In a preferred embodiment the proteorhodopsin comprises a chloroplast transit peptide selected from among a psbX stop-transfer transmembrane domain fused to its C-terminus, a DNAJ transit peptide, a CAB transit peptide, a PGR5 transit peptide, and a psaD transit peptide. In another preferred embodiment the β-carotene monooxygenase is expressed under the control of a promoter selected from among an ethanol inducible gene promoter and a green tissue/leaf-specific promoter selected from among CAB and rbcS. In a preferred embodiment the proteorhodopsin comprises an amino acid substitution selected from among L219E/T206S, M79T, and M79Y, and combinations thereof. In another preferred embodiment the ATP dependent bicarbonate anion transporter localized to the plasma membrane is HLA3.

The transgenic plant of an embodiment disclosed herein may be a C3 plant or a C4 plant such as a transgenic oilseed plant or a transgenic food crop plant which may include the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia*; and *Crambe abyssinica*, wheat, rice, maize (corn), barley, oats, sorghum, rye, and millet; peanuts, chickpeas, lentils, kidney beans, soybeans, lima beans; potatoes, sweet potatoes, and cassavas; soybeans, corn, canola, peanuts, palm, coconuts, safflower, cottonseed, sunflower, flax, olive, and safflower; sugar cane and sugar beets; bananas, oranges, apples, pears, breadfruit, pineapples, and cherries; tomatoes, lettuce, carrots, melons, strawberry, asparagus, broccoli, peas, kale, cashews, peanuts, walnuts, pistachio nuts, almonds; forage and turf grasses; alfalfa, clover; coffee, cocoa, kola nut, poppy; vanilla, sage, thyme, anise, saffron, menthol, peppermint, spearmint and coriander and preferably wheat, rice and canola. The transgenic alga of an embodiment disclosed herein may be selected from among a *Chlorella* species, a *Nannochloropsis* species, and a *Chlamydomonas* species. The heterologous nucleotide sequences are described in an embodiment may be codon-optimized for expression in said transgenic plant or alga. One aspect of the present invention provides for a transgenic plant or alga as described in an embodiment which exhibits enhanced $CO_2$ fixation compared to an otherwise identical control plant grown under the same conditions for example wherein $CO_2$ fixation is enhanced in the range of from about 10% to about 50% compared to that of an otherwise identical control plant grown under the same conditions.

A fourth embodiment provides for a part of said transgenic plant or alga of any embodiment described herein. For example, the part of said transgenic plant may be selected from among a protoplast, a cell, a tissue, an organ, a cutting, an explant, a reproductive tissue, a vegetative tissue, biomass, an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, a callus, propagation materials, germplasm, cuttings, divisions, and propagations.

A fifth embodiment provides for a progeny or derivative of said transgenic plant or alga of any embodiment described herein. For example, the progeny or derivatives may be selected from among clones, hybrids, samples, seeds, and harvested material thereof and may be produced sexually or asexually.

Another embodiment of the present invention provides a method of elevating CET activity in a C3 plant, C4 plant, or alga wherein said method comprises expressing, or overexpressing, in a C3 plant, a C4 plant, or an alga, a combination of heterologous nucleotide sequences encoding an ATP dependent bicarbonate anion transporter localized to the plasma membrane and cyclic electron transfer modulator protein.

Yet another embodiment provides a method of enhancing carbon fixation in a C3 plant, C4 plant, or alga wherein said method comprises expressing, or overexpressing, in a C3 plant, a C4 plant, or an alga, a combination of heterologous nucleotide sequences encoding an ATP dependent bicarbonate anion transporter localized to the plasma membrane and a cyclic electron transfer modulator protein.

Yet another method provides for a method of producing biomass or other products from a C3 plant, C4 plant, or an alga, wherein said products are selected from among starches, oils, fatty acids, triacylglycerols, lipids, cellulose or other carbohydrates, alcohols, sugars, nutraceuticals, pharmaceuticals, fragrance and flavoring compounds, and organic acids wherein said method comprises expressing, or overexpressing, in a C3 plant, a C4 plant, or an alga, a combination of heterologous nucleotide sequences encoding an ATP dependent bicarbonate anion transporter localized to the plasma membrane and a cyclic electron transfer modulator protein. This method further comprises growing said plant or alga and harvesting said biomass or recovering said product from said plant or alga. Another aspect of the present invention provides for biomass or other product produced from a plant or alga selected from among starches, oils, fatty acids, lipids, cellulose or other carbohydrates, alcohols, sugars, nutraceuticals, pharmaceuticals, fragrance and flavoring compounds, and organic acids, made by a method of any one of the method of making a transgenic plant or alga embodiments herein.

Another embodiment provides a method of elevating cyclic electron transfer (CET) activity in a C3 plant, C4 plant, or alga wherein said method comprises expressing, or overexpressing, in a C3 plant, a C4 plant, or an alga, a combination of heterologous nucleotide sequences encoding an ATP dependent bicarbonate anion transporter localized to the plasma membrane, a bicarbonate anion transporter, a carbonic anhydrase, a proteorhodopsin protein targeted to thylakoid membranes; and a β carotene monooxygenase protein.

Another embodiment provides a method of enhancing carbon fixation in a C3 plant, C4 plant, or alga wherein said method comprises expressing, or overexpressing, in a C3 plant, a C4 plant, or an alga, a combination of heterologous nucleotide sequences encoding an ATP dependent bicarbonate anion transporter localized to the plasma membrane, a bicarbonate anion transporter, a carbonic anhydrase, a proteorhodopsin protein targeted to thylakoid membranes; and a β carotene monooxygenase protein.

Another embodiment provides for a method of producing biomass or other products from a C3 plant, C4 plant, or an alga, wherein said products are selected from among starches, oils, fatty acids, triacylglycerols, lipids, cellulose or other carbohydrates, alcohols, sugars, nutraceuticals, pharmaceuticals, fragrance and flavoring compounds, and organic acids wherein said method comprises expressing, or overexpressing, in a C3 plant, a C4 plant, or an alga, a combination of heterologous nucleotide sequences encoding an ATP dependent bicarbonate anion transporter localized to the plasma membrane, a bicarbonate anion transporter, a carbonic anhydrase, a proteorhodopsin protein targeted to thylakoid membranes; and a β carotene monooxygenase protein. The method further comprises growing said plant or alga and harvesting said biomass or recovering said product from said plant or alga.

Another embodiment provides for use of a construct comprising one or more nucleic acids encoding a) a PGR5 protein, and a HLA3 protein;
b) a PGR5 protein, a HLA3 protein and a PGRL1 protein;
c) a PGR5 protein, a HLA3 protein, and a LCIA protein;
d) a PGR5 protein, a HLA3 protein, a LCIA protein and a BCA or HCA2 protein;
e) a PGR5 protein, a HLA3 protein, a PGRL1 protein and a LCIA protein;
f) a PGR5 protein, a HLA3 protein, a PGRL1 protein, a LCIA protein, and a BCA or HCA2 protein;
g) a PGR5 protein, a HLA3 protein, and a BCA or HCA2 protein; or
h) a PGR5 protein, a HLA3 protein, a PGRL1 protein, and a BCA or HCA2 protein for
   i) making a transgenic plant or alga of a first embodiment;
   ii) elevating CET activity in a C3 plant, C4 plant, or alga;

iii) enhancing carbon fixation in a C3 plant, C4 plant, or alga; or iv) producing biomass or other products from a C3 plant, C4 plant, or an alga, wherein said products are selected from among starches, oils, fatty acids, triacylglycerols, lipids, cellulose or other carbohydrates, alcohols, sugars, nutraceuticals, pharmaceuticals, fragrance and flavoring compounds, and organic acids.

Another embodiment provides for use of a construct comprising one or more nucleic acids encoding a) a LCIA protein and a BCA or HCA2 protein; for i) making a transgenic plant or alga of a second embodiment;

ii) elevating CET activity in a C3 plant, C4 plant, or alga;

iii) enhancing carbon fixation in a C3 plant, C4 plant, or alga; or iv) producing biomass or other products from a C3 plant, C4 plant, or an alga, wherein said products are selected from among starches, oils, fatty acids, triacylglycerols, lipids, cellulose or other carbohydrates, alcohols, sugars, nutraceuticals, pharmaceuticals, fragrance and flavoring compounds, and organic acids.

One aspect of the present invention provides for a transgenic plant or alga, comprising within its genome, and expressing or overexpressing, a combination of heterologous nucleotide sequences encoding:

1. i) a PGRL1 protein, a PGR5 protein, and a HLA3 protein; or ii) a PGRL1 protein, a PGR5 protein, a HLA3 protein, a LCIA protein, and a BCA or HCA2 protein; or iii) a Fd1 protein, a HLA3 protein, a LCIA protein, and a BCA or HCA2 protein; or iv) a leaf FNR1 protein, a HLA3 protein, a LCIA protein, and a BCA or HCA2 protein; or v) a proteorhodopsin protein targeted to thylakoid membranes, a HLA3 protein, a LCIA protein, a BCA or HCA2 protein, and a β-carotene monooxygenase.

2. The transgenic plant or alga of 1, wherein said proteorhodopsin comprises a chloroplast transit peptide selected from among a psbX stop-transfer trans-membrane domain fused to its C-terminus, a DNAJ transit peptide, a CAB transit peptide, a PGR5 transit peptide, and a psaD transit peptide.

3. The transgenic plant or alga of 1 or 2, wherein said β-carotene monooxygenase is expressed under the control of a promoter selected from among an ethanol inducible gene promoter and a green tissue/leaf-specific promoter selected from among CAB and rbcS.

4. The transgenic plant or alga of any one of 1-3, wherein said proteorhodopsin comprises an amino acid substitution selected from among L219E/T206S, M79T, and M79Y, and combinations thereof.

5. The transgenic plant of any one of 1-4, which is a C3 plant or a C4 plant.

6. The transgenic plant of any one of 1-5, which is a transgenic oilseed plant or a transgenic food crop plant.

7. The transgenic oilseed plant of 6, which is selected from among plants of the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia*; and *Crambe abyssinica.*

8. The transgenic alga of any one of 1-5, which is selected from among *Chlorella* sp., *Nannochloropsis* sp., and *Chlamydomonas* sp.

9. The transgenic plant or alga of any one of 1-8, wherein said heterologous nucleotide sequences are codon-optimized for expression in said transgenic plant or alga.

10. The transgenic plant or alga of any one of 1-9, which exhibits enhanced $CO_2$ fixation compared to an otherwise identical control plant grown under the same conditions.

11. The transgenic plant or alga of 10, wherein $CO_2$ fixation is enhanced in the range of from about 10% to about 50% compared to that of an otherwise identical control plant grown under the same conditions.

12. A part of said transgenic plant or alga of any one of 1-11.

13. The part of said transgenic plant of 12, which is selected from among a protoplast, a cell, a tissue, an organ, a cutting, an explant, a reproductive tissue, a vegetative tissue, biomass, an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, a callus, propagation materials, germplasm, cuttings, divisions, and propagations.

14. Progeny or derivatives of said transgenic plant or alga of any one of 1-11.

15. The progeny or derivatives of 14, which is selected from among clones, hybrids, samples, seeds, and harvested material thereof.

16. The progeny of 14 or 15, which is produced sexually.

17. The progeny of 14 or 15, which is produced asexually.

Another aspect of the present invention provides for a method selected from among:

18. i) making a transgenic plant or alga of any one of 1-11;

ii) elevating CET activity in a C3 plant, C4 plant, or alga;

iii) enhancing carbon fixation in a C3 plant, C4 plant, or alga; and iv) producing biomass or other products from a C3 plant, C4 plant, or alga, wherein said products are selected from among starches, oils, fatty acids, triacylglycerols, lipids, cellulose or other carbohydrates, alcohols, sugars, nutraceuticals, pharmaceuticals, fragrance and flavoring compounds, and organic acids, wherein said method comprises expressing, or overexpressing, in a C3 plant, a C4 plant, or an alga, a combination of heterologous nucleotide sequences encoding:

a) a PGRL1 protein, a PGR5 protein, and a HLA3 protein; or b) a PGRL1 protein, a PGR5 protein, a HLA3 protein, a LCIA protein, and a BCA or HCA2 protein; or c) a Fd1 protein, a HLA3 protein, a LCIA protein, and a BCA or HCA2 protein; or d) a leaf FNR1 protein, a HLA3 protein, a LCIA protein, and a BCA or HCA2 protein; or e) a proteorhodopsin protein targeted to thylakoid membranes, a HLA3 protein, a LCIA protein, a BCA or HCA2 protein, and a β-carotene monooxygenase.

19. The method of 18, wherein step iv) further comprises growing said plant or alga and harvesting said biomass or recovering said product from said plant or alga.

20. The method of 18 or 19, wherein said proteorhodopsin comprises a chloroplast transit peptide selected from among a psbX stop-transfer trans-membrane domain fused to its C-terminus, a DNAJ transit peptide, a CAB transit peptide, a PGR5 transit peptide, and a psaD transit peptide.

21. The method of any one of 18-20, wherein said β-carotene monooxygenase is expressed under the control of a promoter selected from among an ethanol inducible gene promoter and a green tissue/leaf-specific promoter selected from among CAB and rbcS.

22. The method of any one of 18-21, wherein said proteorhodopsin comprises an amino acid substitution selected from among L219E/T206S, M79T, and M79Y, and combinations thereof.

23. The method of any one of 18-22, wherein said transgenic plant is a C3 plant, a C4 plant, or an alga.

24. The method of any one of 18-23, wherein said transgenic plant is a transgenic oilseed plant or a transgenic food crop plant.

25. The method of 24, wherein said transgenic oilseed plant is selected from among plants of the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard other than *Arabidopsis*; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia*; and *Crambe abyssinica.*

26. The method of any one of 18-23, wherein said alga is selected from among *Chlorella* sp., *Nannochloropsis* sp., and *Chlamydomonas* sp.

27. The method of any one of 18-26, wherein said heterologous nucleotide sequences are codon-optimized for expression in said transgenic plant or alga.

28. The method of any one of 18-27, wherein said transgenic plant or alga exhibits enhanced $CO_2$ fixation compared to an otherwise identical control plant or alga grown under the same conditions.

29. The method of 28, wherein $CO_2$ fixation is enhanced in the range of from about 10% to about 50% compared to that of an otherwise identical control plant or alga grown under the same conditions.

Another aspecxt of the present invention provides for a transgenic plant or alga made by the method of any one of 18-29.

Yet another aspect of the present invention provides for a biomass or other product from a plant or alga, selected from among starches, oils, fatty acids, lipids, cellulose or other carbohydrates, alcohols, sugars, nutraceuticals, pharmaceuticals, fragrance and flavoring compounds, and organic acids, made by the method of any one of 18-29.

In addition to the various embodiments listed above, in the Examples below, and in the claims, this disclosure further variously encompasses the presently disclosed and claimed CCM protein combinations in further combinations with the genes and proteins focusing on engineering pathways that are directly involved in facilitating $CO_2$ transport into leaf chloroplasts, disclosed and claimed in the inventors' previous application PCT International Publication WO 2012/125737. The present disclosure encompasses any combination of genes disclosed herein with any combination of genes disclosed in WO 2012/125737 and in Tables D1-D9 to improve carbon concentrating systems (CCMs) in plants and algae.

Table D1 represents different classes of α-CAs found in mammals.

Table D2-D4 represents representative species, Gene bank accession numbers, and amino acid sequences for various species of suitable CA genes.

Table D5 represents the codon optimized DNA sequence for chloroplast expression in *Chlamydomonas reinhardtii*. In Table D5, the underlines sequences represent restriction sites, and bases changed to optimize chloroplast expression are listed in lower case. Table D6 provides a breakdown of the number and type of each codon optimized.

Representative species and Gene bank accession numbers for various species of bicarbonate transporter are listed below in Tables D8-D9.

Further scope of the applicability of the presently disclosed embodiments will become apparent from the detailed description and drawing(s) provided below. However, it should be understood that the detailed description and specific examples, while indicating preferred embodiments of this disclosure, are given by way of illustration only since various changes and modifications within the spirit and scope of these embodiments will become apparent to those skilled in the art from this detailed description.

BRIEF DESCRIPTION OF THE SEQUENCE LISTING

The disclosure can be more fully understood form the following detailed description and the accompanying Sequence Listing, which form a part of this application.

The sequence descriptions summarize the Sequence Listing attached hereto. The Sequence Listing contains standard symbols and format used for nucleotide and amino acid sequence data comply with the rules set forth in 37 C.F.R. §1.822.

BRIEF DESCRIPTION OF THE DRAWINGS

The above and other aspects, features, and advantages of the present disclosure will be better understood from the following detailed descriptions taken in conjunction with the accompanying drawing(s), all of which are given by way of illustration only, and are not limitative of the presently disclosed embodiments, in which:

FIG. 2(A-B). (A) Growth phenotypes of WT and HLA3 transgenic (T3) *Arabidopsis* initially grown on MS media (plus nitrate, $NO_3$). (B) MS media (plus ammonium ($NH_4$+) and sucrose) or in soil (ammonium only). X indicates plants died. Numbers refer to plant lines.

DETAILED DESCRIPTION OF SEVERAL EMBODIMENTS

Figure 1:
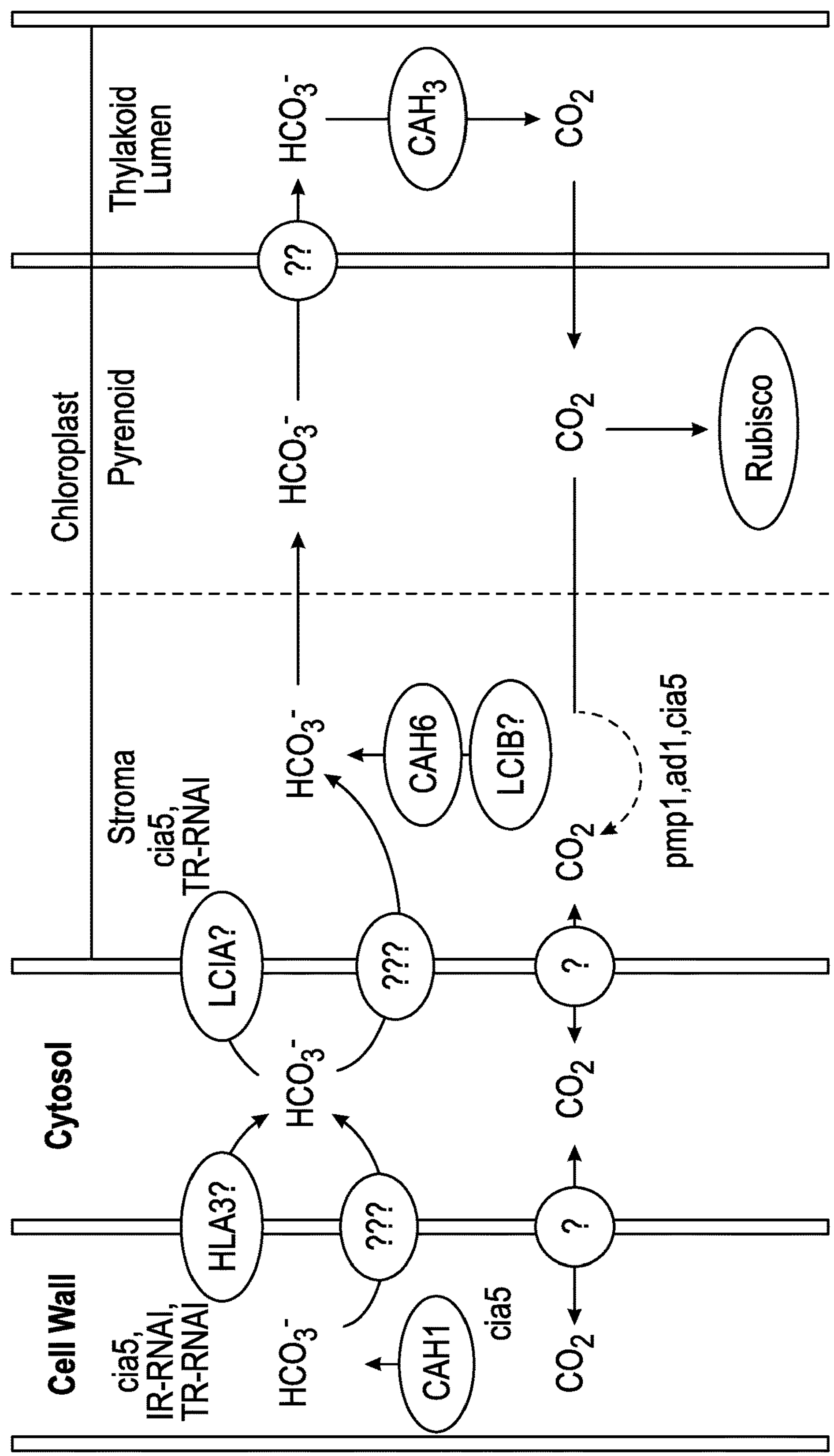
FIG. 1. Model of the *Chlamydomonas* CCM showing the localization of inorganic carbon transporters (HLA3, LCIA) and carbonic anhydrase (CAH: CAH1, CAH3, and CAH6) [5]), and Rubisco. LCIB is an essential protein for CCM in *Chlamydomonas*. It's exact function is unknown.

The following detailed description is provided to aid those skilled in the art in practicing the various embodiments of the present disclosure described herein, including all the methods, uses, compositions, etc., described herein. Even so, the following detailed description should not be construed to unduly limit the present disclosure, as modifications and variations in the embodiments herein discussed may be made by those of ordinary skill in the art without departing from the spirit or scope of the present discoveries.

The present disclosure is explained in greater detail below. This disclosure is not intended to be a detailed catalog of all the different ways in which embodiments of this disclosure can be implemented, or all the features that can be added to the instant embodiments. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which variations and additions do not depart from the scope of the instant disclosure. Hence, the following specification is intended to illustrate some particular embodiments of the disclosure, and not to exhaustively specify all permutations, combinations, and variations thereof.

Any feature, or combination of features, described herein is(are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

The contents of all publications, patent applications, patents, and other references mentioned herein are incorporated by reference herein in their entirety. In case of conflict, the present specification, including explanations of terms, will control.

Definitions

The following definitions are provided to aid the reader in understanding the various aspects of the present disclosure. Unless defined otherwise, all technical and scientific terms used herein have the same meaning as commonly understood by those of ordinary skill in the art to which the disclosure pertains.

As used herein and in the appended claims, the singular forms "a", "an", and "the" include plural referents unless the context clearly dictates otherwise. Thus, for example, reference to "a plant" includes a plurality of such plants, reference to "a cell" includes one or more cells and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ± a range of up to 20%, up to 15%, up to 10%, up to 5%, or up to 4%, 3%, 2%, or 1% compared to the specifically recited value.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary. Furthermore, the use of the term "including", as well as other related forms, such as "includes" and "included", is not limiting.

"BCA" refers to bacterial carbonic anhydrase.

"CCMs" and the like refer to carbon concentrating systems.

"CET" refers to cyclic electron transfer.

"LET" refers to linear electron transfer.

"WT" refers to wild-type.

"Cyclic electron transfer modulator protein" refers to any protein natural or synthetic that improves the separation of charge across the thylakoid membrane resulting in improved photophosphorylation with the production of chemical energy. Examples of such modulators are the PGR5 and PRGL1 reductases, however improved proteins in the electron transport chain such as cytochromes, ATPases, ferredoxin-NADP reductase, NAD(P)H-plastoquinone reductase, and the like are also CET modulator proteins.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art and is understood as included in embodiments where it would be appropriate. Nucleotides may be referred to by their commonly accepted single-letter codes. Unless otherwise indicated, amino acid sequences are written left to right in amino to carboxyl orientation, respectively. Amino acids may be referred to herein by either their commonly known three letter symbols or by the one-letter symbols recommended by the IUPAC-IUM Biochemical Nomenclature Commission. It is further to be understood that all base sizes or amino acid sizes, and all molecular weight or molecular mass values, given for nucleic acids or polypeptides are approximate, and are provided for description purposes and are not to be unduly limiting.

Regarding disclosed ranges, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). Numeric ranges recited with the specification are inclusive of the numbers defining the range and include each integer within the defined range.

As used herein, "altering level of production" or "altering level of expression" means changing, either by increasing or decreasing, the level of production or expression of a nucleic acid sequence or an amino acid sequence (for example a polypeptide, an siRNA, a miRNA, an mRNA, a gene), as compared to a control level of production or expression.

"Conservative amino acid substitutions": It is well known that certain amino acids can be substituted for other amino acids in a protein structure without appreciable loss of biochemical or biological activity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. Thus, various changes can be made in the amino acid sequences disclosed herein, or in the corresponding DNA sequences that encode these amino acid sequences, without appreciable loss of their biological utility or activity.

Proteins and peptides biologically functionally equivalent to the proteins and peptides disclosed herein include amino acid sequences containing conservative amino acid changes in the fundamental amino acid sequence. In such amino acid sequences, one or more amino acids in the fundamental sequence can be substituted, for example, with another amino acid(s), the charge and polarity of which is similar to that of the native amino acid, i.e., a conservative amino acid substitution, resulting in a silent change.

It should be noted that there are a number of different classification systems in the art that have been developed to describe the interchangeability of amino acids for one another within peptides, polypeptides, and proteins. The following discussion is merely illustrative of some of these systems, and the present disclosure encompasses any of the "conservative" amino acid changes that would be apparent to one of ordinary skill in the art of peptide, polypeptide, and protein chemistry from any of these different systems.

As disclosed in U.S. Pat. No. 5,599,686, certain amino acids in a biologically active peptide, polypeptide, or protein can be replaced by other homologous, isosteric, and/or isoelectronic amino acids, wherein the biological activity of the original molecule is conserved in the modified peptide, polypeptide, or protein. The following list of amino acid replacements is meant to be illustrative and is not limiting:

| Original Amino Acid | Replacement Amino Acid(s) |
|---|---|
| Ala | Gly |
| Arg | Lys, ornithine |
| Asn | Gln |
| Asp | Glu |
| Glu | Asp |
| Gln | Asn |
| Gly | Ala |
| Ile | Val, Leu, Met, Nle (norleucine) |
| Leu | Ile, Val, Met, Nle |
| Lys | Arg |
| Met | Leu, Ile, Nle, Val |
| Phe | Tyr, Trp |
| Ser | Thr |
| Thr | Ser |
| Trp | Phe, Tyr |
| Tyr | Phe, Trp |
| Val | Leu, Ile, Met, Nle |

In another system, substitutes for an amino acid within a fundamental sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine. and glutamine; (4) neutral nonpolar (hydrophobic) amino acids such as alanine, leucine, isoleucine, valine, proline, phenylalanine, tryptophan, and methionine.

Conservative amino acid changes within a fundamental peptide, polypeptide, or protein sequence can be made by substituting one amino acid within one of these groups with another amino acid within the same group.

Some of the other systems for classifying conservative amino acid interchangeability in peptides, polypeptides, and proteins applicable to the sequences of the present disclosure include, for example, the following:

Functionally defining common properties between individual amino acids by analyzing the normalized frequencies of amino acid changes between corresponding proteins of homologous organisms (Schulz, G. E. and R. H. Schirmer (1979) Principles of Protein Structure (Springer Advanced Texts in Chemistry), Springer-Verlag). According to such analyses, groups of amino acids can be defined where amino acids within a group exchange preferentially with each other, and therefore resemble each other most in their impact on overall protein structure;

Making amino acid changes based on the hydropathic index of amino acids as described by Kyte and Doolittle (1982) J. Mol. Biol. 157(1):105-32. Certain amino acids can be substituted by other amino acids having a similar hydropathic index or score and still result in a protein with similar biological activity, i.e., still obtain a biological functionally equivalent protein. In making such changes, the substitution of amino acids whose hydropathic indices are within +2 is preferred, those that are within +1 are particularly preferred, and those within +0.5 are even more particularly preferred;

Substitution of like amino acids on the basis of hydrophilicity. U.S. Pat. No. 4,554,101 states that the greatest local average hydrophilicity of a protein, as governed by the hydrophilicity of its adjacent amino acids, correlates with a biological property of the protein. As detailed in this patent, the following hydrophilicity values have been assigned to amino acid residues: arginine (+3.0); lysine (+3.0); aspartate (+3.0.+0.1); glutamate (+3.0.+0.1); serine (+0.3); asparagine (+0.2); glutamine (+0.2); glycine (0); threonine (−0.4); proline (−0.5.+0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).Betts and Russell ((2003), "Amino Acid Properties and Consequences of Substitutions", Bioinformatics for Geneticists, Michael R. Barnes and Ian C. Gray, Eds., John Wiley & Sons, Ltd, Chapter 14, pp. 289-316) review the nature of mutations and the properties of amino acids in a variety of different protein contexts with the purpose of aiding in anticipating and interpreting the effect that a particular amino acid change will have on protein structure and function. The authors point out that features of proteins relevant to considering amino acid mutations include cellular environments, three-dimensional structure, and evolution, as well as the classifications of amino acids based on evolutionary, chemical, and structural principles, and the role for amino acids of different classes in protein structure and function in different contexts. The authors note that classification of amino acids into categories such as those shown in FIG. 14.3 of their review, which involves common physico-chemical properties, size, affinity for water (polar and non-polar; negative or positive charge), aromaticity and aliphaticity, hydrogen-bonding ability, propensity for sharply turning regions, etc., makes it clear that reliance on simple classifications can be dangerous, and suggests that alternative amino acids could be engineered into a protein at each position. Criteria for interpreting how a particular mutation might affect protein structure and function are summarized in section 14.7 of this review, and include first inquiring about the protein, and then about the particular amino acid substitution contemplated.

Biologically/enzymatically functional equivalents of the proteins and peptides disclosed herein can have 10 or fewer conservative amino acid changes, more preferably seven or fewer conservative amino acid changes, and most preferably five or fewer conservative amino acid changes, i.e., 10, 9, 8, 7, 6, 5, 4, 3, 2, or 1 conservative amino acid changes. The encoding nucleotide sequence (e.g., gene, plasmid DNA, cDNA, codon-optimized DNA, or other synthetic DNA) will thus have corresponding base substitutions, permitting it to code for the biologically functionally equivalent form of protein or peptide. Due to the degeneracy of the genetic code, i.e., the existence of more than one codon for most of the amino acids naturally occurring in proteins, other DNA (and RNA) sequences that contain essentially the same genetic information as these nucleic acids, and which encode the same amino acid sequence as that encoded by these nucleic acids, can be used in the methods disclosed herein. This principle applies as well to any of the other nucleotide sequences disclosed herein.

"Control" or "control level" means the level of a molecule, such as a polypeptide or nucleic acid, normally found in nature under a certain condition and/or in a specific genetic background. In certain embodiments, a control level of a molecule can be measured in a cell or specimen that has not been subjected, either directly or indirectly, to a treatment. A control level is also referred to as a wildtype or a basal level. These terms are understood by those of ordinary skill in the art. A control plant, i.e. a plant that does not contain a recombinant DNA that confers (for instance) an enhanced trait in a transgenic plant, is used as a baseline for comparison to identify an enhanced trait in the transgenic plant. A suitable control plant may be a non-transgenic plant of the parental line used to generate a transgenic plant. A control plant may in some cases be a transgenic plant line that comprises an empty vector or marker gene, but does not contain the recombinant DNA, or does not contain all of the recombinant DNAs, in the test plant.

The terms "enhance", "enhanced", "increase", or "increased" refer to a statistically significant increase. For the avoidance of doubt, these terms generally refer to about a 5% increase in a given parameter or value, about a 10% increase, about a 15% increase, about a 20% increase, about a 25% increase, about a 30% increase, about a 35% increase, about a 40% increase, about a 45% increase, about a 50% increase, about a 55% increase, about a 60% increase, about a 65% increase, about 70% increase, about a 75% increase, about an 80% increase, about an 85% increase, about a 90% increase, about a 95% increase, about a 100% increase, or more over the control value. These terms also encompass ranges consisting of any lower indicated value to any higher indicated value, for example "from about 5% to about 50%", etc.

"Expression" or "expressing" refers to production of a functional product, such as, the generation of an RNA transcript from an introduced construct, an endogenous DNA sequence, or a stably incorporated heterologous DNA sequence. A nucleotide encoding sequence may comprise intervening sequence (e.g., introns) or may lack such intervening non-translated sequences (e.g., as in cDNA). Expressed genes include those that are transcribed into mRNA and then translated into protein and those that are transcribed into RNA but not translated (for example, siRNA, transfer RNA, and ribosomal RNA). The term may also refer to a polypeptide produced from an mRNA generated from any of the above DNA precursors. Thus, expression of a nucleic acid fragment, such as a gene or a promoter region of a gene, may refer to transcription of the nucleic acid fragment (e.g., transcription resulting in mRNA or other functional RNA) and/or translation of RNA into a precursor or mature protein (polypeptide), or both.

An "expression cassette" refers to a nucleic acid construct, which when introduced into a host cell, results in transcription and/or translation of a RNA or polypeptide, respectively.

The term "genome" as it applies to a plant cells encompasses not only chromosomal DNA found within the nucleus, but organelle DNA found within subcellular components (e.g., mitochondrial, plastid) of the cell. As used herein, the term "genome" refers to the nuclear genome unless indicated otherwise. However, expression in a plastid genome, e.g., a chloroplast genome, or targeting to a plastid genome such as a chloroplast via the use of a plastid targeting sequence, is also encompassed by the present disclosure.

The term "heterologous" refers to a nucleic acid fragment or protein that is foreign to its surroundings. In the context of a nucleic acid fragment, this is typically accomplished by introducing such fragment, derived from one source, into a different host. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such fragment located in its(their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

A "heterologous" PGRL1 protein or CAB transit peptide protein-encoding nucleotide sequence, etc., can be one or more additional copies of an endogenous PGRL1 protein or CAB transit peptide protein-encoding nucleotide sequence, or a nucleotide sequence from another plant or other source. PGRL1 is a putative ferredoxin-plastoquinone reductase involved in photosynthetic cyclic electron flow. Furthermore, these can be genomic or non-genomic nucleotide sequences. Non-genomic nucleotide sequences encoding such proteins and peptides include, by way of non-limiting examples, mRNA; synthetically produced DNA including, for example, cDNA and codon-optimized sequences for efficient expression in different transgenic plants algae reflecting the pattern of codon usage in such plants; nucleotide sequences encoding the same proteins or peptides, but which are degenerate in accordance with the degeneracy of the genetic code; which contain conservative amino acid substitutions that do not adversely affect their activity, etc., as known by those of ordinary skill in the art.

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences, or homologs. The term "homologous" refers to the relationship between two nucleic acid sequence and/or proteins that possess a "common evolutionary origin", including nucleic acids and/or proteins from superfamilies (e.g., the immunoglobulin superfamily) in the same species of animal, as well as homologous nucleic acids and/or proteins from different species of animal (for example, myosin light chain polypeptide, etc.; see Reeck et al., (1987) Cell, 50:667). Such proteins (and their encoding nucleic acids) may have sequence homology, as reflected by sequence similarity, whether in terms of percent identity or by the presence of specific residues or motifs and conserved positions. The methods disclosed herein contemplate the use of the presently disclosed nucleic and protein sequences, as well as sequences having sequence identity and/or similarity, and similar function.

"Host cell" means a cell which contains a vector and supports the replication and/or expression of the vector. Host cells may be prokaryotic cells such as *E. coli*, or eukaryotic cells such as yeast, insect, amphibian, or mammalian cells. Alternatively, the host cells are monocotyledonous or dicotyledonous plant cells.

The term "introduced" means providing a nucleic acid (e.g., an expression construct) or protein into a cell. "Introduced" includes reference to the incorporation of a nucleic acid into a eukaryotic or prokaryotic cell where the nucleic acid may be incorporated into the genome of the cell, and includes reference to the transient provision of a nucleic acid or protein to the cell. "Introduced" includes reference to stable or transient transformation methods, as well as sexually crossing. Thus, "introduced" in the context of inserting a nucleic acid fragment (e.g., a recombinant DNA construct/expression construct) into a cell, can mean "transfection" or "transformation" or "transduction", and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

The term "isolated" refers to a material such as a nucleic acid molecule, polypeptide, or small molecule, that has been separated from the environment from which it was obtained. It can also mean altered from the natural state. For example, a polynucleotide or a polypeptide naturally present in a living animal is not "isolated" but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as "isolated polypeptides" or "isolated nucleic acid molecules", etc., are polypeptides or nucleic acid molecules that have been purified, partially or substantially, from a recombinant host cell or from a native source.

As used herein, "nucleic acid" or "nucleotide sequence" means a polynucleotide (or oligonucleotide), including single or double-stranded polymers of deoxyribonucleotide or ribonucleotide bases, and unless otherwise indicated, encompasses naturally occurring and synthetic nucleotide analogues having the essential nature of natural nucleotides in that they hybridize to complementary single-stranded nucleic acids in a manner similar to naturally occurring nucleotides. Nucleic acids may also include fragments and modified nucleotide sequences. Nucleic acids disclosed herein can either be naturally occurring, for example genomic nucleic acids, or isolated, purified, non-genomic nucleic acids, including synthetically produced nucleic acid sequences such as those made by solid phase chemical oligonucleotide synthesis, enzymatic synthesis, or by recombinant methods, including for example, cDNA, codon-optimized sequences for efficient expression in different transgenic plants reflecting the pattern of codon usage in such plants, nucleotide sequences that differ from the nucleotide sequences disclosed herein due to the degeneracy of the genetic code but that still encode the protein(s) of interest disclosed herein, nucleotide sequences encoding the presently disclosed protein(s) comprising conservative (or non-conservative) amino acid substitutions that do not adversely affect their normal activity, PCR-amplified nucleotide sequences, and other non-genomic forms of nucleotide sequences familiar to those of ordinary skill in the art.

The protein-encoding nucleotide sequences, and promoter nucleotide sequences used to drive their expression, disclosed herein can be genomic or non-genomic nucleotide sequences. Non-genomic nucleotide protein-encoding sequences and promoters include, for example, naturally-occurring mRNA, synthetically produced mRNA, naturally-occurring DNA, or synthetically produced DNA. Synthetic nucleotide sequences can be produced by means well known in the art, including by chemical or enzymatic synthesis of oligonucleotides, and include, for example, cDNA, codon-optimized sequences for efficient expression in different transgenic plants and algae reflecting the pattern of codon usage in such organisms, variants containing conservative (or non-conservative) amino acid substitutions that do not adversely affect their normal activity, PCR-amplified nucleotide sequences, etc.

"A PGRL1 protein", "a PGR5 protein", "a HLA3 protein", "a CAB transit peptide", "a PGR5 transit peptide", or any other protein or peptide presently broadly disclosed and utilized in any of the CCM methods and plants and algae disclosed herein refers to a protein or peptide exhibiting enzymatic/functional activity similar or identical to the enzymatic/functional activity of the specifically named protein or peptide. Enzymatic/functional activities of the proteins and peptides disclosed herein are described below. “Similar” enzymatic/functional activity of a protein or peptide can be in the range of from about 75% to about 125% or more of the enzymatic/functional activity of the specifically named protein or peptide when equal amounts of both proteins or peptides are assayed, tested, or expressed as described below under identical conditions, and can therefore be satisfactorily substituted for the specifically named proteins or peptides in the present enhanced CCM methods and transgenic plants and algae.

“Nucleic acid construct” or “construct” refers to an isolated polynucleotide which can be introduced into a host cell. This construct may comprise any combination of deoxyribonucleotides, ribonucleotides, and/or modified nucleotides. This construct may comprise an expression cassette that can be introduced into and expressed in a host cell.

“Operably linked” refers to a functional arrangement of elements. A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered “operably linked” to the coding sequence.

The terms “plant” or “plants” that can be used in the present methods broadly include the classes of higher and lower plants amenable to transformation techniques, including angiosperms (monocotyledonous and dicotyledonous plants), gymnosperms, ferns, and unicellular and multicellular algae. The term “plant” also includes plants which have been modified by breeding, mutagenesis, or genetic engineering (transgenic and non-transgenic plants). It includes plants of a variety of ploidy levels, including aneuploid, polyploid, diploid, haploid, and hemizygous. The plant may be in any form including suspension cultures, embryos, meristematic regions, callus tissue, gametophytes, sporophytes, pollen, microspores, whole plants, shoot vegetative organs/structures (e.g. leaves, stems and tubers), roots, flowers and floral organs/structures, seed (including embryo, endosperm, and seed coat) and fruit, plant tissue (e.g. vascular tissue, ground tissue, and the like) and cells, and progeny of same.

Embodiments of the present disclosure also include parts of plants or algae, which can be selected from among a protoplast, a cell, a tissue, an organ, a cutting, an explant, a reproductive tissue, a vegetative tissue, biomass, an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, a callus, propagation materials, germplasm, cuttings, divisions, and propagations.

Other embodiments include progeny or derivatives of transgenic plants and algae disclosed herein selected, for example, from among clones, hybrids, samples, seeds, and harvested material. Progeny can be asexually or sexually produced by methods well known in the art.

Useful C3 and C4 Plants

Plants to which the methods disclosed herein can be advantageously applied include both C3 and C4 plants, including “food crop” and “oilseed” plants, as well as algae.

Food Crop Plants

The term “food crop plant” refers to plants that are either directly edible, or which produce edible products, and that are customarily used to feed humans either directly, or indirectly through animals. Non-limiting examples of such plants include:

1. Cereal crops: wheat, rice, maize (corn), barley, oats, sorghum, rye, and millet;

2. Protein crops: peanuts, chickpeas, lentils, kidney beans, soybeans, lima beans;

3. Roots and tubers: potatoes, sweet potatoes, and cassavas;

4. Oil crops: soybeans, corn, canola, peanuts, palm, coconuts, safflower, cottonseed, sunflower, flax, olive, and safflower;

5. Sugar crops: sugar cane and sugar beets;

6. Fruit crops: bananas, oranges, apples, pears, breadfruit, pineapples, and cherries;

7. Vegetable crops and tubers: tomatoes, lettuce, carrots, melons, asparagus, etc.

8. Nuts: cashews, peanuts, walnuts, pistachio nuts, almonds;

9. Forage and turf grasses;

10. Forage legumes: alfalfa, clover;

11. Drug crops: coffee, cocoa, kola nut, poppy;

12. Spice and flavoring crops: vanilla, sage, thyme, anise, saffron, menthol, peppermint, spearmint, coriander.

In certain embodiments of this disclosure, the food crop plants are soybean, canola, tomato, potato, cassava, wheat, rice, oats, lettuce, broccoli, beets, sugar beets, beans, peas, kale, strawberry, and peanut.

“Oilseed Plants”, “Oil Crop Plants”, “Biofuels Crops”, “Energy Crops”

The terms “oilseed plant” or “oil crop plant”, and the like, to which the present methods and compositions can also be applied, refer to plants that produce seeds or fruit with oil content in the range of from about 1 to 2%, e.g., wheat, to about 20%, e.g., soybeans, to over 40%, e.g., sunflowers and rapeseed (canola). These include major and minor oil crops, as well as wild plant species which are used, or are being investigated and/or developed, as sources of biofuels due to their significant oil production and accumulation.

Exemplary oil seed or oil crop plants useful in practicing the methods disclosed herein include, but are not limited to, plants of the genera *Brassica* (e.g., rapeseed/canola (*Brassica napus; Brassica carinata; Brassica nigra; Brassica oleracea*), *Camelina, Miscanthus*, and *Jatropha*; Jojoba (*Simmondsia chinensis*), coconut; cotton; peanut; rice; safflower; sesame; soybean; mustard; wheat; flax (linseed); sunflower; olive; corn; palm; palm kernel; sugarcane; castor bean; switchgrass; *Borago officinalis; Echium plantagineum; Cuphea hookeriana; Cuphea pulcherrima; Cuphea lanceolata; Ricinus communis; Coriandrum sativum; Crepis alpina; Vernonia galamensis; Momordica charantia*; and *Crambe abyssinica*.

A non-limiting example of a tuber that accumulates significant amounts of reserve lipids is the tuber of *Cyperus esculentus* (chufa or tigernuts), which has been proposed as an oil crop for biofuel production. In the case of chufa, use of a constitutive or tuber-specific promoter would be useful in the methods disclosed herein.

Useful Algae

Algae useful in practicing various methods of the present disclosure include members of the following divisions: *Chlorophyta* and *Heterokontophyta*.

In certain embodiments, useful algae include members of the following classes: Chlorophyceae, Bacillariophyceae, Eustigmatophyceae, and Chrysophyceae. In certain embodiments, useful algae include members of the following genera: *Nannochloropsis, Chlorella, Dunaliella, Scenedesmus, Selenastrum, Oscillatoria, Phormidium, Spirulina, Amphora*, and *Ochromonas*. In one embodiment, members of the genus *Chlorella* are preferred.

Some algal species of particular interest include, without limitation: Bacillariophyceae strains, Chlorophyceae, Cyanophyceae, Xanthophyceae, Chrysophyceae, *Chlorella, Crypthecodinium, Schizocytrium, Nannochloropsis, Ulkenia, Dunaliella, Cyclotella, Navicula, Nitzschia, Cyclotella, Phaeodactylum*, and *Thaustochytrid*.

Non-limiting examples of algae species that can be used with the methods of the present disclosure include, for example, *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlore* Ila *anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Chlamydomonas moewusii Chlamydomonas reinhardtii Chlamydomonas* sp. *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii*, and *Viridiella fridericiana*.

In certain embodiments of this disclosure, the algae are species of *Chlorella, Nannochloropsis*, and *Chlamydomonas* listed above.

Exemplary food crop plant include wheat, rice, maize (corn), barley, oats, sorghum, rye, and millet; peanuts, chickpeas, lentils, kidney beans, soybeans, lima beans; potatoes, sweet potatoes, and cassavas; soybeans, corn, canola, peanuts, palm, coconuts, safflower, cottonseed, sunflower, flax, olive, and safflower; sugar cane and sugar beets; bananas, oranges, apples, pears, breadfruit, pineapples, and cherries; tomatoes, lettuce, carrots, melons, strawberry, asparagus, broccoli, peas, kale, cashews, peanuts, walnuts, pistachio nuts, almonds; forage and turf grasses; alfalfa, clover; coffee, cocoa, kola nut, poppy; vanilla, sage, thyme, anise, saffron, menthol, peppermint, spearmint and coriander and preferably wheat, rice and canola.

The terms "peptide", "polypeptide", and "protein" are used to refer to polymers of amino acid residues. These terms are specifically intended to cover naturally occurring biomolecules, as well as those that are recombinantly or synthetically produced, for example by solid phase synthesis.

The term "promoter" or "regulatory element" refers to a region or nucleic acid sequence located upstream or downstream from the start of transcription and which is involved in recognition and binding of RNA polymerase and/or other proteins to initiate transcription of RNA. Promoters need not be of plant or algal origin. For example, promoters derived from plant viruses, such as the CaMV35S promoter, or from other organisms, can be used in variations of the embodiments discussed herein. Promoters useful in the present methods include, for example, constitutive, strong, weak, tissue-specific, cell-type specific, seed-specific, inducible, repressible, and developmentally regulated promoters.

A skilled person appreciates that a promoter sequence can be modified to provide for a range of expression levels of an operably linked heterologous nucleic acid molecule. Less than the entire promoter region can be utilized and the ability to drive expression retained. However, it is recognized that expression levels of mRNA can be decreased with deletions of portions of the promoter sequence. Thus, the promoter can be modified to be a weak or strong promoter. A promoter is classified as strong or weak according to its affinity for RNA polymerase (and/or sigma factor); this is related to how closely the promoter sequence resembles the ideal consensus sequence for the polymerase. Generally, by “weak promoter” is intended a promoter that drives expression of a coding sequence at a low level. By “low level” is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. The promoter of choice is preferably excised from its source by restriction enzymes, but can alternatively be PCR-amplified using primers that carry appropriate terminal restriction sites. It should be understood that the foregoing groups of promoters are non-limiting, and that one skilled in the art could employ other promoters that are not explicitly cited herein.

The term “purified” refers to material such as a nucleic acid, a protein, or a small molecule, which is substantially or essentially free from components which normally accompany or interact with the material as found in its naturally occurring environment, and/or which may optionally comprise material not found within the purified material’s natural environment. The latter may occur when the material of interest is expressed or synthesized in a non-native environment. Nucleic acids and proteins that have been isolated include nucleic acids and proteins purified by standard purification methods. The term also encompasses nucleic acids and proteins prepared by recombinant expression in a host cell as well as chemically synthesized nucleic acids.

“Recombinant” refers to a nucleotide sequence, peptide, polypeptide, or protein, expression of which is engineered or manipulated using standard recombinant methodology. This term applies to both the methods and the resulting products. As used herein, a “recombinant construct”, “expression construct”, “chimeric construct”, “construct” and “recombinant expression cassette” are used interchangeably herein.

As used herein, the phrase “sequence identity” or “sequence similarity” is the similarity between two (or more) nucleic acid sequences, or two (or more) amino acid sequences. Sequence identity is frequently measured as the percent of identical nucleotide or amino acid residues at corresponding positions in two or more sequences when the sequences are aligned to maximize sequence matching, i.e., taking into account gaps and insertions.

One of ordinary skill in the art will appreciate that sequence identity ranges are provided for guidance only. It is entirely possible that nucleic acid sequences that do not show a high degree of sequence identity can nevertheless encode amino acid sequences having similar functional activity. It is understood that changes in nucleic acid sequence can be made using the degeneracy of the genetic code to produce multiple nucleic acid molecules that all encode substantially the same protein. Means for making this adjustment are well-known to those of skill in the art. When percentage of sequence identity is used in reference to amino acid sequences it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have “sequence similarity” or “similarity”. Means for making this adjustment are well-known to those of skill in the art. Typically this involves scoring a conservative substitution as a partial rather than a full mismatch, thereby increasing the percentage sequence identity.

“Percentage of sequence identity” is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Sequence identity (or similarity) can be readily calculated by known methods, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., J. Mol. Biol. 215: 403-410 (1990) and Altschul et al. Nucl. Acids Res. 25: 3389-3402 (1997)).

One example of an algorithm that is suitable for determining percent sequence identity and sequence similarity is the BLAST algorithm, which is described in (Altschul, S., et al., NCBI NLM NIH Bethesda, Md. 20894; & Altschul, S., et al., J. Mol. Biol. 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff(1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). One measure of similarity provided by the BLAST algorithm is the smallest sum probability (P (N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chern., 17: 149-163 (1993)) and XNU (Claverie and States, Comput. Chern., 17: 191-201 (1993)) low-complexity filters can be employed alone or in combination.

The constructs and methods disclosed herein encompass nucleic acid and protein sequences having sequence identity/sequence similarity at least about 75%, 80%, 85%, 90%, 91%, 92%, 93%, 94%, 95%, 96%, 97%, 98%, 99%, 100% to those specifically and/or sequences having the same or similar function for example if a protein or nucleic acid is identified with a transit peptide and the transit peptide is cleaved leaving the protein sequence without the transit peptide then the sequence identity/sequence similarity is compared to the protein with and/or without the transit peptide.

A "transgenic" organism, such as a transgenic plant, is a host organism that has been stably or transiently genetically engineered to contain one or more heterologous nucleic acid fragments, including nucleotide coding sequences, expression cassettes, vectors, etc. Introduction of heterologous nucleic acids into a host cell to create a transgenic cell is not limited to any particular mode of delivery, and includes, for example, microinjection, floral dip, adsorption, electroporation, vacuum infiltration, particle gun bombardment, whiskers-mediated transformation, liposome-mediated delivery, *Agrobacterium*-mediated transfer, the use of viral and retroviral vectors, etc., as is well known to those skilled in the art.

Conventional techniques of molecular biology, recombinant DNA technology, microbiology, and chemistry useful in practicing the methods of the present disclosure are described, for example, in Green and Sambrook (2012) Molecular Cloning: A Laboratory Manual, Fourth Edition, Cold Spring Harbor Laboratory Press; Ausubel et al. (2003 and periodic supplements) Current Protocols in Molecular Biology, John Wiley & Sons, New York, N.Y.; Amberg et al. (2005) Methods in Yeast Genetics: A Cold Spring Harbor Laboratory Course Manual, 2005 Edition, Cold Spring Harbor Laboratory Press; Roe et al. (1996) DNA Isolation and Sequencing: Essential Techniques, John Wiley & Sons; J. M. Polak and James O'D. McGee (1990) In Situ Hybridization: Principles and Practice; Oxford University Press; M. J. Gait (Editor) (1984) Oligonucleotide Synthesis: A Practical Approach, IRL Press; D. M. J. Lilley and J. E. Dahlberg (1992) Methods in Enzymology: DNA Structure Part A: Synthesis and Physical Analysis of DNA, Academic Press; and Lab Ref: A Handbook of Recipes, Reagents, and Other Reference Tools for Use at the Bench, Edited by Jane Roskams and Linda Rodgers (2002) Cold Spring Harbor Laboratory Press; Burgess and Deutscher (2009) Guide to Protein Purification, Second Edition (Methods in Enzymology, Vol. 463), Academic Press. Note also U.S. Pat. Nos. 8,178,339; 8,119,365; 8,043,842; 8,039,243; 7,303,906; 6,989,265; US20120219994A1; and EP1483367B1. The entire contents of each of these texts and patent documents are herein incorporated by reference.

Preliminary Results: Transgenic Plants Expressing Algal CCM Genes

Previously, reconstitution of a functional inorganic CCM in C3 plants to suppress photo-respiration and enhance photosynthesis was proposed. In WO 2012/125737, it was hypothesized that expression of a minimum of three algal CCM proteins would be sufficient to elevate internal plastid $CO_2$ concentrations high enough to suppress photorespiration. These three algal CCM genes included the *Chlamydomonas* plasma membrane-localized and ATP-dependent bicarbonate transporter, HLA3; the chloroplast envelope localized bicarbonate anion transporter, LCIA; and a chloroplast stromal-localized carbonic anhydrase (HCA-II) to accelerate conversion of bicarbonate into $CO_2$. These genes have individually been shown to be important to the CCM in prior studies ([3-5]). To test this hypothesis, we generated multiple independent transgenic *Arabidopsis* and *Camelina* plants expressing each CCM gene as a single gene construct, as well as a stacked 3-gene construct. The expression of each gene was controlled by the light-regulated Cab1 gene promoter [6].

Figure 6:
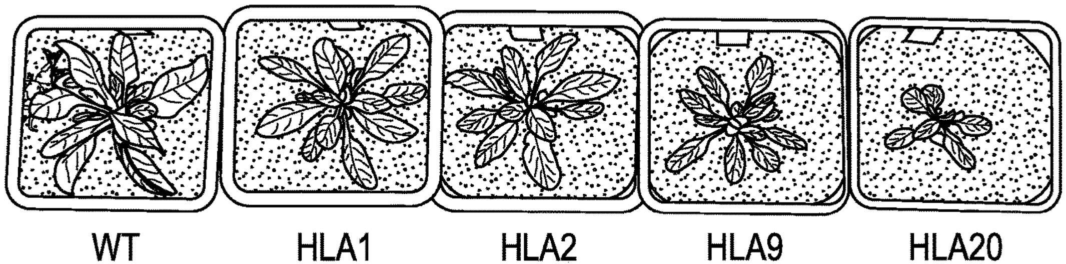
FIG. 6. Phenotype of HLA3 transgenics grown on nitrate. Energy charge and reductive potential of WT and HLA3 transgenic *Arabidopsis*. Adenylate, nucleotide cofactors, and inorganic phosphate levels measured as nmole/gFW for plants grown on nitrate. Values are averages ±SE.

The results of phenotypic analyses of *Arabidopsis* and *Camelina* plants transformed with the single CCM gene constructs were as follows:

HLA3 *Arabidopsis* transgenics varied in their phenotypes, but generally had reduced growth phenotypes relative to wild-type (WT) plants (FIG. 6). When the same plasmid was used to transform *Camelina*, no viable seeds were recovered from any transformation event after multiple attempts, indicating that HLA3 expression was likely toxic to *Camelina.*

Figure 3A:
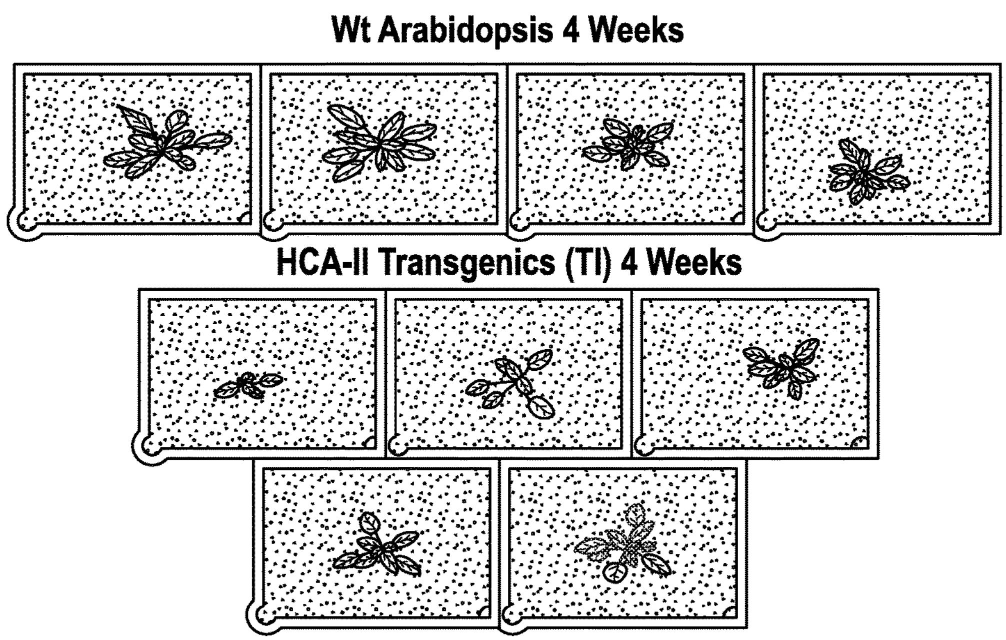
FIG. 3(A-B). (A) Growth phenotypes of WT and HCA-II transgenic (T1) *Arabidopsis* 4 weeks after germination. (B) Growth phenotype of WT *Arabidopsis* (Col-0, left) and the BCA transgenic (T3) (right).
Figure 3B:
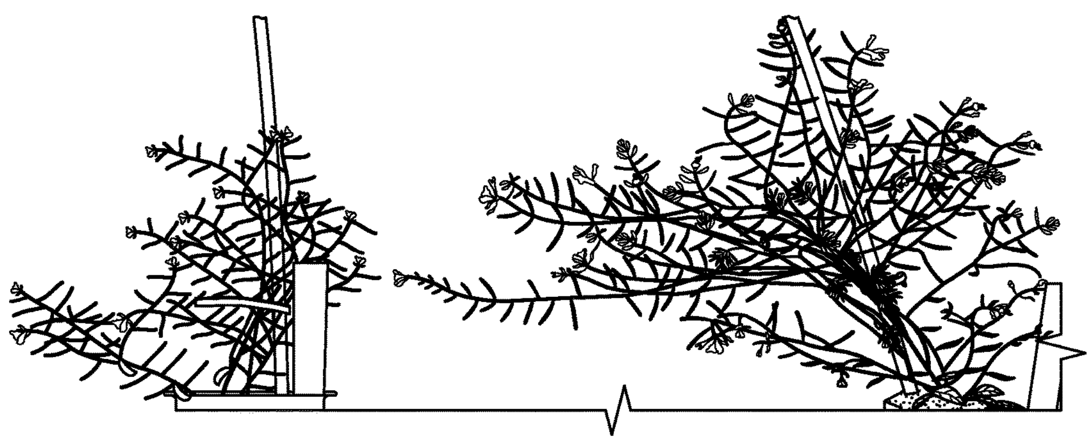
Figure 4:
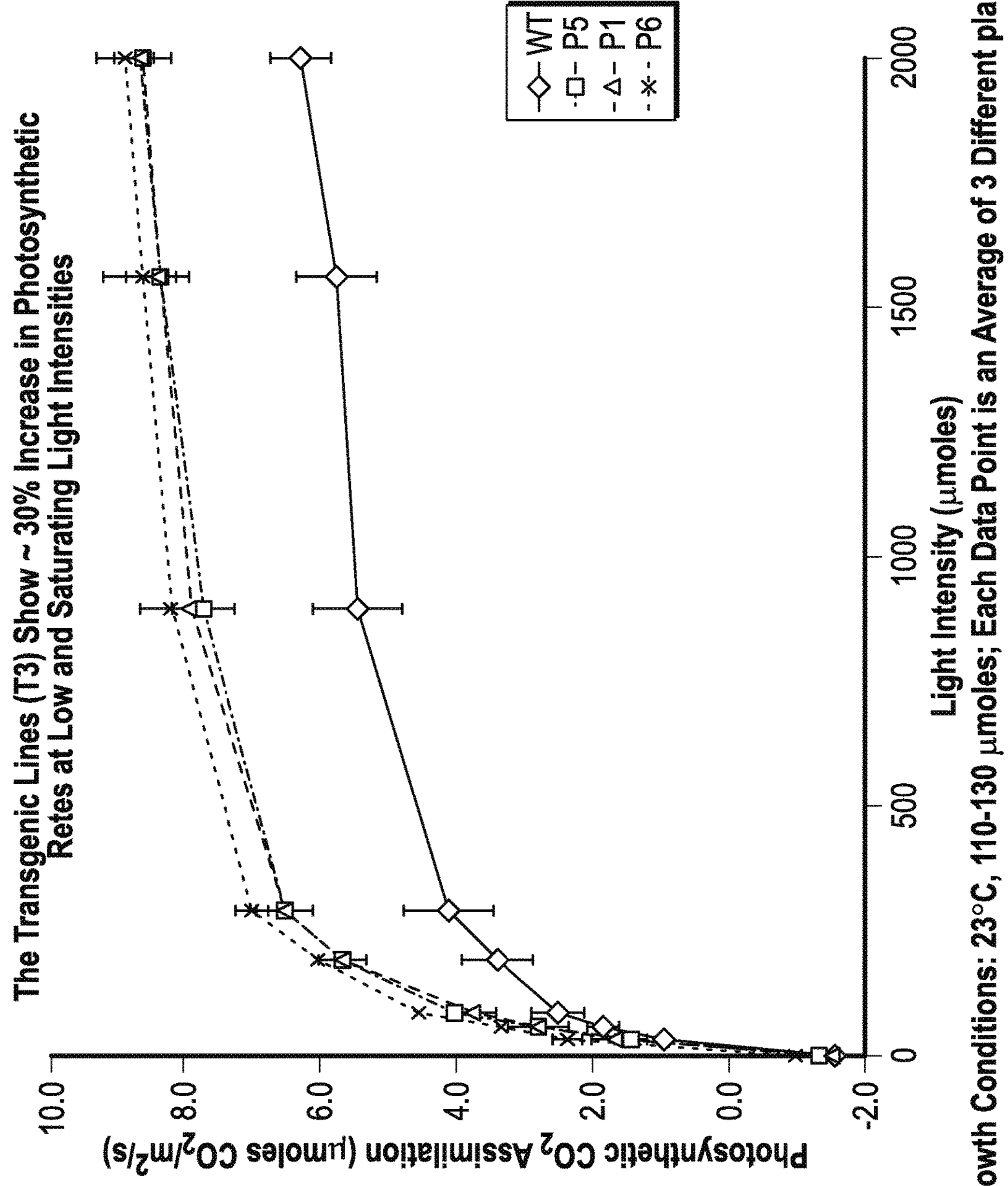
FIG. 4. Photosynthetic assimilation rate of $CO_2$ in three transgenic lines (P1, P5, P6) of *Arabidopsis* expressing BCA (bacterial carbonic anhydrase) measured using a LICOR 6400 gas analyzer. These lines showed ~30% increase in their photosynthetic efficiency when compared to WT *Arabidopsis* (Col.-0).

With respect to carbonic anhydrase (CA) transgenics, we expressed a human carbonic anhydrase-2 (HCA2 (SEQ ID NO:17)) or a bacterial *Neisseria gonorrhoeae* carbonic anhydrase (BCA SEQ ID NO 4)) in the chloroplast stroma [7]. We choose these CAs because each has a turnover number (Kcat=106 sec−1) that is approximately 10× faster than plant/algal CAs In both *Arabidopsis* and *Camelina*, we observed phenotypes that were either similar to WT (HCA2) or substantially larger (BCA) than WT plants (FIG. 3B).

Figure 5A:
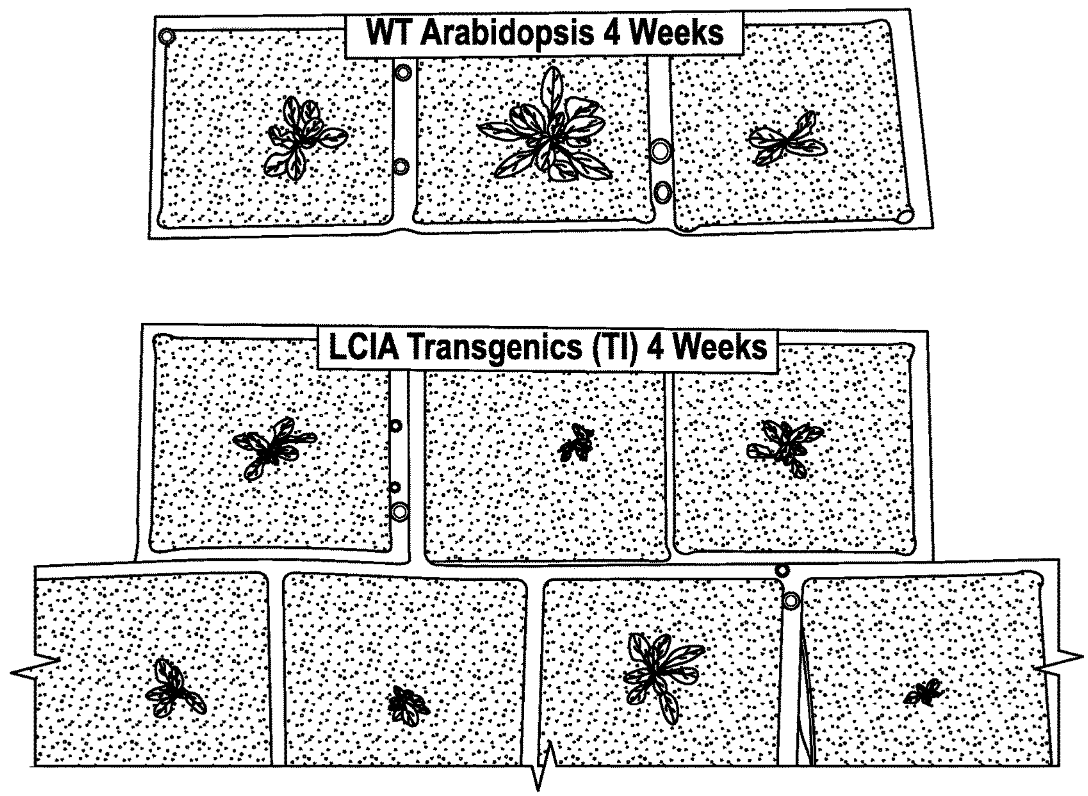
FIG. 5(A-C). (A) Growth phenotypes of WT and LCIA transgenic (T1) *Arabidopsis* plants four weeks after germination. (B) Four-week-old WT (left 4 plants) and independent transgenic Camelina (right 4 plants) expressing LCIA. (C) $CO_2$-dependent photosynthetic rates of WT and LCIA transgenic *Camelina.*
Figure 5B:
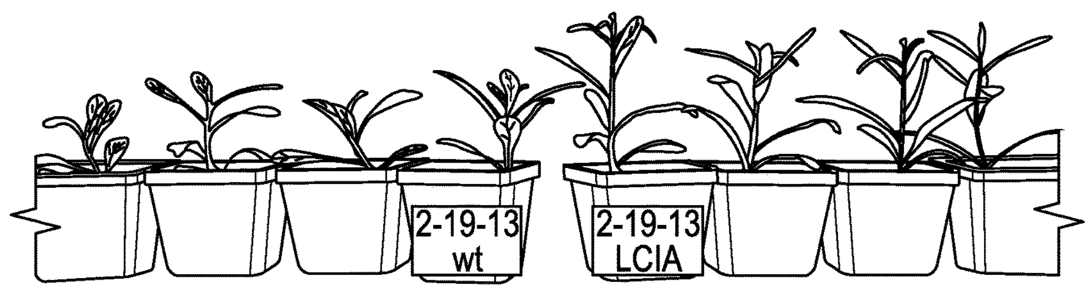

Transgenic *Arabidopsis* plants expressing the LCIA gene were substantially impaired in growth (FIG. 5A). In contrast, *Camelina* LCIA transgenics grew better than WT, had up to 25% higher photosynthetic rates at ambient $CO_2$ concentrations, and had reduced $CO_2$ compensation points (FIG. 5B).

The fact that expression of individual CCM genes impaired growth in C3 plants suggested that additional traits may need to be expressed or silenced to achieve optimal photosynthetic performance.

To determine if we could reconstitute a fully functional CCM complex in C3 plants, we transformed *Arabidopsis* and *Camelina* with a triple-gene CCM construct in which the expression of the HLA3, CA, and LCIA genes was driven by the green-tissue specific Cab1 promoter. In both *Arabidopsis* and *Camelina* there was either a substantial impairment in growth, or the plants did not survive (results not shown).

Thus, co-expression of the HLA3 gene with any other CCM gene(s) impaired growth even in plants in which expression of the other CCM genes, e.g., LCIA in *Camelina*, or BCA in *Arabidopsis*, enhanced growth. These results indicated that HLA3 expression was problematic.

Since the HLA3 protein catalyzes active bicarbonate transport and is the first-dedicated step in the engineered CCM, we re-focused our efforts on trying to determine why HLA3 expression was toxic to plants and how to mitigate its effects. We considered two possible hypotheses for HLA3 toxicity: 1) expression of the HLA3 ABC-transporter increases ATP demand (1 ATP/$CO_2$) for photosynthesis by 25% and depletes cytoplasmic ATP levels [3-5,8] and 2) elevated bicarbonate levels in HLA3 transgenic plants negatively impact cytoplasmic pH levels. With respect to the latter hypothesis, it is noteworthy that unlike cyanobacteria, plants have robust cytoplasmic CA activity, potentially mitigating the effects of elevated bicarbonate levels on cytoplasmic pH.

The Role of ATP Demand and Cyclic Electron Transfer Activity in CCMs

In contrast to air-grown algae (4 ATP/2 NADPH/$CO_2$) and C4 plants (5 ATP/2 NADPH/$CO_2$) which have increased ATP demands for photosynthesis, C3 plants (3 ATP/2 NADPH/$CO_2$) have limited capacity to generate additional ATP for each electron transferred [8-10]. Increasing ATP demand by 25% per carbon fixed in HLA3 transgenic plants, therefore, could deplete cytoplasmic ATP levels as well as alter the redox state of the cell [8,10]. One mechanism to increase ATP synthesis for each light-driven electron transferred is by cyclic electron transfer (CET) activity. Light-driven CET is catalyzed by photosystem I (PSI) mediated charge separation leading to the reduction of ferredoxin (fd) and the PGR5 protein. The PGR5 protein reduces and protonates plastoquinone (PQ). PQH2 is then oxidized by the cytochrome b6f complex (Cyt b6f). Protons released from the oxidation of PQH2 drive ATP synthesis. The electron transfer cycle is completed by the reduction of plastocyanin (PC) by Cyt b6f, which in turn is oxidized by the PSI primary donor P700+. Significantly, molecular studies have demonstrated that genes encoding proteins functional in CET are substantially overexpressed (4-10×) in C4 plants and air-grown algae relative to related C3 species or high $CO_2$ grown algae [9,11-17]. These CET genes include: the Proton Gradient Regulation Genes PGR5 and PGRL1, and certain members of the Fd and ferredoxin NADP reductase (FNR) gene families [8-15]: Accession Nos.: PGR5:NM_126585; PGRL1: NM_179091; Fd: AtFd1: At1g10960; AtFd2:At1g60950; FNR: LFNR1:At5g66190; LFRN2: At1g20020) [15]. The sequence for the PRG5 protein with the transit peptide amino acid sequence underlined is provided as MAAASISAIGCNQTLIGTSF YGGWGSSISGEDYQTMLSKTVAPPQQARVS RKAIRAVPMMKNVNEGKGLF APLVVVTRNL VGKKRFNQLR GKAIALHSQV ITEFCKSIGA DAKQRQGLIRAKKNGERLG FL (SEQ ID NO:1). The transit peptide is cleaved to produce the functional PGR5 protein.

To test the hypothesis that ATP depletion in HLA3 transgenics resulted in growth impairment, we compared the phenotypes of WT and HLA3 transgenics grown on nitrate which would require more linear electron transport (LET) to facilitate the reduction of nitrate. Significantly, the additional ATP produced by LET is not required for conversion of nitrate to ammonium and thus total ATP levels are expected to increase. In contrast, plants grown on ammonium do not require additional LET. Finally, we also grew transgenics on ammonium with sucrose which would presumably provide additional ATP via respiration [15,17]. We hypothesized that growth on nitrate or ammonium with sucrose would provide additional ATP that could potentially drive HLA3 activity.

As shown in FIG. 2B, none of the *Arabidopsis* HLA3 transgenics (4 independent lines) grew in the presence of ammonium, but all HLA3 lines were rescued when grown on ammonium with sucrose. Furthermore, plants grown on ammonium plus sucrose were phenotypically similar to WT (FIG. 2B). In contrast, all HLA3 plants grown on nitrate survived, but some lines (#9, #20) had substantially impaired growth phenotypes. Identical results were observed for the germination and growth of WT and HLA3 transgenic seeds on MS media agar plates using either nitrate (HLA3 transgenics survived) or ammonium (HLA3 transgenics died) as the sole nitrogen source (results not shown). Based on these observations, we propose that increased ATP synthesis associated with nitrate-driven LET and/or sucrose metabolism reduces the depletion of cytoplasmic ATP levels in HLA3 transgenics and rescues them.

This interpretation was corroborated by comparative metabolite analyses of leaf energy charge (EC) status (ATP), inorganic phosphate levels, and leaf reductive potential (RP) of WT and HLA3 transgenic *Arabidopsis* grown on nitrate. As shown in FIG. 6, HLA3 transgenics grown on nitrate had reduced EC and RP ratios relative to WT. Energy charge is defined as ([ATP] +1/2[ADP])/([ATP]+[ADP]+[AMP]). The reduction potential is a measurement of the capacity of the system to gain or lose electrons.

Significantly, inorganic phosphate levels were two-fold higher in HLA3 line #20, while the NADH level was two-fold lower than WT.

These results are consistent with the hypothesis that HLA3 expression places increased ATP demand on plants. This increased ATP demand in HLA3 transgenics may be met in part via NAD(P)H oxidation via the malate/oxaloacetate redox shunt between the mitochondria and chloroplasts [16].

LCIA Phenotype Depends on Plant Species

Figure 5C:
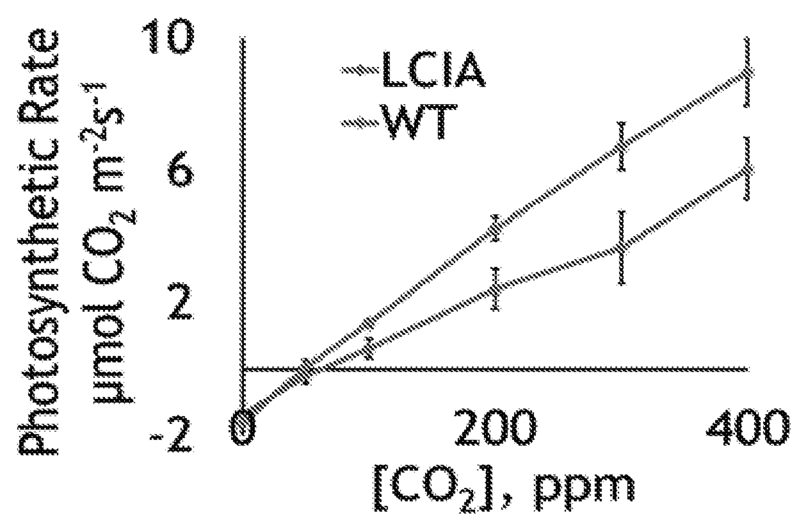

As previously indicated, LCIA expression in transgenic *Arabidopsis* resulted in plants with severely depressed growth phenotypes (FIG. 5A). In contrast, transgenic *Camelina* expressing LCIA had increased growth rates as well as higher $CO_2$-dependent photosynthetic rates relative to WT (FIG. 5B). We propose that the substantially greater carbon sink-strength of *Camelina* relative to *Arabidopsis* accounts for the enhanced growth phenotype observed in *Camelina* LCIA plants. In support of this hypothesis, we observed that *Camelina* LCIA transgenics had higher $CO_2$-dependent rates of photosynthesis and lower $CO_2$ compensation points (40 vs. 53 ppm $CO_2$) than WT plants indicative of facilitated inorganic carbon uptake by LCIA (FIG. 5C).

Overview: Enhancing photosynthetic carbon fixation by increasing ATP production and limiting $CO_2$ diffusion out of artificial CCM lines; Strategies for facilitating CET and ATP synthesis in C3 plants Prior attempts to subvert the limitations of photosynthesis have focused on engineering RuBisCO throughput and specificity [35] by introduction of engineered and non-native forms of the enzyme [36], through alterations in the regenerative capacity of the Calvin cycle [37,38] or by engineering photorespiratory bypasses [39]. These studies produced mixed results, thus advocating for a more comprehensive systems-level approach to enhance and/or redirect photosynthetic carbon flux.

As evidenced by our prior work described above, we postulate that both the carbon assimilatory steps and the light-based generation of ATP and NAPDH must be considered to develop a competent CCM with significantly improved photosynthetic capacity. To demonstrate proof of concept, an *Arabidopsis* line that contains a functional CCM that includes mechanisms to adjust ATP levels to meet transporter demand will be generated.

Enhancing CET and ATP synthesis to support HLA3-dependent bicarbonate uptake

To exploit the expression of an algal CCM in C3 plants requires that we meet the additional energy demands required to actively transport inorganic carbon. As previously discussed in the section entitled "The role of ATP demand and cyclic electron transfer activity in CCMs", C4 plants and algae have robust CET activity, and overexpress a variety of genes involved in CET [13,16,40-45] compared to C3 plants.

Several strategies are identified in the following examples, to increase ATP synthesis to support HLA3-dependent bicarbonate transport. Several of these strategies focus on elevating CET activity in C3 plants. Another approach involves the expression of a green photon-driven bacterial proton pump in thylakoids to supplement proton-driven ATP synthesis. Each approach is designed to complement existing CCM lines in *Arabidopsis, Camelina*, and potato we have created, and are evaluated based upon measured adenylate levels, plant biomass production, and photosynthetic measurements of carbon assimilation. The materials and methods employed in the examples below are for illustrative purposes only, and are not intended to limit the practice of the present embodiments thereto. Any materials and methods similar or equivalent to those described herein as would be apparent to one of ordinary skill in the art can be used in the testing or practice of the present embodiments, i.e., the materials, methods, and examples are illustrative only and not intended to be limiting.

EXAMPLE 1

Enhancing CET Based on Overexpressing the Proton Gradient Regulatory Proteins PGR5 and PGRL1 in C3 Plants Enhancing CET is based on overexpressing the proton gradient regulatory proteins PGR5 and/or PGRL1 which have previously been shown to be important to CET [37].

It has recently been demonstrated that the PGRL1 protein has antimycin A-sensitive (AA), ferredoxin-plastoquinone reductase (FQR) activity [46]. In *Chlamydomonas*, PGRL1 is part of the Cytb6f/PSI supercomplex which mediates CET. Significantly, PGRL1 forms homodimers as well as heterodimers with PGR5 via redox active cysteine residues. Under high-light conditions, thioredoxinred reduces PGRL1 dimers present in grana stacks, increasing the abundance of PGRL1 monomers and enhancing CET [47]. Mutational studies have shown that the PGR5 protein is required for Fd oxidation and PGRL1 reduction, but not for PQ reduction. In addition, it has been shown that PGRL1/PGR5 heterodimers are more active in CET than PGRL1 monomers. In C4 plants PGR5 and PGRL1 expression levels are elevated (4×) relative to C3 plants [9]. Similarly, PGR5 expression is up-regulated in air-grown *Chlamydomonas* (active CCM and HLA3 activity) relative to high $CO_2$ (low CCM) grown cells [16,43]. Significantly, overexpression of PGRL1 and PGR5 has also been shown to increase AA-sensitive CET in transgenic *Arabidopsis* [48]. One embodiment of the present invention provides for an overexpression of PGRL1 gene (SEQ ID NO:106) and PGR5 gene with chloroplast targeting sequence (SEQ ID NO:2) with HLA3 gene (SEQ ID NO:12) or with HLA3 gene (SEQ ID NO:12) and LCIA gene (SEQ ID NO:16) and BCA gene codon optimized for expression in *Arabidopsis* (SEQ ID NO:4) to yield substantially increased photosynthetic rates, particularly in plants with enhanced sink strength (*Camelina* and potato for example). Co-expression of the PGR5 gene (SEQ ID NO:2) along with the HLA3 gene (SEQ ID NO:12) in *Camelina* rescued the HLA3 gene and it was no longer lethal. These results indicate that the PGR5 gene is enabling the production of sufficient ATP to meet the demands of the HLA3 gene product.

Figure 9:
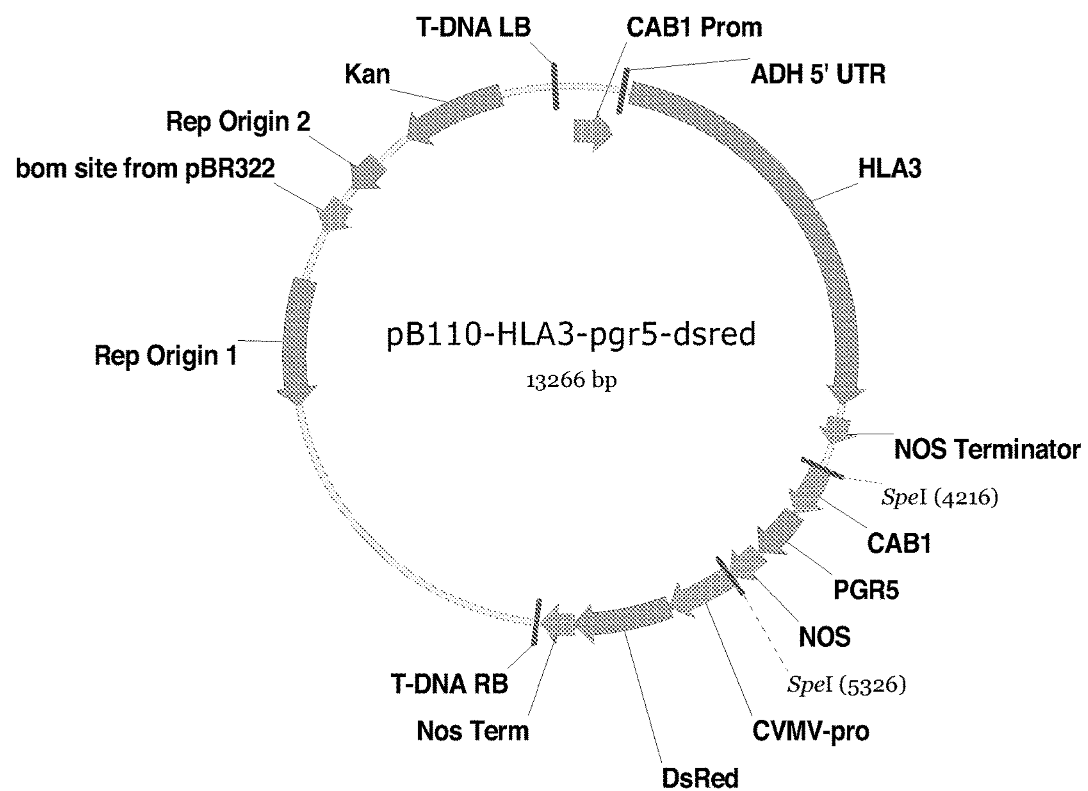
FIG. 9. Plasmid pB110-HLA3-pgr5-dsred (Example 1).

HLA3 (SEQ ID NO:12) and PGR5 (SEQ ID NO:2) are introduced as a double construct into *Arabidopsis* or *Camelina*, by *Agrobacterium*-mediated Ti plasmid transformation using, for example, plasmid pB110-HLA3-pgr5-dsred (FIG. 9). Since PGR5 protein (SEQ ID NO:1) is naturally targeted to the thylakoid membranes, no additional targeting sequences are introduced. Similarly, since HLA3 protein (SEQ ID NO:77) is naturally targeted to the chloroplast envelope, no additional targeting sequences are added. HLA3 is codon optimized for plant expression.

In one embodiment, the expression of each protein is driven by the light sensitive leaf-specific CAB1 promoter (SEQ ID NO:7) and Nos terminator (SEQ ID NO:9) (FIG. 9).

The BCA gene (AAW89307; SEQ ID NO:4), under the control of CAB1 promoter, is introduced in to *Arabidopsis* by *Agrobacterium*-mediated Ti plasmid transformation by floral dip method using the construct shown in FIG. 10.

Figure 10:
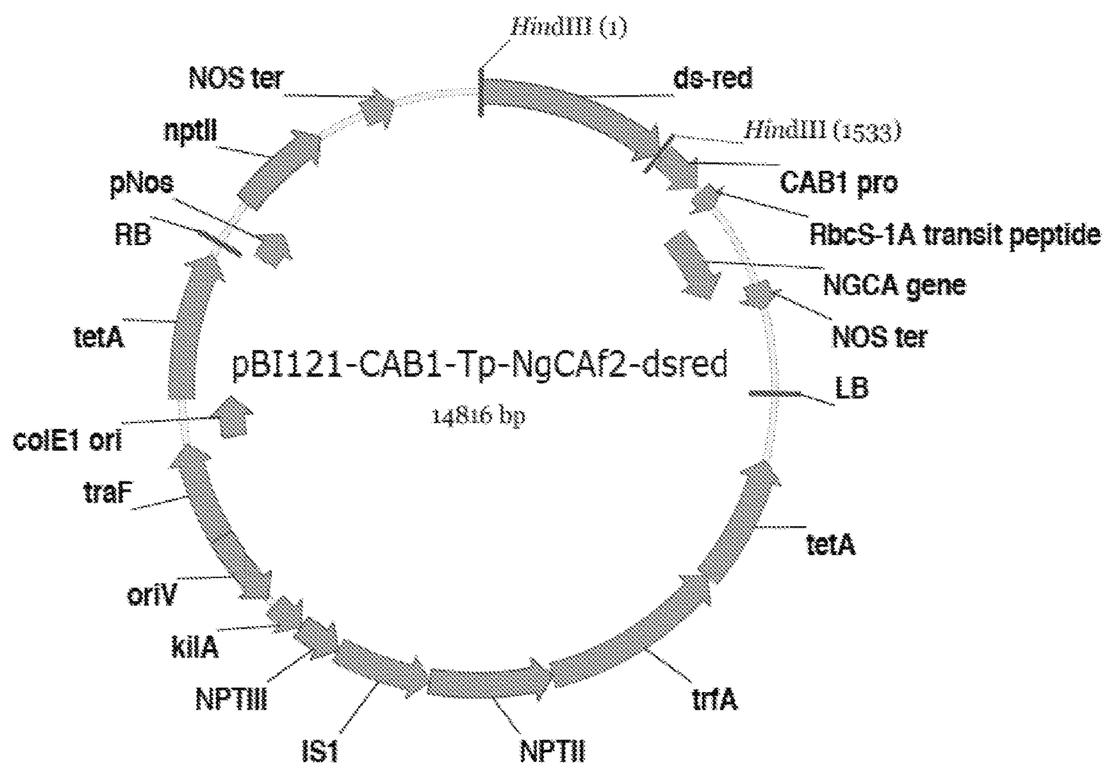
FIG. 10. Plasmid pBI 121-CAB1-Tp-NgCAf2-dsred (Example 1).

As a visual marker, the plasmid also includes a gene for expression of fluorescent DsRed protein under the control of CVMV promoter and Nos terminator (FIG. 10).

Plants are transformed by vacuum infiltration method (Lu and Kang (February, 2008) Plant Cell Rep. 27(2):273-8), and will be screened for biomass yield parameters (including plant weight, height, branching and seed yield) and photosynthetic efficiency measured as $CO_2$ absorption with the aid of a LiCor 6400 gas exchange analyzer.

The PGRL1 gene from *Arabidopsis* (NM_179091 SEQ ID NO:3) will be subcloned into pCambia1301-based binary plasmid under control of the CAB1 promoter (SEQ ID NO:7) and Nos terminator (SEQ ID NO:9). The plasmid will also carry a gene for hygromycin selection marker. *Agrobacterium*-mediated transformation takes place by the standard floral dip method followed by germination of seeds on hygromycin to select for transformants. The expression of PRGL1 will be confirmed by RT-PCR, and the resulting transgenic plant lines will be crossed with HLA3/PGR5 plants and screened for biomass yield and photosynthesis rate ($CO_2$ fixation).

EXAMPLE 2

Determining if Fd1 Gene Overexpression Can Support Algal CCM and Increased Photosynthetic Rates It has recently been demonstrated that specific members of the ferredoxin (Fd) gene family facilitate CET. Overexpression of pea ferredoxin1 (Fd1) enhanced CET at the expense of LET in tobacco [16,40].

Therefore, another embodiment of the present invention provides enhancing ATP production and titrating the expression of the pea Fd1 gene in the three model C3 plants with and without co-expression of the CCM genes to determine if Fd1 overexpression can support the algal CCM and increased photosynthetic rates. Earlier results demonstrated that Fd1 overexpression slightly impaired Linear Electron Transfer (LET), resulting in a stunted phenotype [40]. We expect that the additional ATP demand in HLA3 transgenics, however, will mitigate these effects.

Fd1 gene (At1g10960) will be introduced by *Agrobacterium*-mediated Ti plasmid transformation. Fd1 gene will be subcloned into pCambia1301-based binary plasmid under control of CAB1 promoter (SEQ ID NO:7) and Nos terminator (SEQ ID NO:9). The plasmid will also carry a gene for hygromycin selection as a marker. *Agrobacterium*-mediated transformation takes place by the standard floral dip method, followed by germination of seeds on hygromycin to select for transformants. The expression of FD1 (SEQ ID NO:93) will be confirmed by real time QPCR, and the resulting plant lines exhibiting different levels of FD1 expression will be crossed with CCM-expressing plants and screened for biomass yield and photosynthesis rate with the aid of a LiCor 6400 $CO_2$-gas exchange analyzer.

EXAMPLE 3

Overexpression of Unique Ferredoxin NADP Reductase (FNR) Gene Family Members Associated with CET Yet another embodiment is based on overexpression of unique ferredoxin NADP reductase (FNR) gene family members associated with CET. Leaf FNR (LFNR) catalyzes the reduction of Fd and is involved in both LET and CET [15]. It was recently demonstrated that there are three LFNR gene family members expressed in maize leaves: Accession Nos. BAA88236 (LFNR1), BAA88237 (LFNR2), and ACF85815 (LFNR3).

LFNR-1 was shown to be localized to thylakoid membranes and associated with Cytb6f complexes. LFNR2 was present in thylakoids and stroma associated with Cytb6f complexes. LFNR3 was soluble and not associated with Cytb6f complexes.

Significantly, when plants were grown with nitrate instead of ammonium, expression of LFNR1 and LFNR2 was elevated but not that of LFNR3. In contrast, studies using *Arabidopsis* LFNR1 knockout mutants demonstrated that PGA-dependent oxygen evolution (which requires additional ATP) is more negatively affected than is nitrate-dependent oxygen evolution (no additional ATP demand), suggesting that LFNR1 may play a role in regulating CET [15]. However, this interpretation remains equivocal.

To determine if CET activity and HLA3 mediated inorganic carbon uptake can be altered by differential expression of LFNR1, we will both over-express (CAB1 promoter (SEQ ID NO:7)) and under-express (LFNR1 RNAi) LFNR1 in transgenic *Arabidopsis* to determine the impact of altered LFNR1 expression on functional CCM activity.

For overexpression of the LFNR1, the gene (At5g66190) will be introduced by *Agrobacterium*-mediated Ti plasmid transformation by floral dipping. The LFNR1gene will be subcloned into pCambia1301-based binary plasmid under control of the CAB1 promoter (SEQ ID NO:7) and Nos terminator (SEQ ID NO:9). The plasmid will also carry a gene for hygromycin selection as a marker. The expression of LFNR1 will be confirmed by real time QPCR, the resulting plant lines will be crossed with CCM-expressing plants, and screened for biomass yield and photosynthesis rate with the aid of a LiCor 6400 $CO_2$-gas exchange analyzer.

For downregulaton of the LFNR1 levels, an RNAi construct containing a partial sequence of the LFNR1 (At5g66190 or BAA88236) and reverse complementary sequence of LFNR1 will be subcloned into pCambia1301-based binary plasmid under control of the CAB1 promoter (SEQ ID NO:7) and Nos terminator (SEQ ID NO:9). The plasmid will also carry a gene for hygromycin selection as a marker. The reduced level of LFNR1 expression will be confirmed by real time QPCR.

The resulting lines will be crossed with CCM-expressing lines to generate double mutants. Those mutants will be screened for biomass yield parameters (including plant weight, height, branching and seed yield) and photosynthetic efficiency measured as $CO_2$ absorption with the aid of a LiCor 6400 gas exchange analyzer.

EXAMPLE 4

Facilitated Vectoral Proton Transport Using Proteorhodopsin (PR)

Figure 7:
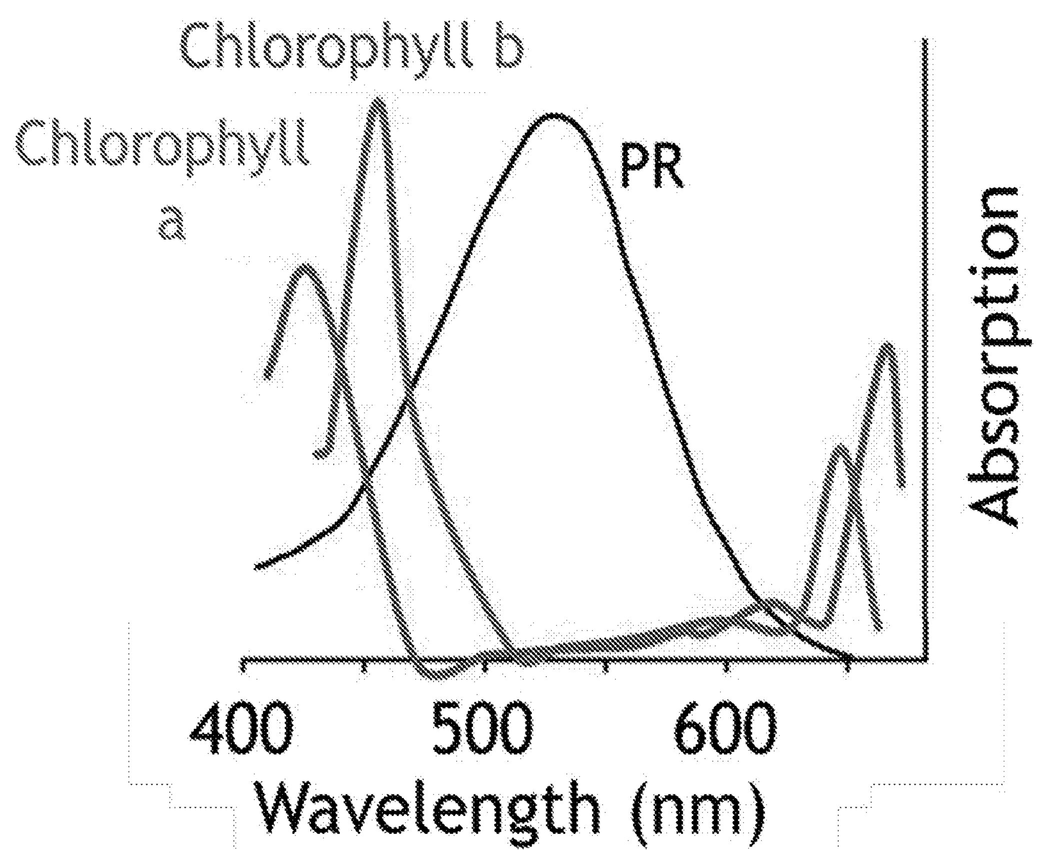
FIG. 7. Photosynthetically active radiation in proteorhodopsin relative to plant-based chlorophyll [49].
Figure 8:
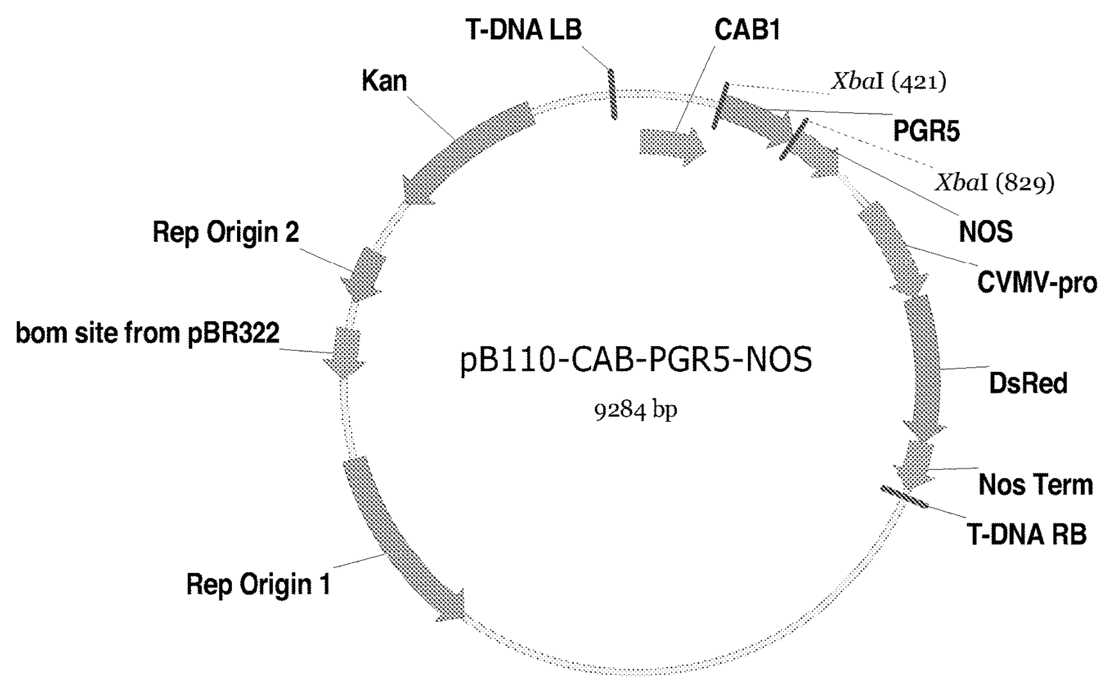
FIG. 8. Plasmid pB110-CAB-PGR5-NOS (Example 1).

In yet another embodiment green photons, not absorbed by chlorophyll, to drive proton transport across thylakoids by expressing modified PR [49]) will be employed to enhance ATP sysnthesis (FIG. 7).

PR is a seven-helix transmembrane-spanning protein similar to bacteriorhodopsin that contains retinal in its active site. Green light-driven cis-trans isomerization of retinal drives vectoral proton transfer across the membrane [50-55]. Significantly, it has been demonstrated that a functional PR could be expressed in a respiration-impaired mutant of *E. coli* when supplemented with exogenous all-trans retinal [56]. More recently, hydrogen production was shown to increase nearly two-fold in PR-expressing *E. coli* when cells were exposed to increasing light intensities (70 to 130 μE), indicating that PR can efficiently absorb light even at low intensities [57]. To the best of our knowledge, retinal complementation of other rhodopsins has not been reported. Significantly, PR-expressing *E. coli* respiratory mutants generated sufficient proton-motive force to support ATP synthesis levels, leading to enhanced cell viability and motility when transgenics were exposed to sunlight as the only energy source.

These results suggest that targeting PR to the thylakoid membrane using appropriate targeting sequences (e.g., nuclear-encoded, N-terminal, light harvesting complex signal sequences) and supplementation with exogenous retinal or retinal derived from β-carotene cleavage) could drive additional ATP synthesis. One concern is that the optical cross section of retinal is small and light harvesting by PR is not supplemented by antenna complexes. This constraint may be overcome in part by overexpressing PR in thylakoids. Regardless, the additional proton gradient necessary to support HLA3 activity is substantially less than that required to support overall $CO_2$ fixation. The best achievable PR expression levels will be determined empirically using different gene promoters, e.g., psaD (SEQ ID NO:10), rbcs (SEQ ID NO:11), and cab1 (SEQ ID NO:7), to drive its expression.

Generation of Improved PR and its Functional Reconstitution in Chloroplasts

PR (AF279106),for example (SEQ ID NO:98),will be introduced into *Arabidopsis, Camelina*, and potato by Ti plasmid transformation and targeted to the thylakoid membrane using the DNAJ transit peptide (At5g21430, SEQ ID NO: 22) or psbX stop-transfer trans-membrane domain (At2g06520 SEQ ID NO:23) fused to the C-terminus of PR [58], or transit peptides from nuclear encoded chloroplast proteins such as CAB (SEQ ID NO:13), PGR5 (SEQ ID NO:14), and psaD (SEQ ID NO:15). Reconstitution with exogenous retinal will be carried out in a manner similar to strategies described for *E. coli*, except that retinal will be painted on the surface of the leaf [56] to demonstrate proof of concept. Retinal reconstitution will be followed by monitoring the absorption of the thylakoid membranes at 540 nm [59].

If exogenously applied retinal is not incorporated into PR, we will express low levels of a plant codon-optimized β-carotene monooxygenase for example (SEQ ID NO:100) in plastids to cleave a small fraction of β-carotene to generate retinal. Non-limiting examples of β-carotene monooxygenases that can be used include, for example, mouse, human, zebra fish, and rat enzymes (Accession Nos. AW044715, AK001592, AJ290390, and NM_053648, respectively). Alternatively, if β-carotene levels are severely depleted, we will transiently express β-carotene monooxygenase under the control of a transient inducible promoter such as an ethanol inducible gene promoter. This is available as an EcoRI/Pstl fragment from Syngenta-Construct: pJL67-5S::AlcR/AlcA::GUS in pMLBART (Weigel World, Max Planck Institute for Developmental Biology, Tubingen, Germany) for periods of time sufficient to fully saturate PR [60,61]. Operation of a functional retinal photocycle in PR will be confirmed by transient absorption spectroscopy [62].

Alternatively, promoters such as the green tissue/leaf-specific promoters such as the CAB (At3g54890 SEQ ID NO:7) and rbcS (At5g38420 SEQ ID NO:11) promoters can be used, for example see SEQ ID NO:5 for the BCA protein with a rbc-1a transit peptide. As the skilled person will be well aware, various promoters may be used to promote the transcription of the nucleic acid of the invention, i.e. the nucleic acid which when transcribed yields an RNA molecule that modulates the expression and/or activity of a protein according to the invention. Such promoters include for example constitutive promoters, inducible promoters (e.g. light inducible promoters, stress-inducible promoters, drought-inducible promoters, hormone-inducible promoters, chemical-inducible promoters, etc.), tissue-specific promoters, developmentally regulated promoters and the like.

Thus, a plant expressible promoter can be a constitutive promoter, i.e. a promoter capable of directing high levels of expression in most cell types (in a spatio-temporal independent manner). Examples of plant expressible constitutive promoters include promoters of bacterial origin, such as the octopine synthase (OCS) and nopaline synthase (NOS) promoters from *Agrobacterium*, but also promoters of viral origin, such as that of the cauliflower mosaic virus (CaMV) 35S transcript (Hapster et al., 1988, Mol. Gen. Genet. 212: 182-190) or 19S RNAs genes (Odell et al., 1985, Nature. 6; 313(6005):810-2; U.S. Pat. No. 5,352,605; WO 84/02913; Benfey et al., 1989, EMBO J. 8:2195-2202), the enhanced 2×35S promoter (Kay at al., 1987, Science 236:1299-1302; Datla et al. (1993), Plant Sci 94:139-149) promoters of the cassava vein mosaic virus (CsVMV; WO 97/48819, U.S. Pat. No. 7,053,205), 2×CsVMV (WO2004/053135) the circovirus (AU 689 311) promoter, the sugarcane bacilliform badnavirus (ScBV) promoter (Samac et al., 2004, Transgenic Res. 13(4):349-61), the figwort mosaic virus (FMV) promoter (Sanger et al., 1990, Plant Mol Biol. 14(3):433-43), the subterranean clover virus promoter No 4 or No 7 (WO 96/06932) and the enhanced 35S promoter as described in U.S. Pat. No. 5,164,316, U.S. Pat. No. 5,196,525, U.S. Pat. No. 5,322,938, U.S. Pat. No. 5,359,142 and U.S. Pat. No. 5,424,200. Among the promoters of plant origin, mention will be made of the promoters of the promoter of the *Arabidopsis thaliana* histone H4 gene (Chaboutéet al., 1987), the ubiquitin promoters (Holtorf et al., 1995, Plant Mol. Biol. 29:637-649, U.S. Pat. No. 5,510,474) of Maize, Rice and sugarcane, the Rice actin 1 promoter (Act-1, U.S. Pat. No. 5,641,876), the histone promoters as described in EP 0 507 698 A1, the Maize alcohol dehydrogenase 1 promoter (Adh-1) (from http://www.patentlens.net/daisy/promoters/242.html)).

A variety of plant gene promoters that regulate gene expression in response to environmental, hormonal, chemical, developmental signals, and in a tissue-active manner can be used for expression of a sequence in plants. Choice of a promoter is based largely on the phenotype of interest and is determined by such factors as tissue (e.g., seed, fruit, root, pollen, vascular tissue, flower, carpel, etc.), inducibility (e.g., in response to heat, cold, drought, light etc.), timing, developmental stage, and the like.

Promoters that can be used to practice this invention include those that are green tissue specific such as the promoter of light harvesting complex protein 2 (Sakamoto et al. Plant Cell Physiology, 1991, 32(3): 385-393) or the promoter of the cytosolic fructose-1, 6-bisphosphatase from rice (Si et al. Acta Botanica Sinica 45: 3(2003): 359-364). Alternative embodiments include light inducible promoters such as promoters of the plant ribulose-biscarboxylase/oxygenase (Rubisco) small subunit promoter (U.S. Pat. No. 4,962,028; WO99/25842) from zea mays and sunflower. Also the small subunit promoter from Chrysanthemum may be used, combined or not combined with the use of the respective terminator (Outchkourov et al., Planta, 216: 1003-1012, 2003).

Additional promoters that can be used to practice this invention are those that elicit expression in response to stresses, such as the RD29 promoters that are activated in response to drought, low temperature, salt stress, or exposure to ABA (Yamaguchi-Shinozaki et al., 2004, Plant Cell, Vol. 6, 251-264; WO12/101118), but also promoters that are induced in response to heat (e.g., see Ainley et al. (1993) Plant Mol. Biol. 22: 13-23), light (e.g., the pea rbcS-3A promoter, Kuhlemeier et al. (1989) Plant Cell 1: 471-478, and the maize rbcS promoter, Schaffher and Sheen (1991) Plant Cell 3: 997-1012); wounding (e.g., wunl, Siebertz et al. (1989) Plant Cell 1: 961-968); pathogens (such as the PR-I promoter described in Buchel et al. (1999) Plant Mol. Biol. 40: 387-396, and the PDF 1.2 promoter described in Manners et al. (1998) Plant Mol. Biol. 38: 1071-1080), and chemicals such as methyl jasmonate or salicylic acid (e.g., see Gatz (1997) Annu. Rev. Plant Physiol. Plant Mol. Biol. 48: 89-108). In addition, the timing of the expression can be controlled by using promoters such as those acting at senescence (e.g., see Gan and Amasino (1995) Science 270:

1986-1988); or late seed development (e.g., see Odell et al. (1994) Plant Physiol. 106: 447-458).

Use may also be made of salt-inducible promoters such as the salt-inducible NHX1 promoter of rice landrace Pokkali (PKN) (Jahan et al., 6th International Rice Genetics symposium, 2009, poster abstract P4-37), the salt inducible promoter of the vacuolar H+-pyrophosphatase from *Thellungiella halophila* (TsVP1) (Sun et al., BMC Plant Biology 2010, 10:90), the salt-inducible promoter of the *Citrus sinensis*gene encoding phospholipid hydroperoxide isoform gpx1 (Avsian-Kretchmer et al., Plant Physiology July 2004 vol. 135, p1685-1696).

In alternative embodiments, tissue-specific and/or developmental stage-specific promoters are used, e.g., promoter that can promote transcription only within a certain time frame of developmental stage within that tissue. See, e.g., Blazquez (1998) Plant Cell 10:791-800, characterizing the *Arabidopsis* LEAFY gene promoter. See also Cardon (1997) Plant J 12:367-77, describing the transcription factor SPL3, which recognizes a conserved sequence motif in the promoter region of the *A. thaliana* floral meristem identity gene API; and Mandel (1995) Plant Molecular Biology, Vol. 29, pp 995-1004, describing the meristem promoter elF4. Tissue specific promoters which are active throughout the life cycle of a particular tissue can be used. Other promoters that can be used to express the nucleic acids of the invention include,; a leaf-specific promoter (see, e.g., Busk (1997) Plant J. 11 :1285 1295, describing a leaf-specific promoter in maize); a tomato promoter active during fruit ripening, senescence and abscission of leaves, a guard-cell preferential promoter e.g. as described in PCT/EP12/065608, and, to a lesser extent, of flowers can be used (see, e.g., Blume (1997) Plant J. 12:731 746); the Blec4 gene from pea, which is active in epidermal tissue of vegetative and floral shoot apices of transgenic alfalfa making it a useful tool to target the expression of foreign genes to the epidermal layer of actively growing shoots or fibers; the ovule-specific BELI gene (see, e.g., Reiser (1995) Cell 83:735-742, GenBank No. U39944); and/or, the promoter in Klee, U.S. Patent No. 5,589,583, describing a plant promoter region is capable of conferring high levels of transcription in meristematic tissue and/or rapidly dividing cells. Further tissue specific promoters that may be used according to the invention include, promoters active in vascular tissue (e.g., see Ringli and Keller (1998) Plant Mol. Biol. 37: 977-988), carpels (e.g., see Ohl et al. (1990) Plant Cell 2.In alternative embodiments, plant promoters which are inducible upon exposure to plant hormones, such as auxins, are used to express the nucleic acids used to practice the invention. For example, the invention can use the auxin-response elements El promoter fragment (AuxREs) in the soybean {Glycine max L.) (Liu (1997) Plant Physiol. 115:397-407); the auxin-responsive *Arabidopsis* GST6 promoter (also responsive to salicylic acid and hydrogen peroxide) (Chen (1996) Plant J. 10: 955-966); the auxin-inducible parC promoter from tobacco (Sakai (1996) 37:906-913); a plant biotin response element (Streit (1997) Mol. Plant Microbe Interact. 10:933-937); and, the promoter responsive to the stress hormone abscisic acid (ABA) (Sheen (1996) Science 274:1900-1902). Further hormone inducible promoters that may be used include auxin-inducible promoters (such as that described in van der Kop et al. (1999) Plant Mol. Biol. 39: 979-990 or Baumann et al., (1999) Plant Cell 11: 323-334), cytokinin-inducible promoter (e.g., see Guevara-Garcia (1998) Plant Mol. Biol. 38: 743-753), promoters responsive to gibberellin (e.g., see Shi et al. (1998) Plant Mol. Biol. 38: 1053-1060, Willmott et al. (1998) Plant Molec. Biol. 38: 817-825) and the like.

In alternative embodiments, nucleic acids used to practice the invention can also be operably linked to plant promoters which are inducible upon exposure to chemicals reagents which can be applied to the plant, such as herbicides or antibiotics. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. Coding sequence can be under the control of, e.g., a tetracycline-inducible promoter, e.g. , as described with transgenic tobacco plants containing the Avena sativa L. (oat) arginine decarboxylase gene (Masgrau (1997) Plant J. 11 :465-473); or, a salicylic acid-responsive element (Stange (1997) Plant J. 11:1315-1324). Using chemically-{e.g. , hormone- or pesticide) induced promoters, i.e., promoter responsive to a chemical which can be applied to the transgenic plant in the field, expression of a polypeptide of the invention can be induced at a particular stage of development of the plant. Use may also be made of the estrogen-inducible expression system as described in U.S. Pat. No. 6,784,340 and Zuo et al. (2000, Plant J. 24: 265-273) to drive the expression of the nucleic acids used to practice the invention.

In alternative embodiments, a promoter may be used whose host range is limited to target plant species, such as corn, rice, barley, wheat, potato or other crops, inducible at any stage of development of the crop.

In alternative embodiments, a tissue-specific plant promoter may drive expression of operably linked sequences in tissues other than the target tissue. In alternative embodiments, a tissue-specific promoter that drives expression preferentially in the target tissue or cell type, but may also lead to some expression in other tissues as well, is used.

According to the invention, use may also be made, in combination with the promoter, of other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed 1990, J. Virol. 64: 1590-1597, for example.

Other regulatory sequences that enhance the expression of the nucleic acid of the invention may also be located within the chimeric gene. One example of such regulatory sequences is introns. Introns are intervening sequences present in the pre-mRNA but absent in the mature RNA following excision by a precise splicing mechanism. The ability of natural introns to enhance gene expression, a process referred to as intron-mediated enhancement (IME), has been known in various organisms, including mammals, insects, nematodes and plants (WO 07/098042, p11-12). IME is generally described as a posttranscriptional mechanism leading to increased gene expression by stabilization of the transcript. The intron is required to be positioned between the promoter and the coding sequence in the normal orientation. However, some introns have also been described to affect translation, to function as promoters or as position and orientation independent transcriptional enhancers (Chaubet-Gigot et al., 2001, Plant Mol Biol. 45(1):17-30, p27-28).

Examples of genes containing such introns include the 5' introns from the rice actin 1 gene (see U.S. Pat. No. 5,641,876), the rice actin 2 gene, the maize sucrose synthase gene (Clancy and Hannah, 2002, Plant Physiol. 130(2):918-29), the maize alcohol dehydrogenase-1 (Adh-1) and Bronze-1 genes (Callis et al. 1987 Genes Dev. 1(10):1183-

200; Mascarenhas et al. 1990, Plant Mol Biol. 15(6):913-20), the maize heat shock protein 70 gene (see U.S. Pat. No. 5,593,874), the maize shrunken 1 gene, the light sensitive 1 gene of *Solanum tuberosum*, and the heat shock protein 70 gene of *Petunia hybrida* (see U.S. Pat. No. 5,659,122), the replacement histone H3 gene from alfalfa (Keleman et al. 2002 Transgenic Res. 11(1):69-72) and either replacement histone H3 (histone H3.3-like) gene of *Arabidopsis thaliana* (Chaubet-Gigot et al., 2001, Plant Mol Biol. 45(1):17-30).

Other suitable regulatory sequences include 5' UTRs. As used herein, a 5' UTR, also referred to as a leader sequence, is a particular region of a messenger RNA (mRNA) located between the transcription start site and the start codon of the coding region. It is involved in mRNA stability and translation efficiency. For example, the 5' untranslated leader of a petunia chlorophyll a/b binding protein gene downstream of the 35S transcription start site can be utilized to augment steady-state levels of reporter gene expression (Harpster et al., 1988, Mol Gen Genet. 212(1):182-90). WO95/006742 describes the use of 5' non-translated leader sequences derived from genes coding for heat shock proteins to increase transgene expression.

The chimeric gene may also comprise a 3' end region, i.e. a transcription termination or polyadenylation sequence, operable in plant cells. As a transcription termination or polyadenylation sequence, use may be made of any corresponding sequence of bacterial origin, such as for example the nos terminator of *Agrobacterium tumefaciens*, of viral origin, such as for example the CaMV 35S terminator, or of plant origin, such as for example a histone terminator as described in published Patent Application EP 0 633 317 A1. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

The expression and targeting of proteorhodopsin to the thylakoid membranes will take advantage of the green energy spectrum that is inaccessible to chlorlophyll. An increase in the amount of ATP is expected under photosynthesis conditions, from proton gradient generated both by the photosystems and the proteorhodopsin pump. Under conditions of inhibition of electron transfer through the photosystems, we should be able to observe a steady rate of ATP synthesis well above the basal rate through the activity of the proteorhodopsin proton pump.

Under normal pH conditions, protons are pumped into the bacterial periplasmic space by PR [50]. The photo-driven retinal cycle begins with photoisomerization of all trans-retinal to 13-cis retinal. The resulting conformational change poises the system for transfer of a proton from the Schiff base (SB; pKa~11) to the counter ion, Asp 97 (pKa~7.5). The proton is transferred to the lumen via a proton-conducting channel, and the SB is reprotonated from the cytoplasm. The mechanism of proton release in PR is not as well understood as in bacteriorhodopsin (BR); however, the main events of the photocycle are expected to be similar to those of BR. One potential challenge for pumping protons by PR in thylakoid membranes is the pH gradient-dependent reversibility of proton transfer by PR. At periplasmic pHs, <5.5, proton flow in PR is reversed, potentially depleting the proton gradient and impairing ATP synthesis. Thus, at the lumenal pH of thylakoids (4.5), reversed proton transduction via PR is possible. One of the critical residues involved in reversible proton flow is Asp97, which acts as the proton acceptor from retinal. The pKa of Asp97 in PR is ~7.5, while the pKa of its counterpart in BR is ~2.5. Due to the extremely low pKa of the counter ion, BR is able to retain its forward pumping activity at pHs as low as 3.5. The ability of PR to act as a proton pump in the thylakoid membrane thus entails maintaining the pumping efficiency at low pH conditions prevailing in the lumen. We propose that vectoral pumping of protons into the thylakoid lumen can be achieved by lowering the pKa of Asp97 and/or by protecting the SB from the lumenal pH through rational, site-specific mutagenesis. The electrostatic environment around the SB in PR is presumably maintained by the counter ions, Asp97, Asp227 (analogous to BR Asp212), Arg94 (analogous to BR Arg82) and His75. In BR, the low pKa of Asp85 is attributed to its strong hydrogen bonding interactions with Thr89 and Arg82 [53,54]. Since, interactions that reduce the pKa of Asp97 will promote proton-pumping activity at low external pH, mutation of Met79 to a residue that can hydrogen bond to His75 and Asp212, like Tyr or Thr, will be explored. These mutations are proposed by overlaying the structures of BR and PR, and identifying residues which are in a position to effect the desired behavior. Finally, the ability of a modified PR to work as an efficient H+ pump at acidic pHs will also entail shielding the SB from the extracellular environment. To this end, a L219E/T206S mutant will be generated, wherein E219 and S206 will form a Glu-Ser gate regulating vectoral proton transfer as occurs in BR.

To determine if any transgenes alter CET or ATP synthesis activity, we will compare the dark reduction kinetics of the photosystem I primary donor, P700+ in WT and transgenic plants, with and without dibromothymoquinone (DBMIB), an inhibitor of Cytb6f-mediated CET. Dark P700+ reduction kinetics are expected to be faster in plants with more active CET. In addition, we will assess the amplitude of the After Glow (AG) thermoluminescence band (-40° C.) associated with CET activity [11,14,16,43,63]. Pool sizes of ATP will also be assessed in WT and transgenic plants by mass spectroscopy.

Figure 11:
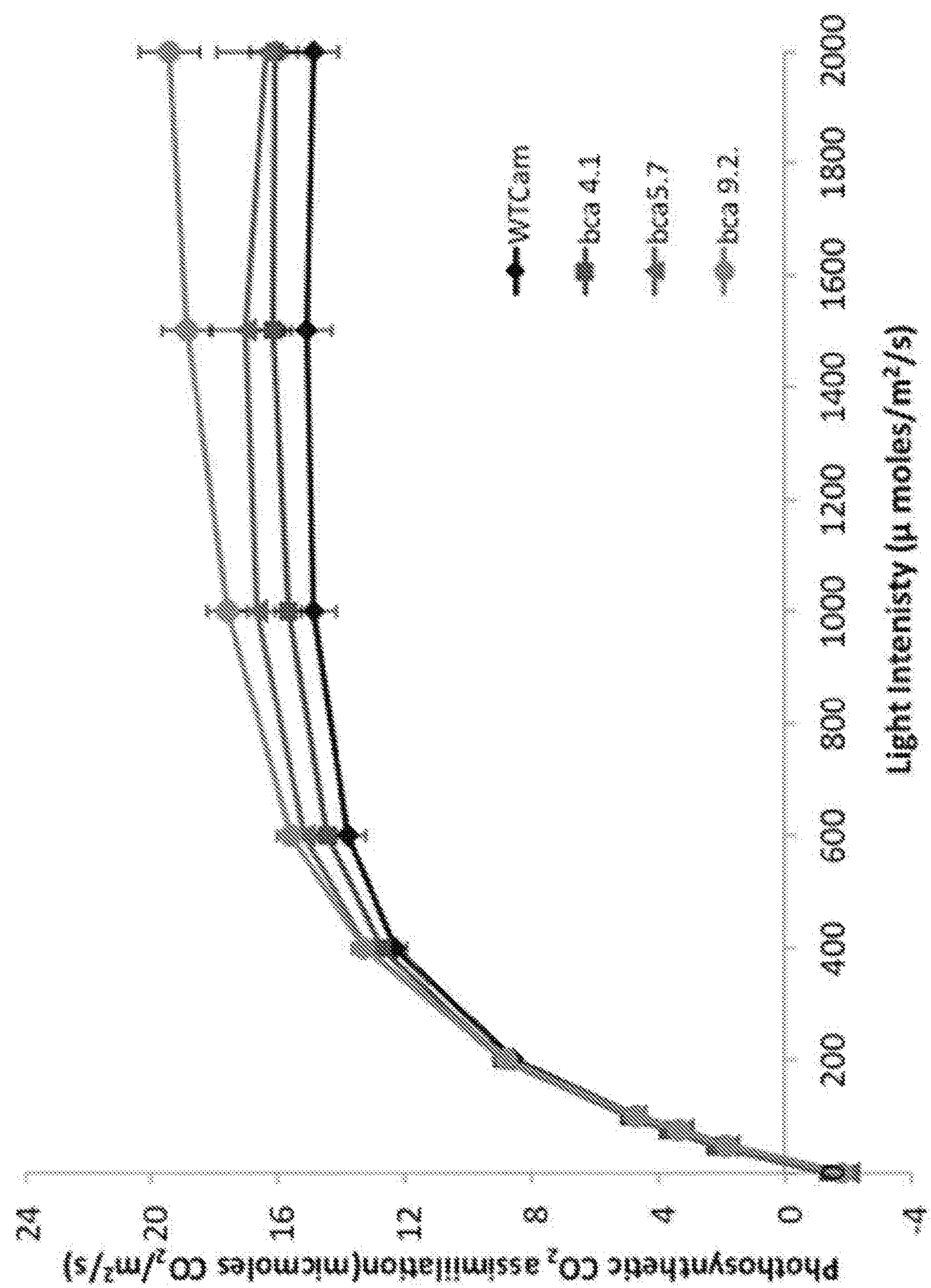
FIG. 11 illustrates light response curves of *Camelina BCA lines.*

Referring now to FIG. 11, additional transgenic *Camelina* lines were produced that expressed the BCA gene (SEQ ID NO:4) in the chloroplast stroma. These lines were produced using the *Agrobacterium*-mediated transformation procedures as described previously. Three lines were evaluated for their ability to accumulate biomass and provide improved photosynthetic rates. Wildtype *Camelina* and the BCA mutant lines were not significantly different at lower light levels (0-400 umol/$m^2$/s) in their ability to assimilate carbon dioxide. However, as light intensity increased the BCA transformants showed between 10 and 30% higher accumulation of $CO_2$ at 2000 μmoles/$m^2$/s than wildtype. The BCA line 9.2 was the highest while lines BCA 4.1 and BCA 5.7 were both about 10% higher than wildtype. This improved ability to assimilate $CO_2$ was reflected in two of the lines (BCA-5.7 and BCA-9.2) into increased biomass accumulation, with these lines having about 15% greater biomass accumulation than wildtype. The BCA-4.1 line did not show improved biomass accumulation compared to control.

Figure 12:
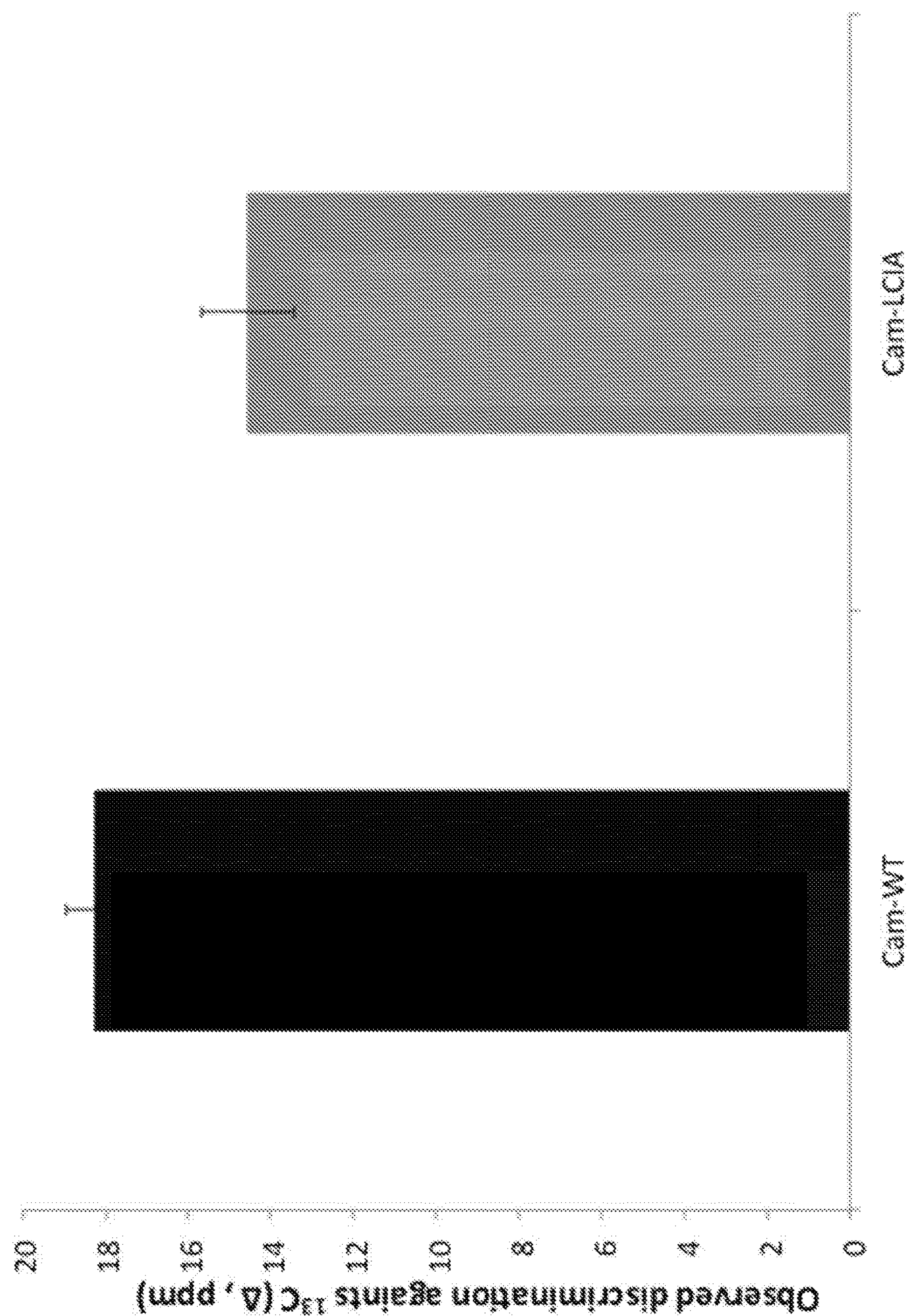
FIG. 12 illustrates expression of LCIA in *Camelina vs WT.*

Referring now to FIG. 12, the ability of the chloroplast enveloped localized bicarbonate transporter bicarbonate transporter (LCIA) protein to transport bicarbonate and improve the capture of inorganic carbon by transgenic *Camelina* was determined following the method of Farquhar and colleagues (1989). LCIA transgenic *Camelina* were produced using the *Agrobacterium*-mediated transformation processed described previously. A LCIA expressing mutant line (CAM-LCIA) was compared to wildtype *Camelina* (Cam-WT) for the observed discrimination of the stable isotope $^{13}C$. This carbon isotope discrimination is expressed as the difference between the $^{13}C$ in the air and in a plant which has been previously exposed to $^{13}CO_2$, the carbon isotope discrimination is symbolized by Δ and expressed in parts per million (ppm) and is described by Farquhar and colleagues (1989). In the LCIA transgenic lines, the observed discrimination by the plant was 20% less than that observed in the wildtype. This indicates that the insertion of LCIA provides the plant the ability to better accumulate and retain inorganic carbon than the wildtype plant and shows decreased "leakiness" vs wildtype. Reference for $^{13}C$ discrimination: Carbon isotope discrimination and photosynthesis, G. D. Farquhar, J. R. Ehlieringer and K. T. Hubick. *Annu. Rev. Plant Physiol. Plant Mol. Biol.* 1989, 40, 503-537.

TABLE D1

| Isoenzyme | Kcat (s-1) | Km (mM) | Kcat/Km ($M^{-1}s^{-1}$) | Ki (nM) | Subcellular localization | Tissue I organ localization |
|---|---|---|---|---|---|---|
| hCAI | $2 \times 10^5$ | 4.0 | $5.0 \times 10^7$ | 250 | cytosol | E, GI |
| hCAII | $1.4 \times 10^6$ | 9.3 | $1.5 \times 10^8$ | 12 | cytosol | E, eye, GI, BO, K, L, T, B |
| hCAIII | $1.0 \times 10^4$ | 33.3 | $3.0 \times 10^8$ | $2 \times 10^5$ | cytosol | SM, A |
| hCAIV | $1.0 \times 10^6$ | 21.5 | $5.1 \times 10^7$ | 74 | membrane | K, L, P, B, C, H |
| hCAVA | $2.9 \times 10^5$ | 10.0 | $2.9 \times 10^7$ | 63 | mitochondria | Li |
| hCAVB | $9.5 \times 10^5$ | 9.7 | $9.8 \times 10^7$ | 54 | mitochondria | H, SM, P, K, SC, GI |
| hCAVI | $3.4 \times 10^5$ | 6.9 | $4.9 \times 10^7$ | 11 | secreted | G |
| hCAVII | $9.5 \times 10^5$ | 11.4 | $8.3 \times 10^1$ | 2.5 | cytosol | CNS |
| hCAVIII | | | | | cytosol | CNS |
| hCAIX | $3.8 \times 10^5$ | 6.9 | $5.5 \times 10^7$ | 25 | transmembrane | TU, GI |
| hCAX | | | | | cytosol | CNS |
| hCAXI | | | | | cytosol | CNS |
| hCAXII | $4.2 \times 10^5$ | 12.0 | $3.5 \times 10^7$ | 5.7 | transmembrane | R, I, RE, eye, TU |
| hCAXIII | $1.5 \times 10^5$ | 13.8 | $1.1 \times 10^7$ | 16 | cytosol | K, B, L, GI, RE |
| hCAXIV | $3.1 \times 10^5$ | 7.9 | $3.9 \times 10^7$ | 41 | transmembrane | K, B, L |
| hCAXV | $4.7 \times 10^5$ | 14.2 | $3.3 \times 10^7$ | 72 | membrane | K |

H = Human;
M = Mouse;
hCAVIII, X, and XI are devoid of catalytic activity.
E = Erthrocyes;
GI = GI tract;
BO = Bone osteoclasts;
K = kidney,
L = Lung;
T = testis;
B = brain;
SM = skeletal muscle;
A = Adipocytes;
P = pancreas;
C = colon;
H = heart;
Li = liver;
SC = spinal cord;
G = salivary and mammary gland;
R = renal;
I = intestinal;
TU = tumors,
RE = Reproductive

TABLE D2

| | Exemplary Type II Carbonic Anhydrases | | |
|---|---|---|---|
| Organism | Sequence | Accession Number | SEQ. ID. NO |
| Human | MSHHWGYGKH NGPEHWHKDF PIAKGERQSP VDIDTHTAKY DPSLKPLSVS YDQATSLRIL NNGHAFNVEF DDSQDKAVLK GGPLDGTYRL IQFHFHWGSL DGQGSEHTVD KKKYAAELHL VHWNTKYGDF GKAVQQPDGL AVLGIFLKVG SAKPGLQKVV DVLDSIKTKG KSADFTNFDP RGLLPESLDY WTYPGSLTTP PLLECVTWIV LKEPISVSSE QVLKFRKLNF NGEGEPEELM VDNWRPAQPL KNRQIKASFK | NP_000056.1 | SEQ. ID. NO. 19 |
| *Macaca fascicularis* (crab-eating macaque) | MSHHWGYGKH NGPEHWHKDF PIAKGQRQSP VDIDTHTAKY DPSLKPLSVS YDQATSLRIL NNGHSFNVEF DDSQDKAVIK GGPLDGTYRL IQFHFHWGSL DGQGSEHTVD KKKYAAELHL VHWNTKYGDF GKAVQQPDGL AVLGIFLKVG SAKPGLQKVV DVLDSIKTKG KSADFTNFDP RGLLPESLDY WTYPGSLTTP PLLECVTWIV LKEPISVSSE QMSKFRKLNF NGEGEPEELM VDNWRPAQPL KNRQIKASFK | BAE91302.1 | SEQ. ID. NO. 24 |

TABLE D2-continued

Exemplary Type II Carbonic Anhydrases

| Organism | Sequence | Accession Number | SEQ. ID. NO |
| --- | --- | --- | --- |
| *Pan troglodytes* | MSHHWGYGKH NGPEHWHKDF PIAKGERQSP VDIDTHTAKY DPSLKPLSVS YGQATSLRIL NNGHAFNVEF DDSQDKAVLK GGPLDGTYRL IQFHFHWGSL DGQGSEHTVD KKKYAAELHL VHWNTKYGDF GKAVQQPDGL AVLGIFLKVG SAKPGLQKVV DVLDSIKTKG KSADFTNFDP HGLLPESLDY WTYPGSLTTP PLLECVTWIV LKEPISVSSE QMLKFRKLNF NGEGEPEELM VDNWRPAQPL KNRQIKASFK | NP_001181853 | SEQ. ID. NO. 25 |
| *Macaca mulatta* | MSHHWGYGKH NGPEHWHKDF PIAKGQRQSP VDINTHTAKY DPSLKPLSVS YDQATSLRIL NNGHSFNVEF DDSQDKAVIK GGPLDGTYRL IQFHFHWGSL DGQGSEHTVD KKKYAAELHL VHWNTKYGDF GKAVQQPDGL AVLGIFLKVG SAKPGLQKVV DVLDSIKTKG KSADFTNFDP RGLLPESLDY WTYPGSLTTP PLLECVTWIV LKEPISVSSE QMSKFRKLNF NGEGEPEELM VDNWRPAQPL KNRQIKASFK | NP_001182346 | SEQ. ID. NO. 26 |
| *Pongo abelii* | MSHHWGYGKH NGPEHWHKDF PIAKGERQSP VDIDTHTAKY DPSLKPLSVC YDQATSLRIL NNGHSFNVEF DDSQDKAVLK GGPLDGTYRL IQFHFHWGSL DGQGSEHTVD KKKYAAELHL VHWNTKYGDF GKAVQQPDGL AVLGIFLKVG SAKPGLQKVV DVLDSIKTKG KCADFTNFDP RGLLPASLDY WTYPGSLTTP PLLECVTWIV LKEPISVSSE QMLKFRKLNF NGEGEPEELM VDNWRPAQPL KKRQIKASFK | XP_002819286 | SEQ. ID. NO. 27 |
| *Callithrix jacchus* | MSHHWGYGKH NGPEHWHKDF PIAKGERQSP VDIDTHTAKY DPSLKPLSVS YDQATSWRIL NNGHSFNVEF DDSQDKAVLK GGPLDGTYRL IQFHFHWGST DGQGSEHTVD KKKYAAELHL VHWNTKYGDF GKAAQQPDGL AVLGIFLKVG SAKPGLQKVV DVLDSIKTKG KSADFTNFDP RGLLPESLDY WTYPGSLTTP PLLESVTWIV LKEPISVSSE QILKFRKLNF SGEGEPEELM VDNWRPAQPL KNRQIKASFK | XP_002759086 | SEQ. ID. NO. 28 |
| *Lemur catta* | MSHHWGYGKH NGPEHWHKDF PIAKGERQSP VDINTGAAKH DPSLKPLSVY YEQATSRRIL NNGHSFNVEF DDSQDKAVLK GGPLDGTYRL IQFHFHWGSL DGQGSEHTVD KKKYAAELHL VHWNTKYGDF GKAVQQPDGL AVLGIFLKVG SAKPGLQKVV DVLDSIKTKG KSADFTNFDP RGLLPESLDY WTYLGSLTTP PLLECVTWIV LKEPISVSSE QMMKFRKLSF SGEGEPEELM VDNWRPAQPL KNRQIKASFK | ADD83028 | SEQ. ID. NO. 29 |
| *Ailuropoda melanoleuca* | MAHHWGYGKH NGPEHWYKDF PIAKGQRQSP VDIDTKAAIH DPALKALCPT YEQAVSQRVI NNGHSFNVEF DDSQDNAVLK GGPLTGTYRL IQFHFHWGSS DGQGSEHTVD KKKYAAELHL VHWNTKYGDF GKAVQQPDGL AVLGIFLKIG DARPGLQKVL DALDSIKTKG KSADFTNFDP RGLLPESLDY WTYPGSLTTP PLLECVTWIV LKEPISVSSE QMLKFRRLNF NKEGEPEELM VDNWRPAQPL HNRQINASFK | XP_002916939 | SEQ. ID. NO. 30 |
| *Equus caballus* | MSHHWGYGQH NGPKHWHKDF PIAKGQRQSP VDIDTKAAVH DAALKPLAVH YEQATSRRIV NNGHSFNVEF DDSQDKAVLQ GGPLTGTYRL IQFHFHWGSS DGQGSEHTVD KKKYAAELHL VHWNTKYGDF GKAVQQPDGL AVVGVFLKVG GAKPGLQKVL DVLDSIKTKG KSADFTNFDP RGLLPESLDY WTYPGSLTTP PLLECVTWIV LREPISVSSE QLLKFRSLNF NAEGKPEDPM VDNWRPAQPL NSRQIRASFK | XP_001488540 | SEQ. ID. NO. 31 |
| *Canis lupus familiaris* | MAHHWGYAKH NGPEHWHKDF PIAKGERQSP VDIDTKAAVH DPALKSLCPC YDQAVSQRII NNGHSFNVEF DDSQDKTVLK GGPLTGTYRL IQFHFHWGSS DGQGSEHTVD KKKYAAELHL VHWNTKYGEF GKAVQQPDGL AVLGIFLKIG GANPGLQKIL DALDSIKTKG KSADFTNFDP RGLLPESLDY WTYPGSLTTP PLLECVTWIV LKEPISVSSE QMLKFRKLNF NKEGEPEELM MDNWRPAQPL HSRQINASFK | NP_001138642 | SEQ. ID. NO. 32 |
| *Oryctolagus cuniculus* | MSHHWGYGKH NGPEHWHKDF PIANGERQSP IDIDTNAAKH DPSLKPLRVC YEHPISRRII NNGHSFNVEF DDSHDKTVLK EGPLEGTYRL IQFHFHWGSS DGQGSEHTVN KKKYAAELHL VHWNTKYGDF GKAVKHPDGL AVLGIFLKIG SATPGLQKVV DTLSSIKTKG KSVDFTDFDP RGLLPESLDY WTYPGSLTTP PLLECVTWIV LKEPITVSSE QMLKFRNLNF NKRAEPEEPM VDNWRPTQPL KGRQVKASFV | NP_001182637 | SEQ. ID. NO. 33 |
| *Ailuropoda melanoleuca* | GPEHWYKDFP IAKGQRQSPV DIDTKAAIHD PALKALCPTY EQAVSQRVIN NGHSFNVEFD DSQDNAVLKG GPLTGTYRLI | EFB24165 | SEQ. ID. NO. 34 |

TABLE D2-continued

| Organism | Sequence | Accession Number | SEQ. ID. NO |
|---|---|---|---|
| | Exemplary Type II Carbonic Anhydrases | | |
| | QFHFHWGSSD GQGSEHTVDK KKYAAELHLV HWNTKYGDFG KAVQQPDGLA VLGIFLKIGD ARPGLQKVLD ALDSIKTKGK SADFTNFDPR GLLPESLDYW TYPGSLTTPP LLECVTWIVL KEPISVSSEQ MLKFRRLNFN KEGEPEELMV DNWRPAQPLH NRQINASFK | | |
| *Sus scrofa* | MSHHWGYDKH NGPEHWHKDF PIAKGDRQSP VDINTSTAVH DPALKPLSLC YEQATSQRIV NNGHSFNVEF DSSQDKGVLE GGPLAGTYRL IQFHFHWGSS DGQGSEHTVD KKKYAAELHL VHWNTKYKDF GEAAQQPDGL AVLGVFLKIG NAQPGLQKIV DVLDSIKTKG KSVEFTGFDP RDLLPGSLDY WTYPGSLTTP PLLESVTWIV LREPISVSSG QMMKFRTLNF NKEGEPEHPM VDNWRPTQPL KNRQIRASFQ | XP_001927840.1 | SEQ. ID. NO. 35 |
| *Callithrix jacchus* | MSHHWGYGKH NGPEHWHKDF PIAKGERQSP VDIDTHTAKY DPSLKPLSVS YDQATSWRIL NNGHSFNVEF DDSQDKAVLK GGPLDGTYRL IQLHLVHWNT KYGDFGKAAQ QPDGLAVLGI FLKVGSAKPG LQKVVDVLDS IKTKGKSADF TNFDPRGLLP ESLDYWTYPG SLTTPPLLES VTWIVLKEPI SVSSEQILKF RKLNFSGEGE PEELMVDNWR PAQPLKNRQI KASFK | XP_002759087 | SEQ. ID. NO. 36 |
| *Mus musculus* | MSHHWGYSKH NGPENWHKDF PIANGDRQSP VDIDTATAQH DPALQPLLIS YDKAASKSIV NNGHSFNVEF DDSQDNAVLK GGPLSDSYRL IQFHFHWGSS DGQGSEHTVN KKKYAAELHL VHWNTKYGDF GKAVQQPDGL AVLGIFLKIG PASQGLQKVL EALHSIKTKG KRAAFANFDP CSLLPGNLDY WTYPGSLTTP PLLECVTWIV LREPITVSSE QMSHFRTLNF NEEGDAEEAM VDNWRPAQPL KNRKIKASFK | NP_033931 | SEQ. ID. NO. 37 |
| *Bos taurus* | MSHHWGYGKH NGPEHWHKDF PIANGERQSP VDIDTKAVVQ DPALKPLALV YGEATSRRMV NNGHSFNVEY DDSQDKAVLK DGPLTGTYRL VQFHFHWGSS DDQGSEHTVD RKKYAAELHL VHWNTKYGDF GTAAQQPDGL AVVGVFLKVG DANPALQKVL DALDSIKTKG KSTDFPNFDP GSLLPNVLDY WTYPGSLTTP PLLESVTWIV LKEPISVSSQ QMLKFRTLNF NAEGEPELLM LANWRPAQPL KNRQVRGFPK | NP_848667 | SEQ. ID. NO. 38 |
| *Oryctolagus cuniculus* | GKHNGPEHWH KDFPIANGER QSPIDIDTNA AKHDPSLKPL RVCYEHPISR RIINNGHSFN VEFDDSHDKT VLKEGPLEGT YRLIQFHFHW GSSDGQGSEH TVNKKKYAAE LHLVHWNTKY GDFGKAVKHP DGLAVLGIFL KIGSATPGLQ KVVDTLSSIK TKGKSVDFTD FDPRGLLPES LDYWTYPGSL TTPPLLECVT WIVLKEPITV SSEQMLKFRN LNFNKRAEPE EP | AAA80531 | SEQ. ID. NO. 39 |
| *Rattus norvegicus* | MSHHWGYSKS NGPENWHKEF PIANGDRQSP VDIDTGTAQH DPSLQPLLIC YDKVASKSIV NNGHSFNVEF DDSQDFAVLK EGPLSGSYRL IQFHFHWGSS DGQGSEHTVN KKKYAAELHL VHWNTKYGDF GKAVQHPDGL AVLGIFLKIG PASQGLQKIT EALHSIKTKG KRAAFANFDP CSLLPGNLDY WTYPGSLTTP PLLECVTWIV LKEPITVSSE QMSHFRKLNF NSEGEAEELM VDNWRPAQPL KNRKIKASFK | NP062164 | SEQ. ID. NO. 40 |

TABLE D3

| Organism | Sequence | Accession Number | SEQ. ID. NO |
|---|---|---|---|
| | Exemplary Type VII Carbonic Anhydrases | | |
| Human | MSLSITNNGH SVQVDFNDSD DRTVVTGGPL EGPYRLKQFH FHWGKKHDVG SEHTVDGKSF PSELHLVHWN AKKYSTFGEA ASAPDGLAVV GVFLETGDEH PSMNRLTDAL YMVRFKGTKA QFSCFNPKCL LPASRHYWTY PGSLTTPPLS ESVTWIVLRE PICISERQMG KFRSLLFTSE DDERIHMVNN FRPPQPLKGR VVKASFRA | | SEQ. ID. NO. 41 |
| *Pongo abelii* | MTGHHGWGYG QDDGPSHWHK LYPIAQGDRQ SPINIISSQA VYSPSLQPLE LSYEACMSLS ITNNGHSVQV DFNDSDDRTV VTGGPLEGPY RLKQFHFHWG KKHDVGSEHT VDGKSFPSEL HLVHWNAKKY STFGEAASAP DGLAVVGVFL ETGDEHPSMN RLTDALYMVR FKGTKAQFSCFNPKSLLPAS RHYWTYPGSL | XP_002826555 | SEQ. ID. NO. 42 |

TABLE D3-continued

Exemplary Type VII Carbonic Anhydrases

| Organism | Sequence | Accession Number | SEQ. ID. NO |
|---|---|---|---|
| | TTPPLSESVT WIVLREPICI SERQMGKFRS LLFTSEDDER IHMVNNFRPP QPLKGRVVKA SFRA | | |
| *Pan troglodytes* | MEFGLSPELS PSRCFKRLLR GSERGRSRSP NERTEPTGQV HGCGDGSGMT GHHGWGYGQD DGPSHWHKLY PIAQGDRQSP INIISSQAVY SPSLQPLELS YEACMSLSIT NNGHSVQVDF NDSDDRTVVT GGPLEGPYRL KQFHFHWGKK HDVGSEHTVD GKSFPSELHL VHWNAKKYST FGEAASAPDG LAVVGVFLET GDEHPSMNRL TDALYMVRFK GTKAQFSCFN PKCLLPASRH YWTYPGSLTT PPLSESVTWI VLREPICISE RQMRKFRSLL FTSEDDERIH MVNNFRPPQP LKGRVVKASF RA | XP_001143159.1 | SEQ. ID. NO. 43 |
| *Callithrix jacchus* | MTGHHGWGYG QDDGPSHWHK LYPIAQGDRQ SPINIISSQA VYSPSLQPLE LSYEACMSLS ITNNGHSVQV DFNDSDDRTV VTGGPLEGPY RLKQFHFHWG KKHDVGSEHT VDGKSFPSEL HLVHWNAKKY STFGEAASAP DGLAVVGVFL ETGDEHPSMN RLTDALYMVR FKGTKAQFSC FNPKCLLPAS WHYWTYPGSL TTPPLSESVT WIVLREPICI SERQMGKFRS LLFTSEDDER VHMVNNFRPP QPLKGRVVKA SFRA | XP_002761099 | SEQ. ID. NO. 44 |
| *Ailuropoda melanoleuca* | GPSQWHKLYP IAQGDRQSPI NIVSSQAVYS PSLKPLELSY EACISLSIAN NGHSVQVDFN DSDDRTVVTG GPLDGPYRLK QFHFHWGKKH SVGSEHTVDG KSFPSELHLV HWNAKKYSTF GEAASAPDGL AVVGVFLETG DEHPSMNRLT DALYMVRFKG TKAQFSCFNP KCLLPASRHY WTYPGSLTTP PLSESVTWIV LREPISISER QMEKFRSLLF TSEDDERIHM VNNFRPPQPL KGRVVKASFR A | EFB15849 | SEQ. ID. NO. 45 |
| *Canis familiaris* | MTGHHCWGYG QNDEIQASLS PSLSTPAGPS QWHKLYPIAQ GDRQSPINIV SSQAVYSPSL KPLELSYEAC ISLSITNNGH SVQVDFNDSD DRTAVTGGPL DGPYRLKQLH FHWGKKHSVG SEHTVDGKSF PSELHLVHWN AKKYSTFGEA ASAPDGLAVV GIFLETGDEH PSMNRLTDAL YMVRFKGTKA QFSCFNPKCL LPASRHYWTY PGSLTTPPLS ESVTWIVLRE PISISERQME KFRSLLFTSE EDERIHMVNN FRPPQPLKGR VVKASFRA | XP_546892 | SEQ. ID. NO. 46 |
| *Bos taurus* | MTGHHGWGYG QNDGPSHWHK LYPIAQGDRQ SPINIVSSQA VYSPSLKPLE ISYESCTSLS IANNGHSVQV DFNDSDDRTV VSGGPLDGPY RLKQFHFHWG KKHGVGSEHT VDGKSFPSEL HLVHWNAKKY STFGEAASAP DGLAVVGVFL ETGDEHPSMN RLTDALYMVR FKGTKAQFSC FNPKCLLPAS RHYWTYPGSL TTPPLSESVT WIVLREPIRI SERQMEKFRS LLFTSEEDER IHMVNNFRPP QPLKGRVVKA SFRA | XP_002694851 | SEQ. ID. NO. 47 |
| *Rattus norvegicus* | MTVLWWPMLR EELMSKLRTG GPSNWHKLYP IAQGDRQSPI NIISSQAVYS PSLQPLELFY EACMSLSITN NGHSVQVDFN DSDDRTVVAG GPLEGPYRLK QLHFHWGKKR DVGSEHTVDG KSFPSELHLV HWNAKKYSTF GEAAAAPDGL AVVGIFLETG DEHPSMNRLT DALYMVRFKD TKAQFSCFNP KCLLPTSRHY WTYPGSLTTP PLSESVTWIV LREPIRISER QMEKFRSLLF TSEDDERIHM VNNFRPPQPL KGRVVKASFQ S | EDL87229 | SEQ. ID. NO. 48 |
| *Oryctolagus cuniculus* | MTGHHGWGYG QDDGGRPSHW HKLYPIAQGD RQSPINIVSS QAVYSPGLQP LELSYEACTS LSIANNGHSV QVDFNDSDDR TVVTGGPLEG PYRLKQFHFH WGKRRDAGSE HTVDGKSFPS ELHLVHWNAR KYSTFGEAAS APDGLAVVGV FLETGNEHPS MNRLTDALYM VRFKGTKAQF SCFNPKCLLP SSRHYWTYPG SLTTPPLSES VTWIVLREPI SISERQMEKF RSLLFTSEDD ERVHMVNNFR PPQPLRGRVV KASFRA | XP_002711604 | SEQ. ID. NO. 49 |
| *Mus musculus* | GQDDGPSNWH KLYPIAQGDR QSPINIISSQ AVYSPSLQPL ELFYEACMSL SITNNGHSVQ VDFNDSDDRT VVSGGPLEGP YRLKQLHFHW GKKRDMGSEH TVDGKSFPSE LHLVHWNAKK YSTFGEAAAA PDGLAVVGVF LETGDEHPSM NRLTDALYMV RFKDTKAQFS CFNPKCLLPT SRHYWTYPGS LTTPPLSESV TWIVLREPIR ISERQMEKFR SLLFTSEDDE RIHMVDNFRP PQPLKGRVVK ASFQA | AAG16230.1 | SEQ. ID. NO. 50 |
| *Monodelphis domestic* | MTGHHGWGYG QEDGPSEWHK LYPIAQGDRQ SPIDIVSSQA VYDPTLKPLV LAYESCMSLS IANNGHSVMV EFDDVDDRTV VNGGPLDGPY RLKQFHFHWG KKHSLGSEHT VDGKSFSSEL HLVHWNGKKY KTFAEAAAAP DGLAVVGIFL ETGDEHASMN RLTDALYMVR FKGTKAQFNS FNPKCLLPMN LSYWTYPGSL TTPPLSESVT WIVLKEPITI SEKQMEKFRS LLFTAEEDEK VRMVNNFRPP QPLKGRVVQA SFRS | XP_001364411.1 | SEQ. ID. NO. 51 |

TABLE D3-continued

Exemplary Type VII Carbonic Anhydrases

| Organism | Sequence | Accession Number | SEQ. ID. NO |
|---|---|---|---|
| *Gallus gallus* | MTGHHSWGYG QDDGPAEWHK SYPIAQGNRQ SPIDIISAKA VYDPKLMPLV ISYESCTSLN ISNNGHSVMV EFEDIDDKTV ISGGPFESPF RLKQFHFHWG AKHSEGSEHT IDGKPFPCEL HLVHWNAKKY ATFGEAAAAP DGLAVVGVFL EIGKEHANMN RLTDALYMVK FKGTKAQFRS FNPKCLLPLS LDYWTYLGSL TTPPLNESVI WVVLKEPISI SEKQLEKFRM LLFTSEEDQK VQMVNNFRPP QPLKGRTVRA SFKA | XP_414152.1 | SEQ. ID. NO. 52 |
| *Taeniopygia guttata* | MTGQHSWGYG QADGPSEWHK AYPIAQGNRQ SPIDIDSARA VYDPSLQPLL ISYESCSSLS ISNTGHSVMV EFEDTDDRTA ISGGPFQNPF RLKQFHFHWG TTHSQGSEHT IDGKPFPCEL HLVHWNARKY TTFGEAAAAP DGLAVVGVFL EIGKEHASMN RLTDALYMVK FKGTKAQFRG FNPKCLLPLS LDYWTYLGSL TTPPLNESVT WIVLKEPIRI SVKQLEKFRM LLFTGEEDQR IQMANNFRPP QPLKGRIVRA SFKA | XP_002190292.1 | SEQ. ID. NO. 53 |

TABLE D4

Exemplary Type XIII Carbonic Anhydrases

| Organism | Sequence | Accession Number | SEQ. ID. NO |
|---|---|---|---|
| Human | MSRLSWGYRE HNGPIHWKEF FPIADGDQQS PIEIKTKEVK YDSSLRPLSI KYDPSSAKII SNSGHSFNVD FDDTENKSVL RGGPLTGSYR LRQVHLHWGS ADDHGSEHIV DGVSYAAELH VVHWNSDKYP SFVEAAHEPD GLAVLGVFLQ IGEPNSQLQK ITDTLDSIKE KGKQTRFTNF DLLSLLPPSW DYWTYPGSLT VPPLLESVTW IVLKQPINIS SQQLAKFRSL LCTAEGEAAA FLVSNHRPPQ PLKGRKVRAS FH | NP_940986.1 | SEQ. ID. NO. 54 |
| *Pan troglodytes* | MSRLSWGYRE HNGPIHWKEF FPIADGDQQS PIEIKTKEVK YDSSLRPLSI KYDPSSAKII SNSGHSFNVD FDDTENKSVL RGGPLTGSYR LRQFHLHWGS ADDHGSEHIV DGVSYAAELH VVHWNSDKYP SFVEAAHEPD GLAVLGVFLQ IGEPNSQLQK ITDTLDSIKE KGKQTRFTNF DPLSLLPPSW DYWTYPGSLT VPPLLESVTW IVLKQPINIS SQQLAKFRSL LCTAEGEAAA FLVSNHRPPQ PLKGRKVRAS FH | XP_001169377.1 | SEQ. ID. NO. 55 |
| *Macaca mulatta* | MSRLSWGYRE HNGPIHWKEF FPIADGDQQS PIEIKTQEVK YDSSLRPLSI KYDPSSAKII SNSGHSFNVD FDDTEDKSVL RGGPLAGSYR LRQFHLHWGS ADDHGSEHIV DGVSYAAELH VVHWNSDKYP SFVEAAHEPD GLAVLGVFLQ IGEPNSQLQK ITDILDSIKE KGKQTRFTNF DPLSLLPPSW DYWTYPGSLT VPPLLESVIW IVLKQPINVS SQQLAKFRSL LCTAEGEAAA FLLSNHRPPQ PLKGRKVRAS FR | XP_001095487.1 | SEQ. ID. NO. 56 |
| *Oryctolagus cuniculus* | MSRISWGYGE HNGPIHWNQF FPIADGDQQS PIEIKTKEVK YDSSLRPLSI KYDPSSAKII SNSGHSFNVD FDDTEDKSVL RGGPLTGNYR LRQFHLHWGS ADDHGSEHVV DGVRYAAELH VVHWNSDKYP SFVEAAHEPD GLAVLGVFLQ IGEYNSQLQK ITDILDSIKE KGKQTRFTNF DPLSLLPSSW DYWTYPGSLT VPPLLESVTW IVLKQPINIS SQQLAKFRSL LCSAEGESAA FLLSNHRPPQ PLKGRKVRAS FH | XP_002710714.1 | SEQ. ID. NO. 57 |
| *Ailuropoda melanoleuca* | MSRLSWGYGE HNGPIHWNKF FPIADGDQQS PIEIKTKEVK YDSSLRPLSI KYDANSAKII SNSGHSFSVD FDDTEDKSVL RGGPLTGSYR LRQFHLHWGS ADDHGSEHVV DGVRYAAELH VVHWNSDKYP SFVEAAHEPD GLAVLGVFLQ IGEHNSQLQK ITDILDSIKE KGKQTRFTNF DPLSLLPPSW DYWTYPGSLT VPPLLESVTW IVLKQPINIS SEQLATFRTL LCTAEGEAAA FLLSNHRPPQ PLKGRKVRAS FH | XP_002916937.1 | SEQ. ID. NO. 58 |
| *Sus scrofa* | MSRFSWGYGE HNGPVHWNEF FPIADGDQQS PIEIKTKEVK YDSSLRPLSI KYDPSSAKII SNSGHSFSVD FDDTEDKSVL RGGPLTGSYR LRQFHLHWGS ADDHGSEHVV DGVKYAAELH VVHWNSDKYP SFVEAAHEPD GLAVLGVFLQ IGEHNSQLQK ITDILDSIKE KGKQTRFTNF DPLSLLPPSW DYWTYPGSLT VPPLLESVTW IILKQPINIS SQQLATFRTL LCTKEGEEAA FLLSNHRPLQ PLKGRKVRAS FH | XP_001924497.1 | SEQ. ID. NO. 59 |

TABLE D4-continued

| Organism | Sequence | Accession Number | SEQ. ID. NO |
|---|---|---|---|
| *Callithrix jacchus* | MSRLSWGYGE HNGPIHWNEF FPIADGDRQS PIEIKAKEVK YDSSLRPLSI KYDPSSAKII SNSGHSFNVD FDDTEDKSVL HGGPLTGSYR LRQFHLHWGS ADDHGSEHVV DGVRYAAELH VVHWNSEKYP SFVEAAHEPD GLAVLGVFLQ IGEPNSQLQK IIDILDSIKE KGKQIRFTNF DPLSLFPPSW DYWTYSGSLT VPPLLESVTW ILLKQPINIS SQQLAKFRSL LCTAEGEAAA FLLSNYRPPQ PLKGRKVRAS FR | XP_002759085.1 | SEQ. ID. NO. 60 |
| *Rattus norvegicus* | MARLSWGYDE HNGPIHWNEL FPIADGDQQS PIEIKTKEVK YDSSLRPLSI KYDPASAKII SNSGHSFNVD FDDTEDKSVL RGGPLTGSYR LRQFHLHWGS ADDHGSEHVV DGVRYAAELH VVHWNSDKYP SFVEAAHESD GLAVLGVFLQ IGEHNPQLQK ITDILDSIKE KGKQTRFTNF DPLCLLPSSW DYWTYPGSLT VPPLLESVTW IVLKQPISIS SQQLARFRSL LCTAEGESAA FLLSNHRPPQ PLKGRRVRAS FY | NP_001128465.1 | SEQ. ID. NO. 61 |
| *Mus musculus* | MARLSWGYGE HNGPIHWNEL FPIADGDQQS PIEIKTKEVK YDSSLRPLSI KYDPASAKIISNSGHSFNVD FDDTEDKSVL RGGPLTGNYR LRQFHLHWGS ADDHGSEHVV DGVRYAAELH VVHWNSDKYP SFVEAAHESD GLAVLGVFLQ IGEHNPQLQK ITDILDSIKE KGKQTRFTNFDPLCLLPSSW DYWTYPGSLT VPPLLESVTW IVLKQPISIS SQQLARFRSL LCTAEGESAA FLLSNHRPPQ PLKGRRVRAS FY | NP_078771.1 | SEQ. ID. NO. 62 |
| *Canis familiaris* | MPPRRHGPNT FLSAGTKGQQ NFWTKNQKSG PIHWNKFFPI ADGDQQSPIE IKTKEVKYDS SLRPLSIKYD ANSAKIISNS GHSFSVDFDD TEDKSVLRGG PLTGSYRLRQ FHLHWGSADD HGSEHVVDGV RYAAELHVVH WNSDKYPSFV EAAHEPDGLA VLGVFLQIGE HNSQLQKITD ILDSIKEKGK QTRFTNFDPL SLLPPSWDYW TYPGSLTVPP LLESVTWIVL KQPINISSQQ LATFRTLLCT AEGEAAAFLL SNHRPPQPLK GRKVRASFH | XP_544159 | SEQ. ID. NO. 63 |
| *Eguus caballus* | MSGPVHWNEF FPIADGDQQS PIEIKTKEVK YDSSLRPLTI KYDPSSAKII SNSGHSFSVG FDDTENKSVL RGGPLTGSYR LRQFHLHWGS ADDHGSEHVV DGVRYAAELH IVHWNSDKYP SFVEAAHEPD GLAVLGVFLQ VGEHNSQLQK ITDTLDSIKE KGKQTLFTNF DPLSLLPPSW DYWTYPGSLT VPPLLESVTW IILKQPINIS SQQLVKFRTL LCTAEGETAA FLLSNHRPPQ PLKGRKVRAS FR | XP_001489984.2 | SEQ. ID. NO. 64 |
| *Bos taurus* | MSGFSWGYGE RDGPVHWNEF FPIADGDQQS PIEIKTKEVR YDSSLRPLGI KYDASSAKII SNSGHSFNVD FDDTDDKSVL RGGPLTGSYR LRQFHLHWGS TDDHGSEHVV DGVRYAAELH VVHWNSDKYP SFVEAAHEPD GLAVLGIFLQ IGEHNPQLQK ITDILDSIKE KGKQTRFTNF DPVCLLPPCR DYWTYPGSLT VPPLLESVTW IILKQPINIS SQQLAAFRTL LCSREGETAA FLLSNHRPPQ PLKGRKVRAS FR | XP_002692875.1 | SEQ. ID. NO. 65 |
| *Monodelphis domestica* | MSRLSWGYCE HNGPVHWSEL FPIADGDYQS PIEINTKEVK YDSSLRPLSI KYDPASAKII SNSGHSFSVD FDDSEDKSVL RGGPLIGTYR LRQFHLHWGS TDDQGSEHTV DGMKYAAELH VVHWNSDKYP SFVEAAHEPD GLAVLGIFLQ TGEHNLQMQK ITDILDSIKE KGKQIRFTNF DPATLLPQSW DYWTYPGSLT VPPLLESVTW IVLKQPITIS SQQLAKFRSL LYTGEGEAAA FLLSNYRPPQ PLKGRKVRAS FR | XP_001366749.1 | SEQ. ID. NO. 66 |
| *Ornithor hynchus anatinus* | MKKGVGSFYE LAVNRWSVVN RVQIMIVESI TEPLLCGSRA LALTLSPTQA LAVAPALALA VVQALALTVV QALALAVSPA LALSVAPALA LAVVQALALA VVQALALAVA QALALAVAQA LALAVAQALA LALPQALALT LPQALALTLS PTLALSVAPA LALAVAPALA LADSPALALA LARPHPSSGS SPALDCELVL FGDCHTVLLK WMRMGNYSSV SPLEERNSSC PLGPIHWNEL FPIADGDRQS PIEIKTKEVK YDSSLRPLSI KYDPTSAKII SNSGHSFSVD FDDTEDKSVL RGGPLSGTYR LRQFHFHWGS ADDHGSEHTV DGMEYSAELH VVHWNSDKYS SFVEAAHEPD GLAVLGIFLK RGEHNLQLQK ITDILDAIKE KGKQMRFTNF DPLSLLPLTR DYWTYPGSLT VPPLLESVIW IIFKQPISIS SQQLAKFRNL LYTAEGEAAD FMLSNHRPPQ PLKGRKVRAS FRS | XP_001507177.1 | SEQ. ID. NO. 67 |

TABLE D5

| Exemplary CA II DNA expression constructs for chloroplast expression | |
|---|---|
| ATGTCCCATC ACTGGGGGTA CGGCAAACAC AACGGACCTG AGCACTGGCA TAAGGACTTC CCCATTGCCA AGGGAGAGCG CCAGTCCCCT GTTGACATCG ACACTCATAC AGCCAAGTAT GACCCTTCCC TGAAGCCCCT GTCTGTTTCC TATGATCAAG CAACTTCCCT GAGGATCCTC AACAATGGTC ATGCTTTCAA CGTGGAGTTT GATGACTCTC AGGACAAAGC AGTGCTCAAG GGAGGACCCC TGGATGGCAC TTACAGATTG ATTCAGTTTC ACTTTCACTG GGGTTCACTT GATGGACAAG GTTCAGAGCA TACTGTGGAT AAAAAGAAAT ATGCTGCAGA ACTTCACTTG GTTCACTGGA ACACCAAATA TGGGGATTTT GGGAAAGCTG TGCAGCAACC TGATGGACTG GCCGTTCTAG GTATTTTTTT GAAGGTTGGC AGCGCTAAAC CGGGCCTTCA GAAAGTTGTT GATGTGCTGG ATTCCATTAA AACAAAGGGC AAGAGTGCTG ACTTCACTAA CTTCGATCCT CGTGGCCTCC TTCCTGAATC CTTGGATTAC TGGACCTACC CAGGCTCACT GACCACCCCT CCTCTTCTGG AATGTGTGAC CTGGATTGTG CTCAAGGAAC CCATCAGCGT CAGCAGCGAG CAGGTGTTGA AATTCCGTAA ACTTAACTTC AATGGGGAGG GTGAACCCGA AGAACTGATG GTGGACAACT GGCGCCCAGC TCAGCCACTG AAGAACAGGC AAATCAAAGC TTCCTTCAAA TAA | SEQ. ID. NO. 94 (human cDNA sequence) |
| gaattcATGTCtCATCAtTGGGGtTAtGGtAAACACAAtGGtCCTGAaCACTGGCATAAaGACTTtCCaATTGCaAAaGGtGAaCGtCAaTCaCCTGTTGAtATtGACACTCATACAGCtAAaTATGACCCTTCttTaAAaCCatTaTCTGTTTCaTATGATCAAGCAACTTCttTacGtATttTaAACAATGGTCATGCTTTtAAtGTaGAaTTTGATGACTCTCAaGAtAAAGCAGTatTaAAaGGtGGtCCatTaGATGGtACTTACcGtTTaATTCAaTTTCACTTTCACTGGGGTTCAtTaGATGGtCAAGGTTCAGAaCATACTGTaGATAAAAAaAAATATGCTGCAGAAtTaCACTTaGTTCACTGGAACACaAAATATGGtGATTTTGGtAAAGCTGTaCAaCAACCTGATGGttTaGCtGTTtTAGGTATTTTTTTaAAaGTTGGtAGtGCTAAACCaGGtCTTCAaAAAGTTGTTGATGTatTaGATTCaATTAAAACAAAaGGtAAaAGTGCTGACTTtACTAAtTTCGATCCTCGTGGttTaCTTCCTGAATCtTTaGATTACTGGACaTAtCCAGGtTCAtTaACaACaCCTCCTCTTtTaGAATGTGTaACaTGGATTGTatTaAAaGAACCaATtAGtGTaAGtAGtGAaCAaGTaTTaAAATTCCGTAAACTTAAtTTCAATGGtGAaGGTGAACCaGAAGAAtTaATGGTtGAtAACTGGCGtCCAGCTCAaCCAtTaAAaAAtcGtCAAATtAAAGCTTCaTTCAAATAAgcatgc | SEQ. ID. NO. 108 (Optimized for chloroplast Expression) |

TABLE D6

| Codons in Human CA II optimized for expression in chloroplast of *Chlamydomonas reinhardtii* | | | | |
|---|---|---|---|---|
| Amino acid | Total number | Number of codons that were optimized | No. of amino acids of each codon | Expected ratio of codons |
| Ser(S) | 18 | 12 | TCT TCA AGT (7:7:5) | 1:1:1 |
| Phe(F) | 12 | 3 | TIT TTC (8:4) | 2:1 |
| Leu(L) | 26 | 19 | TIA CTT (21:5) | 5:1 |
| Val(V) | 17 | 10 | GTT GTA (8:9) | 1:1 |
| Pro(P) | 17 | 6 | CCT CCA (8:9) | 3:4 |
| Thr(T) | 12 | 5 | ACT ACA (5:7) | 2:3 |
| Ala(A) | 13 | 3 | GCT GCA (9:4) | 2:1 |
| Tyr(Y) | 8 | 2 | TAT TAC (6:2) | 2:1 |
| His(H) | 12 | 1 | CAT CAC (6:6) | 1:1 |
| Asn(N) | 10 | 4 | AAT AAC (7:3) | 2.5 1 |
| A(D) | 19 | 3 | GAT GAC (14:5) | 2.5 1 |
| Ile(I) | 9 | 4 | ATT (9) | 1 |
| Met(M) | 2 | 0 | ATG (2) | 1 |
| Gln(Q) | 11 | 7 | CAA (11) | 1 |
| Glu(E) | 13 | 6 | GAA (13) | 1 |
| Lys(K) | 24 | 11 | AAA (24) | 1 |
| Cys(C) | 1 | 0 | TGT (1) | 1 |
| Tf£_(W) | 7 | 0 | TGG (7) | 1 |
| Gly(G) | 22 | 17 | GGT (22) | 1 |
| Arg(R) | 7 | 5 | CGT (7) | 1 |

TABLE D7

| Exemplary algal bicarbonate transporter types | | | | |
|---|---|---|---|---|
| Transport Type | Mechanism | Substrate affinity | Flux rate | Photosynthetic affinity ko.6 |
| BicA | Na+ dependent | Low-medium | High | 90-170 μμM $HC0_{3-}$ |
| SbtA | Na+ dependent $HC0_{3-}$ uptake | High | Low | <5 μM $HC0_3$ |
| Transport Type | Mechanism | Substrate affinity | Flux rate | Photosynthetic affinity ko.6 |
| BicA | Na+ dependent | Low-medium | High | 90-170 μM $HC0_{3-}$ |
| SbtA | Na+ dependent $HC0_{3-}$ uptake | High | Low | <5 μM $HC0_3$ |

TABLE D8

| Exemplary plasma membrane localized Bicarbonate transporters | | | |
|---|---|---|---|
| Organism | Sequence | Accession Number | SEQ. ID. NO |
| *Chlamydomonas reinhardtii* | MLPGLGVILL VLPMQYYFGY KIVQIKLQNA KHVALRSAIM QEVLPAIKLV KYYAWEQFFE NQISKVRREE IRLNFWNCVM KVINVACVFC VPPMTAFVIF TTYEFQRARL VSSVAFTTLS LFNILRFPLV VLPKALRAVS EANASLQRLE AYLLEEVPSG TAAVKTPKNA PPGAVIENGV FHHPSNPNWH LHVPKFEVKP | EDP07736.1 | SEQ. ID. NO. 77 |

TABLE D8 -continued

| Exemplary plasma membrane localized Bicarbonate transporters | | | |
|---|---|---|---|
| Organism | Sequence | Accession Number | SEQ. ID. NO |
| | GQVVAVVGRI AAGKSSLVQA ILGNMVKEHG SFNVGGRISY VPQNPWLQNL SLRDNVLFGE QFDENKYTDV IESCALTLDL QILSNGDQSK AGIRGVNFSG GQRQRVNLAR CAYADADLVL LDNALSAVDH HTAHHIFDKC IKGLFSDKAV VLVTHQIEFM PRCDNVAIMD EGRCLYFGKW NEEAQHLLGK LLPITHLLHA AGSQEAPPAP KKKAEDKAGP QKSQSLQLTL APTSIGKPTE KPKDVQKLTA YQAALIYTWY GNLFLVGVCF FFFLAAQCSR QISDFWVRWW VNDEYKKFPV KGEQDSAATT FYCLIYLLLV GLFYIFMIFR GATFLWWVLK SSETIRRKAL HNVLNAPMGF FLVTPVGDLL LNFTKDQDIM DENLPDAVHF MGIYGLILLA TTITVSVTIN FFAAFTGALI IMTLIMLSIY LPAATALKKA RAVSGGMLVG LVAEVLEGLG VVQAFNKQEY FIEEAARRTN ITNSAVFNAE ALNLWLAFWC DFIGACLVGV VSAFAVGMAK DLGGATVGLA FSNIIQMLVF YTWVVRFISE SISLFNSVEG MAYLADYVPH DGVFYDQRQK DGVAKQIVLP DGNIVPAASK VQVVVDDAAL ARWPATGNIR FEDVWMQYRL DAPWALKGVT FKINDGEKVG AVGRTGSGKS TTLLALYRMF ELGKGRILVD GVDIATLSLK RLRTGLSIIP QEPVMFTGTV RSNLDPFGEF KDDAILWEVL KKVGLEDQAQ HAGGLDGQVD GTGGKAWSLG QMQLVCLARA ALRAVPILCL DEATAAMDPH TEAIVQQTIK KVFDDRTTIT IAHRLDTIIE SLMEYESPSK LLANRDSMFS KLVDKTGPAA AAALRKMAED FWSTRSAQGR NQ | | |
| *Volvox carterif. nagariensis* | MGTISHPARG NDPTAGFFNK EAFGWMFKHV SEARKNGDID LDKMGMPPEN HAHEAYDMFA SNWAAEMKLK DSGAKPSLVR ALRKSFGLVY LLGGVFKCFW STFVITGAFY FVRSLLAHVN GIKDGRLYSK TVSGWCLMAG FTLDAWLLGL SLQRMGYICM SVGIRARAAL VQAVTHKAFR LSSVRADQSA AIVNFVSSDI QKIYDGALEF HYLWTAPFEA AAILALLGYL TNDSMLPGLG VILLVLPLQY FFGYKIIQIK LQNAKHVALR SSILQEVLPA IKLVKYYAWE QFFEDEISKI RREEMRLSFW NAMMKVINVA CVFCVPPMTA FVIFTTYEFQ KARLVSGVAF TTLSLFNILR FPLVVLPKAL RAVSEAHASL QRLESYLLED VPQGTASGGK SSKSSAPGVH IDNAVYHHPS NPNWHLHVPR FDVRPGQVVA VVGRIGAGKS SLVQAILGNM VKEHGSQQVG GRISYVPQNP WLQNLSIRDN VTFGEGWDEN KYEAVIDACA LTMDLQILPQ GDQSKAGIRG VNFSGGQRQR VNLARCAYAD ADLVLLDNAL SAVDHHTAHH IFDKCIKGLF SDKAVVLITH QIEFMPRCDA VAIMDEGRCL YFGKWNEESQ HLLGKLLPIT HLLHAAGSQE APPAAPKKKD DKATPQKSQS LQLTLAPTSI GKPTQKDTKA APKLTAFKAA LIYTYYGNIL LVFVCFITFL AAQTCRQMSD FWVRWWVNDE YKHFPKRTGV REESATKFYA LIYLLLVGLF YFTMVARGST FLWWVLRSSE NIRKKALNNV LNAPMGFFLV TPVGDLLLNF TKDQDIMDEN LPDAIHFMGI YGLILLATTI TVSVTINFFG AFTGFLIIMT LIMLAIYLPA ATALKKARAV SGGQLVGLVA EVLEGLNVVQ AFSKQEYFIE EAARRTDVTN AAVFNAESLN LWLAFWCDLI GASLVGVVSA EAVGLKDQLG AATVGLAFSN IIQMLVFYTW VVRFIAESIS LFNSVEAMAW LADYVPKDGI FYDQKQLDGV AKSITLPDGQ IVPATSKVQV VVDDAALARW PATGNIRFED VWMQYRLDAA WALKGVTFKI NDGEKVGAVG RTGSGKSTTL LALYRMFELG KGRILIDGVD IATLSLKRLR TGLSIIPQEP VMFTGTVRSN LDPFGEFKDD SVLWEVLQKV GLEAQAQHAG GLDGRVDGTG GKAWSLGQMQ LVCLARAALR AVPILCLDEA TAAMDPHTEQ VVQETIKKVF DDRTTITIAH RLDTIIESDK VLVMEAGELK EFAPPAQLLA NRETMFSKLV DKTGPAAAAA LRKMADEHFS KSQARAAAQR H | XP_002950646.1 | SEQ. ID. NO. 69 |
| *Chlorella variabilis* | MVPLLAQRGR IRSQAPRTWH PDPQPLHAER SRQCPGRGVR AAAKRGGGSG GATHKSKKSK ELDEVAAFEQ LMCDWDDAFA ADCYDNERAA RMARLAEEGY QHHGRGFVFV RSRLDKRSRK ARNDSGASKG FGAAAKALSV EQGTPLENNP QLHLLSWTAC YIASSQLDSL GGLFSTQEGV LLPDSGSLLT DGGSGASGSN AADAVGELQR VLRGQDLSQL RGYVGAPPQA RPASGSDDDG SSTTGSNNGA AGEGSEVEEG TAMGGIRRYE PESGELVVLL SCKIGGKPAV GAELLAVAQA EDGKHAPGAS PDTRLCKEPS QSAFDLWSFG WMNKIVPAAR RGEVEVADLP LPEAQQAEPC YEELNTNWEA AVQEAKKAGK EPKLMKVLWK TYGKDIVLAG IFKLMWSVFV ILGAYYFTRS ILMCIRTLEG KDDSIYDTEW KGWVLTGFFF LDAWLLGMML QRMAFNCLKV GIKARAALTT MIARKCYNMA HLTKDTAAEA VGFVASDINK VFEGIQEVHY LWGAPVEAGA ILALLGTLVG VYCIGGVIIV CMVVPLQYYF GYKIIKNKIK NAPNVTERWS IIQEILPAMK LVKYYAWERF FEKHVADMRT RERHYMFWNA VVKTVNVTMV FGVPPMVTFA VLVPYELWHV DSSTSEPYIK PQTAFTMLSL FNVLRFPLVV | EFN52914.1 | SEQ. ID. NO. 70 |

TABLE D8 -continued

| Exemplary plasma membrane localized Bicarbonate transporters | | | |
|---|---|---|---|
| Organism | Sequence | Accession Number | SEQ. ID. NO |
| | LPKAMRCVSE ALRSVGNLEK FLAEPVAPRQ DLEGKPGAQL<br>SKAVLRHEMD TSGFTLRVPE FSVKAGELVA VVGRVGAGKS<br>SILQAMLGNM QTASGLAKCQ HSASSCLPFL VEGTAHSGGR<br>IAYVPQTAWC QNLSLRDNIT FGQPWDEAKY KQVIHACALE<br>LDLAILAAGD QSKAGLRGIN LSGGQRQRLN LARCAYFDGD<br>LVLLDNALSA VDHHTAHHIF EHCVRGMFRD KATVLVTHQV<br>EFLPQCDKVA IMDDGTCVYF GPWNAAAQQL LSKYLPASHL<br>LAAGGNAEQP RDTKKKVVKK EETKKTEDAG KAKRVHSASL<br>TLKSALWEYC WDARWIIFCL SLFFFLTAQA SRQLADYFIR<br>WWTRDHYNKY GVLCIDEGDN PCGPLFYVQY YGILGLLCFI<br>VLMAFRGAFL YTWSLGASYR QHEKSIHRVL YAPLGFFLTT<br>PVGDLLVSFT KDQDVMDDAL PDALYYAGIY GLILLATAIT<br>VSVTIPLFSA LAGGLFVVSG IMLAIYLPAA THLKKLRMGT<br>SGDVVTLIAE ALDGLGVIQA YGKQAYFTTI TSQYVNDAHR<br>ALFGAESLNL WLAFICDFFG ACMVLSVACF GIGQWSTLGS<br>SSVGLAFSQS IQMLVFYTWS IRLVAECIGL FGSAEKIAWL<br>ANHTPQEAGS LDPPSLPGSG ETKAAPKKRG TAGKFLPPLK<br>DEDLAIVPTG GPKLPSGWPR TGVLEFNQVV MKYAPHLPPA<br>LRGVSFKVKS GDKVGVVGRT GSGKSTLLLA LYRMFNLESG<br>AITLDGIDIS TLTLEQLRRG LSVIPQEPTV FSGTVRTNLD<br>PFGEFGADAI LWEALRDCGL EEQVKACGGL DAKLDGTGGN<br>AWSIGQQQLM CLARAALKKV PVLCLDEATA AMDPHTEAHV<br>LEIIERIFSD RTMLTIAHRL DNVIRSDLVV VMDAGQVCEM<br>GTPDELLANP_QSAFSQLVDK TGAASAAALR KMAADFLDER<br>ARGQKLGFKP RPSLEESHIC VAPSPSLILS TLLFPPAFMA<br>NVTALLLPKP VLSHAPVSSQ TVNTYIRLNI IQLQCNVLHP<br>ATKEATWSSR RITFTAHLSS SGSKPPPPLP PLTELPEGRG<br>LDWSSAGYRD GREAIPSPSA KYSAADYGAA GDGVTDDTQA<br>LQVAVAAAHE DDEGGVVYLG AGTFVLTQPL SIAGSNVVIR<br>GAGEDATTIF VPLPLSDVFP GTWSMDASGK VTSPWITRGG<br>FLAFSGRRTK SSDSSTLLAT VAGSVEQGAS VIPVDSTAEF<br>RLGQWVRIII NDASTDASAG GGTLERGSSE VQESETMIAE<br>GATGGGAGVR AQWTGVLHAF EPTVQCSGVE QLTIRFNHSM<br>MAAHLAERGY NAIELEDVVD CWIRQVTILN ADNAIRLRGT<br>DHSTLSGQAC SGGGVVAVVP VWCRRGLPSP ADVTVGVTEL<br>RWEPDTREVN GHHAITVSKG HANLVTRFRI TAPFYHDISL<br>EGGALLNVIS SGGGANLNLD LHRSGPWGNL FSQLGMGLAA<br>RPFDAGGRDG RGAHAGRQNT FWNLQPGDVA AAAPALQPSA<br>AAGDARRLLV DGDSLLHAGT GQARLLRQLE ADDSAEPLLL<br>PSCEFGPLLN FVGGFAGELC KSSGWLVAGL PDDRPDLHAS<br>QVTARLQHGA ADNKTHA | | |
| *Synechococcus elongatus* PCC7942J. | MDFLSNFLMD FVKQLQSPTL SFLIGGMVIA ACGSQLQIPE<br>SICKIIVFML LTKIGLTGGM AIRNSNLTEM VLPALFSVAI<br>GILIVFIARY TLARMPKVKT VDAIATGGLF GAVSGSTMAA<br>ALTLLEEQKI PYEAWAGALY PFMDIPALVT AIVVANIYLN<br>KKKRKEAAFA SAQGAYSKQP VAAGDYSSSS DYPSSRREYA<br>QQESGDHRVK IWPIVEESLQ GPALSAMLLG VALGLFARPE<br>SVYEGFYDPL FRGLLSILML VMGMEAWSRI SELRKVAQWY<br>VVYSIVAPLA HGFIAFGLGM IAHYATGFSM GGVVVLAVIA<br>ASSSDISGPP TLRAGIPSAN PSAYIGASTA IGTPVAIGIA<br>IPLFLGLAQT IGG | ABB57505.1 | SEQ. ID. No. 71 |
| *Synechocystis* sp. PCC 6803 | MDFLSNFLTD FVGQLQSPTL AFLIGGMVIA ALGTQLVIPE<br>AISTIIVFML LTKIGLTGGM AIRNSNLTEM LLPVAFSVIL<br>GILIVFIARF TLAKLPNVRT VDALATGGLF GAVSGSTMAA<br>ALTTLEESKI SYEAWAGALY PFMDIPALVT AIVVANIYLN<br>KRKRKSAAAS IEESFSKQPV AAGDYGDQTD YPRTRQEYLS<br>QQEPEDNRVK IWPIIEESLQ GPALSAMLLG LALGIFTKPE<br>SVYEGFYDPL FRGLLSILML IMGMEAWSRI GELRKVAQWY<br>VVYSLIAPIV HGFIAFGLGM IAHYATGFSL GGVVVLAVIA<br>ASSSDISGPP TLRAGIPSAN PSAYIGSSTA IGTPIAIGVC<br>IPLFIGLAQT LGAG | NP-441340 | SEQ. ID. No. 72 |
| *Nostoc* sp. PCC 712 | MDFFSLFLMD FVKQLQSPTL GFLIGGMVIA ALGSELIIPE<br>AICQIIVFML LTKIGLTGGI AIRNSNLTEM VLPAASAVAV<br>GVLVVFIARY TLAKLPKVNT VDAIATGGLF GAVSGSTMAA<br>ALTLLEEQKI QYEAWAAALY PFMDIPALVT AIVVANIYLN<br>KKKRSAAGEY LSKQSVAAGE YPDQQDYPSS RQEYLRKQQS<br>ADNRVKIWPI VKESLQGPAL SAMLLGIALG LFTQPESVYK<br>SFYDPLFRGL LSILMLVMGM EAWSRIGELR KVAQWYVVYS<br>VVAPLVHGFI AFGLGMIAHY ATGFSLGGVV ILAVIAASSS<br>DISGPPTLRA GIPSANPSAY IGASTAIGTP IAIGLAIPLF<br>LGLAQAIGGR | NP-486174 | SEQ. ID. No. 73 |

TABLE D8 -continued

| Exemplary plasma membrane localized Bicarbonate transporters | | | |
|---|---|---|---|
| Organism | Sequence | Accession Number | SEQ. ID. NO |
| *Cyanothece* sp. PCC 7425 | MDFWSYFLMD FVKQLQSPTL GFLIGGMVIA ALGSQLVIPE AICQIIVFML LTKIGLTGGM AIRNSNLTEM VLPAAFSVIS GILIVFIARY TLAKLPKVRT VDAIATGGLF GAVSGSTMAA ALTLLEEEKI PYEAWAGALY PFMDIPALVT AIVIANIYLN KKKRRAESEA LSKQEYLGKQ SIVAGDYPAQ QDYPSTRQEY LSKQQGPENN RVKIWPIVQE SLQGPALSAM LLGVALGILT KPESVYESFY DPLFRGLLSI LMLVMGMEAW SRIGELRKVA QWYVVYSVVA PFVHGLIAFG LGMFAHYTMG FSMGGVVVLA VIASSSSDIS GPPTLRAGIP SANPSAYIGA STAIGTPIAI GLCIPFFIGL AQTLGGG | YP_002485721 | SEQ. ID. No. 74 |
| *Microcysti aeruginosa* NIES-843 | MDFFSLFVMD FIQQLQSPTL AFLIGGMIIA ALGSELVIPE SICTIIVFML LTKIGLTGGI AIRNSNLTEM VLPMIFAVIV GIIVVFVARY TLANLPKVKV VDAIATGGLF GAVSGSTMAA GLTVLEEQKI PYEAWAGALY PFMDIPALVT AIVVANIYLN KKKQKEAAYD QESFSKQPVA AGNYSDQQDY PSSRQEYLSQ QQPADNRVKI WPIIEESLRG PALSAMLLGL ALGIFTQPES VYKSFYDPLF RGLLSVLMLV MGMEAWSRVG ELRKVAQWYV VYSVIAPFVH GLIAFGLGMI AHYATGFSWG GVVMLAVIAS SSSDISGPPT LRAGIPSANP SAYIGASTAI GTPVAIGLCI PFFVGLAQAL SGG | YP_001661223 | SEQ. ID. No. 75 |
| *Anabaena variabills* ATCC 29413 | MDFVSLFVKD FIAQLQSPTL AFLIGGMIIA ALGSELVIPE SICTIIVFML LTKIGLTGGI AIRNSNLTEM VLPMIFAVIT GITIVFISRY TLAKLPKVKV VDAIATGGLF GAVSGSTMAA GLTVLEEQKM AYEAWAGALY PFMDIPALVT AIVIANIYLN KKKRKEAVYS TEQPVAAGDY PDQKDYPSSR QEYLSQQKGD EDNRVKIWPI IEESLRGPAL SAMLLGLALG LFTQPESVYK SFYDPAFRGL LSILMLVMGM EAWSRIGELR KVAQWYVVYS VVAPFVHGLI AFGLGMIAHY TMNFSMGGVV ILAVIASSSS DISGPPTLRA GIPSANPSAY IGASTAVGTP VAIGLCIPFF LGLAQAIGG | YP_323532 | SEQ. ID. No. 86 |
| *Cyanothece* sp. PCC 880 | MDFLSLFVKD FIIQLQSPTL AFLIGGMVIA ALGSELVIPE SICTIIVFML LTKIGLTGGI AIRNSNLTEM VLPMICAVIV GIVVVFIARY TLAKLPKVNV VDAIATGGLF GAVSGSTMAA GLTVLEEQKI PYEAWAGALY PFMDIPALVT AIVVANIYLN KKKRKATVMQ ESLSKQPVAA GDYPSSRQEY VSQQQPEDNR VKIWPIIEES LRGPALSAML LGLALGILTQ PESVYKGFYD PPFRGLLSIL MLVMGMEAWS RIGELRKVAQ WYVVYSVAAP FIHGLLAFGL GMIAHYTMGF SMGGVVILAV IASSSSDISG PPTLRAGIPS ANPSAYIGAS TAIGTPVAIG LCIPFFVGLA QAIGGF | YP_002371470.1 | SEQ. ID. No. 87 |
| *Arthrospia platensis* str. Paraca | MDFLSGFLTR FLAQLQSPTL GFLIGGMVIA AVNSQLQIPD AIYKFVVFML LMKVGLSGGI AIRGSNLTEM LLPAVFALVT GIVIVFIGRY TLAKLPNVKT VDAIATAGLF GAVSGSTMAA ALTLLEEQGM EYEAWAAALY PFMDIPALVS AIVLASIYVS KQKHSDMADE SLSKHESLSK QPVAAGDYPS KPEYPTTRQE YLSQQRGSAN QGVEIWPIIK ESLQGSALSA LLLGLALGLL TRPESVFQSF YEPLFRGLLS ILMLVMGMEA TARLGELRKV AQWYAVYAFI APLLHGLIAF GLGMIAHVVT GFSLGGVVIL AVIASSSSDI SGPPTLRAGI PSANPSAYIG SSTAVGTPVA IALGIPLYIG LAQALMGG | ZP_06383808.1 | SEQ. ID. No. 88 |

TABLE D9

| Exemplary chloroplast envelope localized Bicarbonate transporters | | | |
|---|---|---|---|
| Organism | Sequence | Accession Number | SEQ. ID. NO |
| *Chlamydomonas reinhardtii* | MQTTMTRPCL AQPVLRSRVL RSPMRVVAAS APTAVTTVVT SNGNGNGHFQ AATTPVPPTP APVAVSAPVR AVSVLTPPQV YENAINVGAY KAGLTPLATF VQGIQAGAYI AFGAFLAISV GGNIPGVAAA NPGLAKLLFA LVFPVGLSMV TNCGAELFTG NTMMLTCALI EKKATWGQLL KNWSVSYFGN FVGSIAMVAA VVATGCLTTN TLPVQMATLK ANLGFTEVLS RSILCNWLVC CAVWSASAAT SLPGRILALW PCITAFVAIG LEHSVANMFV IPLGMMLGAE VTWSQFFFNN LIPVTLGNTI AGVLMMAIAY SISFGSLGKS AKPATA | BAD16681.1 | SEQ. ID. NO. 89 |

TABLE D9 -continued

| Exemplary chloroplast envelope localized Bicarbonate transporters | | | |
|---|---|---|---|
| Organism | Sequence | Accession Number | SEQ. ID. NO |
| *Volvox cartefif. nagariensis* | MQTTMSVTRP CVGLRPLPVR NVRSLIRAQA APQQVSTAVS TNGNGNGVAA ASLSVPAPVA APAQAVSTPV RAVSVLTPPQ VYENAANVGA YKASLGVLAT FVQGIQAGAY IAFGAFLACS VGGNIPGITA SNPGLAKLLF ALVFPVGLSM VTNCGAELYT GNTMMLTCAI FEKKATWAQL VKNWVVSYAG NFVGSIAMVA AVVATGLMAS NQLPVNMATA KSSLGFTEVL SRSILCNWLV CCAVWSASAA TSLPGRILGL WPPITAFVAI GLEHSVANMF VIPLGMMLGA DVTWSQFFFN NLVPVTLGNT IAGVVMMAVA YSVSYGSLGK TPKPATA | XP_002951507.1 | SEQ. ID. NO. 79 |

TABLE D10

| Transit Peptides | | |
|---|---|---|
| Organism | SEQ ID NO | Name |
| *Arabidopsis thaliana* | 8 | Rbcs-1a transit peptide |
| *Arabidopsis thaliana* | 14 | PGR5 transit peptide |
| *Arabidopsis thaliana* | 15 | psaD transit peptide |
| *Arabidopsis thaliana* | 22 | DNAJ transit peptide |
| *Cyanophora paradoxa* | 102 | psaD trasit peptide |
| *Arabidopsis thaliana* | 104 | CAB transit peptide |
| *Arabidopsis thaliana* | 105 | PGR5 transit peptide |

TABLE D11

| Cyclic Electron Transfer modulator proteins | | | | |
|---|---|---|---|---|
| Organism | SEQ ID NO | Name | Accession No. | Function |
| *Arabidopsis thaliana* | 93 | Ferredoxin1 (FD1) | AEE28669.1 | cyclic electron transfer modulator protein |
| *Arabidopsis thaliana* | 95 | Ferredoxin2 (FD2) | AAG40057.1 | cyclic electron transfer modulator protein |
| *Arabidopsis thaliana* | 96 | ferredoxin-NADP(+) oxidoreductase (FNR1) | AT5G66190 partial | cyclic electron transfer modulator protein |
| *Arabidopsis thaliana* | 97 | ferredoxin-NADP(+) oxidoreductase (FNR2) | BAH19611.1 | cyclic electron transfer modulator protein |

An exemplary optimized DNA sequence for the plasma membrane localized bicarbonate transporter is shown in SEQ ID NO. 91

(SEQ ID NO: 91)

```
atgctgcccg gcctgggcgt catcctgctg gtgctgccca tgcagtacta cttcggctac  60
aagatcgtgc agatcaagct gcagaacgcc aagcacgtcg ccctgcgctc cgccatcatg 120
caggaggtgc tgcccgccat caagctggtc aagtactacg cctgggagca gttctttgag 180
aaccagatca gcaaggtccg ccgcgaggag atccgcctca acttctggaa ctgcgtgatg 240
aaggtcatca acgtggcctg cgtgttctgc gtgccgccca tgaccgcctt cgtcatcttc 300
accacctacg agttccagcg cgcccgcctg gtgtccagcg tcgccttcac caccctgtcg 360
ctgttcaaca ttctgcgctt ccccctggtc gtgctgccca aggccctgcg tgccgtgtcc 420
gaggccaacg cgtctctcca gcgcctggag gcctacctgc tggaggaggt gccctcgggc 480
actgccgccg tcaagacccc caagaacgct ccccccggcg ccgtcatcga gaacggtgtg 540
ttccaccacc cctccaaccc caactggcac ctgcacgtgc ccaagttcga ggtcaagccc 600
ggccaggtcg ttgctgtggt gggccgcatc gccgccggca agtcgtccct ggtgcaggcc 660
atcctcggca acatggtcaa ggagcacggc agcttcaacg tgggcggccg catctcctac 720
gtgccgcaga acccctggct gcagaacctg tccctgcgtg acaacgtgct gtttggcgag 780
cagttcgatg agaacaagta caccgacgtc atcgagtcct gcgccctgac cctggacctg 840
cagatcctgt ccaacggtga ccagtccaag gccggcatcc gcggtgtcaa cttctccggt 900
ggccagcgcc agcgcgtgaa cctggcccgc tgcgcctacg ccgacgccga cctggtgctg 960
```

```
ctcgacaacg ccctgtccgc cgtggaccac cacaccgccc accacatctt cgacaagtgc 1020
atcaagggcc tgttctccga caaggccgtg gtgctggtca cccaccagat cgagttcatg 1080
ccccgctgcg acaacgtggc catcatggac gagggccgct gcctgtactt cggcaagtgg 1140
aacgaggagg cccagcacct gctcggcaag ctgctgccca tcacccacct gctgcacgcc 1200
gccggctccc aggaggctcc ccccgccccc aagaagaagg ccgaggacaa ggccggcccc 1260
cagaagtcgc agtcgctgca gctgaccctg gcccccacct ccatcggcaa gcccaccgag 1320
aagcccaagg acgtccagaa gctgactgcc taccaggccg ccctcatcta cacctggtac 1380
ggcaacctgt tcctggttgg cgtgtgcttc ttcttcttcc tggcggctca gtgctctcgc 1440
cagatctccg atttctgggt gcgctggtgg gtgaacgacg agtacaagaa gttccccgtg 1500
aagggcgagc aggactcggc cgccaccacc ttctactgcc tcatctacct gctgctggtg 1560
ggcctgttct acatcttcat gatcttccgc ggcgccactt tcctgtggtg ggtgctcaag 1620
tcctcggaga ccatccgcag gaaggccctg cacaacgtcc tcaacgcgcc catgggcttc 1680
ttcctggtca cgccggtcgg cgacctgctg ctcaacttca ccaaggacca ggacattatg 1740
gatgagaacc tgcccgatgc cgttcacttc atgggcatct acggcctgat tctgctggcg 1800
accaccatca ccgtgtccgt caccatcaac ttcttcgccg ccttcaccgg cgcgctgatc 1860
atcatgaccc tcatcatgct ctccatctac ctgcccgccg ccactgccct gaagaaggcg 1920
cgcgccgtgt ctggcggcat gctggtcggc ctggttgccg aggttctgga gggccttggc 1980
gtggttcagg ccttcaacaa gcaggagtac ttcattgagg aggccgcccg ccgcaccaac 2040
atcaccaact ccgccgtctt caacgccgag gcgctgaacc tgtggctggc tttctggtgc 2100
gacttcatcg gcgcctgcct ggtgggcgtg gtgtccgcct tcgccgtggg catggccaag 2160
gacctgggcg gcgcgaccgt cggcctggcc ttctccaaca tcattcagat gcttgtgttc 2220
tacacctggg tggtccgctt catctccgag tccatctccc tcttcaactc cgtcgagggc 2280
atggcctacc tcgccgacta cgtgccccac gatggtgtct tctatgacca gcgccagaag 2340
gacggcgtcg ccaagcaaat cgtcctgccc gacggcaaca tcgtgcccgc cgcctccaag 2400
gtccaggtcg tggttgacga cgccgccctc gcccgctggc ctgccaccgg caacatccgc 2460
ttcgaggacg tgtggatgca gtaccgcctg gacgctcctt gggctctgaa gggcgtcacc 2520
ttcaagatca acgacggcga gaaggtcggc gccgtgggcc gcaccggctc cggcaagtcc 2580
accacgctgc tggcgctgta ccgcatgttc gagctgggca agggccgcat cctggtcgac 2640
ggcgtggaca tcgccaccct gtcgctcaag cgcctgcgca ccggcctgtc catcattccc 2700
caggagcccg tcatgttcac cggcaccgtg cgctccaacc tggacccctt cggcgagttc 2760
aaggacgatg ccattctgtg ggaggtgctg aagaaggtcg gcctcgagga ccaggcgcag 2820
cacgccggcg gcctggacgg ccaggtcgat ggcaccggcg gcaaggcctg gtctctgggc 2880
cagatgcagc tggtgtgcct ggctcgcgcc gccctgcgcg ccgtgcccat cctgtgcctg 2940
gacgaggcta ccgccgccat ggacccgcac actgaggcca tcgtgcagca gaccatcaag 3000
aaggtgttcg acgaccgcac caccatcacc attgcccacc gcctggacac catcatcgag 3060
tccgacaaga tcatcgtgat ggagcagggc tcgctgatgg agtacgagtc gccctcgaag 3120
ctgctcgcca accgcgactc catgttctcc aagctggtcg acaagaccgg ccccgccgcc 3180
gccgctgcgc tgcgcaagat ggccgaggac ttctggtcca ctcgctccgc gcagggccgc 3240
aaccagtaa
```

An exemplary optimized DNA sequence for Chloroplast envelope localized Bicarbonate transporter is shown in SEQ ID NO: 92

```
                                                            (SEQ ID NO: 92)
atgcagacca ctatgactcg cccttgcctt gcccagcccg tgctgcgatc tcgtgtgctc    60

cggtcgccta tgcgggtggt tgcagcgagc gctcctaccg cggtgacgac agtcgtgacc   120

tcgaatggaa atggcaacgg tcatttccaa gctgctacta cgcccgtgcc ccctactccc   180

gctcccgtcg ctgtttccgc gcctgtgcgc gctgtgtcgg tgctgactcc tcctcaagtg   240

tatgagaacg ccattaatgt tggcgcctac aaggccgggc taacgcctct ggcaacgttt   300

gtccagggca tccaagccgg tgcctacatt gcgttcggcg ccttcctcgc catctccgtg   360

ggaggcaaca tccccggcgt cgccgccgcc aaccccggcc tggccaagct gctatttgct   420

ctggtgttcc ccgtgggtct gtccatggtg accaactgcg gcgccgagct gttcacgggc   480

aacaccatga tgctcacatg cgcgctcatc gagaagaagg ccacttgggg gcagcttctg   540

aagaactgga gcgtgtccta cttcggcaac ttcgtgggct ccatcgccat ggtcgccgcc   600

gtggtggcca ccggctgcct gaccaccaac accctgcctg tgcagatggc caccctcaag   660

gccaacctgg gcttcaccga ggtgctgtcg cgctccatcc tgtgcaactg gctggtgtgc   720

tgcgccgtgt ggtccgcctc cgccgccacc tcgctgcccg gccgcatcct ggcgctgtgg   780

ccctgcatca ccgccttcgt ggccatcggc ctggagcact ccgtcgccaa catgttcgtg   840

attcctctgg gcatgatgct gggcgctgag gtcacgtgga gccagttctt tttcaacaac   900

ctgatccccg tcaccctggg caacaccatt gctggcgttc tcatgatggc catcgcctac   960

tccatctcgt tcggctccct cggcaagtcc gccaagcccg ccaccgcg               1008
```

Those skilled in the art will recognize, or be able to ascertain using no more than routine experimentation, many equivalents to the specific embodiments of the disclosure specifically described herein. For example a transgenic plant or alga of an embodiment disclosed herein further comprising within its genome, and expressing or overexpressing, a combination of heterologous nucleotide sequences encoding additionally a Rubisco (for example SEQ ID NO:107). Further still a transit peptide amino acid sequence at the amine terminal portion of a protein sequence identified herein may be cleaved leaving the protein sequence alone. The percent homology applies to the protein sequence without the transit peptide sequence also. Such equivalents are intended to be encompassed within the scope of the following claims.

REFERENCES CITED

1. Hausler R E, Hirsch H J, Kreuzaler F, Peterhansel C (2002) Overexpression of C(4)-cycle enzymes in transgenic C(3) plants: a biotechnological approach to improve C(3)-photosynthesis. J Exp Bot 53: 591-607.
2. Goldschmidt E E, Huber S C (1992) Regulation of photosynthesis by end-product accumulation in leaves of plants storing starch, sucrose, and hexose sugars. Plant Physiol 99: 1443-1448.
3. Duanmu D, Miller A R, Horken K M, Weeks D P, Spalding M H (2009) Knockdown of limiting-$CO_2$-induced gene HLA3 decreases HCO3-transport and photosynthetic Ci affinity in *Chlamydomonas reinhardtii*. Proc Natl Acad Sci USA 106: 5990-5995.
4. Moroney J V, Jungnick N, Dimario R J, Longstreth D J (2013) Photorespiration and carbon concentrating mechanisms: two adaptations to high O2, low $CO_2$ conditions. Photosynth Res 117: 121-131.
5. Wang Y, Duanmu D, Spalding M H (2011) Carbon dioxide concentrating mechanism in *Chlamydomonas reinhardtii*: inorganic carbon transport and $CO_2$ recapture. Photosynth Res 109: 115-122.
6. Perrine Z, Negi S, Sayre R (2012) Optimization of photosynthetic light energy utilization by microalgae. Algal Research 1: 134-142.
7. Elleby B, Chirica L C, Tu C, Zeppezauer M, Lindskog S (2003) Characterization of carbonic anhydrase from *Neisseria gonorrhoeae*. Eur J Biochem 286: 1613-1619.
8. Subramanian S, Barry A, Pieris S, Sayre R T (2013) Comparative energetics and kinetics of autotrophic lipid and starch metabolism in chlorophytic microalgae: implications for biomass and biofuel production. Biotechnol Biofuels 6: 150.
9. Nakamura N, Iwano M, Havaux M, Yokota A, Munekage Y N (2013) Promotion of cyclic electron transport around photosystem I during the evolution of NADP-malic enzyme-type C4 photosynthesis in the genus Flaveria. New Phytol 199: 832-842.
10. Kramer D M, Evans J R (2011) The importance of energy balance in improving photosynthetic productivity. Plant Physiol 155: 70-78.
11. Alric J (2010) Cyclic electron flow around photosystem I in unicellular green algae. Photosynth Res 106: 47-56.
12. Amunts A, Drory O, Nelson N (2007) The structure of a plant photosystem I supercomplex at 3.4 A resolution. Nature 447: 58-63.
13. Breyton C, Nandha B, Johnson G N, Joliot P, Finazzi G (2006) Redox modulation of cyclic electron flow around photosystem I in C3 plants. Biochemistry 45: 13465-13475.

14. Cardol P, Forti G, Finazzi G (2011) Regulation of electron transport in microalgae. Biochim Biophys Acta 1807: 912-918.
15. Hanke G T, Okutani S, Satomi Y, Takao T, Suzuki A, et al. (2005) Multiple iso-proteins of FNR in *Arabidopsis*: evidence for different contributions to chloroplast function and nitrogen assimilation. Plant Cell Environ 28: 1146-1157.
16. Johnson G N (2011) Physiology of PSI cyclic electron transport in higher plants. Biochim Biophys Acta 1807: 384-389.
17. Okutani S, Hanke G T, Satomi Y, Takao T, Kurisu G, et al. (2005) Three maize leaf ferredoxin:NADPH oxidoreductases vary in subchloroplast location, expression, and interaction with ferredoxin. Plant Physiol 139: 1451-1459.
18. Slewinski T L, Braun D M (2010) Current perspectives on the regulation of whole-plant carbohydrate partitioning. Plant Science 178: 341-349.
19. Arrivault S, Guenther M, Ivakov A, Feil R, Vosloh D, et al. (2009) Use of reverse-phase liquid chromatography, linked to tandem mass spectrometry, to profile the Calvin cycle and other metabolic intermediates in *Arabidopsis rosettes* at different carbon dioxide concentrations. Plant Journal 59: 824-839.
20. Huege J, Sulpice R, Gibon Y, Lisec J, Koehl K, et al. (2007) GC-EI-TOF-MS analysis of in vivo carbon-partitioning into soluble metabolite pools of higher plants by monitoring isotope dilution after ($CO_2$)-C-13 labelling. Phytochemistry 68: 2258-2272.
21. Romisch-Margl W, Schramek N, Radykewicz T, Ettenhuber C, Eylert E, et al. (2007) ($CO_2$)-C-13 as a universal metabolic tracer in isotopologue perturbation experiments. Phytochemistry 68: 2273-2289.
22. Sekiyama Y, Kikuchi J (2007) Towards dynamic metabolic network measurements by multi-dimensional NMR-based fluxomics. Phytochemistry 68: 2320-2329.
23. Szecowka M, Heise R, Tohge T, Nunes-Nesi A, Vosloh D, et al. (2013) Metabolic fluxes in an illuminated *Arabidopsis rosette*. Plant Cell 25: 694-714.
24. Ma F, Jazmin L J, Young J D, Allen D K (Submitted) Isotopically nonstationary 13C flux analysis of *Arabidopsis thaliana* leaf metabolism at varying light intensities. Proc Natl Acad Sci USA.
25. Shastri A A, Morgan J A (2007) A transient isotopic labeling methodology for 13C metabolic flux analysis of photoautotrophic microorganisms. Phytochemistry 68: 2302-2312.
26. Young J D, Shastri A A, Stephanopoulos G, Morgan J A (2011) Mapping photoautotrophic metabolism with isotopically nonstationary (13)C flux analysis. Metab Eng 13: 656-665.
27. Young J D (Submitted) INCA: A computational platform for isotopically nonstationary metabolic flux analysis. Bioinformatics.
28. Young J D, Walther J L, Antoniewicz M R, Yoo H, Stephanopoulos G (2008) An elementary metabolite unit (EMU) based method of isotopically nonstationary flux analysis. Biotechnol Bioeng 99: 686-699.
29. Masclaux-Daubresse C, Chardon F (2011) Exploring nitrogen remobilization for seed filling using natural variation in *Arabidopsis thaliana*. J Exp Bot 62: 2131-2142.
30. Hay R K M, Gilbert R A (2001) Variation in the harvest index of tropical maize: Evaluation of recent evidence from Mexico and Malawi. Annals of Applied Biology 138: 103-109.
31. Russell W A (1985) Evaluation for plant, ear and grain traits of maize cultivars representing seven years of breeding. Maydica 30: 85-96.
32. Sinclair T R (1998) Historical changes in harvest index and crop nitrogen accumulation. Crop Science 38: 638-643.
33. Victorio R G , Moreno U, Black Jr C C (1986) Growth, partitioning, and harvest index of tuber-bearing *Solanum* genotypes grown in two contrasting Peruvian environments. Plant Physiology 82: 103-108.
34. Vos J (1997) The nitrogen response of potato (*Solanum tuberosum* L.) in the field: Nitrogen uptake and yield, harvest index and nitrogen concentration. Potato Research 40: 237-248.
35. Parry M A, Andralojc P J, Scales J C, Salvucci M E, Carmo-Silva A E, et al. (2013) Rubisco activity and regulation as targets for crop improvement. J Exp Bot 64: 717-730.
36. Sage R F (2002) Variation in the k(cat) of Rubisco in C(3) and C(4) plants and some implications for photosynthetic performance at high and low temperature. J Exp Bot 53: 609-620.
37. Henkes S, Sonnewald U, Badur R, Flachmann R, Stitt M (2001) A small decrease of plastid transketolase activity in antisense tobacco transformants has dramatic effects on photosynthesis and phenylpropanoid metabolism. Plant Cell 13: 535-551.
38. Miyagawa Y, Tamoi M, Shigeoka S (2001) Overexpression of a cyanobacterial fructose-1,6-/sedoheptulose-1,7-bisphosphatase in tobacco enhances photosynthesis and growth. Nature Biotechnology 19: 965-969.
39. Peterhansel C, Blume C, Offermann S (2013) Photorespiratory bypasses: how can they work? J Exp Bot 64: 709-715.
40. Blanco N E, Ceccoli R D, Via M V, Voss I, Segretin M E, et al. (2013) Expression of the minor isoform pea ferredoxin in tobacco alters photosynthetic electron partitioning and enhances cyclic electron flow. Plant Physiol 161: 866-879.
41. Busch K B, Deckers-Hebestreit G, Hanke G T, Mulkidjanian A Y (2012) Dynamics of bioenergetic microcompartments. Biol Chem 394: 163-188.
42. Minagawa J (2011) State transitions—the molecular remodeling of photosynthetic supercomplexes that controls energy flow in the chloroplast. Biochim Biophys Acta 1807: 897-905.
43. Peltier G, Tolleter D, Billon E, Cournac L (2010) Auxiliary electron transport pathways in chloroplasts of microalgae. Photosynth Res 106: 19-31.
44. Peng L, Shikanai T (2011) Supercomplex formation with photosystem I is required for the stabilization of the chloroplast NADH dehydrogenase-like complex in *Arabidopsis*. Plant Physiol 155: 1629-1639.
45. Takahashi H, Clowez S, Wollman F A, Vallon O, Rappaport F (2013) Cyclic electron flow is redox-controlled but independent of state transition. Nat Commun 4: 1954.
46. Hertle A P, Blunder T, Wunder T, Pesaresi P, Pribil M, et al. (2013) PGRL1 is the elusive ferredoxin-plastoquinone reductase in photosynthetic cyclic electron flow. Mol Cell 49: 511-523.
47. DalCorso G, Pesaresi P, Masiero S, Aseeva E, Schunemann D, et al. (2008) A complex containing PGRL1 and PGR5 is involved in the switch between linear and cyclic electron flow in *Arabidopsis*. Cell 132: 273-285.

48. Shikanai T (2014) Central role of cyclic electron transport around photosystem I in the regulation of photosynthesis. Current Opinion in Biotechnology 26: 25-30.
49. Walter J M, Greenfield D, Liphardt J (2010) Potential of light-harvesting proton pumps for bioenergy applications. Curr Opin Biotechnol 21: 265-270.
50. Dioumaev A K, Brown L S, Shih J, Spudich E N, Spudich J L, et al. (2002) Proton transfers in the photochemical reaction cycle of proteorhodopsin. Biochemistry 41: 5348-5358.
51. Friedrich T, Geibel S, Kalmbach R, Chizhov I, Ataka K, et al. (2002) Proteorhodopsin is a light-driven proton pump with variable vectoriality. J Mol Biol 321: 821-838.
52. Govindjee R, Ebrey T G, Crofts A R (1980) The quantum efficiency of proton pumping by the purple membrane of Halobacterium halobium. Biophys J 30: 231-242.
53. Govindjee R, Imasheva E S, Misra S, Balashov S P, Ebrey T G, et al. (1997) Mutation of a surface residue, lysine-129, reverses the order of proton release and uptake in bacteriorhodopsin; guanidine hydrochloride restores it. Biophys J 72: 886-898.
54. Govindjee R, Misra S, Balashov S P, Ebrey T G, Crouch R K, et al. (1996) Arginine-82 regulates the pKa of the group responsible for the light-driven proton release in bacteriorhodopsin. Biophys J 71: 1011-1023.
55. Lakatos M, Lanyi J K, Szakacs J, Varo G (2003) The photochemical reaction cycle of proteorhodopsin at low pH. Biophys J 84: 3252-3256.
56. Walter J M , Greenfield D, Bustamante C, Liphardt J (2007) Light-powering *Escherichia coli* with proteorhodopsin. Proc Natl Acad Sci USA 104: 2408-2412.
57. Kim J Y, Jo B H, Jo Y, Cha H J (2012) Improved production of biohydrogen in light-powered *Escherichia coli* by co-expression of proteorhodopsin and heterologous hydrogenase. Microb Cell Fact 11:2.
58. Froehlich J E, Keegstra K (2011) The role of the transmembrane domain in determining the targeting of membrane proteins to either the inner envelope or thylakoid membrane. Plant J 68: 844-856.
59. Beja O, Aravind L, Koonin E V, Suzuki M T, Hadd A, et al. (2000) Bacterial rhodopsin: evidence for a new type of phototrophy in the sea. Science 289: 1902-1906.
60. Lindqvist A, Andersson S (2002) Biochemical properties of purified recombinant human beta-carotene 15,15'-monooxygenase. J Biol Chem 277: 23942-23948.
61. Roslan H A, Salter M G, Wood C D, White M R, Croft K P, et al. (2001) Characterization of the ethanol-inducible alc gene-expression system in *Arabidopsis thaliana*. Plant J 28: 225-235.
62. Cao Y, Brown L S, Sasaki J, Maeda A, Needleman R, et al. (1995) Relationship of proton release at the extracellular surface to deprotonation of the schiff base in the bacteriorhodopsin photocycle. Biophys J 68: 1518-1530.
63. Joliot P, Johnson G N (2011) Regulation of cyclic and linear electron flow in higher plants. Proc Natl Acad Sci USA 108: 13317-13322.
64. Fabre N, Reiter I M, Becuwe-Linka N, Genty B, Rumeau D (2007) Characterization and expression analysis of genes encoding alpha and beta carbonic anhydrases in *Arabidopsis*. Plant Cell Environ 30: 617-629.
65. Bihmidine S, Hunter C T, 3rd, Johns C E, Koch K E, Braun D M (2013) Regulation of assimilate import into sink organs: update on molecular drivers of sink strength. Front Plant Sci 4: 177.
66. Ihemere U, Arias-Garzon D, Lawrence S, Sayre R (2006) Genetic modification of cassava for enhanced starch production. Plant Biotechnol J 4: 453-465.
67. Wunsche J N, Greer D H, Laing W A, Palmer J W (2005) Physiological and biochemical leaf and tree responses to crop load in apple. Tree Physiol 25: 1253-1263.
68. Paul M J, Foyer C H (2001) Sink regulation of photosynthesis. J Exp Bot 52: 1383-1400.
69. Sonnewald U, Lerchi J, Zrenner R, Frommer W (1994) Manipulation of sink-source relations in transgenic plants. Plant Cell Environ 17: 649-658.
70. Sonnewald U, Willmitzer L (1992) Molecular approaches to sink-source interactions. Plant Physiol 99: 1267-1270.
71. Willson W J (1972) Control of crop processes In: Rees A R, Cockshull K E, Hand D W, Hurd R G, editors. Crop Processes in Controlled Environments: London Academic Press. pp. 7-30.
72. Jonik C, Sonnewald U, Hajirezaei M R, Flugge U I, Ludewig F (2012) Simultaneous boosting of source and sink capacities doubles tuber starch yield of potato plants. Plant Biotechnol J 10: 1088-1098.
73. Sweetlove L J, Hill S A (2000) Source metabolism dominates the control of source to sink carbon flux in tuberizing potato plants throughout the diurnal cycle and under a range of environmental conditions. Plant, Cell and Environment 23: 523-529.
74. Allen D K, Goldford J, Gierse J, Mandy D, Diepenbrock C, et al. (2013) (submitted) Quantification of peptide m/z distributions form 13C-labeled cultures with high resolution mass spectrometry. Analytical Chemistry.
75. Choi J, Antoniewicz M R (2011) Tandem mass spectrometry: a novel approach for metabolic flux analysis. Metab Eng 13: 225-233.
76. Allen D K, Libourel I G L, Shachar-Hill Y (2009) Metabolic flux analysis in plants: Coping with complexity. Plant, Cell and Environment 32: 1241-1257.
77. Allen D K, Laclair R W, Ohlrogge J B, Shachar-Hill Y (2012) Isotope labelling of Rubisco subunits provides in vivo information on subcellular biosynthesis and exchange of amino acids between compartments. Plant, Cell and Environment 35: 1232-1244.
78. Allen D K, Shachar-Hill Y, Ohlrogge J B (2007) Compartment-specific labeling information in $^{13}C$ metabolic flux analysis of plants. Phytochemistry 68: 2197-2210.
79. Mandy D, Goldford J, Yang H, Allen D K, Libourel I G L (2013) (submitted) Metabolic flux analysis using 13C peptide label measurements. The Plant Journal.
80. Allen D K, Young J D (2013) Carbon and nitrogen provisions alter the metabolic flux in developing soybean embryos. Plant Physiol 161: 1458-1475.
81. Allen D K, Ohlrogge J B, Shachar-Hill Y (2009) The role of light in soybean seed filling metabolism. Plant Journal 58: 220-234.
82. Jazmin L J, Young J D (2013) Isotopically nonstationary 13C metabolic flux analysis. Methods Mol Biol 985: 367-390.
83. Blankenship R E, Tiede D M, Barber J, Brudvig G W, Fleming G, et al. (2011) Comparing photosynthetic and photovoltaic efficiencies and recognizing the potential for improvement. Science 332: 805-809.
84. Jazmin L J, O'Grady J, Ma F, Allen D K, Morgan J A, et al. (In press) Isotopically nonstationary MFA (INST-MFA) of autotrophic metabolism. Methods Mol Biol.
85. Egnatchik R A, Leamy A K, Noguchi Y, Shiota M, Young J D (In press) Palmitate-induced activation of mitochondrial metabolism promotes oxidative stress and apoptosis in H4IIEC3 rat hepatocytes. Metabolism.

86. Leamy A K, Egnatchik R A, Young J D (2013) Molecular mechanisms and the role of saturated fatty acids in the progression of non-alcoholic fatty liver disease. Prog Lipid Res 52: 165-174.

87. Srour O, Young J D, Eldar Y C (2011) Fluxomers: a new approach for 13C metabolic flux analysis. BMC Syst Biol 5: 129.

88. Young J D, Allen D K, Morgan J A (2014) Isotopomer measurement techniques in metabolic flux analysis II: Mass spectrometry. Methods Mol Biol 1083: 85-108.

89. Egnatchik R A, Leamy A K, Jacobson D A, Young J D (Submitted) ER calcium stimulates mitochondrial alterations in hepatic lipotoxicity. J Biol Chem.

90. Leamy A K, Egnatchik R A, Shiota M, Young J D (Submitted) Modulating lipid fate controls ER stress and lipotoxicity in palmitate-treated hepatic cells. FEBS J.

91. Young J D (In press) Metabolic flux rewiring in mammalian cell cultures. Curr Opin Biotechnol.

92. McAtee A G, Templeton N, Young J D (Submitted) Role of CHO central carbon metabolism in controlling the quality of secreted biotherapeutic proteins. Pharmaceutical Bioprocessing.

93. Duckwall C S, Murphy T A, Young J D (2013) Mapping cancer cell metabolism with(13)C flux analysis: Recent progress and future challenges. J Carcinog 12: 13.

What is claimed is:

1. A transgenic plant or alga, comprising within its genome, and expressing or overexpressing, a combination of heterologous nucleotide sequences encoding:

i) a protein with at least 85% amino acid sequence identity to SEQ ID NO: 77 which has an activity of an ATP-dependent bicarbonate anion transporter localized to the plasma membrane, or ii) a protein with at least 85% amino acid sequence identity to SEQ ID NO: 18 which has an activity of a bicarbonate anion transporter localized to the chloroplast envelope, or iii) a combination thereof;

a protein with at least 85% amino acid sequence identity to SEQ ID NO: 1 which has an activity of a cyclic electron transfer modulator protein;

a protein with at least 85% amino acid sequence identity to SEQ ID NO: 3 which has an activity of a cyclic electron transfer modulator protein; and a protein with at least 85% amino acid sequence identity to SEQ ID NO: 21 which has an activity of a carbonic anhydrase protein.

2. The transgenic plant or alga of claim 1 wherein the bicarbonate anion transporter localized to the chloroplast envelope is an LCIA protein of SEQ ID NO: 18.

3. The transgenic plant or alga of claim 1 wherein the carbonic anhydrase is a BCA protein of SEQ ID NO: 21.

4. The transgenic plant or alga of claim 1 wherein the heterologous nucleotide sequences encode i) SEQ ID NO: 1, and SEQ ID NO: 77; or ii) SEQ ID NO: 1, SEQ ID NO: 77 and SEQ ID NO: 3.

5. The transgenic plant or alga of claim 2 wherein the heterologous nucleotide sequences encode SEQ ID NO: 1, and SEQ ID NO: 77.

6. The transgenic plant or alga of claim 1 wherein the heterologous nucleotide sequences encode (SEQ ID NO: 1), (SEQ ID NO: 77), (SEQ ID NO: 3), (SEQ ID NO: 18), and (SEQ ID NO: 21).

7. The transgenic plant or alga of claim 1, wherein the sequence identity is at least 90% amino acid sequence identity.

8. The transgenic plant of claim 1, which is a C3 plant or a C4 plant.

9. The transgenic plant or alga of claim 1 further comprising a cell-part comprising within its genome, and expressing or overexpressing a combination of heterologous nucleotide sequences encoding:

i) a protein with at least 85% amino acid sequence identity to SEQ ID NO: 77 which has an activity of an ATP-dependent bicarbonate anion transporter localized to the plasma membrane, or ii) a protein with at least 85% amino acid sequence identity to SEQ ID NO: 18 which has an activity of a bicarbonate anion transporter localized to the chloroplast envelope, or iii) a combination thereof;

a protein with at least 85% amino acid sequence identity to SEQ ID NO: 1 which has an activity of a cyclic electron transfer modulator protein;

a protein with at least 85% amino acid sequence identity to SEQ ID NO: 3 which has an activity of a cyclic electron transfer modulator protein; and a protein with at least 85% amino acid sequence identity to SEQ ID NO: 21 which has an activity of a carbonic anhydrase protein.

10. A method of making a transgenic plant or alga of claim 1 wherein said method comprises expressing, or overexpressing, in a C3 plant, a C4 plant, or an alga, a combination of heterologous nucleotide sequences encoding i) a protein with at least 85% amino acid sequence identity to SEQ ID NO: 77 which has an activity of an ATP-dependent bicarbonate anion transporter localized to the plasma membrane, or ii) a protein with at least 85% amino acid sequence identity to SEQ ID NO: 18 which has an activity of a bicarbonate anion transporter localized to the chloroplast envelope, or iii) a combination thereof;

a protein with at least 85% amino acid sequence identity to SEQ ID NO: 1 which has an activity of a cyclic electron transfer modulator protein;

a protein with at least 85% amino acid sequence identity to SEQ ID NO: 3 which has an activity of a cyclic electron transfer modulator protein; and a protein with at least 85% amino acid sequence identity to SEQ ID NO: 21 which has an activity of a carbonic anhydrase protein.

11. A method of elevating CET activity or of enhancing carbon fixation or for producing biomass or other products in a C3 plant, C4 plant, or alga wherein said method comprises expressing, or overexpressing, in a C3 plant, a C4 plant, or an alga, a combination of heterologous nucleotide sequences encoding:

i) a protein with at least 85% amino acid sequence identity to SEQ ID NO: 77 which has an activity of an ATP-dependent bicarbonate anion transporter localized to the plasma membrane, or ii) a protein with at least 85% amino acid sequence identity to SEQ ID NO: 18 which has an activity of a bicarbonate anion transporter localized to the chloroplast envelope, or iii) a combination thereof;

a protein with at least 85% amino acid sequence identity to SEQ ID NO: 1 which has an activity of a cyclic electron transfer modulator protein;

a protein with at least 85% amino acid sequence identity to SEQ ID NO: 3 which has an activity of a cyclic electron transfer modulator protein; and a protein with at least 85% amino acid sequence identity to SEQ ID NO: 21 which has an activity of a carbonic anhydrase protein.

12. The method of claim 11 further comprises growing said plant or alga and harvesting said biomass or recovering said product from said plant or alga.

* * * * *